United States Patent
Dischert et al.

(10) Patent No.: US 10,858,675 B2
(45) Date of Patent: Dec. 8, 2020

(54) MODIFIED MICROORGANISM FOR THE OPTIMIZED PRODUCTION OF 2,4-DIHYDROXYBUTYRATE WITH ENHANCED 2,4-DIHYDROXYBUTYRATE EFFLUX

(71) Applicant: METABOLIC EXPLORER, Saint Beauzire (FR)

(72) Inventors: Wanda Dischert, Vic-le-Comte (FR); Laurence Dumon-Seignovert, Pont du Chateau (FR); Perrine Vasseur, Martres sur Morges (FR); Gwénaëlle Bestel-Corre, Saint Beauzire (FR); Philippe Soucaille, Deyme (FR)

(73) Assignee: METABOLIC EXPLORER, Saint Beauzire (FR)

( * ) Notice: Subject to any disclaimer, the term of this patent is extended or adjusted under 35 U.S.C. 154(b) by 0 days.

(21) Appl. No.: 15/564,943

(22) PCT Filed: Apr. 7, 2016

(86) PCT No.: PCT/EP2016/057660
§ 371 (c)(1),
(2) Date: Oct. 6, 2017

(87) PCT Pub. No.: WO2016/162442
PCT Pub. Date: Oct. 13, 2016

(65) Prior Publication Data
US 2018/0105845 A1 Apr. 19, 2018

(30) Foreign Application Priority Data

Apr. 7, 2015 (EP) .................................... 15305514

(51) Int. Cl.
| | |
|---|---|
| *C12P 7/42* | (2006.01) |
| *C12N 15/52* | (2006.01) |
| *C07K 14/245* | (2006.01) |
| *C07K 14/39* | (2006.01) |
| *C07K 14/395* | (2006.01) |
| *C12N 9/04* | (2006.01) |
| *C12N 9/02* | (2006.01) |
| *C12N 9/18* | (2006.01) |

(52) U.S. Cl.
CPC .............. *C12P 7/42* (2013.01); *C07K 14/245* (2013.01); *C07K 14/39* (2013.01); *C07K 14/395* (2013.01); *C12N 9/0006* (2013.01); *C12N 9/0008* (2013.01); *C12N 9/18* (2013.01); *C12N 15/52* (2013.01); *C12Y 101/01175* (2013.01); *C12Y 301/01068* (2013.01)

(58) Field of Classification Search
None
See application file for complete search history.

(56) References Cited

U.S. PATENT DOCUMENTS 8,758,764 B2 * 6/2014 Masignani ......... C07K 16/1232
424/185.1

FOREIGN PATENT DOCUMENTS

| WO | WO 2013/160762 A2 | 10/2013 |
| WO | WO 2014/009435 A1 | 1/2014 |

OTHER PUBLICATIONS

Altschul et al., "Basic local alignment search tool," Journal of Molecular Biology, vol. 215, No. 3, 1990, pp. 403-410.
Anderson, "Growth requirements of virus-resistant mutants of *Escherichia coil* strain "B"," Proceedings of the National Academy of Sciences, vol. 32, 1946, pp. 120-128.
Bolten et al., "Sampling for metabolome analysis of microorganisms," Analytical Chemistry, vol. 79, No. 10, May 15, 2007, pp. 3843-3849.
Carrier et al., "Library of synthetic 5' secondary structures to manipulate mRNA stability in *Escherichia coli*," Biotechnology Progress, vol. 15, No. 1, 1999 (Published on Web Jan. 9, 1999), pp. 58-64.
Cho et al, "Integrated membrane processes for separation and purification of organic acid from a biomass fermentation process," Industrial & Engineering Chemistry Research, vol. 51, Jun. 28, 2012, pp. 10207-10219.
Daßler et al., "Identification of a major facilitator protein from *Escherichia coli* involved in efflux of metabolites of the cysteine pathway," Molecular Microbiology, vol. 336, No. 5, 2000, pp. 1101-1112.
Datsenko et al., "One-step inactivation of chromosomal genes in *Escherichia coli* K-12 using PCR products," Proceedings of the National Academy of Sciences, vol. 97, No. 12, Jun. 6, 2000, pp. 6640-6645.
Davis et al., "Characterizing the native codon usages of a genome: an axis projection approach," Molecular Biology and Evolution, vol. 28, No. 1, 2011 (Advance Access publication Aug. 2, 2010), pp. 211-221.
Deml et al., "Multiple effects of codon usage optimization on expression and immunogenicity of DNA candidate vaccines encoding the human immunodeficiency virus type 1 Gag protein," Journal of Virology, vol. 75, No. 22, Nov. 2001, pp. 10991-11001.
Dykxhoorn et al., "A set of compatible tac promoter expression vectors," Gene, vol. 177, No. 1-2, 1996, pp. 133-136.

(Continued)

*Primary Examiner* — Hope A Robinson
(74) *Attorney, Agent, or Firm* — Birch, Stewart, Kolasch & Birch, LLP

(57) ABSTRACT

The present invention relates to a recombinant microorganism capable of producing 2,4-dihydroxybutyrate, which is characterized by an increased cellular export, and preferably by a decreased cellular import, of said 2,4 DHB. The invention also relates to a method for the optimized production of 2,4-dihydroxybutyrate by culturing said microorganism in a fermentation medium and recovering 2,4-DHB from said medium.

5 Claims, 2 Drawing Sheets

Specification includes a Sequence Listing.

(56) References Cited

OTHER PUBLICATIONS

Eriksen et al., "Protein design for pathway engineering," Journal of Structural Biology, vol. 185, No. 2, 2014 (Available online Apr. 1, 2013), pp. 234-242.

Gao et al., "Extractive lactic acid fermentation with tri-n-decylamine as the extractant," Enzyme and Microbial Technology, vol. 44, 2009, pp. 350-354.

Graf et al., "Concerted action of multiple cis-acting sequences is required for Rev dependence of late human immunodeficiency virus type 1 gene expression," Journal of Virology, vol. 74, No. 22, Nov. 2000, pp. 10822-10826.

Green et al., "Molecular cloning: a laboratory manual," Ed. 4, Cold Spring Harbor Laboratory Press, vol. 1, 2012, 34 pages.

Harrington et al., "Balanced branching in transcription termination," Proceedings of the National Academy of Sciences, vol. 98, No. 9, Apr. 24, 2001, pp. 5019-5024.

Hiller et al., "Metabolic profiling of *Escherichia coli* cultivations: evaluation of extraction and metabolite analysis procedures," Biotechnology Letters, vol. 29, No. 8, 2007 (Published online May 2007), pp. 1169-1178.

Husson et al., "Multiple-acid equilibria in adsorption of carboxylic acids from dilute aqueous solution," Industrial & Engineering Chemistry Research, vol. 38, No. 2, 1999 (Published on Web Jan. 5, 1999), pp. 502-511.

Kiefer et al., "Determination of carbon labeling distribution of intracellular metabolites from single fragment ions by ion chromatography tandem mass spectrometry," Analytical Biochemistry, vol. 360, 2007 (Available online Jul. 12, 2006), pp. 182-188.

Kim et al., "Simultaneous consumption of pentose and hexose sugars: an optimal microbial phenotype for efficient fermentation of lignocellulosic biomass," Applied Microbiology and Biotechnology, vol. 88, 2010 (Published online Sep. 14, 2010), pp. 1077-1085.

Kurihara et al., "The putrescine importer PuuP of *Escherichia coli* K-12," Journal of Bacteriology, vol. 191, No. 8, Apr. 2009 (Published ahead of print on Jan. 30, 2009), pp. 2776-2782.

Kutukova et al., "The yeaS (leuE) gene of *Escherichia coli* encodes an exporter of leucine, and the Lrp protein regulates its expression," FEBS Letters, vol. 579, No. 21, 2005 (Available online Aug. 10, 2005), pp. 4629-4634.

Lee et al., "Control of substrate access to the active site in methane monooxygenase," Nature, vol. 494, Feb. 21, 2013 (Published online Feb. 10, 2013), pp. 380-384.

Lerner et al., "Low copy number plasmids for regulated low-level expression of cloned genes in *Escherichia coli* with blue/white insert screening capability," Nucleic Acids Research, vol. 18, No. 15, 1990, p. 4631.

Needleman et al., "A general method applicable to the search for similarities in the amino acid sequence of two proteins," Journal of Molecular Biology, vol. 48, No. 3, 1970, pp. 443-453.

Rao et al., "Recovery of lactic acid by reactive distillation," Journal of Applied Sciences, vol. 14, No. 12, 2014, pp. 1289-1293.

Salts, "The ribosome binding site calculator," Methods in Enzymology, Academic Press, vol. 498, 2011, pp. 19-42.

Schügerl, "Integrated processing of biotechnology products," Biotechnology Advances, vol. 18, 2000, pp. 581-599.

Segel, "Enzyme kinetics: Behavior and analysis of rapid equilibrium and steady-state enzyme systems," John Wiley & Sons, Inc., 1993, pp. 44-54 and 100-112.

Van Hecke et al., "Advances in in-situ product recovery (ISPR) in whole cell biotechnology during the last decade," Biotechnology Advances, vol. 32, 2014 (Available online Jul. 27, 2014), pp. 1245-1255.

Zittrich et al., "Quantitative discrimination of carrier-mediated excretion of isoleucine from uptake and diffusion in Corynebacterium glutamicum," Journal of Bacteriology, vol. 176, No. 22, Nov. 1994, pp. 6892-6899.

* cited by examiner

MODIFIED MICROORGANISM FOR THE OPTIMIZED PRODUCTION OF 2,4-DIHYDROXYBUTYRATE WITH ENHANCED 2,4-DIHYDROXYBUTYRATE EFFLUX

INTRODUCTION

The present invention relates to a recombinant microorganism capable of producing 2,4-dihydroxybutyrate, which is characterized by an increased cellular export, and preferably by a decreased cellular import, of said 2,4-dihydroxybutyrate. The invention also relates to a method for the optimized production of 2,4-dihydroxybutyrate by culturing said microorganism in a fermentation medium and recovering 2,4-dihydroxybutyrate from said medium.

2,4-dihydroxybutyric acid (i.e. 2,4-DHB or DHB), also known as 2,4-dihydroxybutanoic acid, 2,4-dihydroxybutyrate or 3-deoxy-L-glycero-tetronic acid, is an industrial chemical compound of high economic interest as it can serve as a precursor for the synthesis of various bulk and fine chemicals, among which the methionine analogs 2-hydroxy-4-(methylthio)-butyrate (HMTB) and 2-keto-4(methylthio)butyrate (KMTB) (both produced at about 800,000 tons per year), gamma-butyrolactone (GBL) (about 500,000 tons/year), as well as many other biotechnological products (over about 1,000,000 tons/year). Notably, HMTB is a well-known food additive widely used in animal nutrition as a low-priced amino acid substitute (US2009/318715), while GBL is known an organic solvent used for cleaning circuit boards, stripping paint, flavoring soy products or even for producing the gamma-hydroxybutyric acid (GHB) drug.

2,4-dihydroxybutyric acid can be produced by converting glyceritol into acrolein, followed by hydration of the yielded 2-deoxyglycerose (3-hydroxypropanal), subsequently treated with cyanide to produce a nitrile, which is then hydrolysed and treated with brucine to isolate the L-enantiomer 2,4-DHB. However, this petrochemical synthesis of DHB is not economically viable as it relies on the use of hazardous materials and conditions, is time-consuming and expensive, and, to this day, no natural metabolic pathway for its biochemical production has been identified.

There is thus a need in the art for producing this highly relevant compound by alternative cost-effective methods, which will reduce dependence on petroleum feedstocks.

Synthetic metabolic pathways appear to be particularly attractive as they provide a green and sustainable way to produce 2,4-DHB, at a lower cost. As a matter of fact, various metabolic engineering approaches relying on recombinant expression of specific enzymes in microorganisms have recently been developed: WO2012/056318, WO2013/160762, WO2014/009435 and EP14306564.7 describe the production of 2,4-DHB by fermentation of glucose in genetically modified microorganisms, via different metabolic pathways. Most of the enzymes identified in these patent applications were obtained either by rational engineering based on structural and mechanistic knowledge of candidate enzymes acting on sterically similar cognate substrates, or by screening of natural enzymes and further improvement by rational design. More specifically, WO2012/056318 discloses three non-naturally occurring enzymes (malate kinase, malate semi-aldehyde dehydrogenase and a DHB dehydrogenase, all being mutated) which can be overexpressed in a microorganism in order to transform the metabolic intermediate (L)-Malate into 2,4-DHB; WO2013/160762 requires the heterogenous expression of various enzymes, some of them being mutated to improve the enzyme activity and/or substrate affinity (malyl-CoA synthetase, and/or succinyl-CoA: (L)-Malate-CoA transferase, and/or malyl-CoA lyase; malyl-CoA reductase; and DHB dehydrogenase) in order to transform the metabolic intermediate malate, or succinyl-CoA, or glycolyl-CoA into 2,4-DHB; while the method of WO2014/009435 relies on the conversion of the metabolic intermediate (L)-homoserine into 2-oxo-4-hydroxybutyrate (OHB) and the reduction of OHB in 2,4-DHB by recombinantly expressing two mutated enzymes (a homoserine transaminase and a DHB reductase). Recently, the company METabolic EXplorer designed an alternative synthetic pathway for the microbial production of 2,4-dihydroxybutyric acid from the 1,2,4-butanetriol metabolic intermediate, in two single steps comprising the oxidation of 1,2,4-butanetriol into 2,4-dihydroxybutanal, followed by the oxidation of 2,4-dihydroxybutanal into 2,4-DHB (patent application not published yet).

These different approaches nevertheless require further improvements. Indeed, microorganisms genetically modified as described above produce 2,4-DHB by fermentation in a limited amount, and a higher production rate and/or yield in line with a desirable industrial scale may be limited by the accumulation of 2,4-DHB within the cells of the microorganism.

The present invention addresses the above discussed need in the art.

In particular, the inventors have surprisingly and unexpectedly discovered that the overall production of 2,4-DHB can be greatly improved, regardless of the selected 2,4-DHB production metabolic pathway, by genetically engineering microorganisms so as to reduce the intracellular 2,4-DHB accumulation. More particularly, this accumulation can be reduced by genetically improving the 2,4-DHB cellular export capacity of the microorganism of interest as well as by genetically attenuating its intracellular import from the 2,4-DHB contained in the culture medium.

The present invention therefore provides herein a microorganism genetically modified for an optimized production of 2,4-dihydroxybutyrate. This microorganism, which is engineered to produce 2,4-DHB, is further genetically modified for reducing intracellular 2,4-dihydroxybutyrate accumulation, in order to optimize its production.

The invention also relates to a method for the optimized production of 2,4-dihydroxybutyrate by fermentation comprising culturing the microorganism of the invention in a culture medium, and recovering the produced 2,4-DHB from the culture medium.

DETAILED DESCRIPTION OF THE INVENTION

It shall be understood that the following detailed description is not limitative and that various modifications, substitutions, omissions, and changes may be made without departing from the scope of the invention. It shall also be understood that the terminology used herein is for the purpose of describing particular embodiments of the invention, and is not intended to be limiting.

Unless stated otherwise, scientific and technical terms used in connection with the present invention shall have the meanings that are commonly understood by those of ordinary skill in the art. Furthermore, unless otherwise required by context, nomenclatures used herein, and techniques of molecular biology, cell culture, are those well-known and commonly used in the art. Such techniques are fully explained in the literature (see Sambrook et al., 2012).

All publications, patents and patent applications cited herein, whether supra or infra, are hereby incorporated by reference in their entirety.

Nevertheless, with respect to the use of different terms throughout the current specification, the following definitions more particularly apply.

The singular forms "a", "an", and "the" include herein plural reference unless the context clearly dictates otherwise. Thus, for example, a reference to "a microorganism" includes a plurality of such microorganisms, and a reference to "an endogenous gene" is a reference to one or more endogenous genes, and so forth.

The terms "comprise", "contain", "involve" or "include" or variations such as "comprises", "comprising", "containing", "involved", "includes", "including" are used herein in an inclusive sense, i.e. to specify the presence of the stated features but not to preclude the presence or addition of further features in various embodiments of the invention.

The term "microorganism", as used herein, refers to a living microscopic organism, which may be a single cell or a multicellular organism and which can generally be found in nature. In the context of the present invention, the microorganism is preferably a bacterium, yeast or fungus. More preferably, the microorganism of the invention is selected among Enterobacteriaceae, Bacillaceae, Clostridiaceae, Streptomycetaceae, Corynebacteriaceae and yeast. Even more preferably, the microorganism of the invention is a species of *Escherichia, Klebsiella, Thermoanaerobacterium, Clostridium Corynebacterium* or *Saccharomyces*. Yet, even more preferably, the microorganism of the invention is selected from *Escherichia coli, Klebsiella pneumoniae, Thermoanaerobacterium thermosaccharolyticum, Clostridium acetobutylicum, Corynebacterium glutamicum* and *Saccharomyces cerevisiae*. Most preferably, the microorganism of the invention is *Escherichia coli*.

The term "recombinant microorganism", "genetically modified microorganism", or "genetically engineered microorganism", as used herein, refers to a microorganism as defined above that is not found in nature and therefore genetically differs from its natural counterpart. In other words, it refers to a microorganism that is modified by introduction and/or by deletion and/or by modification of its genetic elements. Such modification can be performed by genetic engineering, by forcing the development and evolution of new metabolic pathways by culturing the microorganism under specific selection pressure, or by combining both methods (see, e.g. WO2005/073364 or WO2008/116852).

A microorganism genetically modified for the production of 2,4-DHB according to the invention therefore means that said microorganism is a recombinant microorganism as defined above that is capable of producing 2,4-DHB. In other words, said microorganism has been genetically modified to allow production of 2,4-DHB.

As further explained below, the microorganism of the invention can be genetically modified by modulating the expression level of one or more endogenous genes, and/or by expressing one or more heterologous genes in said microorganism.

By "gene", it is meant herein a nucleic acid molecule or polynucleotide that codes for a particular protein (i.e. polypeptide), or in certain cases, for a functional or structural RNA molecule. In the context of the present invention, the genes referred herein encode proteins, such as enzymes, efflux systems or uptake transporters. Genes according to the invention are either endogenous genes or exogenous. By "endogenous gene", it is meant herein that said gene is naturally present in the microorganism, while the term "exogenous gene" (or alternatively, "heterologous gene" or "transgene") refers to a gene is not naturally occurring in the microorganism.

In the context of the present invention, should the microorganism be genetically modified to "modulate" the expression level of one or more endogenous genes, it is meant herein that the expression level of said gene is up-regulated, downregulated (i.e. attenuated), or even completely abolished by comparison to its natural expression level. Such modulation can therefore result in an enhancement of the activity of the gene product, or alternatively, in a lower or null activity of the endogenous gene product.

An endogenous gene can be overexpressed by introducing heterologous sequences which favour upregulation in addition to endogenous regulatory elements or by substituting those endogenous regulatory elements with such heterologous sequences, or by introducing one or more supplementary copies of the endogenous gene into the chromosome or a plasmid within the microorganism. Endogenous gene activity and/or expression level can also be modified by introducing mutations into their coding sequence to modify the gene product. A deletion of an endogenous gene can also be performed to inhibit totally its expression within the microorganism. Another way to modulate the expression of an endogenous gene is to exchange its promoter (i.e. wild type promoter) with a stronger or weaker promoter to up or down regulate the expression level of this gene. Promoters suitable for such purpose can be homologous or heterologous and are well-known in the art. It is within the skill of the person in the art to select appropriate promoters for modulating the expression of an endogenous gene.

In addition, or alternatively, the microorganism of the invention can be genetically modified to express one or more exogenous genes, provided that said genes are introduced into the microorganism with all the regulatory elements necessary for their expression in the host microorganism. The modification or "transformation" of microorganisms with exogenous DNA is a routine task for those skilled in the art. In the context of the present invention, the term "overexpression" or "overexpressing" is also used herein in relation to the expression of exogenous genes in the microorganism.

In order to express an exogenous gene in a microorganism, such gene can be directly integrated into the microorganism chromosome, or be expressed extra-chromosomally by plasmids or vectors within the microorganism. A variety of plasmids, which differ in respect of their origin of replication and of their copy number in a cell, are well known in the art and can be easily selected by the skilled practitioner for such purpose. Exogenous genes according to the invention are advantageously homologous genes.

In the context of the invention, the term "homologous gene" or "homolog" not only refers to a gene inherited by two species (i.e. microorganism species) by a theoretical common genetic ancestor, but also includes genes which may be genetically unrelated that have, nonetheless, evolved to encode proteins which perform similar functions and/or have similar structure (i.e. functional homolog). Therefore the term "functional homolog" refers herein to a gene that encodes a functionally homologous protein.

Using the information available in databases such as Uniprot (for proteins), Genbank (for genes), or NCBI (for proteins or genes), those skilled in the art can easily determine the sequence of a specific protein and/or gene of a microorganism, and identify based on this sequence the one of equivalent genes, or homologs, in another microorganism. This routine work can be performed by a sequence alignment of a specific gene sequence of a microorganism with gene sequences or the genome of other microorganisms, which can be found in the above mentioned databases. Such sequence alignment can advantageously be performed using the BLAST algorithm developed by Altschul et al. (1990). Once a sequence homology has been established between those sequences, a consensus sequence can be derived and used to design degenerate probes in order to clone the corresponding homolog gene of the related microorganism. These routine methods of molecular biology are well known to those skilled in the art.

It shall be further understood that, in the context of the present invention, should an exogenous gene encoding a protein of interest be expressed in a specific microorganism, a synthetic version of this gene is preferably constructed by replacing non-preferred codons or less preferred codons with preferred codons of said microorganism which encode the same amino acid. It is indeed well-known in the art that codon usage varies between microorganism species, which may impact the recombinant expression level of the protein of interest. To overcome this issue, codon optimization methods have been developed, and are extensively described in Graf et al. (2000), Deml et al. (2001) or Davis & Olsen (2011). Several softwares have been developed for codon optimization determination such as the GeneOptimizer® software (Lifetechnologies) or the OptimumGene™ software (GenScript). In other words, the exogenous gene encoding a protein of interest is preferably codon-optimized for expression in a specific microorganism.

The microorganism according to the invention can also be genetically modified to increase or decrease the activity of one or more proteins.

Increasing such activity can be obtained by improving the protein catalytic efficiency, by decreasing protein turnover, by decreasing messenger RNA (mRNA) turnover, by increasing transcription of the gene, or by increasing translation of the mRNA.

Improving the protein catalytic efficiency means increasing the kcat and/or decreasing the Km for a given substrate and/or a given cofactor, and/or increasing the Ki for a given inhibitor. Kcat, Km and Ki are Michaelis-Menten constants that the man skilled in the art is able to determine (Segel, 1993). Decreasing protein turnover means stabilizing the protein. Methods to improve protein catalytic efficiency and/or decrease protein turnover are well known from the man skilled in the art. Those include rational engineering with sequence and/or structural analysis and directed mutagenesis, as well as random mutagenesis and screening. Mutations can be introduced by site-directed mutagenesis by conventional methods such as Polymerase Chain Reaction (PCR), by random mutagenesis techniques, for example via mutagenic agents (Ultra-Violet rays or chemical agents like nitrosoguanidine (NTG) or ethylmethanesulfonate (EMS)) or DNA shuffling or error-prone PCR. Stabilizing the protein can also be achieved by adding a "tag" peptide sequence either at the N-terminus or the C-terminus of the protein. Such tags are well known in the art, and include, among others, the Glutathione-S-Transferase (GST).

Decreasing mRNA turnover can be achieved by modifying the gene sequence of the 5'-untranslated region (5'-UTR) and/or the coding region, and/or the 3'-UTR (Carrier and Keasling, 1999).

Increasing the transcription of a gene, whether endogenous or exogenous, can be achieved by increasing the number of its copies within the microorganism and/or by using a promoter leading to a higher level of expression of the gene compared to the wild type promoter. In the context of the present invention, the term "overexpression" or "overexpressing" is also used to designate an increase in transcription of a gene in a microorganism.

As indicated above, to increase the number of copies of a gene in the microorganism, said gene can be encoded chromosomally or extra-chromosomally. When the gene of interest is to be encoded on the chromosome, several copies of the gene can be introduced on the chromosome by methods of genetic recombination, which are well-known to in the art (e.g. gene replacement). When the gene is to be encoded extra-chromosomally in the microorganism, it can be carried by different types of plasmid that differ in respect to their origin of replication depending on the microorganism in which they can replicate, and by their copy number in the cell. The microorganism transformed by said plasmid can contain 1 to 5 copies of the plasmid, or about 20 copies of it, or even up to 500 copies of it, depending on the nature of the plasmid. Examples of low copy number plasmids which can replicate in *E. coli* include, without limitation, the pSC101 plasmid (tight replication), the RK2 plasmid (tight replication), as well as the pACYC and pRSF1010 plasmids, while an example of high copy number plasmid which can replicate in *E. coli* is pSK bluescript II.

Promoters which can increase the expression level of a gene are also well-known to the skilled person in the art, and can be homologous (originating from same species) or heterologous (originating from a different species). Examples of such promoters include, without limitation, the promoters Ptrc, Ptac, Plac, and the lambda promoter cl. These promoters can also be induced ("inducible promoters") by a particular compound or by specific external condition like temperature or light.

Increasing translation of the mRNA can be achieved by modifying the Ribosome Binding Site (RBS). A RBS is a sequence on mRNA that is bound by the ribosome when initiating protein translation. It can be either the 5' cap of a mRNA in eukaryotes, a region 6-7 nucleotides upstream of the start codon AUG in prokaryotes (called the Shine-Dalgarno sequence), or an internal ribosome entry site (IRES) in viruses. By modifying this sequence, it is possible to change the protein translation initiation rate, to proportionally alter its production rate, and control its activity inside the cell. It is also possible to optimize the strength of a RBS sequence to achieve a targeted translation initiation rate by using the software RBS CALCULATOR (Salis, 2011). It is within the skill of the person in the art to select the RBS sequence based on the nature of the mRNA.

Decreasing the activity of a protein can mean either decreasing its specific catalytic activity by mutating the gene encoding said protein so as to change the corresponding amino acid sequence and/or decreasing concentrations of the protein in the cell by mutating the nucleotide sequence or by deleting the coding region of said gene.

As used herein, the term "efflux system", "efflux pump", "efflux transporter", or "exporter" refers to a protein assembly that exports substrate molecules from the cytoplasm and/or periplasm of a cell, in an energy dependent manner. An efflux system is therefore typically located in the cytoplasmic membrane of the cell (spanning the cytoplasmic membrane). Notably, in gram-negative bacteria, such as *Escherichia coli*, the efflux system may span the periplasmic space and there may also be portion of the efflux system, which spans the outer membrane. Bacterial efflux systems are well-known in the art, notably for instance via the classification system of transport mechanisms described by Milton H. Saier Jr. of the University of California in San Diego (website: www.tcdb.org/), and are generally classified as either primary active transporters which use adenosine triphosphate (ATP) as a source of energy, or as secondary active transporters in which transport is driven by the electrochemical potential difference of the transported substrate (uniporters) or by coupling to the transport of a second substrate (e.g. hydrogen or sodium ions) from or to the outside of the cell (antiporters and symporters). Five superfamilies of bacterial efflux transporters have so far been identified, based on their amino acid sequence and the energy source used to export their substrates, and include the major facilitator superfamily (MFS), the ATP-binding cassette superfamily (ABC), the small multidrug resistance family (SMR), the resistance-nodulation-cell division superfamily (RND), and the Multi antimicrobial extrusion protein family (MATE). In the context of the present invention, the efflux systems export 2,4-DHB as a substrate from the cellular cytoplasm and/or periplasm in the culture medium into which the microorganism is grown. To this day, such efflux systems exporting 2,4-DHB remained unknown. It is an object of the invention to identify efflux systems that are capable of exporting 2,4-DHB. The capacity of a candidate efflux system to export 2,4-DHB from the cell(s) can be assessed by measuring in vitro the extracellular amount of 2,4-DHB produced from cells naturally expressing or overexpressing said efflux system compared to control cells which do not express this system. This also can be done by measuring the intracellular concentration of 2,4-DHB in the cell(s). Inhibition of export can further be evaluated by measuring the ability of a known inhibitor of this efflux system to reduce the export of 2,4-DHB from the cell(s) or to increase the concentration of 2,4-DHB inside the cell(s). To do so, one skilled in the art may adapt protocols according to the evaluation of extraction and metabolite analysis procedures for testing efflux systems of various substrates that have been extensively described in the literature and patent applications (e.g. Kutukova et al., 2005; Hiller et al., 2007; Kiefer et al., 2007; Bolten et al., 2007; Zittrich & Kramer, 1994; Dassler et al., 2000; WO2005/085463; EP1239041). Examples of suitable efflux systems according to the invention are further described below, notably in Table 1.

By "uptake transporter", "uptake system", "uptake pump" or "uptake porter", it is meant herein a protein assembly that imports substrate molecules into the cytoplasm and/or periplasm of a cell, in an energy dependent or independent manner (active or passive uptake). Similarly to efflux systems, uptake transporters can be located in the cytoplasmic and/or periplasmic membrane of a cell. Bacterial uptake transporters are well-known in the art, and have been classified for instance by Milton H. Saier Jr. of the University of California in San Diego (website: www.tcdb.org/)]. In the context of the present invention, the uptake transporters import 2,4-DHB as a substrate from the culture medium into which the microorganism is grown into the cellular cytoplasm and/or periplasm of said microorganism. To this day, such efflux systems exporting 2,4-DHB remained unknown. It is an object of the invention to identify uptake transporters that are capable of importing 2,4-DHB. The capacity of a candidate uptake transporter to import 2,4-DHB into the cell(s) can be assessed by measuring the intracellular amount of 2,4-DHB contained in cells naturally expressing or overexpressing said transporter compared to control cells which do not express this transporter. Inhibition of import can further be evaluated by measuring the ability of a known inhibitor of this transporter to reduce the uptake of 2,4-DHB into the cell(s). To do so, one skilled in the art may adapt protocols for testing uptake transporters of various substrates that have been extensively described in the literature and patent application (Kurihara et al., 2009; Hiller et al., 2007; Kiefer et al., 2007; Bolten et al., 2007; WO2014029592). Examples of suitable uptake transporters according to the invention are further described below, notably in Table 1.

In a general manner, the relevance of the genetic modification of the efflux and/or uptake system specific of the 2,4-DHB is monitored via the improvement of the production of said molecule and/or via the resistance to high amount of said molecule. In the latter, the growth rate of the recombinant strains is measured and considered as the sign of the reduction of the concentration of 2,4-DHB inside the cell.

By "gene encoding an efflux system or an uptake transporter", it is meant herein a polynucleotide or nucleic acid sequence encoding said system or transporter. In the case of overexpression of exogenous genes encoding an efflux system, one skilled person in the art will readily recognize that the inserted polynucleotide sequence need not be identical and may be "substantially identical" to the sequence of the gene from which it was derived. Indeed, because of codon degeneracy, a number of polynucleotide sequences will encode the same protein. Besides, as explained above, the exogenous gene encoding a protein of interest is preferably codon-optimized for expression in a specific microorganism. Said definition applies mutatis mutandis to genes encoding other proteins of the invention.

By "functional variants", it is meant herein proteins that structurally differ from the amino acid sequence of a protein of reference but that generally retain all the essential functional characteristics of said protein of reference. A variant of a protein may be a naturally-occurring variant or a non-naturally occurring variant. Such non-naturally occurring variants of the reference protein can be made, for example, by mutagenesis techniques on the encoding nucleic acids or genes, for example by random mutagenesis or site-directed mutagenesis.

Structural differences may be limited in such a way that the amino acid sequence of reference protein and the amino acid sequence of the variant may be closely similar overall, and identical in many regions. Structural differences may result from conservative or non-conservative amino acid substitutions, deletions and/or additions between the amino acid sequence of the reference protein and the variant. The only proviso is that, even if some amino acids are substituted, deleted and/or added, the biological activity of the amino acid sequence of the reference protein is retained by the variant. That is to say, in the context of the present invention, the variant of an efflux system is capable to export 2,4-DHB from the cell(s) of the microorganism while the variant of an uptake transporter is capable to import 2,4-DHB into the cell(s) of the microorganism. The capacity of the variants to exhibit such activity can be assessed according to the in vitro tests described above. It must however be noted that the activity of said variants may differ in its 2,4-DHB export or import efficiency compared to the activity of the amino acid sequences of the efflux systems or uptake transporters of reference.

"Functional variants" of efflux systems or uptake transporters according to the present invention include, but are not limited to, proteins having amino acid sequences which are at least 80% identical after alignment to the amino acid sequence encoding said efflux systems or uptake transporters. Preferably, said variants have 85%, 90%, 95% sequence identity to said efflux systems or uptake transporters, and more preferably have 96%, 97%, 98%, 99%, or 99,999% sequence identity to said efflux systems or uptake transporters.

Sequence identity between amino acid sequences can be determined by comparing a position in each of the sequences which may be aligned for the purposes of comparison. When a position in the compared sequences is occupied by the same amino acid, then the sequences are identical at that position. A degree of sequence identity between proteins is a function of the number of identical amino acid residues at positions shared by the sequences of said proteins.

To determine the percentage of identity between two amino acid sequences, the sequences are aligned for optimal comparison. For example, gaps can be introduced in the sequence of a first amino acid sequence for optimal alignment with the second amino acid sequence. The amino acid residues at corresponding amino acid positions are then compared. When a position in the first sequence is occupied by the same amino acid residue as the corresponding position in the second sequence, the molecules are identical at that position.

The percentage of identity between the two sequences is a function of the number of identical positions shared by the sequences. Hence % identity=number of identical positions/total number of overlapping positions×100.

Optimal alignment of sequences may be conducted by the global homology alignment algorithm of Needleman and Wunsch (1972), by computerized implementations of this algorithm or by visual inspection. The best alignment (i.e., resulting in the highest percentage of identity between the compared sequences) generated by the various methods is selected.

In other words, the percentage of sequence identity is calculated by comparing two optimally aligned sequences, determining the number of positions at which the identical amino acid occurs in both sequences to yield the number of matched positions, dividing the number of matched positions by the total number of positions and multiplying the result by 100 to yield the percentage of sequence identity.

The term "carbohydrate" refers herein to any carbon source capable of being metabolized by a microorganism and containing at least one carbon atom, two atoms of hydrogen and one atom of oxygen. The carbohydrate of the invention is preferably selected from the group consisting of monosaccharides such as glucose, fructose, mannose, galactose and the like, disaccharides such as sucrose, cellobiose, maltose, lactose and the like, oligosaccharides such as raffinose, stacchyose, maltodextrins and the like, polysaccharides such as cellulose, hemicellulose, starch and the like, methanol, formaldehyde and glycerol. According to a preferred embodiment of the invention, the source of carbon is advantageously a carbohydrate comprising 3, 6 or 12 carbon atoms, or any combination thereof. In a more preferred embodiment of the invention, the source of carbon is selected from xylose, glycerol, glucose, galactose, fructose, lactose, maltose, sucrose, and any combination thereof.

Reduction of Intracellular 2,4-DHB Accumulation

In a first aspect, the present invention is directed to a microorganism genetically modified for producing 2,4-dihydroxybutyrate by fermentation, wherein said microorganism is further genetically modified for reducing intracellular 2,4-dihydroxybutyrate accumulation, thereby optimizing 2,4-dihydroxybutyrate production.

According to a preferred embodiment of the invention, the genetic modification for reducing intracellular 2,4-dihydroxybutyrate accumulation is:
  i) an overexpression of at least one gene encoding an efflux system; and/or
  ii) an attenuation of the expression or the deletion of at least one gene encoding an uptake transporter.

The efflux system to be overexpressed is more preferably selected from the group consisting of monocarboxylate efflux systems, formate efflux systems, lactate efflux systems, malate efflux systems, succinate efflux systems, aromatic carboxylic acid efflux systems, functional variants thereof, and any combination thereof.

More preferably, said efflux system is selected from the group consisting of:
  monocarboxylate efflux systems of amino acid sequence SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, and SEQ ID NO:19,
  formate efflux systems of amino acid sequence SEQ ID NO:21,
  lactate efflux systems of amino acid sequence SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, and SEQ ID NO:53,
  malate efflux systems of amino acid sequence SEQ ID NO:55, SEQ ID NO:57, SEQ ID NO:59, and SEQ ID NO:61,
  succinate efflux systems of amino acid sequence SEQ ID NO:63, SEQ ID NO:65, and SEQ ID NO:67,
  aromatic carboxylic acid efflux systems of amino acid sequence SEQ ID NO:69 and SEQ ID NO:71,
  functional variants thereof having at least 80% sequence identity to said amino acid sequences, and
  any combination thereof.

Even more preferably, said efflux system is selected from the group consisting of:
  monocarboxylate efflux systems of amino acid sequence SEQ ID NO:1,
  lactate efflux systems of amino acid sequence SEQ ID NO:23,
  lactate efflux systems of amino acid sequence SEQ ID NO:25,
  functional variants thereof having at least 80% sequence identity to said amino acid sequences, and
  any combination thereof.

The uptake transporter to be attenuated or deleted is more preferably selected from the group consisting of alpha-ketoglutarate uptake transporters, lactate uptake transporters, glycolate uptake transporters, acetate uptake transporters, propionate uptake transporters, pantothenate uptake transporters, succinate and acetate uptake transporters, acetoacetate uptake transporters, gluconate uptake transporters, functional variants thereof, and any combination thereof.

More preferably, said uptake transporter is selected from the group consisting of:
  alpha-ketoglutarate uptake transporters of amino acid sequence SEQ ID NO:73,
  lactate uptake transporters of amino acid sequence SEQ ID NO:75,
  glycolate uptake transporters of amino acid sequence SEQ ID NO:77, acetate uptake transporters of amino acid sequence SEQ ID NO:79 and SEQ ID NO:81,
propionate uptake transporters of amino acid sequence SEQ ID NO:83,
pantothenate uptake transporters of amino acid sequence SEQ ID NO:85,
succinate and acetate uptake transporters of amino acid sequence SEQ ID NO:87,
acetoacetate uptake transporters of amino acid sequence SEQ ID NO:89,
gluconate uptake transporters of amino acid sequence SEQ ID NO:91,
uptake transporters of amino acid sequence SEQ ID NO:93,
functional variants thereof having at least 80% sequence identity to said amino acid sequences, and
any combination thereof.

Even more preferably, said uptake transporter is selected from the group consisting of:
alpha-ketoglutarate uptake transporters of amino acid sequence SEQ ID NO:73,
lactate uptake transporters of amino acid sequence SEQ ID NO:75,
glycolate uptake transporters of amino acid sequence SEQ ID NO:77,
functional variants thereof having at least 80% sequence identity to said amino acid sequences, and
any combination thereof.

The above mentioned efflux systems and uptake transporters are well-known in the art, and are described below in Table 1 and Examples 2 and 3.

TABLE 1

Proteins and genes of the invention for reducing 2,4 DHB intracellular accumulation

| | Substrates(*) | Proteins names | Genes names | Origin (Genus species) | SEQ ID NO (protein and gene) | Database (protein and/or gene) | Accession number in the database (protein and/or gene) |
|---|---|---|---|---|---|---|---|
| Efflux systems | Monocarboxylate | uncharacterized MFS-type transporter YhjX | yhjX | Escherichia coli (strain K12) | 1<br>2 | Uniprot<br>Genbank | P37662<br>948066 |
| | | probable transporter MCH1; Monocarboxylate transporter homolog 1 | MCH1 | Saccharomyces cerevisiae (strain ATCC 204508/ S288c) | 3<br>4 | Uniprot<br>Genbank | Q07376<br>NP_010229 |
| | | probable transporter MCH2 | MCH2 | Saccharomyces cerevisiae (strain ATCC 204508/ S288c) | 5<br>6 | Uniprot<br>Genbank | P36032<br>853659 |
| | | uncharacterized transporter ESBP6 | ESBP6/ MCH3 | Saccharomyces cerevisiae (strain ATCC 204508/ S288c) | 7<br>8 | Uniprot<br>Genbank | P53918<br>855598 |
| | | riboflavin transporter MCH5 | MCH5 | Saccharomyces cerevisiae (strain ATCC 204508/ S288c) | 9<br>10 | Uniprot<br>Genbank | Q08777<br>854483 |
| | | mitochondrial nicotinamide adenine dinucleotide transporter 1 | YIA6 | Saccharomyces cerevisiae (strain ATCC 204508/ S288c) | 11<br>12 | Uniprot<br>Genbank | P40556<br>854811 |
| | | putative uncharacterized protein An04g01190 | An04g01190 | Aspergillus niger (strain CBS 513.88/ FGSC A1513) | 13<br>14 | Uniprot | A2QHV6 |
| | | potential mitochondrial FAD transporter | FLX1 | Candida albicans (strain SC5314/ ATCC MYA-2876) | 15<br>16 | Uniprot<br>Genbank | Q5AH06<br>3637489 |
| | | YALI0E16478p | YALI0_E16478g | Yarrowia lipolytica (strain CLIB 122/ E 150) | 17<br>18 | Uniprot<br>Genbank | Q6C5N9<br>2911597 |
| | | KLLA0D14036p | KLLA0D14036g | Kluyveromyces lactis (strain ATCC 8585/ CBS 2359/DSM 70799/NBRC 1267/ NRRL Y-1140/ WM37) | 19<br>20 | Uniprot<br>Genbank | Q6CQV1<br>2893083 |
| | formate | probable formate transporter 1 | focA | Escherichia coli (strain K12) | 21<br>22 | Uniprot<br>Genbank | P0AC23<br>945513 |
| | lactate | carboxylic acid transporter protein homolog | JEN1 | Saccharomyces cerevisiae (strain ATCC 204508/ S288c) | 23<br>24 | Uniprot<br>Genbank | P36035<br>853663 |

TABLE 1-continued

Proteins and genes of the invention for reducing 2,4 DHB intracellular accumulation

| Substrates(*) | Proteins names | Genes names | Origin (Genus species) | SEQ ID NO (protein and gene) | Database (protein and/or gene) | Accession number in the database (protein and/or gene) |
|---|---|---|---|---|---|---|
| | inner membrane metabolite transport protein YhjE | yhjE | Escherichia coli (strain K12) | 25<br>26 | Uniprot<br>Genbank | P37643<br>948807 |
| | sugar transporter | N036_00275 | Enterococcus gallinarum EGD-AAK12 | 27<br>28 | Uniprot | U1DFZ6 |
| | arabinose efflux permease family protein | DesyoDRAFT_2343 | Desulfosporosinus youngiae DSM 17734 | 29<br>30 | Uniprot | H5XUX1 |
| | metabolite transport protein | KPRYC492_12290 | Klebsiella pneumoniae RYC492 | 31<br>32 | Uniprot | M5QHT5 |
| | putative metabolite transport protein YjhB | yjhB | Escherichia coli (strain K12) | 33<br>34 | Uniprot<br>Genbank | P39352<br>948807 |
| | sialic acid transporter (Permease) NanT | NA | Klebsiella pneumoniae IS22 | 35<br>36 | Uniprot | W1AXB5 |
| | putative sialic acid transporter | SEEM1923_12410 | Salmonella enterica subsp. enterica serovar Miami str. 1923 | 37<br>38 | Uniprot | V1W715 |
| | putative sialic acid transporter | nanT | Citrobacter freundii UCI 32 | 39<br>40 | Uniprot | X7HN77 |
| | putative metabolite transport protein YyaJ | yyaJ | Bacillus subtilis (strain 168) | 41<br>42 | Uniprot<br>Genbank | P37514<br>937884 |
| | JEN2 | JEN2 | Kluyveromyces lactis (Candida sphaerica) | 43<br>44 | Uniprot | Q6RFG1 |
| | putative niacin/nicotinamide transporter NaiP | naiP/yceI | Bacillus subtilis (strain 168) | 45<br>46 | Uniprot<br>Genbank | O34691<br>938365 |
| | accumulation of dyads protein 2 | ADY2 | Saccharomyces cerevisiae (strain ATCC 204508/S288c) | 47<br>48 | Uniprot<br>Genbank | P25613<br>850368 |
| | MFS transporter | N234_34710 | Ralstonia pickettii DTP0602 | 49<br>50 | Uniprot<br>Genbank | U3QYA7<br>17106842 |
| | inner membrane protein yaaH | L415_00010 | Klebsiella pneumoniae UCICRE4 | 51<br>52 | Uniprot | V3GU98 |
| | inner membrane protein yaaH | WEU_00424 | Citrobacter sp. KTE32 | 53<br>54 | Uniprot | R8VK11 |
| malate | predicted protein | AO090023000318 | Aspergillus oryzae (strain ATCC 42149/RIB 40) | 55<br>56 | Uniprot | Q2UHT6 |
| | malic acid transport protein | mae1 | Schizosaccharomyces pombe (strain 972/ATCC 24843) | 57<br>58 | Uniprot<br>Genbank | P50537<br>2543334 |
| | C4-dicarboxylate transporter/malic acid transport protein | BW33_03544 | Pseudomonas sp. RIT288 | 59<br>60 | Uniprot | A0A031G165 |
| | C4-dicarboxylate transporter/malic acid transport protein | mae1 | Erwinia billingiae (strain Eb661) | 61<br>62 | Uniprot<br>Genbank | D8MJJ9<br>9434188 |
| succinate | anaerobic C4-dicarboxylate transporter DcuA | dcuA | Escherichia coli (strain K12) | 63<br>64 | Uniprot<br>Genbank | P0ABN5<br>948659 |
| | anaerobic C4-dicarboxylate transporter DcuB | dcuB | Escherichia coli (strain K12) | 65<br>66 | Uniprot<br>Genbank | P0ABN9<br>948641 |
| | anaerobic C4-dicarboxylate transporter DcuC | dcuC | Escherichia coli (strain K12) | 67<br>68 | Uniprot<br>Genbank | P0ABP3<br>945000 |

TABLE 1-continued

Proteins and genes of the invention for reducing 2,4 DHB intracellular accumulation

|  | Substrates(*) | Proteins names | Genes names | Origin (Genus species) | SEQ ID NO (protein and gene) | Database (protein and/or gene) | Accession number in the database (protein and/or gene) |
|---|---|---|---|---|---|---|---|
|  | aromatic carboxylic acid | p-hydroxy-benzoic acid efflux pump subunits AaeA and AeaB | aaeA and aaeB | Escherichia coli (strain K12) | 69, 71 70, 72 | Uniprot Genbank | P46482, P46481 947748, 947747 |
| Uptake transporters | alpha-ketoglutarate | alpha-ketoglutarate permease | kgtP | Escherichia coli (strain K12) | 73 74 | Uniprot Genbank | P0AEX3 947069 |
|  | lactate | L-lactate permease | lldP | Escherichia coli (strain K12) | 75 76 | Uniprot Genbank | P33231 948114 |
|  | glycolate | glycolate permease GlcA | glcA | Escherichia coli (strain K12) | 77 78 | Uniprot Genbank | Q46839 947259 |
|  | acetate | cation/acetate symporter ActP | actP | Escherichia coli (strain K12) | 79 80 | Uniprot Genbank | P32705 948575 |
|  |  | inner membrane protein YbhL | YbhL | Escherichia coli (strain K12) | 81 82 | Uniprot Genbank | P0AAC4 945401 |
|  | propionate | sodium/proline symporter | putP | Escherichia coli (strain K12) | 83 84 | Uniprot Genbank | P07117 945602 |
|  | pantothenate | sodium/pantothenate symporter | panF | Escherichia coli (strain K12) | 85 86 | Uniprot Genbank | P16256 947752 |
|  | succinate and acetate | succinate-acetate/proton symporter SatP | satP | Escherichia coli (strain K12) | 87 88 | Uniprot Genbank | P0AC98 944792 |
|  | acetoacetate | short-chain fatty acids transporter | atoE | Escherichia coli (strain K12) | 89 90 | Uniprot Genbank | P76460 946721 |
|  | gluconate | DsdX permease | DsdX | Escherichia coli (strain K12) | 91 92 | Uniprot Genbank | P08555 949103 |
|  | unknown | uncharacterized protein YbhM | YbhM | Escherichia coli (strain K12) | 93 94 | Uniprot Genbank | P75769 949001 |

(NA = non available; *: substrates known in the art for being exported from the cytoplasm and/or periplasm of the cell by said efflux systems, or for being imported into the cytoplasm and/or periplasm of the cell by said uptake transporters)

Metabolic Pathways for the Production of 2,4-DHB

As stated above, the microorganism according to the invention is genetically modified to produce 2,4-DHB. It is within the skill of the person in the art to engineer such microorganism. Indeed, various genetically engineered metabolic pathways have been described in the art for producing 2,4-DHB in microorganisms, notably in patent applications WO2012/056318, WO2013/160762 and WO2014/009435 (all incorporated herein by reference), depending on the metabolic intermediate of interest from which 2,4-DHB can be derived. Examples of such metabolic intermediate include, without limitation, 1,2,4-butanetriol, (L)-malate, (L)malyl-CoA, and (L)-homoserine.

It is thus a preferred embodiment of the invention to provide a microorganism in which intracellular 2,4-dihydroxybutyrate accumulation are reduced by the genetic modifications as described above, and which is also genetically modified to convert at least one of the following metabolic intermediate into 2,4-dihydroxybutyrate:
 iii) 1,2,4-butanetriol;
 iv) (L)-malate;
 v) (L)malyl-CoA; and
 vi) (L)-homoserine.

The skilled person in the art would readily understand that the preferred embodiments related to the reduction of intracellular 2,4-dihydroxybutyrate accumulation as described above can be combined with the preferred embodiment related to 2,4-DHB production further described below.

Production of 2,4-dihydroxybutyrate Via the 1,2,4-butanetriol Pathway

A possible synthetic pathway for the microbial production of 2,4-dihydroxybutyric acid from the 1,2,4-butanetriol metabolic intermediate can be performed in two single steps, requiring successively the oxidation of 1,2,4-butanetriol into 2,4-dihydroxybutanal, followed by the oxidation of 2,4-dihydroxybutanal into 2,4-DHB.

Preferably, the microorganism of the invention as described above is genetically modified for converting 1,2, 4-butanetriol into 2,4-dihydroxybutyrate, according to the following modifications:
 overexpression of at least one polynucleotide encoding an oxidoreductase acting on the CH—OH group of donors, thereby converting 1,2,4-butanetriol into 2,4-dihydroxybutanal; and
 overexpression of at least one polynucleotide encoding an oxidoreductase acting on the aldehyde or oxo group of donors, thereby converting 2,4-dihydroxybutanal into 2,4-dihydroxybutyrate.

Examples of oxidoreductases acting on the CH—OH group of donors include, without limitation, EC 1.1.1 enzymes (oxidoreductases with NAD+ or NADP+ as acceptor, also known as NAD+/NADP+ oxidoreductases), EC 1.1.2 enzymes (oxidoreductases with a cytochrome as acceptor), EC 1.1.3 enzymes (oxidoreductases with oxygen as acceptor), EC 1.1.4 enzymes (oxidoreductases with a disulphide as an acceptor), EC 1.1.5 enzymes (oxidoreductases with a quinone or similar compound as acceptor), EC 1.1.98 enzymes (oxidoreductases with other known acceptors), and EC 1.1.99 enzymes (oxidoreductases with other acceptors).

Examples of oxidoreductases acting on the aldehyde or oxo group of donors include, without limitation, EC 1.2.1 enzymes (oxidoreductases with NAD+ or NADP+ as acceptor, also known as NAD+/NADP+ oxidoreductases), EC 1.2.2 enzymes (oxidoreductases with a cytochrome as acceptor), EC 1.2.3 enzymes (oxidoreductases with oxygen as acceptor), EC 1.2.4 enzymes (oxidoreductases with a disulphide as acceptor), EC 1.2.5 enzymes (oxidoreductases with a quinone or similar compound as acceptor), EC 1.2.7 enzymes (oxidoreductases with an iron-sulfur protein as acceptor), and EC 1.2.99 enzymes (oxidoreductases with other acceptors).

Enzymes displaying the above activities are well-known in the art and can be easily identified by the skilled person in the art, from example from publicly available databases such as BRENDA.

In order to oxidize 1,2,4-butanetriol into 2,4-dihydroxybutanal, the oxidoreductase acting on the CH—OH group of donors (EC 1.1 enzyme) is preferably selected from the group consisting of alcohol dehydrogenases (or aldehyde reductase), lactaldehyde reductases, glyoxylate reductases, didehydrogluconate reductases, and any combination thereof. More preferably, said EC 1.1 oxidoreductase is an alcohol dehydrogenase (or aldehyde reductase) or a lactaldehyde reductase. Yet, even more preferably, said EC 1.1 oxidoreductase is an NAD+/NADP+ oxidoreductase acting on the CH—OH group of donors (i.e. an EC 1.1.1 enzyme), or an oxidoreductase acting on the CH—OH group of donors with other acceptors (i.e. an EC 1.1.99 enzyme). Most preferably, said EC 1.1 enzyme is an EC 1.1.1 enzyme. It is within the skill of the person in the art to select the EC 1.1 enzymes that are suitable for the purposes of the invention, and identify their corresponding gene (i.e. nucleotide) sequences.

Particularly preferred oxidoreductases acting on the CH—OH group of donors (EC 1.1 enzymes) are described in Table 2 below: alcohol dehydrogenases include, without limitation, the enzymes of amino acid sequence SEQ ID NO:95 to SEQ ID NO:134; lactaldehyde reductases include, without limitation, the enzyme of amino acid sequence SEQ ID NO:135; glyoxylate reductases include, without limitation, the enzymes of amino acid sequence SEQ ID NO:136 and SEQ ID NO:137, and the didehydrogluconate reductases include, without limitation the enzymes of amino acid sequence SEQ ID NO:138 and SEQ ID NO:139.

In a particularly preferred embodiment of the present invention, the oxidoreductase acting on the CH—OH group of donors (EC 1.1 enzyme) is an enzyme of amino acid sequence SEQ ID NO:130 or SEQ ID NO:135.

As indicated above, in order to oxidize 2,4-dihydroxybutanal into 2,4-dihydroxybutyrate, the microorganism of the invention is genetically modified so as to overexpress at least one gene encoding an oxidoreductase acting on the aldehyde or oxo group of donors (EC 1.2 enzyme).

Accordingly, the oxidoreductase acting on the aldehyde or oxo group of donors (EC 1.2 enzyme) is preferably selected from the group consisting of aldehyde dehydrogenases, aldehyde oxidases, and any combination thereof. More preferably, said EC 1.2 oxidoreductase is an aldehyde dehydrogenase. Yet, even more preferably, said EC 1.2 oxidoreductase is an NAD+/NADP+ oxidoreductase acting on the aldehyde or oxo group of donors (i.e. an EC 1.2.1 enzyme), or an oxidoreductase acting on the aldehyde or oxo group of donors with oxygen as acceptor (i.e. an EC 1.2.3 enzyme). Most preferably, said EC 1.2 enzyme is an EC 1.2.1 enzyme. It is within the skill of the person in the art to select the EC 1.2 enzymes that are suitable for the purposes of the invention, and identify their corresponding gene (i.e. nucleotide) sequences.

Particularly preferred oxidoreductases acting on the aldehyde or oxo group of donors (EC 1.2 enzymes) are described in Table 2 below: aldehyde dehydrogenases include, without limitation, the enzymes of amino acid sequence SEQ ID NO:140 to SEQ ID NO:154; aldehyde oxidases include, without limitation, the enzyme of amino acid sequence SEQ ID NO:155.

In a particularly preferred embodiment of the present invention, the oxidoreductase acting on the aldehyde or oxo group of donors (EC 1.2 enzyme) is an enzyme of sequence amino acid SEQ ID NO:140, SEQ ID NO:148 or SEQ ID NO:149.

As well-known to the skilled person in the art, the intermediate metabolite 1,2,4-butanetriol can be generated by the microorganism by fermentation of xylose as a carbon source. Such conversion can be achieved by further genetically engineering the microorganism, as described in patent application EP15305096.8, WO2008/091288 and US2013/0203141, incorporated herein by reference.

Accordingly, the microorganism is preferably further genetically modified to convert xylose into 1,2,4-butanetriol, said genetic modification being an overexpression at least one the following genes:

a gene encoding a xylose dehydrogenase, a gene encoding a xylonolactonase, a gene encoding a xylonate dehydratase, a gene encoding a 3-deoxy-D-glycero-pentulosonate (DGP) decarboxylase, a gene encoding 1,2,4-butanetriol dehydrogenase, and any combination thereof, Said enzymes are well-known in the art, of which preferred ones are described below in Table 2 and Example 1 (pathway 1).

Yet, according to a preferred embodiment, the microorganism of the invention is further genetically modified for providing reducing power and/or energy for 2,4-dihydroxybutyrate production and microorganism growth from a carbon source other than xylose, and/or at least partially, preferably totally, inhibiting carbon catabolite repression.

Said genetic modifications are particularly advantageous as they optimize 2,4-DHB production, by first, using an alternative carbon source rather than xylose for the provision of reducing power and/or energy, so that the xylose can be exclusively converted into 2,4-dihydroxybutyrate; and second, by reducing carbon catabolite repression which is observed in microorganisms which may favour some carbon sources over others. Notably, most naturally occurring microorganisms, among which *Escherichia coli*, prefer using glucose over other sugars even if they are capable of metabolizing an array of monosaccharides (Kim et al., 2010). It is thus preferred herein to inhibit this catabolite repression in microorganisms that are not capable of co-utilizing xylose and another sugar in an effective manner.

Accordingly, in order to provide reducing power and/or energy for 2,4-dihydroxybutyrate production and microorganism growth from a carbon source other than xylose, the microorganism according to the invention is preferably genetically modified by deleting and/or attenuating at least one gene selected from the group consisting of:
- a gene encoding a xylose isomerase,
- a gene encoding a xylulose kinase,
- a gene encoding a 3-deoxy-D-glycero-pentulosonate aldolase,
- a gene encoding a keto-acid dehydrogenase, and
- any combination thereof.

Said enzymes are well-known in the art, and are described in patent application US2013/0203141, incorporated herein by reference. These enzymes are notably known for using xylose or other metabolites that produces a carbon flux which may compete with the conversion of xylose into 2,4-dihydroxybutyrate. Preferred enzymes for providing said reducing power and/or energy according to the invention are described below in Table 2 and Example 1 (pathway 1).

Still, in a preferred embodiment, the genetic modification which allows the inhibition of carbon catabolite repression is selected from at least one of the following:
- deletion of a gene encoding a glucose permease of the phosphotransferase system,
- deletion of a gene encoding a phosphocarrier Hpr protein,
- expression, preferably from a constitutive or inducible promoter not regulated by cAMP-CRP, of a gene and/or operon involved in a sugar importer system wherein said sugar is a carbon source other than xylose,
- expression of a gene encoding an xylose transporter, such as a symporter or an ABC transporter, preferably from a constitutive or inducible promoter not regulated by cAMP-CRP,
- overexpression of a gene encoding a glucose symporter,
- overexpression of a gene encoding a glucose facilitator,
- overexpression of a gene encoding a glucokinase,
- modulation of the expression of a gene involved in cAMP levels, preferably of a gene encoding adenylate cyclase,
- modulation of the expression a gene encoding a CRP and/or a CRP-like protein,
- expression of a gene encoding a cAMP-independent CRP protein, preferably from a constitutive or inducible promoter not regulated by cAMP-CRP, and
- any combination thereof.

Said enzymes are well-known in the art, of which preferred ones are described below in Table 2 and Example 1 (pathway 1).

More preferably, for the co-utilization of xylose and glucose, a deletion of a gene encoding a phosphotransferase and/or a phosphocarrier Hpr protein is advantageously combined with an overexpression of a gene encoding a glucose permease or a glucose facilitator, along with an overexpression of a gene encoding a glucokinase.

According to a further preferred embodiment, the microorganism of the invention comprises another genetic modification of at least one gene involved in the production of NADPH as a source of reducing power. Indeed, reducing enzymes such as dehydrogenases are in need of reducing power available in the microorganism, particularly in the form of NADPH. Strategies for increasing NADPH availability in the cell are well known in the art, and have notably been reviewed by Lee et al. (2013) and also described by U.S. Pat. No. 8,088,620, WO2012/055798 and EP14305691.9, herein incorporated by reference.

According to the present invention, the genetic modification for improving the production of NADPH, and therefore its availability in the microorganism, is preferably selected from:
- overexpression of a gene or operon encoding a membrane-bound transhydrogenase,
- deletion or attenuation of a gene encoding a soluble transhydrogenase,
- overexpression of a gene encoding a NADPH generating glyceraldehyde 3-phosphate dehydrogenase,
- deletion or attenuation of a gene encoding a phosphoglucose isomerase,
- deletion or attenuation of a gene encoding a phosphofructokinase,
- overexpression of a gene encoding a glucose-6-phosphate dehydrogenase,
- overexpression of a mutant gene encoding a lipoamide dehydrogenase capable of generating NADPH,
- overexpression of a gene encoding a bi-functional NAD(P)H-hydrate repair enzyme, and
- any combination thereof.

The deletion or attenuation of a gene encoding a phosphofructokinase is more preferably combined with an overexpression of a gene encoding a glucose-6-phosphate dehydrogenase, in order to increase the flux of NADPH through the pentose phosphate pathway.

More preferably, the genetic modification for improving the production of NADPH is selected from:
- overexpression of a gene encoding a membrane-bound transhydrogenase,
- deletion or attenuation of a gene encoding a phosphoglucose isomerase and/or a soluble transhydrogenase, and
- overexpression of a gene encoding a NADPH generating glyceraldehyde 3-phosphate dehydrogenase.

Said enzymes are well-known in the art, of which preferred ones are described below in Table 2 and Example 1 (pathway 1).

Production of 2,4-dihydroxybutyrate Via the (L)-malate Pathway

An alternative synthetic pathway for the microbial production of 2,4-dihydroxybutyric acid uses (L)-malate as a metabolic intermediate. It is within the skill of the person in the art to engineer microorganisms capable of converting (L)-malate into 2,4-DHB. Indeed, microorganisms genetically modified for converting (L)-malate into 2,4-DHB, and methods for engineering said microorganisms, are well-known in the art and have notably been described in patent application WO2012/056318, incorporated herein by reference.

Accordingly, the microorganism of the invention is genetically modified for converting (L)-malate into 2,4-dihydroxybutyrate, according to the following modifications:
- overexpression of at least one gene encoding a malate kinase, thereby converting malate into 4-phospho-malate;
- overexpression of at least one gene encoding a malate semialdehyde dehydrogenase, thereby converting 4-phospho-malate into malate-4-semialdehyde; and
- overexpression of at least one gene encoding a DHB dehydrogenase, thereby converting malate-4-semialdehyde into 2,4-dihydroxybutyrate.

Said enzymes are well-known in the art, of which preferred ones are described below in Table 2 and Example 1 (pathway 3).

Preferably, said malate kinase is of amino acid sequence SEQ ID NO:198, said malate semialdehyde dehydrogenase is of amino acid sequence SEQ ID NO:199, and said DHB dehydrogenase is of amino acid sequence SEQ ID NO:200.

Production of 2,4-dihydroxybutyrate Via the (L)malyl-CoA Pathway

Another alternative synthetic pathway for the microbial production of 2,4-dihydroxybutyric acid uses (L)malyl-CoA as a metabolic intermediate. It is within the skill of the person in the art to engineer microorganisms capable of converting (L)malyl-CoA into 2,4-DHB. Indeed, microorganisms genetically modified for converting (L)malyl-CoA into 2,4-DHB, and methods for engineering said microorganisms, are well-known in the art and have notably been described in patent application WO2013/160762, incorporated herein by reference.

Accordingly, the microorganism of the invention is genetically modified for converting (L)malyl-CoA into 2,4-dihydroxybutyrate, according to the following modifications:
  overexpression of at least one gene encoding a malyl-CoA reductase, thereby converting malyl-CoA into malate-4-semialdehyde; and
  overexpression of at least one gene encoding a DHB dehydrogenase, thereby converting malate-4-semialdehyde into 2,4-dihydroxybutyrate.

Still preferably, said microorganism is further genetically modified for converting:
  (L)malate into (L)malyl-CoA by overexpression of at least one gene encoding a malyl-CoA synthetase; or
  succinylCoA into (L)malyl-CoA by overexpression of at least one gene encoding a succinyl-CoA:(L)malate-CoA transferase; or
  glyoxylate into (L)malyl-CoA by overexpression of at least one gene encoding a malyl-CoA lyase.

Said enzymes are well-known in the art, of which preferred ones are described below in Table 2 and Example 1 (pathway 4).

Preferably, said malyl-CoA reductase is of amino acid sequence SEQ ID NO:201, said DHB dehydrogenase is of amino acid sequence SEQ ID NO:200, and said malyl-CoA lyase is of amino acid sequence SEQ ID NO:202, Further preferred genetic modifications are described below in Example 1 (pathway 4).

Production of 2,4-dihydroxybutyrate Via the (L)-homoserine Pathway

Yet, another synthetic pathway for the microbial production of 2,4-dihydroxybutyric acid uses (L)-homoserine as a metabolic intermediate. It is within the skill of the person in the art to engineer microorganisms capable of converting (L)-homoserine into 2,4-DHB. Indeed, microorganisms genetically modified for converting (L)-homoserine into 2,4-DHB, and methods for engineering said microorganisms, are well-known in the art and have notably been described in patent application WO2014/009435, incorporated herein by reference or in patent application EP14306564.7 (not yet published).

Accordingly, the microorganism of the invention is genetically modified for converting (L)-homoserine into 2,4-dihydroxybutyrate, according to the following modifications:
  overexpression of at least one gene encoding an enzyme selected from the group consisting of homoserine oxidases, homoserine dehydrogenases, homoserine transaminases and any combination thereof, thereby converting (L)-homoserine into 2-oxo-4-hydroxybutyrate; and
  overexpression of at least one gene encoding a 2-oxo-4-hydroxybutyrate (OHB) reductase, thereby converting 2-oxo-4-hydroxybutyrate (OHB) into 2,4-dihydroxybutyrate.

Said enzymes are well-known in the art, of which preferred ones are described below in Table 2 and Example 1 (pathway 2).

Preferably, said homoserine dehydrogenase is of amino acid sequence SEQ ID NO:203, and said 2-oxo-4-hydroxybutyrate (OHB) reductase is of amino acid sequence SEQ ID NO:204.

Further preferred genetic modifications are described below in Example 1 (pathway 2).

TABLE 2

Proteins and genes of the invention for producing 2,4-DHB

| Enzyme full name(s) | Gene name | Origin (Genus species) | SEQ ID NO (protein and/or gene) | Database (protein and/or gene) | Accession number in the database (protein and/or gene) | Version number in the database (protein and/or gene) |
|---|---|---|---|---|---|---|
| oxidoreductases acting on the CH—OH group of donors (EC 1.1) 1. alcohol dehydrogenases belonging to EC 1.1 | | | | | | |
| S-(hydroxymethyl) glutathione dehydrogenase alcohol dehydrogenase class-III | frmA/ adhC | *Escherichia coli* (strain K12) | 95 | Uniprot | P25437 | ND |
| alcohol dehydrogenase, propanol-preferring | adhP/ yddN | *Escherichia coli* (strain K12) | 96 | Uniprot | P39451 | ND |
| probable alcohol dehydrogenase | yiaY | *Escherichia coli* (strain K12) | 97 | Uniprot | P37686 | ND |
| ethanolamine utilization protein EutG | eutG/ yffV | *Escherichia coli* (strain K12) | 98 | Uniprot | P76553 | ND |
| alcohol dehydrogenase YqhD | yqhD | *Escherichia coli* (strain K12) | 99 | Uniprot | Q46856 | ND |

TABLE 2-continued

Proteins and genes of the invention for producing 2,4-DHB

| Enzyme full name(s) | Gene name | Origin (Genus species) | SEQ ID NO (protein and/or gene) | Database (protein and/or gene) | Accession number in the database (protein and/or gene) | Version number in the database (protein and/or gene) |
|---|---|---|---|---|---|---|
| uncharacterized protein YeaE | yeaE | *Escherichia coli* (strain K12) | 100 | Uniprot | P76234 | ND |
| oxidoreductase YdhF | ydhF | *Escherichia coli* (strain K12) | 101 | Uniprot | P76187 | ND |
| uncharacterized protein YhdN | yhdN | *Escherichia coli* (strain K12) | 102 | Uniprot | P36677 | ND |
| uncharacterized zinc-type alcohol dehydrogenase-like protein YbdR | ybdR | *Escherichia coli* (strain K12) | 103 | Uniprot | P77316 | ND |
| uncharacterized oxidoreductase YbdH | ybdH | *Escherichia coli* (strain K12) | 104 | Uniprot | P45579 | ND |
| uncharacterized zinc-type alcohol dehydrogenase-like protein YdjJ | ydjJ | *Escherichia coli* (strain K12) | 105 | Uniprot | P77280 | ND |
| uncharacterized zinc-type alcohol dehydrogenase-like protein YdjL | ydjL | *Escherichia coli* (strain K12) | 106 | Uniprot | P77539 | ND |
| NADH-dependent butanol dehydrogenase B | bdhB | *Clostridium acetobutylicum* | 107 | Uniprot | Q04945 | ND |
| NADH-dependent butanol dehydrogenase A | bdhA | *Clostridium acetobutylicum* | 108 | Uniprot | Q04944 | ND |
| NADH-dependent butanol dehydrogenase | CA_C3392 | *Clostridium acetobutylicum* | 109 | Uniprot | Q97DT0 | ND |
| alcohol dehydrogenase 1 | ADH1 | *Saccharomyces cerevisiae* | 110 | Uniprot | P00330 | ND |
| alcohol dehydrogenase 2 | ADH2 | *Saccharomyces cerevisiae* | 111 | Uniprot | P00331 | ND |
| alcohol dehydrogenase 3 | ADH3 | *Saccharomyces cerevisiae* | 112 | Uniprot | P07246 | ND |
| alcohol dehydrogenase 4 | ADH4 | *Saccharomyces cerevisiae* | 113 | Uniprot | P10127 | ND |
| general stress protein 69 | yhdN | *Bacillus subtilis* (strain 168) | 114 | Uniprot | P80874 | ND |
| putative oxidoreductase | GOX1615 | *Gluconobacter oxydans* | 115 | Uniprot | Q5FQJ0 | ND |
| aldehyde reductase Ahr | ahr | *Escherichia coli* (strain K12) | 116 | Uniprot | P27250 | ND |
| aldo-keto reductase family 4 member C9 | AKR4C9 | *Arabidopsis thaliana* | 117 | Uniprot | Q0PGJ6 | ND |
| prostaglandin f2-alpha synthase | A4UTP6 | *Leishmania donovani* | 118 | Uniprot | A4UTP6 | ND |
| aldehyde reductase YahK | yahK | *Escherichia coli* (strain K12) | 119 | Uniprot | P75691 | ND |
| protein tas | tas/ ygdS | *Escherichia coli* (strain K12) | 120 | Uniprot | P0A9T4 | ND |
| long-chain primary alcohol dehydrogenase AdhA | adhA | *Thermoanaerobacter ethaolicus* | 121 | Uniprot | Q9F282 | ND |
| (R,R)-butanediol dehydrogenase | bdhA | *Bacillus subtilis* (strain 168) | 122 | Uniprot | O34788 | ND |
| (R,R)-butanediol dehydrogenase | bdh1 | *Saccharomyces cerevisiae* | 123 | Uniprot | P39714 | ND |
| L-2,3-butanediol dehydrogenase/acetoin reductase | butA | *Corynebacterium glutamicum* | 124 | Uniprot | Q8NMA4 | ND |
| diacetyl reductase [(S)-acetoin forming] | budC | *Klebsiella pneumoniae* | 125 | Uniprot | Q48436 | ND |
| slaC | slaC | *Serratia marcescens* | 126 | Uniprot | F8U1P6 | ND |
| glycerol dehydrogenase | gldA | *Escherichia coli* (strain K12) | 127 | Uniprot | P0A9S5 | ND |
| L-2,3-butanediol dehydrogenase | budC | *Corynebacterium Glutanicum* | 128 | Uniprot | Q9ZNN8 | ND |
| glycerol 2-dehydrogenase (NADP(+)) | gld2 | *Hypocrea jecorina* | 129 | Uniprot | Q0GYU4 | ND |

TABLE 2-continued

Proteins and genes of the invention for producing 2,4-DHB

| Enzyme full name(s) | Gene name | Origin (Genus species) | SEQ ID NO (protein and/or gene) | Database (protein and/or gene) | Accession number in the database (protein and/or gene) | Version number in the database (protein and/or gene) |
|---|---|---|---|---|---|---|
| 1,3-propanediol dehydrogenase | dhaT | *Clostridium butyricum* | 130 | Uniprot | Q0G9F1 | ND |
| 1,3-propanediol dehydrogenase | dhaT | *Citrobacter Freundii* | 131 | Uniprot | P45513 | ND |
| 1,3-propanediol dehydrogenase | dhaT | *Klebsiella pneumoniae* | 132 | Uniprot | Q59477 | ND |
| NDMA-dependent alcohol dehydrogenase | ND | *Rhodoccus erythropolis* | 133 | Uniprot | P81747 | ND |
| NDMA-dependent alcohol dehydrogenase | ND | *Amycolatopsis methanolica* | 134 | Uniprot | P80175 | ND |
| 2. lactaldehyde reductases belonging to EC 1.1 | | | | | | |
| lactaldehyde reductase | fucO | *Escherichia coli* (strain K12) | 135 | Uniprot | P0A9S1 | ND |
| 3. glyoxylate reductases belonging to EC 1.1 | | | | | | |
| glyoxylate/hydroxypyruvate reductase A | ghrA/ ycdW | *Escherichia coli* (strain K12) | 136 | Uniprot | P75913 | ND |
| glyoxylate/hydroxypyruvate reductase B | ghrB/ yiaE | *Escherichia coli* (strain K12) | 137 | Uniprot | P37666 | ND |
| 4. didehydrogluconate reductases belonging to EC 1.1 | | | | | | |
| 2,5-diketo-D-gluconic acid reductase A | dkgA/ yqhE | *Escherichia coli* (strain K12) | 138 | Uniprot | Q46857 | ND |
| 2,5-diketo-D-gluconic acid reductase B | dkgB/ yafB | *Escherichia coli* (strain K12) | 139 | Uniprot | P30863 | ND |
| oxidoreductases acting on the aldehyde or oxogroup of donors (EC 1.2) 1. aldehyde dehydrogenases belonging to EC 1.2 | | | | | | |
| aldehyde dehydrogenase PuuC | puuC | *Escherichia coli* (strain K12) | 140 | Uniprot | P23883 | ND |
| aldehyde dehydrogenase | KPN_01018 | *Klebsiella pneumoniae* | 141 | Uniprot | A6T782 | ND |
| potassium-activated aldehyde dehydrogenase, mitochondrial | ALD4 | *Saccharomyces cerevisiae* | 142 | Uniprot | P46367 | ND |
| aldehyde dehydrogenase 5, mitochondrial | ALD5 | *Saccharomyces cerevisiae* | 143 | Uniprot | P40047 | ND |
| succinate semialdehyde dehydrogenase [NAD(P)+] Sad | sad | *Escherichia coli* (strain K12) | 144 | Uniprot | P76149 | ND |
| succinate-semialdehyde dehydrogenase [NADP(+)] GabD | gabD | *Escherichia coli* (strain K12) | 145 | Uniprot | P25526 | ND |
| gamma-aminobutyraldehyde dehydrogenase | prr/ ydcW | *Escherichia coli* (strain K12) | 146 | Uniprot | P77674 | ND |
| glutarate-semialdehyde dehydrogenase DavD | davD | *Pseudomonas putida* | 147 | Uniprot | Q88RC0 | ND |
| lactaldehyde dehydrogenase | aldA | *Escherichia coli* (strain K12) | 148 | Uniprot | P25553 | ND |
| aldehyde dehydrogenase B | aldB/ yiaX | *Escherichia coli* (strain K12) | 149 | Uniprot | P37685 | ND |

TABLE 2-continued

Proteins and genes of the invention for producing 2,4-DHB

| Enzyme full name(s) | Gene name | Origin (Genus species) | SEQ ID NO (protein and/or gene) | Database (protein and/or gene) | Accession number in the database (protein and/or gene) | Version number in the database (protein and/or gene) |
|---|---|---|---|---|---|---|
| lactaldehyde dehydrogenase | MJ1411 | Methanocaldococcus jannaschii | 150 | Uniprot | Q58806 | ND |
| aldehyde dehydrogenase YbcD | ycbD | Bacillus licheniformis | 151 | Uniprot | Q65NX0 | ND |
| 2-aminomuconic 6-semialdehyde dehydrogenase | amnC | Pseudomonas sp. | 152 | Uniprot | Q9KWS5 | ND |
| phenylacetaldehyde dehydrogenase | feaB | Escherichia coli (strain K12) | 153 | Uniprot | P80668 | ND |
| N-succinylglutamate 5-semialdehyde dehydrogenase | astD | Escherichia coli (strain K12) | 154 | Uniprot | P76217 | ND |
| 2. aldehyde oxidases belonging to EC 1.2 | | | | | | |
| indole-3-acetaldehyde oxidase | AO1 | Zea mays (maize) | 155 | Uniprot | O23887 | ND |
| xylose dehydrogenase | xdh | Caulobacter crescentus | 156 | ND | ND | ND |
| | xdh | Haloarcula marismortui | ND | Genbank | AAW78223 | AAW78223.1 GI: 58429660 |
| | NA | Burkholderia fugorum LB400 | ND | Genbank | GN088955 | GN088955.1 GI: 226882916 |
| | gfo2 | Haloferax volcanii DS2 | ND | NCBI | YP_003533786 | YP_003533786.1 GI: 292653888 |
| xylonolactonase (xylolactone hydrolase) | xylC | Caulobacter crescentus | 157 | ND | ND | ND |
| D-xylonate dehydratase | yjhG | Escherichia coli | 158 | ND | ND | ND |
| Alcohol dehydrogenase (NADPH dependant 1,2,4-butanetriol dehydrogenase; NADPH dependant 1,4-butanediol dehydrogenase) | yagF | Escherichia coli | 159 | ND | ND | ND |
| | adhP | Escherichia coli | 160 | ND | ND | ND |
| | yqhD | Escherichia coli | 161 | ND | ND | ND |
| 3-deoxy-D-glycero-pentulosonic acid decarboxylase (3-deoxy-D-glycero-pentulosonate decarboxylase; benzoylformate decarboxylase; 2-keto acid decarboxylase) | mdlC | Pseudomonas putida | 162 | ND | ND | ND |
| D-xylose isomerase | xylA | Escherichia coli | 163 | ND | ND | ND |
| D-xylulose kinase | xylB | Escherichia coli | 164 | ND | ND | ND |
| 3-deoxy-D-glero-pentulosonic acid aldolase | yjhH | Escherichia coli | 165 | ND | ND | ND |
| | yagE | Escherichia coli | 166 | ND | ND | ND |
| keto-acid dehydrogenase | yiaE | Escherichia coli | 167 | ND | ND | ND |
| D-xylulose kinase | ycdW | Escherichia coli | 168 | ND | ND | ND |
| glucose phophotransferase Enzyme IIBC(Glc) (glucose permease) | ptsG | Escherichia coli | 169 | ND | ND | ND |
| EIIA(Glc), phosphocarrier for glucose PTS transport (Carbohydrate repression resistance) | crr | Escherichia coli | 170 | ND | ND | ND |
| histine protein (PTS system histidine phosphocarrier protein HPr, (phosphohistidinoprotein-hexose phosphotransferase) | ptsH/ hpr | Escherichia coli | 171 | ND | ND | ND |
| lactose permease | lacY | Escherichia coli | 172 | ND | ND | ND |
| membrane subunit of the maltose ABC transporter | malF | Escherichia coli | 173 | ND | ND | ND |
| EIIA(Glc), phosphocarrier for glucose PTS transport (Carbohydrate repression resistance) | malG | Escherichia coli | 174 | ND | ND | ND |
| importer of sucrose | scrKYABR | Salmonella typhimurium | 175 | ND | ND | ND |

TABLE 2-continued

Proteins and genes of the invention for producing 2,4-DHB

| Enzyme full name(s) | Gene name | Origin (Genus species) | SEQ ID NO (protein and/or gene) | Database (protein and/or gene) | Accession number in the database (protein and/or gene) | Version number in the database (protein and/or gene) |
|---|---|---|---|---|---|---|
| sucrose:proton symport transport system | cscBKAR | *Escherichia coli* | 176 | ND | ND | ND |
| importer of xylose | xylFGH | *Escherichia coli* | 177 | ND | ND | ND |
| glucose permease (galactose:H+ symporter) | galP | *Escherichia coli* | 178 | ND | ND | ND |
| glucose facilitator | glf | *Zymomonas mobilis* | 179 | ND | ND | ND |
| glucokinase | glk | *Zymomonas mobilis* | 180 | ND | ND | ND |
| importer of xylose | glk | *Escherichia coli* | 181 | ND | ND | ND |
| adenylate cyclase | cyaA | *Escherichia coli* | 182 | ND | ND | ND |
| CRP (cAMP receptor protein; cAMP-activated global transcription factor) and mutated CRP (*) | crp crp* | *Escherichia coli* *Escherichia coli* | 183 184 185 186 187 | ND ND ND ND ND | ND ND ND ND ND | ND ND ND ND ND |
| CRP-like protein (catabolite control protein A) | ccpA | *Bacillus subtilis* | ND | NCBI | NC_000964 (entire genome) | NC_000964.3 GI: 255767013 |
| membrane-bound transhydrogenase (membrane bound proton translocating pyridine nucleotide transhydrogenase) | pntAB | *Escherichia coli* | 188 | ND | ND | ND |
| soluble pyridine nucleotide transhydrogenase | sthA/ udhA | *Escherichia coli* | 189 | ND | ND | ND |
| NADP-dependent glyceraldehyde-3-phosphate dehydrogenase | gapN | *Streptococcus mutans* | 190 | ND | ND | ND |
| NADH generating glyceraldehyde-3-phosphate (Glyceraldehyde 3-phosphate dehydrogenase A) | gapA | *Escherichia coli* | 191 | ND | ND | ND |
| glucose-6-phosphate isomerase (phosphoglucose isomerase) | pgi | *Escherichia coli* | 192 | ND | ND | ND |
| phospho-fructokinase (6-phospho-fructokinase-1) | pfkA | *Escherichia coli* | 193 | ND | ND | ND |
| glucose-6-phosphate 1-dehydrogenase | zwf | *Escherichia coli* | 194 | ND | ND | ND |
| NADPH generating dihydrolipoamide dehydrogenase (lipoamide dehydrogenase), and its mutated version (*) | lpd lpd* | *Escherichia coli* *Escherichia coli* | 195 196 | ND ND | ND ND | ND ND |
| Bifunctional NAD(P)H-hydrate repair enzyme (NAD(P)HX epimerase/ NAD(P)HX dehydratase) | yjeF (nnr) | *Escherichia coli* | 197 | ND | ND | ND |
| malate kinase variant | lysC E119G-E250K | *Escherichia coli* | 198 | ND | ND | ND |
| malate semialdehyde dehydrogenase variant | asd E241Q | *Escherichia coli* | 199 | ND | ND | ND |
| DHB dehydrogenase variant | ssr H39R-N43H | *Metallosphaera sedula* | 200 | ND | ND | ND |
| malyl-CoA reductase variant | mcr Y206P | *Sulfolobus tokodaii* | 201 | ND | ND | ND |
| malyl-CoA lyase | mcl | *Methylobacter extorquens* | 202 | ND | ND | ND |
| homoserine dehydrogenase | ilvE | *Escherichia coli* | 203 | ND | ND | ND |
| 2-oxo-4-hydroxybutyrate reductase | ldhA | *Lactococcus lactis* | 204 | ND | ND | ND |

(NA = non-available; ND = non disclosed)

Methods for the Production of 2,4-DHB

In another aspect, the present invention relates to a method for the production of 2,4-dihydroxybutyrate comprising:

a) culturing a genetically modified microorganism as described above in a culture medium comprising a carbon source, under fermentation conditions allowing conversion of said carbon source into 2,4-dihydroxybutyrate, and b) recovering the 2,4-dihydroxybutyrate from said culture medium.

Fermentation mediums and sources of carbon are well known in the art. According to the invention, the terms "fermentative process", "fermentation" or "culture" are used interchangeably to refer to the experimental conditions allowing the growth of a given microorganism. The growth of a microorganism is generally performed in fermenters with an appropriate growth medium adapted to the microorganism being used.

An "appropriate culture medium" means herein a medium (e.g., a sterile, liquid media) comprising nutrients essential or beneficial to the maintenance and/or growth of the microorganism such as carbon sources or carbon substrates; nitrogen sources, for example peptone, yeast extracts, meat extracts, malt extracts, urea, ammonium sulfate, ammonium chloride, ammonium nitrate and ammonium phosphate; phosphorus sources, for example monopotassium phosphate or dipotassium phosphate; trace elements (e.g., metal salts) for example magnesium salts, cobalt salts and/or manganese salts; as well as growth factors such as amino acids and vitamins.

In a preferred embodiment of the invention, the carbon source, preferably the carbohydrate, is derived from renewable feed-stock, such as vegetable biomass.

The person skilled in the art can easily determine the culture conditions necessary for growing the microorganism according to the invention. In particular, it is well know that bacteria can be fermented at a temperature comprised between 20° C. and 55° C., preferentially between 25° C. and 40° C. *E. coli* can more particularly be cultured at a temperature comprised between about 30° C. and about 37° C.

The method of the invention can be performed either in a batch process, in a fed-batch process or in a continuous process, and under aerobic, micro-aerobic or anaerobic conditions.

A fermentation "under aerobic conditions" means that oxygen is provided to the culture by dissolving gas into the liquid phase of the culture. This can be achieved by (1) sparging oxygen containing gas (e.g. air) into the liquid phase, or (2) shaking the vessel containing the culture medium in order to transfer the oxygen contained in the head space into the liquid phase. The main advantage of the fermentation under aerobic conditions is that the presence of oxygen as an electron acceptor improves the capacity of the strain to produce more energy under the form of ATP for cellular processes, thereby improving the general metabolism of the strain.

Micro-aerobic conditions can be used herein and are defined as culture conditions wherein low percentages of oxygen (e.g. using a mixture of gas containing between 0.1 and 10% of oxygen, completed to 100% with nitrogen) are dissolved into the liquid phase.

By contrast, "anaerobic conditions" are defined as culture conditions wherein no oxygen is provided to the culture medium. Strictly anaerobic conditions can be obtained by sparging an inert gas like nitrogen into the culture medium to remove traces of other gas. Nitrate can be used as an electron acceptor to improve ATP production by the strain and improve its metabolism.

According to a preferred embodiment, the method of the invention further comprises a step c) of purifying the 2,4-DHB of step b).

Methods for purifying carboxylic acids and in particular hydroxyacids are well known in the art, and have notably been described in WO2002/090312, WO2002/022544 and WO2012/153042, which are incorporated herein by reference. The purification of 2,4-DHB can be performed either after the fermentation is finished or during the fermentation by in situ product recovery including extractive fermentation (Van Hecke et al., 2014).

In either case microorganisms may be removed by passing through a device, preferably through a filter with a cut-off in the range from 20 to 200 kDa, where solid/liquid separation takes place. It is also feasible to employ a centrifuge, a suitable sedimentation device or a combination of these devices, it being especially preferred to first separate at least part of the microorganisms by sedimentation and subsequently to feed the fermentation broth, which has been partly relieved of the microorganisms, to ultrafiltration or to a centrifugation device.

After the microorganisms have been removed, the 2,4-DHB contained in the resulting fermentation solution may be purified by precipitation with calcium hydroxide followed by a reacidification with sulfuric acid, however this process generates high loads of calcium sulfate that then needs to be eliminated (Schügerl, 2000). Alternatively 2,4-DHB may be precipitated by adding to the fermentation solution, for example, ammonium compounds to produce an ammonium salt of 2,4-DHB. This ammonium salt can then be removed from the fermentation solution by adding an organic extractant and subsequently heating the resulting mixture, whereby the ammonium salt is concentrated in the organic phase. 2,4-DHB can then be isolated from this phase, for example, by further extraction steps, to give pure 2,4-DHB (WO2002/090312).

In a more simple process without any need for further purification or extraction steps, 2,4-DHB may be purified by using activated charcoal or functionalized resins, but in a relatively inefficient way (Husson & King 1999). Based on the same interaction principle, 2,4-DHB may be purified by ion-exchange or hydrophobic chromatography. Alternatively, 2,4-DHB may be purified by electrodialysis, reverse osmosis, ultrafiltration or nanofiltration (Cho et al., 2012). In that case 2,4-DHB is recovered as an aqueous solution.

In the case of extractive fermentation, 2,4-DHB may be purified from the fermentation broth by liquid-liquid extraction, using for example, amine compounds, such as tri-n-decylamine (Gao et al., 2009). Alternatively 2,4-DHB may be recovered by reactive distillation by for example, esterification with an alcohol such as butanol (Rao et al., 2014).

The present invention will be better understood in the light of the following examples, which are solely provided for illustrative purposes. Nevertheless, the skilled artisan will readily understand that these detailed examples are not limitative and that various modifications, substitutions, omissions, and changes may be made without departing from the scope of the invention.

DRAWINGS

EXAMPLES

The present invention is further defined in the following examples. It should be understood that these examples, while indicating preferred embodiments of the invention, are given by way of illustration only. From above disclosure and these examples, the man skilled in the art can make various changes of the invention to adapt it to various uses and conditions without modifying the essentials means of the invention.

Exemplary genes and enzymes required for constructing microorganisms with these capabilities are described as well as methods for cloning and transformation, monitoring product formation and using the engineered microorganisms for production.

In particular, examples show modified *Escherichia coli* (*E. coli*) strains, but these modifications can easily be performed in other microorganisms of the same family.

*Escherichia coli* belongs to the Enterobacteriaceae family, which comprises members that are Gram-negative, rod-shaped, non-spore forming and are typically 1-5 µm in length. Most members have flagella used to move about, but a few genera are non-motile. Many members of this family are a normal part of the gut flora found in the intestines of humans and other animals, while others are found in water or soil, or are parasites on a variety of different animals and plants. *E. coli* is one of the most important model organism, but other important members of the Enterobacteriaceae family include *Klebsiella*, in particular *Klebsiella terrigena*, *Klebsiella planticola* or *Klebsiella oxytoca, Pantoea* and *Salmonella*.

Protocols

Several protocols have been used to construct 2,4-dihydroxy-butanoic acid producing strains described in the following examples.

Protocol 1 (Chromosomal modifications by homologous recombination, selection of recombinants and antibiotic cassette excision) and protocol 2 (Transduction of phage P1) used in this invention have been fully described in the patent application WO2013/001055.

Protocol 3: Construction of recombinant plasmids Recombinant DNA technology is well described and known by the man skilled in the art.

Briefly, the DNA fragments are PCR amplified using oligonucleotides (the person skilled in the art is able to design) and MG1655 *E. coli* K-12 or other microorganism genomic DNA as matrix (according to the targeted gene to be amplified). The DNA fragments and selected plasmid are digested with compatible restriction enzymes, ligated and then transformed in competent cells. Transformants are analysed and recombinant plasmids of interest are verified by DNA sequencing.

Figure 1:
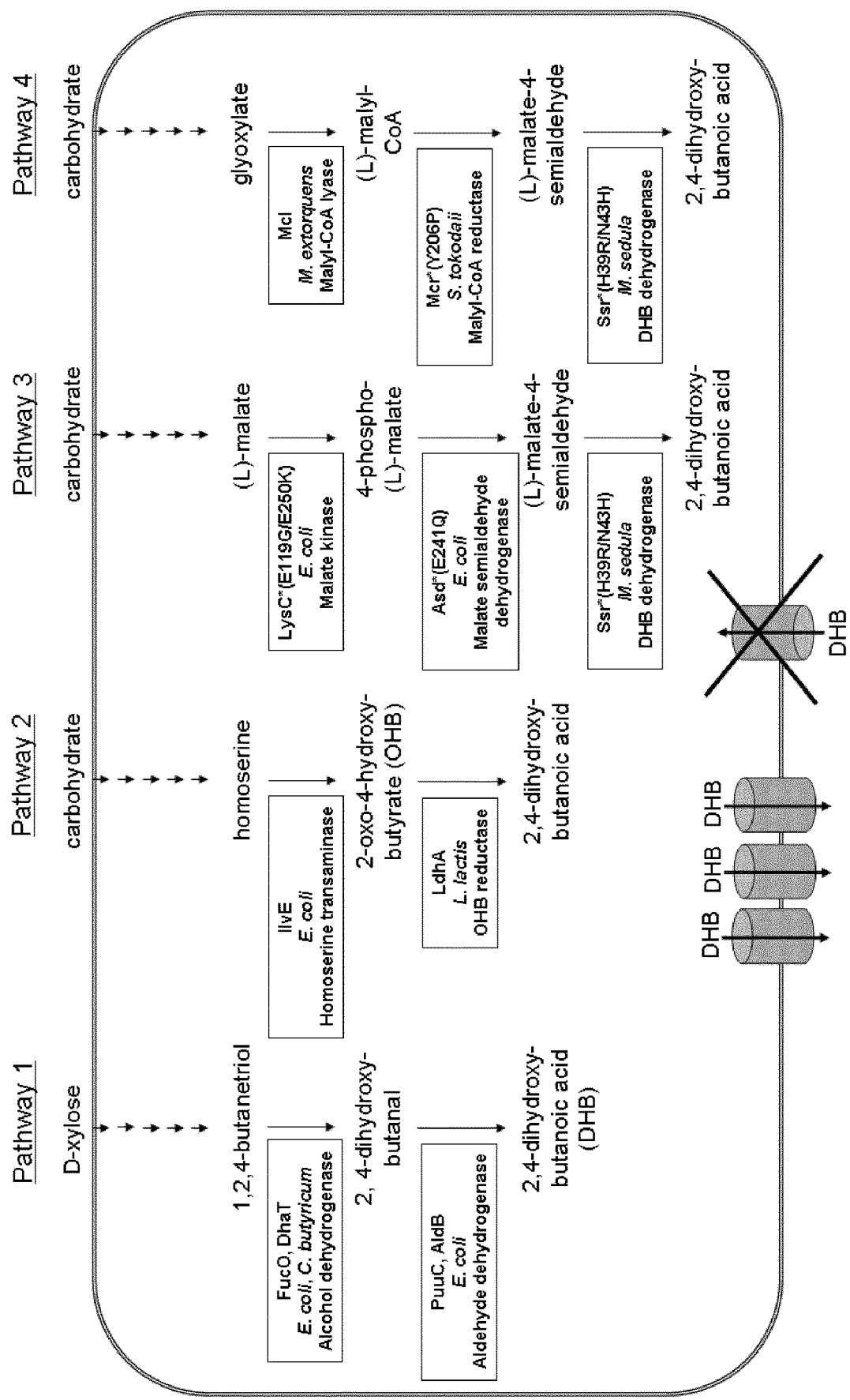
FIG. 1 represents the four metabolic pathways for 2,4-DHB production (*: genes that are optionally attenuated or deleted).

Example 1: Construction of 2,4-DHB Producing Strains From 4 Different Metabolic Pathways in MG1655 *E. coli*—FIG. 1—Construction of Strains 1 to 7

Pathway 1: Production of 2,4-DHB from xylose by Overproduction of Enzymes From a New Pathway in MG1655 *E. coli*—Construction of Strains 1 to 4.

Figure 2:
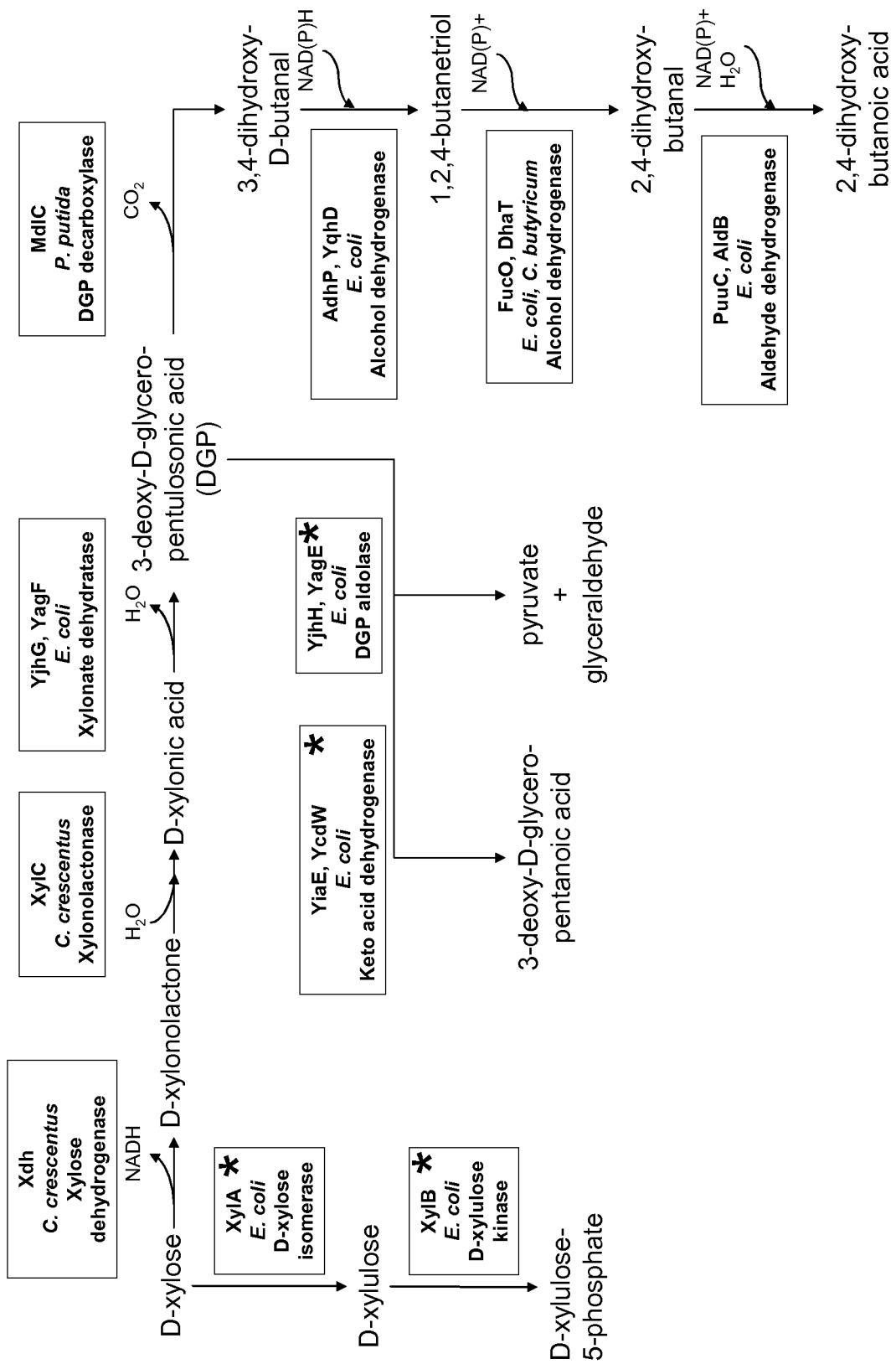
FIG. 2 represents the metabolic pathway for the conversion of D-xylose into 2,4-DHB (*: genes that are optionally attenuated or deleted).

*Escherichia coli* strain MG1655 was modified to produce 2,4-dihydroxybutanoic acid (2,4-DHB) from D-xylose using the pathway illustrated in FIG. 2. The work seeks to maximize the carbon flux toward the production of 2,4-DHB and so to remove all the enzymes involved in other xylose consuming pathways or involved in conversion of 2,4-DHB-intermediate-compounds, which represents a loss of product.

In addition to the genes naturally expressed by *E. coli* (yjhG gene of sequence SEQ ID NO:158 and yagF gene of sequence SEQ ID NO:159, encoding for xylonate dehydratases, and adhP gene of sequence SEQ ID NO:160 and yqhD gene of sequence SEQ ID NO:161 encoding alcohol dehydrogenases—NAD(P)H-dependant 1,2,4-butanetriol dehydrogenases), the genes coding for the following enzymes; the xylose dehydrogenase and the xylonolactonase of *Caulobacter crescentus* (xdh [CC0821 on CauloCyc, SEQ ID NO:156] and xylC [CC0820 on CauloCyc, SEQ ID NO:157], respectively), the 3-deoxy-D-glycero-pentulosonate decarboxylase of *Pseudomonas putida* (mdlC gene of sequence SEQ ID NO:162), the alcohol dehydrogenase—NAD(P)+-dependant 2,4-dihydroxy-butanal dehydrogenase of *E. coli* or *Clostridium butyricum* (fucO gene from *E. coli* encoding the enzyme of sequence SEQ ID NO:135 or dhaT gene form *C. butyricum* encoding the enzyme of sequence SEQ ID NO:130, respectively), and the aldehyde dehydrogenase of *E. coli* (puuC gene from *E. coli* encoding the enzyme of sequence SEQ ID NO:140 or aldB gene from *E. coli* encoding the enzyme of sequence SEQ ID NO:149) were separately expressed with a Ptrc artificial promoter (sequence given in patent WO 2007/0770441) and their own ribosome binding site, using a pCL1920 plasmid (Lerner & Inouye, 1990). In fact, genes xdh, xylC, mdlC, were first cloned on the pCL1920 plasmid giving the plasmid pDHB0001, and then fucO or dhaT and puuC or aldB were sequentially cloned on the plasmid pDHB0001 giving rise to the 4 combinations, with the resulting plasmids pDHB0002 to pDHB0005, as described in table below.

| Couple of genes cloned into the pDHB0001 plasmid overexpressing xdh, xylC, mdlC genes | | | | |
|---|---|---|---|---|
| | fucO, puuC | fucO, aldB | dhaT, puuC | dhaT, aldB |
| Resulting plasmids | pDHB0002 | pDHB0003 | pDHB0004 | pDHB0005 |

Moreover, in order to block the native xylose catabolic pathway, the genes encoding for the D-xylose isomerase (xylA gene of sequence SEQ ID NO:163) and the D-xylulose kinase (xylB gene of sequence SEQ ID NO:164) were deleted from the *E. coli* MG1655 chromosome using the homologous recombination strategy described by Datsenko & Wanner, 2000, and according to Protocol 1. More precisely, to delete xylAB operon, a PCR product carrying the antibiotic resistance gene together with FRT sites surrounded by sequences homologous to up-stream and down-stream regions of xylAB operon was generated with primers of SEQ ID NO:205 and SEQ ID NO:206 and introduced into *E. coli* MG1655 selected strain in which the pKD46 vector was previously transformed.

To avoid the degradation of the 3-deoxy-D-glycero pentulosonic acid (DGP), the genes encoding the keto acid dehydrogenases (yiaE gene of sequence SEQ ID NO:167; and ycdW gene of sequence SEQ ID NO:168) and the DGP aldolases (yjhH gene of sequence SEQ ID NO:165; and yagE gene of sequence SEQ ID NO:166) were also deleted using the same homologous recombination strategy. More precisely, to delete yjhH gene (SEQ ID NO:165), a PCR product carrying the antibiotic resistance gene together with FRT sites, surrounded by sequences homologous to up-stream and downstream regions of yjhH gene, was generated with primers of SEQ ID NO:207 and SEQ ID NO:208 and introduced into *E. coli* MG1655 selected strain in which the pKD46 vector was previously transformed. To delete the yagE gene (SEQ ID NO:166), a PCR product carrying the antibiotic resistance gene together with FRT sites, surrounded by sequences homologous to up-stream and downstream regions of yagE gene, was generated with primers of SEQ ID NO:209 and SEQ ID NO:210 and introduced into *E. coli* MG1655 selected strain in which the pKD46 vector was previously transformed. To delete the yiaE gene (SEQ ID NO:167), a PCR product carrying the antibiotic resistance gene together with FRT sites, surrounded by sequences homologous to up-stream and downstream regions of yiaE gene, was generated with primers of SEQ ID NO:211 and SEQ ID NO:212 and introduced into *E. coli* MG1655 selected strain in which the pKD46 vector was previously transformed. To delete the ycdW gene (SEQ ID NO:168), a PCR product carrying the antibiotic resistance gene together with FRT sites, surrounded by sequences homologous to up-stream and downstream regions of the ycdW gene, was generated with primers of SEQ ID NO:213 and SEQ ID NO:214 and introduced into *E. coli* MG1655 selected strain in which the pKD46 vector was previously transformed.

As the yjhH gene belongs together with yjhG (SEQ ID NO:158) and yjhI to the yjhIHG operon, the sequences homologous to up-stream and downstream regions of yjhH must be chosen as to not alter the expression of surrounding genes. It was the same for yagE gene (SED ID NO:166) which belongs to yagEF operon. The man skilled in the art knows how to remove a DNA sequence from an operon while keeping the open reading frame of the rest of the operon.

To suppress the catabolite repression, the glucose phophotransferase enzyme IIBC(Glc) encoded by the ptsG gene (SEQ ID NO:169), was deleted by using the homologous recombination strategy described by Datsenko & Wanner, 2000 (according to Protocol 1) as described in patent application EP 14305691.9, in particular in Example 2 of said document (referred herein as SEQ ID NO:215 and SEQ ID NO:216). The appropriate PCR product was introduced into *E. coli* MG1655 selected strain in which the pKD46 vector was previously transformed.

Each time a different antibiotic resistance gene was used among kanamycin, chloramphenicol, gentamycin, tetracycline, blasticidin or spectinomycin.

Before using *E. coli* MG1655 optimized strain, the antibiotic cassettes were removed from ΔxylAB, ΔyjhH, ΔyagE, ΔyiaE, ΔycdW and ΔptsG modifications using the Flp recombinase as described by Datsenko & Wanner, 2000 (according to Protocol 1).

Improving of the 2,4-DHB Acid Production by Increasing the NADPH Availability of the Producing Strain The 1,2,4-butanetriol dehydrogenases, encoded by adhP and yqhD, are in need of reducing power available in the organism, particularly in form of NADPH, so the genes involved in NADPH production were overexpressed.

The membrane bound proton translocating pyridine nucleotide transhydrogenase encoded by the pntAB operon (SEQ ID NO:188) was overproduced by replacing the endogenous promoter and ribosome binding site of pntA gene of *Escherichia coli* MG1655 by the inducible Ptrc promoter (from the plasmid pTRC99A, Amersham Pharmacia) and the define ribosome binding site RBS120 (from RBS Calculator software), as described in patent application EP 14305691.9 in particular in Example 4 of said document (referred herein as SEQ ID NO:217). The appropriate PCR product described in patent application EP 14305691.9 was generated and introduced into *E. coli* MG1655 selected strain in which the pKD46 vector was previously transformed.

The soluble pyridine nucleotide transhydrogenase encoded by the sthA gene (previously known as udhA, and of sequence SEQ ID NO:189) was deleted by using the homologous recombination strategy described by Datsenko & Wanner, 2000 (according to Protocol 1) and as described in patent application WO 2012/055798, in particular in Example 2 of said application (referred herein as SEQ ID NO:218 and SEQ ID NO:219). The appropriate PCR product was generated and introduced into *E. coli* MG1655 selected strain in which the pKD46 vector was previously transformed.

The phosphofructokinase encoded by the pfkA gene (SEQ ID NO:193) was deleted by using the homologous recombination strategy described by Datsenko & Wanner, 2000 (according to Protocol 1), and as described in patent application EP 14305691.9, in particular in Example 5 of said document (referred herein as SEQ ID NO:220 and SEQ ID NO:221). The appropriate PCR product was generated and introduced into *E. coli* MG1655 selected strain in which the pKD46 vector was previously transformed.

Each time a different antibiotic resistance gene was used among kanamycin, chloramphenicol, gentamycin, tetracycline, blasticidin or spectinomycin.

Before using *E. coli* MG1655 optimized strain, the antibiotic cassettes were removed from the pntAB, sthA and pfkA loci using the Flp recombinase according to Protocol 1.

Finally, each plasmid pDHB0002, pDHB0003, pDHB0004 or pDHB0005 described above was introduced into different *E. coli* MG1655-derived mutant strains.

A non-exclusive examples of constructed strains are listed in Table 3.

TABLE 3

| Strain | Relevant genotype |
| --- | --- |
| Strain 1 | MG1655 ΔxylAB ΔyjhH ΔyagE ΔyiaE ΔycdW ΔptsG Ptrc01/OP01/RBS120-pntAB ΔsthA ΔpfkA pDHB0002) |
| Strain 2 | MG1655 ΔxylAB ΔyjhH ΔyagE ΔyiaE ΔycdW ΔptsG Ptrc01/OP01/RBS120-pntAB ΔsthA ΔpfkA (pDHB0003) |
| Strain 3 | MG1655 ΔxylAB ΔyjhH ΔyagE ΔyiaE ΔycdW ΔptsG Ptrc01/OP01/RBS120-pntAB ΔsthA ΔpfkA (pDHB0004) |
| Strain 4 | MG1655 ΔxylAB ΔyjhH ΔyagE ΔyiaE ΔycdW ΔptsG Ptrc01/OP01/RBS120-pntAB ΔsthA ΔpfkA (pDHB0005) |

Pathway 2: Production of 2,4-DHB from homoserine by Overproduction of homoserine transaminase and 2-oxo-4-hydroxybutyrate reductase Enzymes in MG1655 *E. coli*— Construction of Strain 5.

The synthetic pathway for the conversion of homoserine into 2,4-DHB is expressed in a *E. coli* strain MG1655 strain with enhanced production of homoserine.

To improve homoserine production, the mutated allele encoding the bifunctional aspartokinase/homoserine dehydrogenase of *E. coli* with reduced feed-back resistance to threonine (thrA*1 gene of sequence SEQ ID NO:222 with point mutation to change the phenylalanine amino acid in position 318 into serine) and the gene encoding the pyruvate carboxylase of *Rhizobium etli* (pycre gene of sequence SEQ ID NO:223) were separately overexpressed (not in operon) from the plasmid pCL1920 (Lerner & Inouye, 1990). More precisely, thrA*1 gene was overexpressed from the IPTG-inducible trc promoter (SEQ ID NO:224) regulated by the repressor LacI encoded by lacI gene, both obtained from the plasmid pTRC99A (Stratagene), and the pycre gene was overexpressed from the promoter of gapA gene (SEQ ID NO:225), giving the pME101-thrA*1-PgapA-pycre-TT07 plasmid. More precisely, one example of pME101-thrA*1 plasmid is described in patent WO2007/077041, added in reference in this patent application. One example of obtaining the PgapA-pycre-TT07 amplicon and cloning it into a pCL1920 vector is described in patent WO2012/055798, added in reference in this patent application.

To avoid the degradation of the homoserine, the genes encoding the homoserine kinase (thrB gene of sequence SEQ ID NO:226), the threonine synthase (thrC gene of sequence SEQ ID NO:227) and the homoserine O-succinyl-transferase (metA gene of sequence SEQ ID NO:228) were attenuated on the E. coli MG1655 chromosome.

To attenuate expression of thrBC operon, the natural promoter of the operon thrBC and ribosome binding site (RBS) of thrB gene were replaced by an artificial one by using the homologous recombination strategy described by Datsenko & Wanner, 2000 (according to Protocol 1). More precisely, a PCR product carrying the transcriptional terminator (T7Te transcriptional terminator of the T7 bacteriophage, Harrington et al., 2001, SEQ ID NO:229), the artificial trc promoter and RBS (SEQ ID NO:230) and an antibiotic resistance gene together with FRT sites, surrounded by sequences homologous to thrB gene and to the up-stream region of thrB gene on the chromosome (SEQ ID NO:231 and SEQ ID NO:232), was introduced into E. coli MG1655 selected strain in which the pKD46 vector was previously transformed.

metA gene was attenuated to the same manner. More precisely, a PCR product carrying the transcriptional terminator (T7Te transcriptional terminator of the T7 bacteriophage, Harrington et al., 2001, SEQ ID NO:229), the artificial trc promoter and RBS (SEQ ID NO:230) and a resistance gene together with FRT sites, surrounded by sequences homologous to metA gene and to the up-stream region of metA gene on the chromosome (SEQ ID NO:233 and SEQ ID NO:234), was introduced into E. coli MG1655 selected strain in which the pKD46 vector was previously transformed.

To convert homoserine into 2,4-DHB, the genes encoding the homoserine transmaminase from E. coli (ilvE gene from E. coli encoding the enzyme of sequence SEQ ID NO:203) and the 2-oxo-4-hydroxybutyrate (OHB) reductase from Lactococcus lactis (ldhA gene from L. lactis encoding the enzyme of sequence SEQ ID NO:204) were overexpressed in a same operon from the IPTG-inducible tac promoter (SEQ ID NO:235) obtained from the plasmid pEXT20 (Dykxhoorn et al., 1996) and the T7 RBS (SEQ ID NO:236) obtained from the plasmid pET28a (Novagen) into the pEXT20 vector, giving the pEXT20-DHB plasmid. More precisely, one example of construction of the pEXT20-DHB plasmid is described in patent WO2014/009435.

To optimize carbon flux in 2,4-DHB biosynthesis pathway, the genes encoding the D-lactate dehydrogenase (IdhA gene from E. coli encoding the enzyme of sequence SEQ ID NO:237), the alcohol dehydrogenase (adhE gene of sequence SEQ ID NO:238), and the pyruvate kinases (pykA gene of sequence SEQ ID NO:239 and pykF gene of sequence SEQ ID NO:240) were also deleted from the E. coli MG1655 chromosome.

More precisely, one example of construction of the gene deletions ΔldhA and ΔadhE in a producing strain and excision of the resistance gene are described in patent WO2014/009435. One example of construction of the gene deletions ΔpykA and ΔpykF in a producing strain and excision of the resistance gene are described in patent WO2009/043803, added in reference in this patent application.

To increase the glucose import into the cell, the gene dgsA (or mlc) (dgsA gene of sequence SEQ ID NO:241), coding for transcriptional dual regulator that controls the expression of a number of genes encoding enzymes of the Escherichia coli phosphotransferase (PTS) and phosphoenolpyruvate (PEP) systems, was deleted. Another way to increase the glucose import into the cell was to overproduce PtsG (IICGlc) (ptsG gene from E. coli encoding the enzyme of sequence SEQ ID NO:169), the transmembrane partner of the glucose phosphotransfer system. One example of construction of the gene deletion ΔdgsA and introduction in a producing strain and excision of the resistance gene are described in patent WO2013/001055, added in reference in this patent application. One example of overexpression of ptsG gene is to construct and introduce the following plasmid pCC1BACVB01-PlacIq-lacI-TT02-Ptrc01/OP01/RBS01*2-ptsG-TT07 in a producing strain, as described in patent WO2013/001055.

According to the wanted combination of the deletion, each deletion was introduced into a construction strain previously transformed with the pKD46 plasmid. Each time a different antibiotic resistance gene was used among kanamycin, chloramphenicol, gentamycin, tetracycline, blasticidin or spectinomycin. When necessary and before plasmid introduction, the antibiotic cassettes were removed from thrBC, metA, ldhA, adhE, dgsA, pykA or pykF loci using the Flp recombinase as described by Datsenko & Wanner, 2000 (according to Protocol 1).

The different plasmids were introduced into different E. coli MG1655-derived mutant strains.

A non-exclusive examples of constructed strains are listed in Table 4.

TABLE 4

| Strain | Relevant genotype |
|---|---|
| Strain 5 | MG1655 ΔldhA ΔadhE Ptrc244*1/E01/RBS08-metA Ptrc244*1/E01/RBS08-thrBC ΔpykA ΔpykF ΔdgsA (pME101-thrA*1-PgapA-pycre-TT07) (pCC1BAC-PlacIq-lacI-TT02-Ptrc01/OP01/RBS01*2-ptsG-TT07) (pEXT20-DHB) |

Pathway 3: Production of 2,4-DHB from Malate by Overproduction of Enzymes of a Synthetic Pathway, Comprising Malate Kinase, Malate semialdehyde dehydrogenase and 2,4-DHB dehydrogenase in MG1655 E. coli—Construction of Strain 6

The synthetic pathway for the conversion of malate into 2,4-DHB is expressed in a E. coli MG1655 strain.

To convert malate into 2,4-DHB, the mutated allele of lysC from E. coli encoding the malate kinase (lysC E119G E250K gene from E. coli encoding the enzyme of sequence SEQ ID NO:198 with point mutations to change the glutamate amino acid in position 119 into glycine, and the glutamate amino acid in position 250 into lysine), the mutated allele of asd from E. coli encoding the malate semialdehyde dehydrogenase (asd E241Q gene from E. coli encoding the enzyme of sequence SEQ ID NO:199 with point mutation to change the glutamate amino acid in position 241 into glutamine), and the mutated allele of ssr from *Metallosphaera sedula* encoding the DHB dehydrogenase (ssr H39R-N43H gene from *M. sedula* encoding the enzyme of sequence SEQ ID NO:200 with point mutations to change the histidine amino acid in position 39 into arginine, the asparagine amino acid in position 43 into histidine and other silent mutations to optimize the coding sequence for maximum expression in *E. coli*, using the GeneOptimizer® software of Geneart (Life Technologie)) were overexpressed in a same operon from the IPTG-inducible tac promoter (SEQ ID NO:235) obtained from the plasmid pEXT20 (Dykxhoorn et al., 1996) and the T7 RBS (SEQ ID NO:236) obtained from the plasmid pET28a (Novagen) into the pET28a vector, giving the pTAC-DHB plasmid. More precisely, one example of construction of the pTAC-DHB plasmid is described in patent WO2012/056318, added in reference in this patent application.

The pTAC-DHB plasmid was introduced into *E. coli* MG1655 strain, giving rise to the strain 27.

A non-exclusive example of constructed strain is listed in Table 5.

TABLE 5

| Strain | Relevant genotype |
| --- | --- |
| Strain 6 | MG1655 (pTAC-DHB) |

Pathway 4: Production of 2,4-DHB from Malate and/or succinyl-CoA and/or glyoxylate by Overproduction of Enzymes of a Synthetic Pathway, Comprising a malyl-CoA Synthetase and/or a succinyl-CoA:(L)-malate CoA Transferase and/or a malyl-CoA lyase, a malyl-CoA Reductase and a DHB Dehydrogenase in MG1655 *E. coli*—Construction of Strain 7.

The synthetic pathway for the conversion of glyoxylate into 2,4-DHB is expressed in a *E. coli* MG1655 strain.

To convert glyoxylate into 2,4-DHB, the genes encoding the malyl-CoA lyase from *Methylobacter extorquens* (mcl gene from *M. extorquens* encoding the enzyme of sequence SEQ ID NO:202 optimized for expression in *E. coli*), the malyl-CoA reductase (malonyl-CoA reductase) from *Sulfolobus tokodaii* (mcr gene from *S. tokodaii* encoding the enzyme of sequence SEQ ID NO:201 with point mutation to change the tyrosine amino acid in position 206 into proline) and the DHB dehydrogenase (succinic semialdehyde reductase) from *Metallosphaera sedula* (ssr gene from *M. sedula* encoding enzyme of sequence SEQ ID NO:200 optimized for expression in *E. coli* and with point mutation to change the histidine amino acid in position 39 into arginine and point mutation to change the asparagine amino acid in position 43 into histidine) were overexpressed in a same operon from the IPTG-inducible tac promoter (SEQ ID NO:236) obtained from the plasmid pACT3 (Dykxhoorn et al., 1996), plasmid into which the 3 genes were cloned, giving the pACT3-MCL-DHB plasmid. More precisely, one example of construction of the pACT3-MCL-DHB plasmid is described in patent WO2013/160762.

To optimize carbon flux in 2,4-DHB biosynthesis pathway and in particular the availability of glyoxylate, the genes encoding the phosphate acetyltransferase (pta gene of sequence SEQ ID NO:242), the malate synthase (aceB gene of sequence SEQ ID NO:243), and the transcriptional regulator of the glyoxylate bypass operon (iclR gene of sequence SEQ ID NO:244) were deleted from the *E. coli* MG1655 chromosome.

More precisely, one example of construction of the gene deletions Δpta, ΔaceB and ΔiclR, introduction in a producing strain and excision of resistance gene are described in patent WO2013/160762.

According to the wanted combination of the deletion, each deletion was introduced into a construction strain previously transformed with the pKD46 plasmid. Each time a different antibiotic resistance gene was used among kanamycin, chloramphenicol, gentamycin, tetracycline, blasticidin or spectinomycin. When necessary and before plasmid introduction, the antibiotic cassettes were removed from pta, aceB, or iclR loci using the Flp recombinase as described by Datsenko & Wanner, 2000 (according to Protocol 1).

The plasmid pACT3-MCL-DHB was introduced into different *E. coli* MG1655-derived mutant strains optimized for 2,4-DHB production.

A non-exclusive example of constructed strain is listed in Table 6.

TABLE 6

| Strain | Relevant genotype |
| --- | --- |
| Strain 7 | MG1655 Δpta ΔiclR ΔaceB (pACT3-MCL-DHB) |

Example 2: Optimization of 2,4-DHB Production by Overproduction of 2.4-DHB Exporter in 2,4-DHB Producing Strains from 4 Different Metabolic Pathways in MG1655 *E. coli*—Construction of Strains 8 to 38

In order to promote the export of 2,4-DHB and in consequence improved the production of 2,4-DHB, one of the following genes encoding for exporters was overexpressed with a Ptrc artificial promoter (sequence given in patent WO 2007/0770441) and their own ribosome binding site, using a pCL1920 plasmid (Lerner & Inouye, 1990). The genes overexpressed are genes encoding the monocarboxylate MFS (major facilitator superfamily)-type transporter from *E. coli* (yhjX gene of sequence SEQ ID NO:2), the carboxylic acid (lactate) transporter from *S. cerevisiae* (JEN1 gene of sequence SEQ ID NO:24), the inner membrane metabolite (lactate) transport protein from *E. coli* (yhjE gene of sequence SEQ ID NO:26) and the malic acid transport protein from *Schizosaccharomyces pombe* (mae1 gene of sequence SEQ ID NO:58). According to the 2,4-DHB production pathway optimized in *E. coli* MG1655-modified strains, the gene encoding the exporter was cloned into an empty pCL1920 plasmid or into a pCL1920 plasmid carrying genes for 2,4-DHB production and described above (pDHB0002 to pDHB0005, plus pME101-thrA*1-PgapA-pycre-TT07).

The resulting plasmids are pDHB0006 to pDHB00029, as described in table below.

|  |  | Gene encoding exporter cloned into pCL1920-type plasmid | | | |
| --- | --- | --- | --- | --- | --- |
|  |  | yhjX | JEN1 | yhjE | mae1 |
| Backbone pCL1920-type plasmid | pCL1920 empty | pDHB0006 | pDHB0007 | pDHB0008 | pDHB0009 |
|  | pDHB0002 | pDHB0010 | pDHB0011 | pDHB0012 | pDHB0013 |
|  | pDHB0003 | pDHB0014 | pDHB0015 | pDHB0016 | pDHB0017 |
|  | pDHB0004 | pDHB0018 | pDHB0019 | pDHB0020 | pDHB0021 |
|  | pDHB0005 | pDHB0022 | pDHB0023 | pDHB0024 | pDHB0025 |
|  | pME101-thrA*1-PgapA-pycre-TT07 | pDHB0026 | pDHB0027 | pDHB0028 | pDHB0029 |

Theses plasmids were introduced separately in different E. coli MG1655-derived mutant strains optimized for 2,4-DHB production and in wild type MG1655.

A non-exclusive example of constructed strains is listed in Table 7.

TABLE 7

| Strain | Relevant genotype |
| --- | --- |
| Pathway 1 | |
| Strain 8 | MG1655 ΔxylAB ΔyjhH ΔyagE ΔyiaE ΔycdW ΔptsG Ptrc01/OP01/RBS120-pntAB DudhA DpfkA (pDHB00010) |
| Strain 9 | MG1655 ΔxylAB ΔyjhH ΔyagE ΔyiaE ΔycdW ΔptsG Ptrc01/OP01/RBS120-pntAB DudhA DpfkA (pDHB00011) |
| Strain 10 | MG1655 ΔxylAB ΔyjhH ΔyagE ΔyiaE ΔycdW ΔptsG Ptrc01/OP01/RBS120-pntAB DudhA DpfkA (pDHB00012) |
| Strain 11 | MG1655 ΔxylAB ΔyjhH ΔyagE ΔyiaE ΔycdW ΔptsG Ptrc01/OP01/RBS120-pntAB DudhA DpfkA (pDHB00013) |
| Strain 12 | MG1655 ΔxylAB ΔyjhH ΔyagE ΔyiaE ΔycdW ΔptsG Ptrc01/OP01/RBS120-pntAB DudhA DpfkA (pDHB0014) |
| Strain 13 | MG1655 ΔxylAB ΔyjhH ΔyagE ΔyiaE ΔycdW ΔptsG Ptrc01/OP01/RBS120-pntAB DudhA DpfkA (pDHB0015) |
| Strain 14 | MG1655 ΔxylAB ΔyjhH ΔyagE ΔyiaE ΔycdW ΔptsG Ptrc01/OP01/RBS120-pntAB DudhA DpfkA (pDHB0016) |
| Strain 15 | MG1655 ΔxylAB ΔyjhH ΔyagE ΔyiaE ΔycdW ΔptsG Ptrc01/OP01/RBS120-pntAB DudhA DpfkA (pDHB0017) |
| Strain 16 | MG1655 ΔxylAB ΔyjhH ΔyagE ΔyiaE ΔycdW ΔptsG Ptrc01/OP01/RBS120-pntAB DudhA DpfkA (pDHB00018) |
| Strain 17 | MG1655 ΔxylAB ΔyjhH ΔyagE ΔyiaE ΔycdW ΔptsG Ptrc01/OP01/RBS120-pntAB DudhA DpfkA (pDHB00019) |
| Strain 18 | MG1655 ΔxylAB ΔyjhH ΔyagE ΔyiaE ΔycdW ΔptsG Ptrc01/OP01/RBS120-pntAB DudhA DpfkA (pDHB00020) |
| Strain 19 | MG1655 ΔxylAB ΔyjhH ΔyagE ΔyiaE ΔycdW ΔptsG Ptrc01/OP01/RBS120-pntAB DudhA DpfkA (pDHB00021) |
| Strain 20 | MG1655 ΔxylAB ΔyjhH ΔyagE ΔyiaE ΔycdW ΔptsG Ptrc01/OP01/RBS120-pntAB DudhA DpfkA (pDHB0022) |
| Strain 21 | MG1655 ΔxylAB ΔyjhH ΔyagE ΔyiaE ΔycdW ΔptsG Ptrc01/OP01/RBS120-pntAB DudhA DpfkA (pDHB0023) |
| Strain 22 | MG1655 ΔxylAB ΔyjhH ΔyagE ΔyiaE ΔycdW ΔptsG Ptrc01/OP01/RBS120-pntAB DudhA DpfkA (pDHB0024) |
| Strain 23 | MG1655 ΔxylAB ΔyjhH ΔyagE ΔyiaE ΔycdW ΔptsG Ptrc01/OP01/RBS120-pntAB DudhA DpfkA (pDHB0025) |
| Pathway 2 | |
| Strain 24 | MG1655 ΔldhA ΔadhE Ptrc244*1/E01/RBS08-metA Ptrc244*1/E01/RBS08-thrBC ΔpykA ΔpykF ΔdgsA (pCC1BAC-Placlq-lacI-TT02-Ptrc01/OP01/RBS01*2-ptsG-TT07) (pEXT20-DHB) (pDHB0026) |
| Strain 25 | MG1655 ΔldhA ΔadhE Ptrc244*1/E01/RBS08-metA Ptrc244*1/E01/RBS08-thrBC ΔpykA ΔpykF ΔdgsA (pCC1BAC-Placlq-lacI-TT02-Ptrc01/OP01/RBS01*2-ptsG-TT07) (pEXT20-DHB) (pDHB0027) |
| Strain 26 | MG1655 ΔldhA ΔadhE Ptrc244*1/E01/RBS08-metA Ptrc244*1/E01/RBS08-thrBC ΔpykA ΔpykF ΔdgsA (pCC1BAC-Placlq-lacI-TT02-Ptrc01/OP01/RBS01*2-ptsG-TT07) (pEXT20-DHB) (pDHB0028) |

TABLE 7-continued

| Strain | Relevant genotype |
|---|---|
| Strain 27 | MG1655 ΔldhA ΔadhE Ptrc244*1/E01/RBS08-metA Ptrc244*1/E01/RBS08-thrBC ΔpykA ΔpykF ΔdgsA (pCC1BAC-Placlq-lacI-TT02-Ptrc01/OP01/RBS01*2-ptsG-TT07) (pEXT20-DHB) (pDHB0029) |

Pathway 3

| Strain 28 | MG1655 (pTAC-DHB) (pDHB0006) |
| Strain 29 | MG1655 (pTAC-DHB) (pDHB0007) |
| Strain 30 | MG1655 (pTAC-DHB) (pDHB0008) |

Pathway 4

| Strain 31 | MG1655 Δpta ΔiclR ΔaceB (pACT3-MCL-DHB) (pDHB0006) |
| Strain 32 | MG1655 Δpta ΔiclR ΔaceB (pACT3-MCL-DHB) (pDHB0007) |
| Strain 33 | MG1655 Δpta ΔiclR ΔaceB (pACT3-MCL-DHB) (pDHB0008) |
| Strain 34 | MG1655 Δpta ΔiclR ΔaceB (pACT3-MCL-DHB) (pDHB0009) |

MG1655

| Strain 35 | MG1655 (pDHB0006) |
| Strain 36 | MG1655 (pDHB0007) |
| Strain 37 | MG1655 (pDHB0008) |
| Strain 38 | MG1655 (pDHB0009) |

Example 3: Optimization of 2,4-DHB Production by Overproduction of 2.4-DHB Exporter Combined with Deletion of 2.4-DHB Importer in 2,4-DHB Producing Strains from 4 Different Metabolic Pathways in MG1655 E. coli—Construction of Strains 39 to 131

In order to avoid the re-import of 2,4-DHB and in consequence improved the production of 2,4-DHB, one of the following genes encoding for importers was deleted from the E. coli MG1655 chromosome using the homologous recombination strategy described by Datsenko & Wanner, 2000, and according to Protocol 1. The genes deleted are the genes encoding the alpha-ketoglutarate permease (kgtP gene of sequence SEQ ID NO:74), the L-lactate permease (lldP gene of sequence SEQ ID NO:76) and the glycolate permease (glcA gene of sequence SEQ ID NO:78). More precisely, to delete kgtP gene, a PCR product carrying the antibiotic resistance gene together with FRT sites surrounded by sequences homologous to up-stream and down-stream regions of kgtP gene, was generated with primers of SEQ ID NO:245 and SEQ ID NO:246 and introduced into E. coli MG1655 selected strain in which the pKD46 vector was previously transformed. To delete lldP gene, a PCR product carrying the antibiotic resistance gene together with FRT sites surrounded by sequences homologous to up-stream and downstream regions of lldP gene, was generated with primers of SEQ ID NO:247 and SEQ ID NO:248 and introduced into E. coli MG1655 selected strain in which the pKD46 vector was previously transformed. To delete glcA gene, a PCR product carrying the antibiotic resistance gene together with FRT sites surrounded by sequences homologous to up-stream and downstream regions of glcA gene, was generated with primers of SEQ ID NO:249 and SEQ ID NO:250 and introduced into E. coli MG1655 selected strain in which the pKD46 vector was previously transformed.

Each time an antibiotic resistance gene was chosen among kanamycin, chloramphenicol, gentamycin, tetracycline, blasticidin or spectinomycin. When necessary and before plasmid introducing, the antibiotic cassettes were removed from kgtP or lldP or glcA locus using the Flp recombinase as described by Datsenko & Wanner, 2000 (according to Protocol 1).

Each deletion was separately introduced in different E. coli MG1655-derived mutant strains optimized for 2,4-DHB production and in wild type MG1655. The resulting strains are listed in the table below.

A non-exclusive example of constructed strains is listed in Table 8.

TABLE 8

| | | Deleted gene encoding a 2,4-DHB importer | | |
|---|---|---|---|---|
| | | kgtP | lldP | glcA |
| Pathway 1 | | | | |
| Backbone 2,4-DHB producing strain | Strain 8 | Strain 39 | Strain 40 | Strain 41 |
| | Strain 9 | Strain 42 | Strain 43 | Strain 44 |
| | Strain 10 | Strain 45 | Strain 46 | Strain 47 |
| | Strain 11 | Strain 48 | Strain 49 | Strain 50 |
| | Strain 12 | Strain 51 | Strain 52 | Strain 53 |
| | Strain 13 | Strain 54 | Strain 55 | Strain 56 |
| | Strain 14 | Strain 57 | Strain 58 | Strain 59 |
| | Strain 15 | Strain 60 | Strain 61 | Strain 62 |
| | Strain 16 | Strain 63 | Strain 64 | Strain 65 |
| | Strain 17 | Strain 66 | Strain 67 | Strain 68 |
| | Strain 18 | Strain 69 | Strain 70 | Strain 71 |
| | Strain 19 | Strain 72 | Strain 73 | Strain 74 |
| | Strain 20 | Strain 75 | Strain 76 | Strain 77 |
| | Strain 21 | Strain 78 | Strain 79 | Strain 80 |
| | Strain 22 | Strain 81 | Strain 82 | Strain 83 |
| | Strain 23 | Strain 84 | Strain 85 | Strain 86 |
| Pathway 2 | | | | |
| | Strain 24 | Strain 87 | Strain 88 | Strain 89 |
| | Strain 25 | Strain 90 | Strain 91 | Strain 92 |
| | Strain 26 | Strain 93 | Strain 94 | Strain 95 |
| | Strain 27 | Strain 96 | Strain 97 | Strain 98 |
| Pathway 3 | | | | |
| | Strain 28 | Strain 99 | Strain 100 | Strain 101 |
| | Strain 29 | Strain 102 | Strain 103 | Strain 104 |
| | Strain 30 | Strain 105 | Strain 106 | Strain 107 |
| Pathway 4 | | | | |
| | Strain 31 | Strain 108 | Strain 109 | Strain 110 |
| | Strain 32 | Strain 111 | Strain 112 | Strain 113 |
| | Strain 33 | Strain 114 | Strain 115 | Strain 116 |
| | Strain 34 | Strain 117 | Strain 118 | Strain 119 |

TABLE 8-continued

| | Deleted gene encoding a 2,4-DHB importer | | | |
|---|---|---|---|---|
| | kgtP | lldP | glcA | |
| | MG1655 | | | |
| MG1655 strain | Strain 35 | Strain 120 | Strain 121 | Strain 122 |
| | Strain 36 | Strain 123 | Strain 124 | Strain 125 |
| | Strain 37 | Strain 126 | Strain 127 | Strain 128 |
| | Strain 38 | Strain 129 | Strain 130 | Strain 131 |

Example 4: Bacteria Growth and Production of 2,4-dihydroxy-butanoic Acid in Presence of High Amount of 2,4-DHB in Medium Broth Conditions of Cultivation for Strains Carrying Pathway 1:

Production strains were evaluated in 500 ml baffled Erlenmeyer flasks using modified M9 medium (Anderson, 1946) that was supplemented with 30 g/l MOPS, 20 g/L D-xylose and 10 g/l glucose and adjusted at pH 6,8. Spectinomycin was added at a concentration of 50 mg·L−1 when it was necessary in preculture and culture. A preculture was grown at 37° C. in LB medium (Sigma). After 24 hours of growth, it was used to inoculate a 50 mL culture of modified M9 medium to an $OD_{600}$ of about 0.2, at 30° C. and 200 rpm.

Conditions of Cultivation for Strains Carrying Pathways 2, 3 and 4:

Production strains were evaluated in 500 ml baffled Erlenmeyer flasks using modified M9 medium (Anderson, 1946) that was supplemented with 20 g·L−1 MOPS and 20 g·L−1 glucose and adjusted at pH 6,8. Spectinomycin was added at a concentration of 50 mg·L−1, ampicillin at 100 mg·L−1 and chloramphenicol at 25 mg·L−1 when it was necessary in preculture and culture. A preculture was grown at 37° C. in LB medium (Sigma). After 24 hours of growth, it was used to inoculate a 50 mL culture of modified M9 medium to an $OD_{600}$ of about 0.2, at 30° C. and 200 rpm. IPTG was added at a concentration comprise between 100 and 1000 μmol·L−1 according to the copy number of the plasmid used in the cell at the beginning of the culture or when the $OD_{600}$ of the growth cultures reached 1.

When sugars in the culture medium were exhausted, the culture was centrifuged and the broth analysed for 2,4-dihydroxy-butanoic acid by LC-MS/MS.

The 2,4-dihydroxy-butanoic acid titer was expressed as followed:

$$Titer_{DHB} = \frac{2,4\text{-dihydroxy-butanoic-acid (mg)}}{\text{volume }(L)}$$

The growth rate of each strain was also monitored as indicative of tolerance towards high 2,4-dihydroxy-butanoic concentrations in culture medium. In such case, strains were evaluated in 250 ml baffled Erlenmeyer flasks. A preculture was grown at 37° C. in LB medium (Sigma) and after 24 hours, it was used to inoculate to an $OD_{600}$ of about 0.2 a 25 mL culture of modified M9 medium, which was supplemented with 10 g/L of glucose (plus 10 g/L of xylose in case of strains containing pathway 1 (strains 1 to 4; strains 8 to 23 and strains 39 to 86)), at 30° C. and 200 rpm. A concentration of 10 g/L of 2,4-DHB (outsourcing from Sigma Aldrich) was added or not to the medium broth and after 24 hours of growth, the $OD_{600}$ was measured and calculated growth rate of each strain between the two conditions were compared.

TABLE 9

Impact of 10 g/L of 2,4-DHB in the medium on the growth rate of MG1655 modified to reduce the accumulation of 2,4-DHB inside the cells. Signs (−): means 5% slower growth in presence of 2,4-DHB compared to growth rate in absence of 2,4-DHB; (−−): means 10% slower growth; (=): means same growth rate (no impact of the DHB concentration in the medium); (+): means 5% faster growth and (++): means 10% faster growth in presence of 2,4-DHB.

| Strains | Impact of 10 g/L of 2,4-DHB on the growth rate of the modified strains |
|---|---|
| WT MG1655 | − |
| Strains with overexpression of a DHB efflux system | |
| Strain 35 | = |
| Strain 36 | = |
| Strain 37 | = |
| Strain 38 | = |
| Strains with overexpression of a DHB efflux system plus the deletion of a DHB uptake system | |
| Strain 120 | + |
| Strain 121 | + |
| Strain 122 | + |

As can be seen in table 9 above, the growth rate of the MG1655 in presence of 10 g/L of 2,4-DHB is restored upon the overexpression of genes encoding specific efflux system (strains 35 to 38) and even improved a little when both one uptake system is deleted and the efflux system overproduced (stains 120 to 122).

The combination of the two modifications to reduce the 2,4-DHB accumulation in the bacterium were tested for all the exporter systems with similar results as shown above (data not shown for strains 123 to 131).

TABLE 10

Impact of 10 g/L of 2,4-DHB in the medium on the growth rate of 2,4-DHB producing strains modified to reduce the accumulation of 2,4-DHB inside the cells. Signs (−): means 5% slower growth in presence of 2,4-DHB compared to growth rate in absence of 2,4-DHB; (−−): means 10% slower growth; (=): means same growth rate (no impact of the DHB concentration in the medium); (+): means 5% faster growth and (++): means 10% faster growth in presence of 2,4-DHB.

| Strains | Impact of 10 g/L of 2,4-DHB on the growth rate of the modified strains |
|---|---|
| Strain 5 (pathway 2) | −− |
| Strain 6 (pathway 3) | −− |
| Strains with overexpression of a DHB efflux system | |
| Strain 24 | = |
| Strain 25 | = |
| Strain 26 | = |
| Strain 27 | = |
| Strain 28 | = |
| Strain 29 | = |
| Strain 30 | = |
| Strains with overexpression of a DHB efflux system plus the deletion of a DHB uptake system | |
| Strain 87 | + |
| Strain 88 | + |
| Strain 89 | + |
| Strain 99 | + |
| Strain 100 | + |
| Strain 101 | + |

As can be seen in table 10 above, strains 5 and 6, modified with the pathway 2 or 3 for the production of 2,4-DHB are sensitive to high concentration of 2,4-DHB, since their growth rate is decreased in presence of 10 g/L of 2,4-DHB. Nevertheless, their respective growth rate can be restored upon the overexpression of genes encoding specific 2,4-DHB efflux system and even improved a little when both one uptake system is deleted and the efflux system overproduced. We found out that the modifications to reduce the accumulation of 2,4-DHB inside the cell improve the growth rate of the strains.

The combination of the two modifications to reduce the 2,4-DHB accumulation in the bacterium were tested for all the producing strains (pathways 1 and 4), with similar results as shown above (data not shown for strains 8 to 23 and 31 to 34; strains 39 to 86 and strains 108 to 119).

TABLE 11

2,4-dihydroxy-butanoic acid (DHB) concentration in the medium for each culture.

| Strains | 2,4-DHB concentration in fermentation cultures |
|---|---|
| Strain 5 (pathway 2) | 12 |
| Strain 6 (pathway 3) | 3 |
| Strains with overexpression of a DHB efflux system | |
| Strain 24 | 14 |
| Strain 25 | 13 |
| Strain 26 | 13 |
| Strain 27 | 14 |
| Strain 28 | 4 |
| Strain 29 | 3.5 |
| Strain 30 | 3.5 |
| Strains with overexpression of a DHB efflux system plus he deletion of a DHB uptake system | |
| Strain 87 | 15 |
| Strain 88 | 14 |
| Strain 89 | 14.5 |
| Strain 99 | 4.5 |
| Strain 100 | 4 |
| Strain 101 | 4.5 |

As can be seen in table 11 above, the production of 2,4-dihydroxy-butanoic acid (DHB) is improved either upon overexpression of DHB export system or by the combination of the overexpression of the efflux system and deletion of the uptake system, for each 2,4-DHB producer strain.

The improvement of the DHB production was observed for all the different backgrounds of producing strains (pathways 1, 2, 3 and 4) carrying at least one modification to reduce the accumulation of the 2,4-DHB in the cell.

The intracellular concentration of 2,4-DHB was measured for all the tested strains according to the following protocol.

samples were collected during exponential phase and stored on ice (No Quenching)

2 washing steps were performed at 4° C. with a physiological salt solution concentrated 3× to prevent leakage of metabolites we wash the cells with.

Some tests were performed to select the best solution between water, physiological water and concentrated physiological water 3×, 5× or 10×. Glutamate was used as reference (Bolten et al, 2007).

Cell pellets were recovered and either kept at −20° C. or extracted.

Extraction was done with hot ethanol in HEPES buffer

The quantification of 2,4-DHB was done by GCMS

The theoretical value used in calculations for the cytoplasmic volume of the cell is 2,3-2,5 mL/g of cell dry weight.

Results for strains were consistent with the respective mutations. In presence of the overexpression of the 2,4-DHB efflux system as well as for the combination of the overexpression of the export and attenuation of the 2,4-DHB uptake system, the intracellular concentration of the said compound is decreased compared to the non-modified microorganism.

REFERENCES

Altschul S, Gish W, Miller W, Myers E, Lipman D J, J. Mol. Biol, 1990, 215 (3): 403-410.
Anderson, Proc. Natl. Acad. Sci. USA., 1946, 32:120-128.
Bolten C J, Kiefer P, Letisse F, Portais J C, Wittmann C., Anal Chem., 2007, 79(10):3843-9.
Carrier T & Keasling J, Biotechnol Prog., 1999, 15(1): 58-64.
Cho Y H, Lee H D, Park H B., Ind. Eng. Chem. Res., 2012, 51:10207-10219.
Dassler et al., Mol Microbiol., 2000, 36(5):1101-12.
Datsenko K A & Wanner B L, Proc Natl Acad Sci USA., 2000, 97: 6640-6645.
Davis J J & Olsen G J., Mol. Biol. Evol., 2011, 28(1):211-221.
Deml L, Bojak A, Steck S, Graf M, Wild J, Schirmbeck R, Wolf H, Wagner R., 2011, J. Virol., 75(22): 10991-11001.
Dykxhoorn D M, St Pierre R, Linn T., Gene, 1996, 177(1-2):133-6.
Gao M T, Shimamura T, Ishida N, Nagamori E, Takahashi H, Umemoto S, Omasa T, Ohtake H, Enzyme Microb Tech, 2009, 44:350-354.
Graf M, Bojak A, Deml L, Bieler K, Wolf H, Wagner R., 2000, J. Virol., 74(22): 10/22-10826.
Harrington K J, Laughlin R B, Liang S. Proc Natl Acad Sci USA., 2001, 98(9):5019-24.
Hiller J, Franco-Lara E, Weuster-Botz D. Biotechnol Lett. 2007, 29(8):1169-78.
Husson S M & King J C., Ind. Eng. Chem. Res., 1999, 38:502-511.
Kiefer P, Nicolas C, Letisse F, Portais J C., Anal Biochem., 2007, 360:182-8.
Kim, J. H. et al., Appl. Microbiol. Biotechnol., 2010, 88, 1077-1085.
Kurihara S, Tsuboi Y, Oda S; Guk Kim H; Kumagai H; Suzuki H, J Bacteriol, 2009, 191(8), 2776-2782.
Kutukova E A, Livshits V A, Altman I P, Ptitsyn L R, Zyiatdinov M H, FEBS Lett., 2005, 579(21), 4629-4634.
Lee S, McCormick M, Lippard S, Cho U, Nature, 2013, 494: 380-384.
Lerner C. G. and Inouye M., Nucleic Acids Research, 1990, 18(15):4631.
Needleman and Wunsch, J. Mol. Biol., 1972, 48(3), 443-453.
Rao V V B, Kumar P S, Sailu C, Rao S R M, J. Applied Sci., 2014, 14(12):1289-1293.
Salis H, Methods Enzymol., 2011, 498:19-42.
Sambrook et al., Molecular cloning: A laboratory manual 4th edition, Cold Spring Harbor Laboratory Press—Cold Spring Harbor, N.Y., USA, 2012.
Schürgel K, Biotechnol Advances, 2000, 18:581-599.
Segel I H, Enzyme kinetics, 1993, John Wiley & Sons, pp. 44-54 and 100-112.
Van Kecke W, Kaur G, De Wever H., Biotechnol Advances, 2014, 32:1245-1255.
Zittrich and Krämer., J Bacteriol., 1994, 176(22):6892-9.

The invention claimed is:

1. An *Escherichia coli* microorganism genetically modified for producing 2,4-dihydroxybutyrate by fermentation, wherein said microorganism is genetically modified for reducing intracellular 2,4-dihydroxybutyrate accumulation, thereby optimizing 2,4-dihydroxybutyrate production, said genetic modification for reducing intracellular 2,4-dihydroxybutyrate accumulation comprising an overexpression of a gene encoding a monocarboxylate efflux system having the amino acid sequence of SEQ ID NO: 1 and, wherein the microorganism is genetically modified to convert at least one of the following metabolic intermediates into 2,4-dihydroxybutyrate:

1,2,4-butanetriol, wherein said genetic modification comprises:
overexpression of at least one gene encoding an oxidoreductase acting on the CH—OH group of donors (EC 1.1 enzyme) having the amino acid sequence of SEQ ID NO: 130 or SEQ ID NO: 135, and
overexpression of at least one gene encoding an oxidoreductase acting on the aldehyde or oxo group of donors (EC 1.2 enzyme) having the amino acid sequence of SEQ ID NO:140, SEQ ID NO: 148 or SEQ ID NO: 149;

(L)-malate, wherein said genetic modification comprises:
overexpression of at least one gene encoding a malate kinase having the amino acid sequence of SEQ ID NO: 198, thereby converting malate into 4-phospho-malate;
overexpression of at least one gene encoding a malate semialdehyde dehydrogenase having the amino acid sequence of SEQ ID NO: 199, thereby converting 4-phospho-malate into malate-4-semialdehyde; and
overexpression of at least one gene encoding a DHB dehydrogenase having the amino acid sequence SEQ ID NO: 200, thereby converting malate-4-semialdehyde into 2,4-dihydroxybutyrate;

(L) malyl-CoA, wherein said genetic modification comprises:
overexpression of at least one gene encoding a malyl-CoA reductase having the amino acid sequence of SEQ ID NO: 201, thereby converting malyl-CoA into malate-4-semialdehyde; and
overexpression of at least one gene encoding a DHB dehydrogenase, thereby converting malate-4-semialdehyde into 2,4-dihydroxybutyrate having the amino acid sequence of SEQ ID NO: 200; and (L)-homoserine, wherein said genetic modification comprises:
overexpression of at least one gene encoding a homoserine transaminase having the amino acid sequence of SEQ ID NO: 203, thereby converting (L)-homoserine into 2-oxo-4-hydroxybutyrate; and overexpression of at least one gene encoding a 2-oxo-4-hydroxybutyrate (OHB) reductase having the amino acid sequence of SEQ ID NO: 204, thereby converting 2-oxo-4-hydroxybutyrate (OHB) into 2,4-dihydroxybutyrate; and.

2. The microorganism according to claim 1, wherein said microorganism further comprises an overexpression of at least one gene encoding an efflux system selected from the group consisting of:

lactate efflux system having the amino acid sequence of SEQ ID NO:23, lactate efflux system having the amino acid sequence of SEQ ID NO:25, and a combination thereof.

3. A method for the production of 2,4-dihydroxybutyrate comprising:

a) culturing the *Escherichia coli* of claim 1 in a culture medium comprising a carbon source other than xylose, under fermentation conditions allowing conversion of said carbon source into 2,4-dihydroxybutyrate, and b) recovering the 2,4-dihydroxybutyrate from said culture medium.

4. The microorganism according to claim 1, wherein said microorganism is further genetically modified to reduce intracellular 2,4-dihydroxybutyrate accumulation by, attenuation of the expression or the deletion of at least one gene encoding an uptake transporter selected from the group consisting of:

alpha-ketoglutarate uptake transporters of amino acid sequence SEQ ID NO:73, lactate uptake transporters of amino acid sequence SEQ ID NO:75, glycolate uptake transporters of amino acid sequence SEQ ID NO:77, acetate uptake transporters of amino acid sequence SEQ ID NO:79 and SEQ ID NO:81, propionate uptake transporters of amino acid sequence SEQ ID NO:83, pantothenate uptake transporters of amino acid sequence SEQ ID NO:85, succinate and acetate uptake transporters of amino acid sequence SEQ ID NO:87, acetoacetate uptake transporters of amino acid sequence SEQ ID NO:89, gluconate uptake transporters of amino acid sequence SEQ ID NO:91, uptake transporters of amino acid sequence SEQ ID NO:93, and any combination thereof.

5. The microorganism according to claim 4, wherein said uptake transporter is selected from the group consisting of:

alpha-ketoglutarate uptake transporter having the amino acid sequence of SEQ ID NO:73, lactate uptake transporter having the amino acid sequence of SEQ ID NO:75, glycolate uptake transporter having the amino acid sequence of SEQ ID NO:77, and any combination thereof.

* * * * *

SEQUENCE LISTING

<160> NUMBER OF SEQ ID NOS: 250

<210> SEQ ID NO 1
<211> LENGTH: 402
<212> TYPE: PRT
<213> ORGANISM: Escherichia coli

<400> SEQUENCE: 1

```
Met Thr Pro Ser Asn Tyr Gln Arg Thr Arg Trp Leu Thr Leu Ile Gly
1               5                   10                  15

Thr Ile Ile Thr Gln Phe Ala Leu Gly Ser Val Tyr Thr Trp Ser Leu
            20                  25                  30

Phe Asn Gly Ala Leu Ser Ala Lys Leu Asp Ala Pro Val Ser Gln Val
        35                  40                  45

Ala Phe Ser Phe Gly Leu Leu Ser Leu Gly Leu Ala Ile Ser Ser Ser
    50                  55                  60

Val Ala Gly Lys Leu Gln Glu Arg Phe Gly Val Lys Arg Val Thr Met
65                  70                  75                  80

Ala Ser Gly Ile Leu Leu Gly Leu Gly Phe Phe Leu Thr Ala His Ser
                85                  90                  95

Asp Asn Leu Met Met Leu Trp Leu Ser Ala Gly Val Leu Val Gly Leu
            100                 105                 110

Ala Asp Gly Ala Gly Tyr Leu Leu Thr Leu Ser Asn Cys Val Lys Trp
        115                 120                 125

Phe Pro Glu Arg Lys Gly Leu Ile Ser Ala Phe Ala Ile Gly Ser Tyr
    130                 135                 140

Gly Leu Gly Ser Leu Gly Phe Lys Phe Ile Asp Thr Gln Leu Leu Glu
145                 150                 155                 160

Thr Val Gly Leu Glu Lys Thr Phe Val Ile Trp Gly Ala Ile Ala Leu
                165                 170                 175

Leu Met Ile Val Phe Gly Ala Thr Leu Met Lys Asp Ala Pro Lys Gln
            180                 185                 190

Glu Val Lys Thr Ser Asn Gly Val Val Glu Lys Asp Tyr Thr Leu Ala
        195                 200                 205

Glu Ser Met Arg Lys Pro Gln Tyr Trp Met Leu Ala Val Met Phe Leu
    210                 215                 220

Thr Ala Cys Met Ser Gly Leu Tyr Val Ile Gly Val Ala Lys Asp Ile
225                 230                 235                 240

Ala Gln Ser Leu Ala His Leu Asp Val Val Ser Ala Ala Asn Ala Val
                245                 250                 255

Thr Val Ile Ser Ile Ala Asn Leu Ser Gly Arg Leu Val Leu Gly Ile
            260                 265                 270

Leu Ser Asp Lys Ile Ala Arg Ile Arg Val Ile Thr Ile Gly Gln Val
        275                 280                 285

Ile Ser Leu Val Gly Met Ala Ala Leu Leu Phe Ala Pro Leu Asn Ala
    290                 295                 300

Val Thr Phe Phe Ala Ala Ile Ala Cys Val Ala Phe Asn Phe Gly Gly
305                 310                 315                 320

Thr Ile Thr Val Phe Pro Ser Leu Val Ser Glu Phe Gly Leu Asn
                325                 330                 335

Asn Leu Ala Lys Asn Tyr Gly Val Ile Tyr Leu Gly Phe Gly Ile Gly
            340                 345                 350

Ser Ile Cys Gly Ser Ile Ala Ser Leu Phe Gly Gly Phe Tyr Val
        355                 360                 365
```

```
Thr Phe Tyr Val Ile Phe Ala Leu Leu Ile Leu Ser Leu Ala Leu Ser
    370                 375                 380

Thr Thr Ile Arg Gln Pro Glu Gln Lys Met Leu Arg Glu Ala His Gly
385                 390                 395                 400

Ser Leu
```

<210> SEQ ID NO 2
<211> LENGTH: 1209
<212> TYPE: DNA
<213> ORGANISM: Escherichia coli

<400> SEQUENCE: 2

```
atgacacctt caaattatca gcgtacccgc tggctgacac tcatcggtac tatcattacc    60
cagtttgcgc tggggtcggt ttatacctgg agcctgttta atggcgcgct tccgccaag   120
ctggatgcgc cggtaagcca ggtcgctttc tctttcggct tgttaagtct ggggctggca   180
atttcgtctt ctgttgcggg caaattacag gaacgttttg cgttaaacg cgtcaccatg    240
gcttccggca ttttgctggg attaggcttc ttcctgacac gcattctga caacctgatg    300
atgctgtggt taagcgccgg tgtgctggtg gactggcag atggcgcggg ttatctgctg    360
acgctctcta actgtgtgaa gtggttcccg gagcgtaaag gtctgatctc cgcgttcgct   420
atcggttctt atggtctggg tagcctgggt ttcaaattta tcgacacgca gctgctggaa   480
acggtcggtc tggaaaaaac ctttgtgatt tggggagcga ttgcgctgtt gatgattgtt   540
ttcggcgcaa cgttaatgaa agacgcacca aaacaggaag tgaaaaccag caatggtgtg   600
gtggagaaag attacacgct ggcagagtcg atgcgtaaac cgcagtactg gatgttagcg   660
gtaatgttcc tgaccgcctg catgagcggc ctgtacgtga ttggggtagc gaaagatatc   720
gcccaaagtc tggcacacct gatgtggtt tccgcagcca atgcagtcac tgttatttcc   780
atcgccaacc tttcaggtcg tctggtgctg ggtattctgt ctgacaaaat cgcccgtatc   840
cgtgttatta ccattggtca ggtgatatcg ctggtgggta tggcggcccct gctgtttgca   900
ccattgaatg cagtgacgtt ctttgcagcg attgcctgcg tggcatttaa ctttggcggc   960
actattaccg tctttccgtc actggtcagt gagttctttg cctcaataa cctggcgaaa  1020
aactacggtg tgatttatct cggtttcggt atcggtagca tttgtggttc gattatcgcc  1080
tcactgtttg gcggcttcta tgtgaccttc tacgtgattt cgccctgct gattctgtca  1140
ttggcgcttt ctacgacgat tcgtcagcca gagcagaaaa tgttgcgtga ggcgcatggc  1200
tccctttaa                                                         1209
```

<210> SEQ ID NO 3
<211> LENGTH: 486
<212> TYPE: PRT
<213> ORGANISM: Saccharomyces cerevisiae

<400> SEQUENCE: 3

```
Met Pro Leu Ser Lys Val Glu His Tyr Leu Ser Tyr His Thr Arg Leu
1               5                   10                  15

Leu Leu Pro His Val Leu Ser Leu Gln Ser Ser His Arg Val Ala Tyr
            20                  25                  30

Ile Phe Ser Leu Leu Ser Ala Val Ser Thr Gly Phe Ile Thr Leu Ile
        35                  40                  45

Ser Leu Tyr Ser Gln Pro Trp Gln Lys His Leu Asn Tyr Ser Ser Trp
    50                  55                  60

Gln Ile Asn Thr Ile Ala Ser Met Thr Asn Leu Gly Met Tyr Leu Thr
```

```
                65                  70                  75                  80
        Pro Pro Ile Leu Gly Met Ile Ala Asp Ser His Gly Pro Ile Thr Leu
                            85                  90                  95
        Ser Leu Leu Ala Ile Ile Gly Phe Ile Pro Ser Tyr Ser Tyr Leu Ala
                           100                 105                 110
        Tyr Val Phe Asn His Pro Glu Leu Ser Leu Gly Gly Asn Gly Asp Ser
                           115                 120                 125
        Ser Phe Asn Leu Ser Ile Ile Cys Phe Val Phe Ile Gly Ile Ser Thr
                           130                 135                 140
        Ser Ala Leu Tyr Phe Ser Ala Leu Leu Thr Cys Thr Lys Leu Tyr Pro
        145                 150                 155                 160
        His Thr Lys Leu Leu Ser Ile Ser Leu Pro Thr Thr Cys Tyr Gly Ile
                           165                 170                 175
        Ser Ser Val Val Gly Ser Gln Leu Leu Arg Ile Lys Trp Phe Trp Ser
                           180                 185                 190
        Ser Asn Ala Ser Ser Ser Ser Asn Ser Asp Leu Asn Leu Gly Arg
                           195                 200                 205
        Val Phe Gln Thr Phe Ala Leu Val Tyr Val Ile Gly Leu Leu Ala
                           210                 215                 220
        Trp Ile Ala Thr Ser Val Val Ser Leu Leu His Phe Asn Glu Glu Gln
        225                 230                 235                 240
        Asp Asn Gln Lys Arg Leu Asp Asp Gln Thr Asp Val Glu Gln Ser Pro
                           245                 250                 255
        Leu Leu Glu Arg Ser Asn His Val Gln Glu Lys Phe Thr Gln Thr Met
                           260                 265                 270
        Leu Arg Ile Phe Ser Asp Pro Val Thr Tyr Ile Leu Ala Val Ser Ile
                           275                 280                 285
        Leu Leu Ser Leu Gly Pro Leu Glu Met Phe Ile Ala Asn Met Gly Ser
                           290                 295                 300
        Leu Thr Asn Leu Leu Val Gln Leu Asp Ala Pro Thr Leu Ser Thr Lys
        305                 310                 315                 320
        Leu Leu Ser Thr Tyr Ala Leu Ser Ser Thr Phe Thr Arg Leu Leu Thr
                           325                 330                 335
        Gly Ile Val Ala Asp Phe Phe Ala Lys Lys Ile Ser Ile Lys Trp
                           340                 345                 350
        Ile Leu Leu Thr Phe Leu Ser Leu Gly Val Cys Ala Gln Leu Phe Leu
                           355                 360                 365
        Leu Lys Met Thr Ser Ser Ala Ser Pro Trp Gly Leu Val Pro Thr Gly
                           370                 375                 380
        Ser Leu Val Gly Ile Val Tyr Gly Gly Leu Phe Thr Val Tyr Pro Thr
        385                 390                 395                 400
        Leu Val Leu Leu Val Trp Gly Glu Arg Ser Phe Gly Thr Val Tyr Gly
                           405                 410                 415
        Ser Leu Leu Ile Ala Pro Ala Ile Gly Ser Met Ile Phe Cys Met Leu
                           420                 425                 430
        Tyr Ala Lys Phe Tyr Asp Ser Arg Cys Met Ser Gly Gly Asp Leu
                           435                 440                 445
        Arg Asn Pro Ser Cys Ile Ser Ala Val Tyr Lys Tyr Ser Ser Ile Ala
        450                 455                 460
        Phe Val Val Ser Ala Val Leu Ser Ala Val Val Phe Trp Lys Leu Lys
        465                 470                 475                 480
        Ser Arg Lys Leu Arg Ile
                           485
```

<210> SEQ ID NO 4
<211> LENGTH: 1461
<212> TYPE: DNA
<213> ORGANISM: Saccharomyces cerevisiae

<400> SEQUENCE: 4

```
atgcctctat caaaggtgga gcactacctt tcataccata cgcgcttact cttacccat      60
gttttgtctc ttcagtcatc acatcgtgtt gcatacatct tttcgctatt atctgcggtg   120
tcaactggct tcattacttt gatatctctt tactctcaac cgtggcagaa acatttaaat   180
tattcctcat ggcaaatcaa caccatcgct agtatgacta atttggggat gtacttgacg   240
ccaccaatct tggggatgat cgctgattct catggcccca ttactttaag tcttttagcc   300
atcatagggt tcatacctag ctattcatat ctggcttacg ttttaatca tccggagtta    360
tctctcggag gaaatggtga ctcatcattc aatctatcca tcatttgttt cgttttcata   420
ggtatatcaa caagcgcttt atactttagc gctttactga catgcactaa gctatatcct   480
catacaaaac tactatccat tagcttacca acgacatgtt atggtatttc ttctgtagtc   540
ggttctcaac tgctaagaat caatggttc tggtcctcta acgcaagttc ttcctcgtcc    600
aatagtgact taaacctggg aagagtattc caaacatttg ccctcgttta tgtcgttatt   660
gggctacttg catggatagc caccagcgtg gtatacacttt tgcattttaa tgaagagcaa   720
gacaaccaaa aacggctgga tgatcaaact gatgtggaac aatcaccgct gttagaacga   780
agtaatcatg ttcaagaaaa gtttacgcag acgatgctaa ggatctttag tgatcctgtg   840
acatatatcc tagcggtatc aattttgtta tcacttgggc ccctcgagat gtttattgcc   900
aatatgggat cactgactaa cctgctagtc caattagatg cgccaacctt atctacaaag   960
ttgttatcca catcgcgct atcttccact tttacgagat tgctcacagg catagtggca   1020
gacttcttcg ccaagaaaaa aatatcaatt aaatggatcc tgttgacttt cctttcatta  1080
ggggtatgtg cacaactgtt tttattgaaa atgacctctt cagcgtcacc ctggggggcta 1140
gtacctacag gatcattggt tggaattgta tacggtggac ttttcactgt ttatccgacg  1200
ctggtcctgt tagtatgggg cgaacgctca ttcgggactg tttacggtag cttactaatt  1260
gcacctgcta taggttctat gatatttgc atgttgtatg ccaaatttta cgattctcgc   1320
tgtatgagtg gcggaggaga tctgcgaaat ccgtcctgta tttcggctgt ctacaagtac  1380
agcagtatcg cattcgttgt atccgctgtt ctttcagctg tagtattttg gaaattaaaa  1440
agtagaaaac tcagaattta a                                             1461
```

<210> SEQ ID NO 5
<211> LENGTH: 473
<212> TYPE: PRT
<213> ORGANISM: Saccharomyces cerevisiae

<400> SEQUENCE: 5

```
Met Ser Glu Glu Arg His Glu Asp His His Arg Asp Val Glu Asn Lys
 1               5                  10                  15

Leu Asn Leu Asn Gly Lys Asp Asp Ile Asn Gly Asn Thr Ser Ile Ser
            20                  25                  30

Ile Glu Val Pro Asp Gly Gly Tyr Gly Trp Phe Ile Leu Leu Ala Phe
        35                  40                  45

Ile Leu Tyr Asn Phe Ser Thr Trp Gly Ala Asn Ser Gly Tyr Ala Ile
    50                  55                  60
```

```
Tyr Leu Ala His Tyr Leu Glu Asn Asn Thr Phe Ala Gly Gly Ser Lys
 65                  70                  75                  80

Leu Asp Tyr Ala Ser Ile Gly Gly Leu Ala Phe Ser Cys Gly Leu Phe
                 85                  90                  95

Phe Ala Pro Val Ile Thr Trp Leu Tyr His Ile Phe Ser Ile Gln Phe
            100                 105                 110

Ile Ile Gly Leu Gly Ile Leu Phe Gln Gly Ala Ala Leu Leu Leu Ala
        115                 120                 125

Ala Phe Ser Val Thr Leu Trp Glu Ile Tyr Leu Thr Gln Gly Val Leu
    130                 135                 140

Ile Gly Phe Gly Leu Ala Phe Ile Phe Ile Pro Ser Val Thr Leu Ile
145                 150                 155                 160

Pro Leu Trp Phe Arg Asn Lys Arg Ser Leu Ala Ser Gly Ile Gly Thr
                165                 170                 175

Ala Gly Ser Gly Leu Gly Gly Ile Val Phe Asn Leu Gly Met Gln Ser
            180                 185                 190

Ile Leu Gln Lys Arg Gly Val Lys Trp Ala Leu Ile Ala Gln Cys Ile
        195                 200                 205

Ile Cys Thr Ser Leu Ser Thr Ile Ala Leu Met Leu Thr Arg Thr Thr
    210                 215                 220

His Gln Gly Leu Arg Gln His Lys Arg Ser Tyr Lys Phe Glu Leu Leu
225                 230                 235                 240

Asp Tyr Asp Val Leu Ser Asn Phe Ala Val Trp Leu Leu Phe Gly Phe
                245                 250                 255

Val Ser Phe Ala Met Leu Gly Tyr Val Val Leu Leu Tyr Ser Leu Ser
            260                 265                 270

Asp Phe Thr Val Ser Leu Gly Tyr Thr Ser Lys Gln Gly Ser Tyr Val
        275                 280                 285

Ser Cys Met Val Ser Val Gly Ser Leu Leu Gly Arg Pro Ile Val Gly
    290                 295                 300

His Ile Ala Asp Lys Tyr Gly Ser Leu Thr Val Gly Met Ile Leu His
305                 310                 315                 320

Leu Val Met Ala Ile Leu Cys Trp Ala Met Trp Ile Pro Cys Lys Asn
                325                 330                 335

Leu Ala Thr Ala Ile Ala Phe Gly Leu Leu Val Gly Ser Ile Met Gly
            340                 345                 350

Thr Ile Trp Pro Thr Ile Ala Ser Ile Val Thr Arg Ile Val Gly Leu
        355                 360                 365

Gln Lys Leu Pro Gly Thr Phe Gly Ser Thr Trp Ile Phe Met Ala Ala
    370                 375                 380

Phe Ala Leu Val Ala Pro Ile Ile Gly Leu Glu Leu Arg Ser Thr Asp
385                 390                 395                 400

Thr Asn Gly Asn Asp Tyr Tyr Arg Thr Ala Ile Phe Val Gly Phe Ala
                405                 410                 415

Tyr Phe Gly Val Ser Leu Cys Gln Trp Leu Leu Arg Gly Phe Ile Ile
            420                 425                 430

Ala Arg Asp Glu Ile Ala Val Arg Glu Ala Tyr Ser Ala Asp Gln Asn
        435                 440                 445

Glu Leu His Leu Asn Val Lys Leu Ser His Met Ser Lys Cys Leu Phe
    450                 455                 460

Arg Tyr Lys Gln Leu Pro Arg Arg Val
465                 470
```

<210> SEQ ID NO 6
<211> LENGTH: 1422
<212> TYPE: DNA
<213> ORGANISM: Saccharomyces cerevisiae

<400> SEQUENCE: 6

```
atgtccgaag aacggcatga agatcatcat agggatgttg aaaataaatt gaatttaaat      60
ggtaaagacg atattaacgg gaatacctca atctcgatcg aggtgcctga tggaggatat     120
gggtggttta ttcttcttgc ttttattctg tacaactttt ctacttgggg ggcaaattct     180
ggttatgcta tttatttagc gcattattta gagaataata cttttgctgg tgggagtaaa     240
ttagactatg cttctatagg tgggttagca ttcagttgtg acttttttt tgccccagtt     300
ataacatggc tttatcatat attttcaatt caattcatta taggcttagg gatactgttt     360
caagggcag cgctactgct tgcagctttt tctgtcacac tctgggaaat ttatctcacg     420
caaggcgttt taattggatt cggtttagca tttattttca tacccagtgt cacactcatc     480
ccactatggt tcagaaataa aagatcttta gcctctggta taggaactgc tggaagcggg     540
ttaggtggta ttgtctttaa cttgggaatg caaagtattc tacaaaagag gggcgttaaa     600
tgggcgctca ttgctcagtg cataaatagc acatcactta gcaccattgc gcttatgttg     660
accagaacaa cacatcaagg cctacgtcaa cataagagat cttacaaatt tgaattgcta     720
gattatgatg tgcttttcaaa tttcgcggtc tggttacttt ttggatttgt atcatttgct     780
atgttaggat atgttgtcct tttgtattcc ttgtctgatt ttaccgttag tttaggttat     840
actagtaagc aaggctcata cgtatcgtgc atggtgagtg tcggctctct gctgggacga     900
ccaattgtgg gtcacattgc tgataaatat ggatcactaa cagttggcat gatattgcac     960
cttgtcatgg ccatccttg ttgggccatg tggatacctt gtaaaaattt ggccactgcg    1020
atagcttttg gattattggt tggttctatt atgggaacaa tttggccaac aattgcttca    1080
attgttacac gcattgttgg tcttcaaaag cttcctggta cctttggtag tacctggatt    1140
tttatggcgg cttttgcctt agttgccccc ataatcggtc tggaacttcg ttcaactgat    1200
acgaatggaa acgattatta tcgtacagca atattcgtgg ttttgcgta ctttggtgtt    1260
agtttatgcc aatggctatt gagagggttt ataatagctc gagatgagat tgctgtgcgt    1320
gaagcctatt cagctgacca aaatgaattg catttaaacg ttaagttatc acatatgagt    1380
aaatgtcttt ttcgttataa acaattacct aggagagtct aa                      1422
```

<210> SEQ ID NO 7
<211> LENGTH: 673
<212> TYPE: PRT
<213> ORGANISM: Saccharomyces cerevisiae

<400> SEQUENCE: 7

```
Met Ser Thr His Ser Asn Asp Tyr Phe Ser Ala Ser Ser Gly Met Val
1               5                   10                  15

Ser Glu Thr Ser Ser Glu Val Ser Ile Asn Ser Ser Gln Pro Val
            20                  25                  30

Ser Phe Ser Lys Ala Ser Ile Ala Ala Pro Val Pro Cys Ser Asp Leu
        35                  40                  45

His Ser Thr Lys Ser Asn Asp Ala Ser Arg Lys Leu Ser Ile Ser Arg
    50                  55                  60

Thr Leu Thr Asn Arg Leu Asn Asp Ile Lys Lys Ala Val Asp Asp Asp
65                  70                  75                  80

Asn Leu Gln Thr Glu Glu Asn Ser Ala Asp Val Asn Lys Ile Leu Glu
```

```
                     85                  90                  95
Ser Arg Phe Asp Val Ala Asp Ala Ile Arg Leu Gln His Asn Glu Ser
                    100                 105                 110

Val Gln Ser Lys Leu Asn Ile Pro Val Thr His Thr Thr Ala Gly
                115                 120                 125

Ala Ser Leu Ser Ala Pro Ser Ser Ala Phe Ser Ala Ser Ile
130                 135                 140

Gln Asn Asp Thr Thr Glu His Lys Ala Ser Met Asp Ser Lys Leu Met
145                 150                 155                 160

Arg Asn Arg Leu Tyr Pro Ala Ser Thr Lys His Ser Gly Lys Asp Leu
                165                 170                 175

Glu Ala Gln Gly Ile Thr Glu Phe Glu Pro Asp Glu Pro Thr Val Lys
                180                 185                 190

Lys Val Phe Thr Asn Lys Ser Thr Gly Gln Leu Glu Leu Pro Pro Asp
                195                 200                 205

Gly Gly Tyr Gly Trp Val Val Thr Phe Cys Val Phe Leu Thr Met Phe
                210                 215                 220

Ser Thr Trp Gly Cys Asn Ala Ser Phe Gly Val Asp Leu Ala Tyr Tyr
225                 230                 235                 240

Leu Asn His Asp Thr Tyr Pro Gly Ala Ser Lys Tyr Asp Tyr Ala Leu
                245                 250                 255

Ile Ala Gly Leu Thr Val Phe Leu Gly Gln Leu Leu Ser Pro Leu Val
                260                 265                 270

Met Ala Leu Met Arg Ile Ile Gly Leu Arg Thr Thr Met Leu Phe Gly
                275                 280                 285

Asp Ala Val Met Leu Ala Ala Tyr Leu Leu Ala Ser Phe Thr Thr Lys
290                 295                 300

Leu Trp Gln Leu Tyr Val Thr Gln Gly Phe Met Val Gly Cys Ser Ile
305                 310                 315                 320

Ser Leu Ile Phe Val Pro Ala Thr Thr Val Leu Pro Gly Trp Phe Leu
                325                 330                 335

Lys Lys Arg Ala Val Ala Met Gly Val Ser Leu Leu Gly Thr Gly Ala
                340                 345                 350

Gly Gly Val Val Tyr Gly Leu Ala Thr Asn Lys Met Leu Ser Asp Phe
                355                 360                 365

Gly Asn Thr Arg Trp Cys Leu Arg Ile Ile Gly Ile Ser Cys Ser Ile
                370                 375                 380

Ser Val Leu Val Ala Ile Ala Leu Leu Lys Glu Arg Asn Pro Thr Pro
385                 390                 395                 400

Ala Ile Gly Leu Lys Ser Pro Arg Ala Met Phe Glu Gln Leu Lys Ala
                405                 410                 415

Met Phe Ser Leu Lys Val Ile Thr Lys Pro Phe Val Val Leu Ile Ala
                420                 425                 430

Leu Trp Phe Met Phe Ala Leu Phe Ala Tyr Asn Met Met Val Phe Thr
                435                 440                 445

Leu Ser Ser Tyr Ala Ile Ser Lys Gly Leu Ser Ser His Asp Ala Ser
450                 455                 460

Thr Leu Thr Ala Ile Leu Asn Gly Ser Gln Ser Ile Gly Arg Pro Leu
465                 470                 475                 480

Met Gly Leu Ala Gly Asp Lys Phe Gly Arg Ala Asn Val Thr Ile Val
                485                 490                 495

Leu Thr Thr Leu Leu Thr Ile Tyr Met Phe Ala Phe Trp Ile Pro Ala
                500                 505                 510
```

His Thr Phe Val Gln Leu Ile Phe Phe Ser Ile Leu Val Gly Ser Cys
            515                 520                 525

Val Gly Val Ala Asn Val Met Asn Thr Val Leu Ile Ala Asp Met Val
    530                 535                 540

Lys Pro Glu Glu Phe Leu Pro Ala Trp Ala Phe Val Asn Tyr Cys Gly
545                 550                 555                 560

Ala Pro Phe Leu Leu Val Cys Glu Val Ile Ala Gln Ala Leu Thr Val
                565                 570                 575

Glu Lys Asp Lys Ser Asn Pro Tyr Leu His Ala Gln Ile Phe Cys Gly
            580                 585                 590

Cys Cys Phe Ile Ala Ala Leu Ile Leu Ile Ser Ile Leu Arg Glu Tyr
        595                 600                 605

Ser Ile Arg Met Lys Leu Thr Glu Arg Gln Ala Met Thr Asn Glu Lys
        610                 615                 620

Leu Lys Glu Trp Lys Ala Ser Glu Tyr Asp Thr Asp Ser Ala Asp Glu
625                 630                 635                 640

Asp Trp Gly Lys Leu Lys Glu Arg Lys Thr Lys Tyr Asp Leu Leu Leu
                645                 650                 655

Gly Pro Gly Ile Lys Lys Tyr Phe Leu Arg Met Val Tyr Pro Met Lys
            660                 665                 670

Val

<210> SEQ ID NO 8
<211> LENGTH: 2022
<212> TYPE: DNA
<213> ORGANISM: Saccharomyces cerevisiae

<400> SEQUENCE: 8
atgtcaacgc actcaaacga ctactttct gcttcttccg gaatggtctc tgagacatcg      60
tccgaggttt cttcgataaa ctcttcacag cctgtatcat tctctaaggc ttctattgct     120
gctccggttc catgctctga tctacacagc accaagtcga acgatgcatc gagaaaattg     180
tctattagta ggacgttaac taatcggctc aacgacatta aaaaggctgt cgatgacgac     240
aacttgcaga cggaagaaaa ttccgcagac gttaataaaa tattagaatc tagatttgac     300
gtggccgatg ccattaggct acagcacaat gagtcagtcc agtcaaagtt aaacatccca     360
gtcacacaca ccacgactgc aggcgcctcg ttgtcggcac catcttcctc tgcttttctct     420 gcttcttcta ttcaaaatga tactacagaa cataaagctt ccatggactc caaactcatg     480
aggaatagac tatatccggc ttccacgaaa cactccggta aggatcttga gcccaagga     540 ataaccgaat cgagcctga tgaaccgact gtaaaaaaag tattcaccaa caagtctacc     600
gggcagctgg aactgccccc cgacggtggt tatggctggg tcgtgacatt ctgtgtgttc     660
ttgaccatgt tttccacgtg gggctgcaac gcatccttcg gtgtcgacct tgcctactac     720
ttaaaccatg atacttaccc tggtgcttcg aagtacgatt atgccttaat tgctggccta     780
actgtctttc tcggtcaact cttatccccc cttgtgatgg cactgatgag ataaattggt     840
ctgcggacca ccatgctttt tggtgatgct gtaatgcttg ccgcatatct cttggcctcc     900
tttactacca agttatggca attgtatgtc acccaaggtt ttatggtcgg ttgttcaata     960
tcactgattt tcgttccagc aacaaccgtc ttaccaggat ggttcttgaa aaaaagagct    1020
gtcgcaatgg gtgtctcatt attgggtacc ggtgctggtg gtgtcgttta cggtttggct    1080
acaaacaaaa tgctttctga ctttggaaat acccggtggt gccttcgtat cataggcata    1140

-continued

| | |
|---|---|
| tcgtgtagca taagtgttct agttgctatt gcgctcttaa aagaaagaaa ccctacacct | 1200 |
| gccataggat tgaaatcgcc tcgggccatg tttgaacagc tcaaagcaat gttttcatta | 1260 |
| aaggttataa ctaagccatt tgtggtactt attgcattat ggttcatgtt cgcattattt | 1320 |
| gcctacaata tgatggtttt tactttatct tcatacgcaa tctcgaaagg attatcatcg | 1380 |
| cacgacgctt ccacattgac tgccattttg aacggctcgc aatccatcgg aagacctctg | 1440 |
| atgggtttag cgggagataa gtttggtagg caaacgtaa cgatcgtatt aaccactttg | 1500 |
| ttaacaatat atatgtttgc gttctggatc cccgctcata cgtttgttca actcatcttt | 1560 |
| ttttcaattc tagttggctc atgcgttggt gtcgccaacg tcatgaatac cgttctgatt | 1620 |
| gccgatatgg ttaaaccaga agagtttttg cccgcttggg ccttcgtcaa ctactgtggt | 1680 |
| gcgcctttct tattggtttg tgaggtgatt gcccaggcat tgacggtgga gaaagataag | 1740 |
| agcaatcctt acttacatgc acaaattttt tgcggttgct gctttattgc cgcactaatt | 1800 |
| ttaatttcta tccttcgtga atattctatc aggatgaaat taacggaaag acaagctatg | 1860 |
| acaaacgaga agttaaaaga atggaaggca agcgaatacg ataccgattc tgccgatgaa | 1920 |
| gattggggta aattaaaaga aagaaagact aaatatgacc ttcttttagg tccgggcatt | 1980 |
| aaaaaatact tcctaagaat ggtatatcca atgaaggtct ag | 2022 |

<210> SEQ ID NO 9
<211> LENGTH: 521
<212> TYPE: PRT
<213> ORGANISM: Saccharomyces cerevisiae

<400> SEQUENCE: 9

Met Ser Ser Asp Ser Leu Thr Pro Lys Asp Thr Ile Val Pro Glu Glu
1               5                   10                  15

Gln Thr Asn Gln Leu Arg Gln Pro Asp Leu Asp Glu Asp Ser Ile His
            20                  25                  30

Tyr Asp Pro Glu Ala Asp Asp Leu Glu Ser Leu Glu Thr Thr Ala Ser
        35                  40                  45

Tyr Ala Ser Thr Ser Val Ser Ala Lys Val Tyr Thr Lys Lys Glu Val
    50                  55                  60

Asn Lys Gly Thr Asp Ile Glu Ser Gln Pro His Trp Gly Glu Asn Thr
65                  70                  75                  80

Ser Ser Thr His Asp Ser Asp Lys Glu Glu Asp Ser Asn Glu Glu Ile
                85                  90                  95

Glu Ser Phe Pro Glu Gly Gly Phe Lys Ala Trp Val Val Thr Phe Gly
            100                 105                 110

Cys Phe Leu Gly Leu Ile Ala Cys Phe Gly Leu Leu Asn Ser Thr Gly
        115                 120                 125

Val Ile Glu Ser His Leu Gln Asp Asn Gln Leu Ser Glu Ser Val
    130                 135                 140

Ser Thr Ile Gly Trp Leu Phe Ser Leu Phe Leu Phe Val Cys Ser Ala
145                 150                 155                 160

Ser Cys Ile Ile Ser Gly Thr Tyr Phe Asp Arg Asn Gly Phe Arg Thr
                165                 170                 175

Ile Met Ile Val Gly Thr Val Phe His Val Ala Gly Leu Phe Ala Thr
            180                 185                 190

Ala Asn Ser Thr Lys Tyr Trp His Phe Ile Leu Ser Phe Ala Ile Val
        195                 200                 205

Cys Gly Phe Gly Asn Gly Ile Val Leu Ser Pro Leu Val Ser Val Pro
    210                 215                 220

```
Ala His Tyr Phe Phe Lys Arg Arg Gly Thr Ala Leu Ala Met Ala Thr
225                 230                 235                 240

Ile Gly Gly Ser Val Gly Val Val Phe Pro Ile Met Leu Arg Ser
            245                 250                 255

Phe Phe Ser Met Lys Ser Asp Thr Asp Pro Thr Tyr Gly Phe Val Trp
        260                 265                 270

Gly Ile Arg Thr Leu Gly Phe Leu Asp Leu Ala Leu Leu Thr Leu Ser
    275                 280                 285

Ile Ile Leu Val Lys Glu Arg Leu Pro His Val Ile Glu Asn Ser Lys
290                 295                 300

Asp Gly Glu Ser Arg Trp Arg Tyr Ile Leu Arg Val Tyr Ile Leu Gln
305                 310                 315                 320

Cys Phe Asp Ala Lys Ala Phe Leu Asp Met Lys Tyr Leu Phe Cys Val
                325                 330                 335

Leu Gly Thr Val Phe Ser Glu Leu Ser Ile Asn Ser Ala Leu Thr Tyr
            340                 345                 350

Tyr Gly Ser Tyr Ala Thr Ser His Gly Ile Ser Ala Asn Asp Ala Tyr
        355                 360                 365

Thr Leu Ile Met Ile Ile Asn Val Cys Gly Ile Pro Gly Arg Trp Val
370                 375                 380

Pro Gly Tyr Leu Ser Asp Lys Phe Gly Arg Phe Asn Val Ala Ile Ala
385                 390                 395                 400

Thr Leu Leu Thr Leu Phe Ile Val Met Phe Val Gly Trp Leu Pro Phe
                405                 410                 415

Gly Thr Asn Leu Thr Asn Met Tyr Val Ile Ser Ala Leu Tyr Gly Phe
            420                 425                 430

Cys Ser Gly Ser Val Phe Ser Leu Leu Pro Val Cys Cys Gly Gln Ile
        435                 440                 445

Ser Lys Thr Glu Glu Phe Gly Lys Arg Tyr Ser Thr Met Tyr Phe Val
450                 455                 460

Val Gly Phe Gly Thr Leu Val Gly Ile Pro Ile Thr Gly Ala Ile Ile
465                 470                 475                 480

Ser Ile Lys Thr Thr Ala Asp Tyr Gln His Tyr Ile Ile Phe Cys Gly
                485                 490                 495

Leu Ala Thr Phe Val Ser Ala Val Cys Tyr Ile Ile Ser Arg Ala Tyr
            500                 505                 510

Cys Val Gly Phe Lys Trp Val Arg Phe
        515                 520

<210> SEQ ID NO 10
<211> LENGTH: 1566
<212> TYPE: DNA
<213> ORGANISM: Saccharomyces cerevisiae

<400> SEQUENCE: 10
atgagctcag acagtttaac gcctaaagac actatagttc agaagaaca aaccaaccaa      60 ctgcggcaac ctgatttaga tgaggatagc atacattatg atccagaagc tgatgattta     120
gagtcattag agactactgc ctcttacgcg tcaacgtcgg tgtcggcaaa ggtgtatacc     180
aagaaggaag taaataaagg aactgacatt gaaagccaac acattggggt gaaaataccc    240
tcgagcacgc acgacagtga caagaagaa gattccaatg aagaaattga aagcttcccg     300
gagggtggat caaggcttg gttgtgaca ttttggttgct tcttgggtct aattgcatgc    360
tttggtttat taaactcaac gggggtcata gaaagtcatc tacaggacaa tcaattatcc   420
```

```
agtgaaagtg tttctaccat tggttggctg ttttctttgt ttcttttttgt ttgctctgcc    480 tcatgtatca ttagtggtac ttactttgat agaaatggat ttaggacaat tatgattgtg    540
ggcacggttt ttcatgtagc cggtctgttc gctaccgcca actctactaa atattggcac    600
ttcatactgt cctttgccat tgtctgcggg ttcggtaatg gtattgtact gagtccccta    660
gtaagtgttc ccgcccacta tttttttaag agacgtggta ctgcattggc aatggccact    720
attggtggta gtgtgggtgg cgtcgttttc ccaattatgt tgcgtagttt cttctctatg    780
aagtcagaca ctgatccaac ttatggattt gtttggggca ttagaacttt aggatttta    840 gatttggctt tgctaactct gtcaatcatt ttagtcaaag agaggttacc acatgttatc    900
gaaaattcca agatggtga gtcacgttgg agatacatac tcagagttta tattctgcaa    960
tgttttgatg cgaaggcttt cctggatatg aaatatcttt tttgtgtcct gggaacggta    1020
tttagtgagt tatccattaa ttcagctctt acttattatg gatcatacgc caccagccat    1080
ggaatttctg ctaatgacgc ctacaccttg attatgatta taaatgtctg cggcataccc    1140
gggagatggg ttcctggcta tttgagcgat aagttcggta ggtttaacgt cgcaattgca    1200
actctactca ctctatttat cgtcatgttt gttggttggt taccatttgg taccaatttg    1260
acaaatatgt acgttattag tgccctatat ggattttgtt ctggaagcgt tttctcctta    1320
cttcctgttt gctgtggcca gatatctaaa acggaagagt tcgtaaacg ttactctaca    1380 atgtacttcg ttgtcggttt cggtacttta gtcggcattc cgataacagg tgccattatc    1440
tctatcaaga caacggccga ttaccaacac tatattattt tttgcggttt ggcaactttt    1500
gtaagcgctg tttgctacat aatttcgaga gcatactgtg ttggcttcaa gtgggtcaga    1560
ttttaa                                                              1566
```

<210> SEQ ID NO 11
<211> LENGTH: 373
<212> TYPE: PRT
<213> ORGANISM: Saccharomyces cerevisiae

<400> SEQUENCE: 11

```
Met Thr Gln Thr Asp Asn Pro Val Pro Asn Cys Gly Leu Leu Pro Glu
1               5                   10                  15

Gln Gln Tyr Cys Ser Ala Asp His Glu Glu Pro Leu Leu Leu His Glu
            20                  25                  30

Glu Gln Leu Ile Phe Pro Asp His Ser Ser Gln Leu Ser Ser Ala Asp
        35                  40                  45

Ile Ile Glu Pro Ile Lys Met Asn Ser Ser Thr Glu Ser Ile Ile Gly
    50                  55                  60

Thr Thr Leu Arg Lys Lys Trp Val Pro Leu Ser Ser Thr Gln Ile Thr
65                  70                  75                  80

Ala Leu Ser Gly Ala Phe Ala Gly Phe Leu Ser Gly Val Ala Val Cys
                85                  90                  95

Pro Leu Asp Val Ala Lys Thr Arg Leu Gln Ala Gln Gly Leu Gln Thr
            100                 105                 110

Arg Phe Glu Asn Pro Tyr Tyr Arg Gly Ile Met Gly Thr Leu Ser Thr
        115                 120                 125

Ile Val Arg Asp Glu Gly Pro Arg Gly Leu Tyr Lys Gly Leu Val Pro
    130                 135                 140

Ile Val Leu Gly Tyr Phe Pro Thr Trp Met Ile Tyr Phe Ser Val Tyr
145                 150                 155                 160
```

-continued

```
Glu Phe Ser Lys Lys Phe Phe His Gly Ile Phe Pro Gln Phe Asp Phe
                165                 170                 175

Val Ala Gln Ser Cys Ala Ala Ile Thr Ala Gly Ala Ala Ser Thr Thr
            180                 185                 190

Leu Thr Asn Pro Ile Trp Val Val Lys Thr Arg Leu Met Leu Gln Ser
        195                 200                 205

Asn Leu Gly Glu His Pro Thr His Tyr Lys Gly Thr Phe Asp Ala Phe
    210                 215                 220

Arg Lys Leu Phe Tyr Gln Glu Gly Phe Lys Ala Leu Tyr Ala Gly Leu
225                 230                 235                 240

Val Pro Ser Leu Leu Gly Leu Phe His Val Ala Ile His Phe Pro Ile
                245                 250                 255

Tyr Glu Asp Leu Lys Val Arg Phe His Cys Tyr Ser Arg Glu Asn Asn
            260                 265                 270

Thr Asn Ser Ile Asn Leu Gln Arg Leu Ile Met Ala Ser Ser Val Ser
        275                 280                 285

Lys Met Ile Ala Ser Ala Val Thr Tyr Pro His Glu Ile Leu Arg Thr
    290                 295                 300

Arg Met Gln Leu Lys Ser Asp Ile Pro Asp Ser Ile Gln Arg Arg Leu
305                 310                 315                 320

Phe Pro Leu Ile Lys Ala Thr Tyr Ala Gln Glu Gly Leu Lys Gly Phe
                325                 330                 335

Tyr Ser Gly Phe Thr Thr Asn Leu Val Arg Thr Ile Pro Ala Ser Ala
            340                 345                 350

Ile Thr Leu Val Ser Phe Glu Tyr Phe Arg Asn Arg Leu Glu Asn Ile
        355                 360                 365

Ser Thr Met Val Ile
    370
```

<210> SEQ ID NO 12
<211> LENGTH: 1122
<212> TYPE: DNA
<213> ORGANISM: Saccharomyces cerevisiae

<400> SEQUENCE: 12

```
atgacacaga ctgataatcc tgtccccaac tgcggtttac tgcccgagca gcagtattgc    60
tctgcagacc atgaagagcc actgttgttg catgaagaac aattgatatt ccctgatcat   120
tcctcccaac tgtcctcagc agatatcatc gagcccatca gatgaacag cagtactgag    180
tcaattatag gacaacgct gcgaaagaaa tgggtaccac tatcctcaac tcagatcaca   240
gctctttccg gcgcatttgc tggattctta tcaggtgtgg cagtatgtcc cctcgatgtt   300
gccaaaacgc gattgcaagc acaaggacta caaactaggt tcgagaaccc ctactatagg   360
gggataatgg ggacattaag tactatagta agagacgaag gcccgcgggg cctctacaaa   420
gggctggtac cgattgtcct gggctacttc ccaacctgga tgatatactt ctccgtgtat   480
gaattcagca aaaagttctt tcacggcatc ttcccacagt ttgattttgt tgctcagtca   540
tgtgctgcaa tcacggcagg cgctgcatct accaccttga ccaacccaat ctgggttgtg   600
aagacaagac ttatgctgca atcaaacctc ggtgagcacc ccacacatta caaaggcact   660
ttcgatgcat tcagaaagct atttatcag gaagggttta agcattata tgcggggctg   720
gtcccctcat tatagggct atttcatgtg ctatccatt tccctatata cgaagatttg   780
aaggtaagat tcactgcta ttctcgggag aacaacacca actccatcaa cttgcaacgg   840
ttgatcatgg catcgtccgt ctctaagatg attgcatcag cagtaacata tccgcacgaa   900
```

```
attttacgaa ccagaatgca actgaaatca gatataccag attccattca acgacgtctg    960
ttccccctca ttaaagcaac ttatgcacaa gagggactaa agggatttta ttctggattt   1020
actactaacc tagtacgaac cattccggcc tcggcaatca ctctagtgtc ctttgagtat   1080
ttcagaaacc gcctagaaaa tattagcact atggtaattt aa                      1122
```

<210> SEQ ID NO 13
<211> LENGTH: 392
<212> TYPE: PRT
<213> ORGANISM: Aspergillus niger

<400> SEQUENCE: 13

```
Met Phe Ser Glu Gly His Gly Pro Ser Gly Ala Ala Ser Gly Ser Gln
1               5                   10                  15

Glu Gln Gln Gly Thr Thr Ser Asp Ser Ser Pro Ser Ser Thr Leu His
            20                  25                  30

Val Ser Ala Glu Ser Pro Ser Gln Pro Thr Leu Leu Asp Arg Phe Glu
        35                  40                  45

Met Leu Ala Thr Arg Val Pro Asp Tyr Tyr Ile Thr Pro Phe Cys Gly
    50                  55                  60

Ala Ser Ala Gly Val Ala Ser Gly Ile Val Thr Cys Pro Leu Asp Val
65                  70                  75                  80

Ile Lys Thr Lys Leu Gln Ala Gln Gly Gly Phe Ala Arg Arg Arg Gly
                85                  90                  95

Lys Ala Val Glu Ala Lys Thr Leu Tyr Arg Gly Met Leu Gly Thr Gly
            100                 105                 110

Arg Val Ile Trp Arg Glu Asp Gly Ile Arg Gly Leu Tyr Gln Gly Leu
        115                 120                 125

Gly Pro Met Leu Leu Gly Tyr Leu Pro Thr Trp Ala Val Tyr Leu Ala
    130                 135                 140

Val Tyr Asp Arg Ser Arg Glu Tyr Phe Tyr Glu Thr Thr Asp Ser Trp
145                 150                 155                 160

Trp Leu Ser Arg Gly Tyr Ala Ser Ile Thr Ala Gly Ala Cys Ser Thr
                165                 170                 175

Leu Ala Thr Asn Pro Ile Trp Val Ile Lys Thr Arg Leu Met Ser Gln
            180                 185                 190

Ser Leu Arg Ser Ser Ser Glu Gly Tyr Arg Ala Pro Trp Gln Tyr Lys
        195                 200                 205

Asn Thr Trp Asp Ala Ala Arg Lys Met Tyr Arg Ser Glu Gly Ile Arg
    210                 215                 220

Ser Phe Tyr Ser Gly Leu Thr Pro Ala Leu Leu Gly Leu Ala His Val
225                 230                 235                 240

Ala Ile Gln Phe Pro Leu Tyr Glu Tyr Leu Lys Met Ala Phe Thr Gly
                245                 250                 255

Tyr Ser Ile Gly Glu His Pro Asp Thr Gly Ser Ser His Trp Val Gly
            260                 265                 270

Ile Thr Ser Ala Thr Phe Leu Ser Lys Arg Thr Ser Pro Ala Ala Ser
        275                 280                 285

Pro Glu Glu Ile Ser Phe Arg Gly Gly Met Asp His Pro Gln Gly His
    290                 295                 300

Ser Arg Pro Pro Gly Ala Ala Ser Ser Asp Gly Met Pro Asn Arg Pro
305                 310                 315                 320

Arg Tyr Thr Gly Ile Ile Arg Thr Cys Gln Thr Ile Leu Arg Glu Glu
                325                 330                 335
```

```
Gly Trp Arg Ala Phe Tyr Ser Gly Ile Gly Thr Asn Leu Phe Arg Ala
            340                 345                 350

Val Pro Ala Ala Met Thr Thr Met Leu Thr Tyr Glu Tyr Leu Lys Lys
            355                 360                 365

Thr Ile Gly His Val Gln His Glu Gly Glu Leu Lys Leu Gln Lys Leu
            370                 375                 380

Glu Ala Thr Ser Asp Ser Gly Ile
385                 390
```

<210> SEQ ID NO 14
<211> LENGTH: 1179
<212> TYPE: DNA
<213> ORGANISM: Aspergillus niger

<400> SEQUENCE: 14

```
atgttctctg aaggccatgg cccttcgggg gctgccagcg gctctcaaga gcagcagggt      60
acaacttcgg acagttcgcc ttcgtcgacg cttcatgtat cggccgagtc cccatcccag     120
cccactcttc tcgatcgctt cgaaatgctc gctacacgtg tgccggatta ttacatcacg     180
ccgttctgcg gggccagtgc gggcgtagcc tcgggaattg tcacctgccc tctcgatgtg     240
atcaagacca agctgcaggc tcagggtggg ttcgcgcgac gacgtggcaa ggcggtcgag     300
gccaaaacac tgtaccgggg catgctagga actggacgag taatatggcg ggaggatggt     360
attcgaggcc tttatcaagg attgggtccc atgctcctgg atacctgccg acgtgggcc     420
gtctatttgg cggtctacga tcggtctcgg gagtatttct acgaaacaac agatagttgg     480
tggctctcac gaggttacgc ctccataacg gcgggcgctt gctcgaccct tgcgacgaat     540
ccaatttggg tgattaagac acgacttatg tcacagagcc tccggtcgag cagcgaaggc     600
taccgggctc cttggcaata caaaaacaca tgggatgcgg cccgcaaaat gtacagaagt     660
gaagggattc gttcgttcta ctccggcctt accccagcgc tgctgggggct ggcgcatgtg     720
gccatccagt ccctctttta cgaatatctg aagatggcgt ttactggcta tagtattggc     780
gaacatcccg atactggcag ctcacactgg gtgggcatta catctgcgac attcctgagt     840
aagaggacat caccggcggc ctcacccgaa gagatctcgt tccgcggcgg gatggatcac     900
ccccagggtc atagcaggcc cccgggtgct gcttcgtcgg acggaatgcc aatcgaccc     960
cggtacacgg gaatcattcg cacatgccag accattctga gaagaaagg ctggcgcgcg    1020
ttctactctg ggatcggcac gaatctgttc cgggcggtcc cggctgcgat gactaccatg    1080
ctcacttatg agtacttgaa gaaaacgatt ggacacgtgc aacatgaggg agagctgaag    1140
ttgcagaagc tggaggccac atcagacagt ggaatctaa                           1179
```

<210> SEQ ID NO 15
<211> LENGTH: 316
<212> TYPE: PRT
<213> ORGANISM: Candida albicans

<400> SEQUENCE: 15

```
Met Glu Leu Asn Thr Thr Asp Lys Gln Val His Thr Arg Arg Phe Ser
1               5                   10                  15

Ser Arg Glu Ile Glu Val Ile Ser Gly Leu Leu Ala Gly Phe Ser Thr
            20                  25                  30

Thr Ile Val Thr His Pro Leu Asp Val Ile Lys Ile Arg Leu Gln Leu
            35                  40                  45

Ser Arg Asp Thr Pro Lys Thr Thr His Pro Leu Glu Ser Ile Ile Ser
```

```
                    50                  55                  60
Val Ile Lys Lys Ile Asn Gln Asp Ala Lys Val Ala Tyr Lys Leu Asn
 65                  70                  75                  80

His Lys Pro Lys Ala Phe Asn Tyr Leu Ile Gln Tyr Arg Gly Ile
                     85                  90                  95

Thr Pro Asn Leu Ile Gly Asn Ile Ser Ala Trp Gly Ile Tyr Phe Ala
                100                 105                 110

Leu Tyr Ala Glu Phe Lys Ser Lys Val Lys Thr Asn Asn Thr Thr Met
            115                 120                 125

Asn Tyr Phe Ala Ser Ser Val Leu Ala Gly Leu Ser Thr Ser Ile Ile
        130                 135                 140

Thr Asn Pro Leu Trp Val Leu Lys Thr Arg Ile Leu Gly Ser Ser Arg
145                 150                 155                 160

Asn Glu Ser Asn Ala Tyr Arg Ser Val Thr Asp Gly Ile Arg Gln Met
                165                 170                 175

Leu Ala Lys Glu Gly Ile Thr Ser Phe Trp Lys Gly Thr Ile Pro Ser
            180                 185                 190

Leu Phe Ser Val Val Gln Ala Ser Leu Gln Ile Thr Ile Tyr Asp His
        195                 200                 205

Ile Lys Val Tyr Leu Ser Ser Pro His His Lys Ser Glu Ser Ile Gly
    210                 215                 220

Ala Thr Ser His Leu Ser Thr Trp Gln Tyr Leu Tyr Ser Ser Ala Ser
225                 230                 235                 240

Ser Lys Ile Ile Ser Met Leu Ile Leu Tyr Pro Thr Gln Val Val Arg
                245                 250                 255

Ser Arg Leu Gln Tyr Ser Gln Asp Ser Ser Ser Ile Val Ser Ile
            260                 265                 270

Val Lys Glu Leu Tyr Tyr Lys Glu Gly Gly Leu Lys Gly Phe Tyr Lys
        275                 280                 285

Gly Ile Gly Ala Asn Ile Leu Arg Val Leu Pro Ala Thr Cys Val Thr
    290                 295                 300

Phe Val Ala Tyr Glu Asn Val Lys Arg Tyr Leu Met
305                 310                 315

<210> SEQ ID NO 16
<211> LENGTH: 951
<212> TYPE: DNA
<213> ORGANISM: Candida albicans

<400> SEQUENCE: 16
atggagttga acacaaccga caagcaagtg catactcgcc gttttctttc acgtgaaatt        60
gaagttatat caggcttgct tgctggattc tcaacaacaa tcgtcaccca cccctagat       120 gttatcaaga tcagattaca attatctcga gatacaccca aaactacgca tcctttggaa      180
tcaataatat ctgtgatcaa aaagataaac caagatgcaa agtagcata caaattgaat       240 cacaagccca aggcattcaa ttatttgatc agtactatc gaggaatcac tccaaacttg       300
atcggaaaca tttctgcttg gggtatctat tttgccttgt atgccgaatt taaaagtaaa      360
gttaagacaa acaatactac aatgaattat tttgcctcgt cggtattagc ggggttatcg     420
acgtccatta taactaatcc attatgggtg ttgaaaacac gaatattagg aagttcaaga    480
aatgaatcca atgcttatag atcagttaca gatggcataa gacaaatgct agcaaaagaa   540
ggaataacca gcttctggaa aggaaccatt cccagtcttt ttctggttgt acaagcaagt  600
ttacaaatta ccatctatga ccatatcaaa gtgtatttac tgagtcctca tcataagtca  660
```

```
gaaagtattg gtgcaacgtc tcatttgtca acttggcagt acttgtattc ttcagcatcg    720
tcgaaaatca ttagtatgtt gattctatat cccacccagg tcgttagatc acggctacag    780
tattcccaag actcttcact gagtattgtt tccatagtta aagagttgta ctataaagaa    840
ggaggattaa aggggttcta caaggaataa ggtgcaaata ttctaagagt tctacctgca    900
acgtgtgtta cttttgttgc ttatgagaac gtcaaaagat atcttatgta a             951
```

<210> SEQ ID NO 17
<211> LENGTH: 306
<212> TYPE: PRT
<213> ORGANISM: Yarrowia lipolytica

<400> SEQUENCE: 17

```
Met Ser Ser Gln Asn Ser His Asn Ile Leu His Glu Thr His Leu Leu
1               5                   10                  15

Ser Asp Thr Ser Ile His Ala Ile Ala Gly Ala Leu Ala Gly Thr Leu
            20                  25                  30

Ser Gly Ile Val Val Cys Pro Leu Asp Val Ile Lys Thr Arg Leu Gln
        35                  40                  45

Ala Glu Gly Ala Leu Asp Lys Gln Arg Gly Ser Leu Lys Gly Gly Leu
    50                  55                  60

Thr Arg Thr Met Asp Ser Ile Val Lys His Asp Gly Val Arg Gly Leu
65                  70                  75                  80

Tyr Arg Gly Val Ile Pro Ile Ile Leu Gly Tyr Ser Pro Thr Trp Met
                85                  90                  95

Ile Tyr Phe Ala Val Tyr Glu Lys Ser Lys Tyr Leu Leu Ser Thr Val
            100                 105                 110

Pro Gln Leu Asp Pro Tyr Pro Phe Phe Ser His Cys Leu Ser Ala Leu
        115                 120                 125

Gly Ala Gly Ala Ala Ser Thr Thr Ile Thr Asn Pro Ile Trp Val Val
    130                 135                 140

Lys Thr Arg Leu Met Ser Gln Gly Arg Asn Thr Pro Trp His Tyr Ser
145                 150                 155                 160

Gly Thr Trp Asp Ala Phe Lys Thr Met Tyr Lys Thr Asp Gly Ile Lys
                165                 170                 175

Val Phe Tyr Ser Gly Leu Gly Pro Ala Leu Leu Gly Leu Ser His Val
            180                 185                 190

Ala Ile Gln Phe Pro Met Tyr Glu Lys Leu Lys Val Met Leu Gly Val
        195                 200                 205

Ser Pro Asp Ser Asn Lys Pro Asn Pro Trp Ala Val Thr Val Ala Ser
    210                 215                 220

Ser Leu Ser Lys Met Ile Ala Ser Ala Ile Thr Tyr Pro His Glu Ile
225                 230                 235                 240

Val Arg Thr Arg Met Gln Ile Gln Ser Lys Asp Gly Gln Tyr Arg Gly
                245                 250                 255

Ile Ile Ala Ser Phe Lys Lys Leu Tyr Gln Glu Glu Gly Phe Arg Ile
            260                 265                 270

Phe Tyr Thr Gly Phe Gly Thr Asn Leu Leu Arg Thr Val Pro Ala Ser
        275                 280                 285

Ala Ile Thr Leu Leu Ser Phe Glu Met Ile Ser Ser Arg Leu Lys Gln
    290                 295                 300

Ile Leu
305
```

<210> SEQ ID NO 18
<211> LENGTH: 921
<212> TYPE: DNA
<213> ORGANISM: Yarrowia lipolytica

<400> SEQUENCE: 18

```
atgtcgtccc aaaactcgca caacatcctc catgagacgc atctgttgtc ggacaccagc      60
atccacgcca tagccggcgc cctggcaggc acgctctctg gtatcgtggt gtgtcctctc     120
gacgtgatca agacccggtt gcaggcagaa ggagctctcg acaagcagag aggctcactc     180
aagggcggcc tcacccgtac aatggactcc attgtcaagc atgacggcgt gcggggcctg     240
taccgaggag tgatccccat cattctgggc tactcgccca cctggatgat ttattttgcc     300
gtctacgaaa aatcaaaata tttattgtcc accgtgcccc agttggaccc ctatcccttc     360
ttttcgcatt gtctgtcggc tctgggcgcc ggagccgcct ccaccaccat caccaacccc     420
atctgggtcg tcaaaaccag actcatgtcc cagggccgca cacccctg gcactactct       480
ggcacctggg acgccttcaa aaccatgtac aaaaccgacg gaatcaaagt cttctactcg     540
ggtctgggcc ccgctcttct gggcctctcc cacgtggcca ttcagttccc catgtacgag     600
aagctcaagg tgatgctcgg agtcagtcca gactccaaca aacccaaccc ctgggcagtc     660
acggtggcct cgtcactgtc caagatgatc gcgtcggcaa tcacctaccc acacgagatt     720
gtgcggaccc gaatgcagat ccagagtaaa gacggccagt atcgtggcat cattgcatcg     780
ttcaagaaac tctaccagga gagggcttc cgaatcttct acacgggctt cggcaccaac     840
ctgcttagaa ccgtgcccgc ctctgccatc accctgcttt cgtttgagat gatttccagc     900
cgcctcaaac agatcccttta g                                              921
```

<210> SEQ ID NO 19
<211> LENGTH: 431
<212> TYPE: PRT
<213> ORGANISM: Kluyveromyces lactis

<400> SEQUENCE: 19

```
Met Ala Ser Ser Ile Ser Ala Ala Lys Thr Asp Asn Cys Gly Thr Asp
1               5                   10                  15

Asn Ile Ala Thr Gly Arg Ser Met Gly Gln Gly Leu Val Ala Glu Glu
            20                  25                  30

Glu Ile Asp Lys Val Leu Lys Gln Asp Val Gly Asp Ala Val Thr Ala
        35                  40                  45

Thr Ala Gly Thr Ala Ala Val Ala Ala Val Ala Ser Gly Ser Val Thr
    50                  55                  60

Val Ser Ser Gly Val Asn Ser Gly Cys Ser Ser Arg Ser Gly Ala Ile
65                  70                  75                  80

Asp Leu Glu Gly Ser Ser Ser Arg His Gly Leu Ser Ile Val Arg Glu
                85                  90                  95

Glu Gly His Phe Asn Asp Thr Glu Ile Thr Ala Leu Ser Gly Ala Leu
            100                 105                 110

Ala Gly Phe Leu Ala Gly Val Ile Val Cys Pro Leu Asp Val Ala Lys
        115                 120                 125

Thr Arg Leu Gln Ala Gln Gly Leu Gln Leu Asn Gly Pro Val Thr Arg
    130                 135                 140

Pro Val Gly Ser Val Ala Thr Thr Phe Gly Gly Lys Tyr Tyr Ser Gly
145                 150                 155                 160

Ile Trp Gly Thr Leu Thr Thr Ile Val Arg Asp Glu Ser Ile Arg Gly
```

```
                165                 170                 175
Leu Tyr Lys Gly Ile Val Pro Ile Val Leu Gly Tyr Phe Pro Thr Trp
            180                 185                 190

Met Ile Tyr Phe Ser Val Tyr Glu Arg Cys Lys Leu Ser Tyr Pro Arg
            195                 200                 205

Tyr Phe Asn Asn Ser Glu Phe Leu Ser His Ser Met Ser Ala Leu Thr
            210                 215                 220

Ala Gly Ala Ile Ser Thr Thr Leu Thr Asn Pro Ile Trp Val Val Lys
225                 230                 235                 240

Thr Arg Leu Met Leu Gln Ser Gly Lys Asn Ile Lys Gly Met Thr His
                245                 250                 255

Tyr Lys Asn Thr Leu Asp Ala Phe Ile Lys Ile Tyr Lys Val Glu Gly
            260                 265                 270

Ile Lys Ser Phe Tyr Ser Gly Leu Ile Pro Ser Leu Phe Gly Leu Leu
            275                 280                 285

His Val Ala Ile His Phe Pro Val Tyr Glu Lys Leu Lys Lys Val Leu
            290                 295                 300

His Cys Tyr Pro Ser Gly Arg Pro Asn Gln Glu Thr Met Asn Val Asn
305                 310                 315                 320

Gly Asn Ser Asn Pro Gln Thr Thr Gly Ser Thr Asn Phe Gln Leu Gly
                325                 330                 335

Arg Leu Ile Val Ala Ser Cys Gly Ser Lys Met Ile Ala Ser Thr Leu
            340                 345                 350

Thr Tyr Pro His Glu Ile Leu Arg Thr Arg Leu Gln Leu Lys Ser Asp
            355                 360                 365

Met Lys Pro Ser Ile Lys Ser Ile Ile Arg Thr Thr Tyr Ala Lys Glu
            370                 375                 380

Gly Ile Arg Gly Phe Tyr Ser Gly Phe Leu Thr Asn Met Phe Arg Thr
385                 390                 395                 400

Val Pro Ala Ser Ala Ile Thr Leu Val Ser Phe Glu Tyr Phe Arg Lys
                405                 410                 415

His Phe Lys Leu Trp Asn Asp Ser Ile Glu Val Glu Arg Gly Gly
            420                 425                 430

<210> SEQ ID NO 20
<211> LENGTH: 1296
<212> TYPE: DNA
<213> ORGANISM: Kluyveromyces lactis

<400> SEQUENCE: 20
atggcatctt cgatcagtgc tgcaaaaact gacaattgtg gtactgataa tatagcaact    60
ggacggtcga tgggtcaagg attggttgcg gaggaggaga tagataaagt actcaagcag   120
gatgtcggag atgcagtgac agcaacagct ggcacggcag ctgtcgctgc cgtagcgtct   180
ggttctgtca ctgtcagttc gggcgtgaac tccggttgta gttctagatc cggcgctata   240
gacttggaag gttcttcgag ccgacatgga cttagtattg taagggaaga ggggcatttc   300
aacgatacag aaattacagc attgagtggt gcattggctg ggttcttggc cggtgtcatc   360
gtatgtccgt ggatgttgc caagactagg ttacaggctc aaggtttgca acttaatggt   420
ccggtgactc gtccggtcgg tagtgttgct accacgtttg gagggaaata ttacagtggt   480
atctggggaa ctctcacgac gattgtacga gacgaatcca ttagaggatt gtacaagggg   540
atagtaccga tagttctggg gtacttcccg acatggatga tatattttc agtttacgaa   600 cgatgtaagc tatcgtaccc tcggtatttc aacaattcgg agtttctttc gcattcgatg   660
```

```
tctgctttga ctgcaggagc catttccaca acgctcacga acccgatctg ggtcgttaag      720
acacggttaa tgcttcagtc aggtaagaat attaagggca tgacgcatta caaaaacacc      780
ttggacgcat ttattaagat atacaaagtc gaaggaatca agagttttta ctccggggttg     840 atcccatcgt tgtttggatt attacatgta gctatacact tccccgtata cgaaaaactg      900
aagaaggttt tgcattgtta cccaagtggt agacctaatc aggaaactat gaacgtcaac      960
ggtaacagta acccacagac taccggttct acaaattttc agttgggacg gttgatcgtt     1020
gcatcctgtg ggtcaaagat gatcgcttca acgctcacct accctcatga aatactaaga     1080
accaggttac aactgaaatc tgatatgaaa ccttccatta aatcgataat acgaacgact     1140
tatgcaaagg aagggataag agggttttat tcgggtttcc taactaatat gttcagaact     1200
gtaccggcat cagcaattac tttagtctcg tttgaatact tcaggaagca tttcaaactt     1260
tggaacgata gtatagaggt agaaagggggc ggatag                              1296
```

```
<210> SEQ ID NO 21
<211> LENGTH: 285
<212> TYPE: PRT
<213> ORGANISM: Escherichia coli

<400> SEQUENCE: 21

Met Lys Ala Asp Asn Pro Phe Asp Leu Leu Leu Pro Ala Ala Met Ala
1               5                   10                  15

Lys Val Ala Glu Glu Ala Gly Val Tyr Lys Ala Thr Lys His Pro Leu
            20                  25                  30

Lys Thr Phe Tyr Leu Ala Ile Thr Ala Gly Val Phe Ile Ser Ile Ala
        35                  40                  45

Phe Val Phe Tyr Ile Thr Ala Thr Thr Gly Thr Gly Thr Met Pro Phe
    50                  55                  60

Gly Met Ala Lys Leu Val Gly Gly Ile Cys Phe Ser Leu Gly Leu Ile
65                  70                  75                  80

Leu Cys Val Val Cys Gly Ala Asp Leu Phe Thr Ser Thr Val Leu Ile
                85                  90                  95

Val Val Ala Lys Ala Ser Gly Arg Ile Thr Trp Gly Gln Leu Ala Lys
            100                 105                 110

Asn Trp Leu Asn Val Tyr Phe Gly Asn Leu Val Gly Ala Leu Leu Phe
        115                 120                 125

Val Leu Leu Met Trp Leu Ser Gly Glu Tyr Met Thr Ala Asn Gly Gln
    130                 135                 140

Trp Gly Leu Asn Val Leu Gln Thr Ala Asp His Lys Val His His Thr
145                 150                 155                 160

Phe Ile Glu Ala Val Cys Leu Gly Ile Leu Ala Asn Leu Met Val Cys
                165                 170                 175

Leu Ala Val Trp Met Ser Tyr Ser Gly Arg Ser Leu Met Asp Lys Ala
            180                 185                 190

Phe Ile Met Val Leu Pro Val Ala Met Phe Val Ala Ser Gly Phe Glu
        195                 200                 205

His Ser Ile Ala Asn Met Phe Met Ile Pro Met Gly Ile Val Ile Arg
    210                 215                 220

Asp Phe Ala Ser Pro Glu Phe Trp Thr Ala Val Gly Ser Ala Pro Glu
225                 230                 235                 240

Asn Phe Ser His Leu Thr Val Met Asn Phe Ile Thr Asp Asn Leu Ile
                245                 250                 255
```

```
Pro Val Thr Ile Gly Asn Ile Ile Gly Gly Leu Leu Val Gly Leu
        260                 265                 270

Thr Tyr Trp Val Ile Tyr Leu Arg Glu Asn Asp His His
        275                 280                 285

<210> SEQ ID NO 22
<211> LENGTH: 858
<212> TYPE: DNA
<213> ORGANISM: Escherichia coli

<400> SEQUENCE: 22
gtgaaagctg acaacccttt tgatctttta cttcctgctg caatggccaa agtggccgaa      60
gaggcgggtg tctataaagc aacgaaacat ccgcttaaga ctttctatct ggcgattacc     120
gccggtgttt tcatctcaat cgcattcgtc ttctatatca cagcaaccac tggcacaggc     180
acaatgccct tcggcatggc aaaactggtt ggcggcattt gcttctctct ggggctgatt     240
ctttgtgttg tctgcggagc cgatctcttt acttccaccg tgttgattgt tgttgctaag     300
gcgagtgggc gcatcacctg gggtcagttg gcgaaaaact ggctaaatgt ctattttggc     360
aacctggtcg gcgcactgct gtttgtactt ttaatgtggc tttccggcga gtatatgacc     420
gcaaatggtc aatggggact aaacgtccta caaaccgccg accacaaagt gcaccatact     480
tttattgagg ccgtctgtct tggtatcctg gcaaacctga tggtatgtct ggcagtatgg     540
atgagttatt ctggccgcag cctgatggac aaagcgttca ttatggtgct gccggtcgcg     600
atgtttgttg ccagcggttt tgagcacagt atcgcaaaca tgtttatgat cccgatgggt     660
attgtaatcc gcgacttcgc atccccggaa ttttggaccg cagtcggttc tgcaccggaa     720
aatttttctc acctgaccgt gatgaatttc atcactgata acctgattcc ggttacgatc     780
ggcaacatta tcggtggtgg tttgttggtt gggttgacat actgggtcat ttacctgcgt     840
gaaaacgacc accattaa                                                   858

<210> SEQ ID NO 23
<211> LENGTH: 616
<212> TYPE: PRT
<213> ORGANISM: Saccharomyces cerevisiae

<400> SEQUENCE: 23

Met Ser Ser Ser Ile Thr Asp Glu Lys Ile Ser Gly Glu Gln Gln Gln
1               5                   10                  15

Pro Ala Gly Arg Lys Leu Tyr Tyr Asn Thr Ser Thr Phe Ala Glu Pro
            20                  25                  30

Pro Leu Val Asp Gly Glu Gly Asn Pro Ile Asn Tyr Glu Pro Glu Val
        35                  40                  45

Tyr Asn Pro Asp His Glu Lys Leu Tyr His Asn Pro Ser Leu Pro Ala
    50                  55                  60

Gln Ser Ile Gln Asp Thr Arg Asp Glu Leu Leu Glu Arg Val Tyr
65                  70                  75                  80

Ser Gln Asp Gln Gly Val Glu Tyr Glu Asp Glu Asp Lys Pro
            85                  90                  95

Asn Leu Ser Ala Ala Ser Ile Lys Ser Tyr Ala Leu Thr Arg Phe Thr
            100                 105                 110

Ser Leu Leu His Ile His Glu Phe Ser Trp Glu Asn Val Asn Pro Ile
        115                 120                 125

Pro Glu Leu Arg Lys Met Thr Trp Gln Asn Trp Asn Tyr Phe Phe Met
    130                 135                 140
```

Gly Tyr Phe Ala Trp Leu Ser Ala Ala Trp Ala Phe Phe Cys Val Ser
145                 150                 155                 160

Val Ser Val Ala Pro Leu Ala Glu Leu Tyr Asp Arg Pro Thr Lys Asp
            165                 170                 175

Ile Thr Trp Gly Leu Gly Leu Val Leu Phe Val Arg Ser Ala Gly Ala
                180                 185                 190

Val Ile Phe Gly Leu Trp Thr Asp Lys Ser Ser Arg Lys Trp Pro Tyr
        195                 200                 205

Ile Thr Cys Leu Phe Leu Phe Val Ile Ala Gln Leu Cys Thr Pro Trp
    210                 215                 220

Cys Asp Thr Tyr Glu Lys Phe Leu Gly Val Arg Trp Ile Thr Gly Ile
225                 230                 235                 240

Ala Met Gly Gly Ile Tyr Gly Cys Ala Ser Ala Thr Ala Ile Glu Asp
                245                 250                 255

Ala Pro Val Lys Ala Arg Ser Phe Leu Ser Gly Leu Phe Phe Ser Ala
            260                 265                 270

Tyr Ala Met Gly Phe Ile Phe Ala Ile Ile Phe Tyr Arg Ala Phe Gly
                275                 280                 285

Tyr Phe Arg Asp Asp Gly Trp Lys Ile Leu Phe Trp Phe Ser Ile Phe
    290                 295                 300

Leu Pro Ile Leu Leu Ile Phe Trp Arg Leu Leu Trp Pro Glu Thr Lys
305                 310                 315                 320

Tyr Phe Thr Lys Val Leu Lys Ala Arg Lys Leu Ile Leu Ser Asp Ala
                325                 330                 335

Val Lys Ala Asn Gly Gly Glu Pro Leu Pro Lys Ala Asn Phe Lys Gln
            340                 345                 350

Lys Met Val Ser Met Lys Arg Thr Val Gln Lys Tyr Trp Leu Leu Phe
                355                 360                 365

Ala Tyr Leu Val Val Leu Val Gly Pro Asn Tyr Leu Thr His Ala
    370                 375                 380

Ser Gln Asp Leu Leu Pro Thr Met Leu Arg Ala Gln Leu Gly Leu Ser
385                 390                 395                 400

Lys Asp Ala Val Thr Val Ile Val Val Thr Asn Ile Gly Ala Ile
                405                 410                 415

Cys Gly Gly Met Ile Phe Gly Gln Phe Met Glu Val Thr Gly Arg Arg
            420                 425                 430

Leu Gly Leu Leu Ile Ala Cys Thr Met Gly Cys Phe Thr Tyr Pro
                435                 440                 445

Ala Phe Met Leu Arg Ser Glu Lys Ala Ile Leu Gly Ala Gly Phe Met
    450                 455                 460

Leu Tyr Phe Cys Val Phe Gly Val Trp Gly Ile Leu Pro Ile His Leu
465                 470                 475                 480

Ala Glu Leu Ala Pro Ala Asp Ala Arg Ala Leu Val Ala Gly Leu Ser
                485                 490                 495

Tyr Gln Leu Gly Asn Leu Ala Ser Ala Ala Ser Thr Ile Glu Thr
            500                 505                 510

Gln Leu Ala Asp Arg Tyr Pro Leu Glu Arg Asp Ala Ser Gly Ala Val
                515                 520                 525

Ile Lys Glu Asp Tyr Ala Lys Val Met Ala Ile Leu Thr Gly Ser Val
        530                 535                 540

Phe Ile Phe Thr Phe Ala Cys Val Phe Val Gly His Glu Lys Phe His
545                 550                 555                 560

Arg Asp Leu Ser Ser Pro Val Met Lys Lys Tyr Ile Asn Gln Val Glu

```
                    565                 570                 575
        Glu Tyr Glu Ala Asp Gly Leu Ser Ile Ser Asp Ile Val Glu Gln Lys
                580                 585                 590

Thr Glu Cys Ala Ser Val Lys Met Ile Asp Ser Asn Val Ser Lys Thr
                595                 600                 605

Tyr Glu His Ile Glu Thr Val
            610             615

<210> SEQ ID NO 24
<211> LENGTH: 1851
<212> TYPE: DNA
<213> ORGANISM: Saccharomyces cerevisiae

<400> SEQUENCE: 24
atgtcgtcgt caattacaga tgagaaaata tctggtgaac agcaacaacc tgctggcaga      60
aaactatact ataacacaag tacatttgca gagcctcctc tagtggacgg agaaggtaac     120
cctataaatt atgagccgga agtttacaac ccggatcacg aaaagctata ccataaccca     180
tcactgcctg cacaatcaat tcaggataca agagatgatg aattgctgga aagagtttat     240
agccaggatc aaggtgtaga gtatgaggaa gatgaagagg ataagccaaa cctaagcgct     300
gcgtccatta aaagttatgc tttaacgaga tttacgtcct tactgcacat ccacgagttt     360
tcttgggaga atgtcaatcc catacccgaa ctgcgcaaaa tgacatggca gaattggaac     420 tatttttta tgggttattt tgcgtggttg tctgcggctt gggccttctt ttgcgtttca     480
gtatcagtcg ctccattggc tgaactatat gacagaccaa ccaaggacat cacctggggg     540
ttgggattgg tgttatttgt tcgttcagca ggtgctgtca tatttggttt atggacagat     600
aagtcttcca gaaagtggcc gtacattaca tgtttgttct tatttgtcat tgcacaactc     660
tgtactccat ggtgtgacac atacgagaaa tttctgggcg taaggtggat aaccggtatt     720
gctatgggag gaatttacgg atgtgcttct gcaacagcga ttgaagatgc acctgtgaaa     780
gcacgttcgt tcctatcagg tctattttt tctgcttacg ctatggggtt catatttgct     840
atcatttttt acagagcctt tggctacttt agggatgatg ctggaaaat attgttttgg     900 tttagtattt ttctaccaat tctactaatt ttctggagat tgttatggcc tgaaacgaaa     960
tacttcacca aggttttgaa agcccgtaaa ttaatattga gtgacgcagt gaaagctaat    1020
ggtggcgagc tctaccaaa agccaacttt aaacaaaaga tggtatccat gaagagaaca    1080
gttcaaaagt actggttgtt gttcgcatat ttggttgttt tattggtggg tccaaattac    1140
ttgactcatg cttctcaaga cttgttgcca accatgctgc gtgcccaatt aggcctatcc    1200
aaggatgctg tcactgtcat tgtagtggtt accaacatcg gtgctatttg tgggggtatg    1260
atatttggac agttcatgga agttactgga agaagattag ccctattgat tgcatgcaca    1320
atgggtggtt gcttcaccta ccctgcattt atgttgagaa gcgaaaaggc tatattaggt    1380
gccggtttca tgttatattt ttgtgtcttt ggtgtctggg gtatcctgcc cattcacctt    1440
gcagagttgg cccctgctga tgcaagggct ttggttgccg gtttatctta ccagctaggt    1500
aatctagctt ctgcagcggc ttccacgatt gagacacagt tagctgatag atacccatta    1560
gaaagagatg cctctggtgc tgtgattaaa gaagattatg ccaaagttat ggctatcttg    1620
actggttctg ttttcatctt cacatttgct tgtgttttg ttggccatga gaaattccat    1680
cgtgatttgt cctctcctgt tatgaagaaa tatataaacc aagtggaaga atacgaagcc    1740
gatggtcttt cgattagtga cattgttgaa caaaagacgg aatgtgcttc agtgaagatg    1800
```

```
attgattcga acgtctcaaa gacatatgag gagcatattg agaccgttta a            1851
```

<210> SEQ ID NO 25
<211> LENGTH: 440
<212> TYPE: PRT
<213> ORGANISM: Escherichia coli

<400> SEQUENCE: 25

```
Met Gln Ala Thr Ala Thr Thr Leu Asp His Glu Gln Glu Tyr Thr Pro
1               5                   10                  15

Ile Asn Ser Arg Asn Lys Val Leu Val Ala Ser Leu Ile Gly Thr Ala
                20                  25                  30

Ile Glu Phe Phe Asp Phe Tyr Ile Tyr Ala Thr Ala Ala Val Ile Val
            35                  40                  45

Phe Pro His Ile Phe Phe Pro Gln Gly Asp Pro Thr Ala Ala Thr Leu
        50                  55                  60

Gln Ser Leu Ala Thr Phe Ala Ile Ala Phe Val Ala Arg Pro Ile Gly
65                  70                  75                  80

Ser Ala Val Phe Gly His Phe Gly Asp Arg Val Gly Arg Lys Ala Thr
                85                  90                  95

Leu Val Ala Ser Leu Leu Thr Met Gly Ile Ser Thr Val Val Ile Gly
            100                 105                 110

Leu Leu Pro Gly Tyr Ala Thr Ile Gly Ile Phe Ala Pro Leu Leu Leu
        115                 120                 125

Ala Leu Ala Arg Phe Gly Gln Gly Leu Gly Leu Gly Gly Glu Trp Gly
    130                 135                 140

Gly Ala Ala Leu Leu Ala Thr Glu Asn Ala Pro Pro Arg Lys Arg Ala
145                 150                 155                 160

Leu Tyr Gly Ser Phe Pro Gln Leu Gly Ala Pro Ile Gly Phe Phe Phe
                165                 170                 175

Ala Asn Gly Thr Phe Leu Leu Leu Ser Trp Leu Leu Thr Asp Glu Gln
            180                 185                 190

Phe Met Ser Trp Gly Trp Arg Val Pro Phe Ile Phe Ser Ala Val Leu
        195                 200                 205

Val Ile Ile Gly Leu Tyr Val Arg Val Ser Leu His Glu Ser Pro Val
    210                 215                 220

Phe Glu Lys Val Ala Lys Ala Lys Lys Gln Val Lys Ile Pro Leu Gly
225                 230                 235                 240

Thr Leu Leu Thr Lys His Val Arg Val Thr Val Leu Gly Thr Phe Ile
                245                 250                 255

Met Leu Ala Thr Tyr Thr Leu Phe Tyr Ile Met Thr Val Tyr Ser Met
            260                 265                 270

Thr Phe Ser Thr Ala Ala Ala Pro Val Gly Leu Gly Leu Pro Arg Asn
        275                 280                 285

Glu Val Leu Trp Met Leu Met Met Ala Val Ile Gly Phe Gly Val Met
    290                 295                 300

Val Pro Val Ala Gly Leu Leu Ala Asp Ala Phe Gly Arg Arg Lys Ser
305                 310                 315                 320

Met Val Ile Ile Thr Thr Leu Ile Ile Leu Phe Ala Leu Phe Ala Phe
                325                 330                 335

Asn Pro Leu Leu Gly Ser Gly Asn Pro Ile Leu Val Phe Ala Phe Leu
            340                 345                 350

Leu Leu Gly Leu Ser Leu Met Gly Leu Thr Phe Gly Pro Met Gly Ala
        355                 360                 365
```

| Leu | Leu | Pro | Glu | Leu | Phe | Pro | Thr | Glu | Val | Arg | Tyr | Thr | Gly | Ala | Ser |
|-----|-----|-----|-----|-----|-----|-----|-----|-----|-----|-----|-----|-----|-----|-----|-----|
| 370 |     |     |     |     | 375 |     |     |     |     | 380 |     |     |     |     |     |

| Phe | Ser | Tyr | Asn | Val | Ala | Ser | Ile | Leu | Gly | Ala | Ser | Val | Ala | Pro | Tyr |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

| Ile | Ala | Ala | Trp | Leu | Gln | Thr | Asn | Tyr | Gly | Leu | Gly | Ala | Val | Gly | Leu |
|-----|-----|-----|-----|-----|-----|-----|-----|-----|-----|-----|-----|-----|-----|-----|-----|
|     |     |     |     | 405 |     |     |     |     | 410 |     |     |     |     | 415 |     |

| Tyr | Leu | Ala | Ala | Met | Ala | Gly | Leu | Thr | Leu | Ile | Ala | Leu | Leu | Leu | Thr |
|-----|-----|-----|-----|-----|-----|-----|-----|-----|-----|-----|-----|-----|-----|-----|-----|
|     |     |     | 420 |     |     |     |     | 425 |     |     |     |     | 430 |     |     |

| His | Glu | Thr | Arg | His | Gln | Ser | Leu |
|-----|-----|-----|-----|-----|-----|-----|-----|
|     |     |     | 435 |     |     |     | 440 |

<210> SEQ ID NO 26
<211> LENGTH: 1323
<212> TYPE: DNA
<213> ORGANISM: Escherichia coli

<400> SEQUENCE: 26

| atgcaagcaa | cagccacaac | actcgaccac | gagcaagaat | acacgccgat | caactcgcgt | 60 |
| aataaagtcc | ttgtcgcctc | tctcattggc | acagccattg | agttcttcga | cttttacatt | 120 |
| tacgccactg | cggccgttat | tgtgtttccg | catatcttct | cccgcagggg | cgatcctacg | 180 |
| gcagcaacgc | tacagtcgct | cgccaccttc | gccatcgcct | cgtcgcgcg  | ccccattggc | 240 |
| tctgccgttt | ttggtcattt | tggcgatcgc | gttgggcgta | aagcgacgct | ggtcgcctcg | 300 |
| ttgctaacga | tggggatttc | gaccgtggtg | attggtctgc | tgccgggcta | tgccacgatt | 360 |
| ggtattttcg | ccccgctgct | gctggcgctg | gctcgatttg | gtcagggtct | ggcttaggc  | 420 |
| ggtgaatggg | gcggcgcggc | gctgctggcg | actgaaaacg | ccccaccgcg | caaacgtgca | 480 |
| ctgtatggct | cctttccgca | gctgggcgca | ccgattggct | tcttctttgc | caatggcact | 540 |
| ttcttgctgc | tttcctggct | actgaccgac | gagcagttta | tgagctgggg | ctggcgtgtg | 600 |
| ccatttatct | ctcggcggt  | gctggtcatt | atcggcctgt | atgttcgcgt | gtcgctgcat | 660 |
| gagtcgccgg | tgtttgagaa | agtcgctaaa | gcgaaaaaac | aggtgaagat | cccgctgggt | 720 |
| acgctgctga | ccaaacatgt | tcgcgtaacc | gtactgggta | cgttcattat | gctggcaacc | 780 |
| tatacgctgt | tttacatcat | gacggtctac | tctatgacct | ttagtaccgc | cgccgcgcca | 840 |
| gttgggcttg | gcctgccgcg | taacgaagtg | ttgtggatgt | tgatgatggc | agttattggt | 900 |
| tttgcgtga  | tggtgccagt | cgctggatta | ctggctgatg | cctttggtcg | ccgtaaaagc | 960 |
| atggtaatca | tcaccacgct | gatcatcctg | ttcgcgctgt | cgcctttaa  | cccactgctc | 1020 |
| ggttctggca | acccgattct | ggttttgcc  | ttcctgctgc | tggggttaag | tctgatgggg | 1080 |
| ctgaccttcg | ggccaatggg | tgcgctgtta | ccagagctgt | tccgacaga  | agtgcgttac | 1140 |
| accggagcat | cgttctctta | caactagcg  | tcgattctcg | gggcttccgt | tgcgccatat | 1200 |
| atcgcagcct | ggttgcagac | taactacggg | ctaggtgcgg | tggggttata | tctggcggcg | 1260 |
| atggctggct | tgacgttaat | cgccctgctg | ctgacccatg | agacgcgaca | tcagtcgttg | 1320 |
| taa        |            |            |            |            |            | 1323 |

<210> SEQ ID NO 27
<211> LENGTH: 410
<212> TYPE: PRT
<213> ORGANISM: Enterococcus gallinarum

<400> SEQUENCE: 27

| Met | His | Gly | Trp | Thr | Ser | Arg | Gln | Arg | Asn | Ala | Ala | Ile | Ala | Ser | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Leu Ser Trp Thr Leu Asp Ala Phe Asp Phe Leu Leu Val Phe Leu
            20                  25                  30

Leu Ser Asp Ile Ala His Ser Phe His Val Asp Leu Glu Glu Val Thr
            35                  40                  45

Leu Ala Ile Leu Leu Thr Leu Ala Val Arg Pro Val Gly Ala Leu Ile
50                      55                  60

Phe Gly Arg Ala Ala Glu Lys Phe Gly Arg Lys Pro Ile Leu Met Leu
65                  70                  75                  80

Asn Ile Val Phe Phe Ser Ala Phe Glu Leu Leu Ser Ala Ala Pro
                85                  90                  95

Ser Leu Met Leu Phe Phe Leu Leu Arg Val Leu Tyr Gly Val Ala Met
            100                 105                 110

Gly Gly Ile Trp Gly Val Ala Ser Ser Leu Ala Met Glu Thr Ile Pro
            115                 120                 125

Asp Arg Ser Arg Gly Leu Met Ser Gly Leu Phe Gln Ala Gly Tyr Pro
130                     135                 140

Phe Gly Tyr Leu Leu Ala Ala Val Ala Tyr Gly Leu Leu Phe Glu Gln
145                     150                 155                 160

Leu Gly Trp Arg Gly Met Phe Val Ile Gly Ala Ala Pro Val Leu Leu
                165                 170                 175

Leu Pro Phe Ile Tyr Phe Cys Val Glu Glu Ser Pro Val Trp Gln Ala
            180                 185                 190

Ala Arg Gln Asn Lys Glu Ser Thr Ala Leu Leu Pro Val Leu Arg Ser
            195                 200                 205

His Trp Lys Leu Cys Leu Tyr Leu Val Val Leu Met Ala Ala Phe Asn
            210                 215                 220

Phe Phe Ser His Gly Thr Gln Asp Leu Tyr Pro Val Phe Leu Lys Val
225                     230                 235                 240

Gln His Gly Phe Glu Pro Lys Thr Val Ser Ile Ile Ala Val Cys Tyr
                245                 250                 255

Asn Ile Ala Ser Ile Ile Gly Val Phe Phe Gly Ser Leu Ser Glu
            260                 265                 270

Lys Ile Gly Arg Arg Lys Ala Ile Met Ile Ala Ala Met Leu Ala Leu
            275                 280                 285

Pro Val Ile Pro Leu Trp Ala Phe Ala Ser Gly Ser Leu Ala Leu Gly
            290                 295                 300

Ala Gly Ala Phe Leu Met Gln Phe Met Val Gln Gly Ala Trp Gly Val
305                     310                 315                 320

Ile Pro Thr Trp Leu Asn Glu Leu Val Pro Ala Asn Thr Arg Ala Val
                325                 330                 335

Leu Pro Gly Phe Val Tyr Gln Leu Gly Asn Leu Leu Ala Ser Val Asn
            340                 345                 350

Ala Thr Leu Gln Ala Ser Ile Ala Gln His His Gly His Asn Tyr Gly
            355                 360                 365

Leu Ala Met Ala Leu Val Ala Gly Thr Val Ala Ile Val Ile Thr Val
            370                 375                 380

Leu Thr Phe Phe Gly Arg Glu Gly Arg Val Ile Gln Ser Ala Gly Ala
385                     390                 395                 400

Gly His His Gln Pro Leu Ser Thr Ser Arg
                405                 410

<210> SEQ ID NO 28
<211> LENGTH: 1233

<212> TYPE: DNA
<213> ORGANISM: Enterococcus gallinarum

<400> SEQUENCE: 28

```
atgcacggct ggacctcacg acagcgtaat gcggcgatag ccagttttt aagctggacg      60
ctcgatgctt tcgactttt cctgttagtt tttttactga gcgatatcgc ccactcgttt     120
catgtcgacc ttgaggaggt cactctggcg attctgctga ctctggccgt gcggcccgtc    180
ggcgcgctaa ttttcggcag gcggcggag aagtttggtc gcaaaccaat cctgatgctc     240
aacattgtgt tcttctcggc ttttgagctg ctctccgccg ccgcgccgtc gttgatgctg    300
tttttcctgc tgcgggtgct gtacggcgtg gcgatgggcg ggatctgggg cgtggcctct    360
tcgctggcga tggagacgat ccccgaccgc tcgcgcggcc tgatgtccgg cctgttccag    420
gcgggatacc ccttcggcta tttgctggcg gccgtcgcct acgggctgct gtttgaacaa    480
ctcggctggc gcgggatgtt tgtcattggc gccgcgccgg tgcttctgct gccgtttatc    540
tatttctgcg tcgaggagtc tccggtttgg caggcggcca gcagaataa agagagtacg     600
gccctgctgc cggtactgcg tagccactgg aagctgtgcc tgtacctggt ggtgctgatg    660
gcggctttca acttcttctc tcacgggacg caggatcttt accggtcttt tttgaaagtt    720
cagcacggct tcgagcctaa aacggtcagc atcatcgcgg tctgctataa catcgcctcg    780
atcattggtg gagtgttctt cggttcgctg tcggagaaga ttggccgacg caaagcgatt    840
atgatcgccg ccatgctggc gctgccggtc attccactgt gggctttcgc cagcggctcg    900
ctggcgctgg gggcggggc gttcctgatg cagtttatgg tccagggggc ctgggggtg     960
atccccacct ggctcaatga actggtcccg gccaacaccc gggcggtgct gcccggcttc   1020
gtctaccagc tgggtaattt gctggcttcg gtgaatgcca ctctccaggc atcaatcgcc   1080
cagcatcatg ggcataacta cggcctggca atggccctgg tggccgggac ggtggcgatt   1140
gtcattaccg tcctgacctt ttttggtcgc gaaggccggg tgatccaatc cgcaggagcg   1200
ggacatcacc agccgctctc caccagccgt taa                               1233
```

<210> SEQ ID NO 29
<211> LENGTH: 419
<212> TYPE: PRT
<213> ORGANISM: Desulfosporosinus youngiae

<400> SEQUENCE: 29

```
Met Ala Glu Leu Ser Tyr Asn Gln Lys Ile Ile Ala Asp Pro Leu Lys
1               5                   10                  15

Tyr Lys Tyr Lys Ala Leu Thr Gly Ala Ile Leu Gly Tyr Met Phe Asp
                20                  25                  30

Ala Gln Asp Phe Met Val Leu Ala Leu Val Ile Pro Leu Leu Val Lys
            35                  40                  45

Thr Trp Gly Ile Ser Leu Ala Ser Ala Gly Leu Ile Ser Thr Ala Thr
        50                  55                  60

Ile Phe Gly Ala Ala Leu Ser Gly Tyr Leu Trp Gly Pro Met Ile Asp
65                  70                  75                  80

Lys Phe Gly Arg Lys Lys Met Leu Ile Leu Cys Leu Ala Trp Phe Gly
                85                  90                  95

Ile Phe Thr Phe Leu Cys Gly Phe Ala Thr Asn Tyr Thr Gln Leu Ile
                100                 105                 110

Leu Leu Arg Phe Ile Ala Gly Ile Gly Leu Gly Gly Glu Trp Val Ile
            115                 120                 125
```

```
Gly Ala Ala Leu Ile Ser Glu Phe Phe Pro Pro Glu Gln Arg Ala Arg
    130                 135                 140

Ala Thr Ser Ala Val Gln Ser Gly Trp Pro Leu Gly Tyr Ala Leu Ala
145                 150                 155                 160

Leu Gly Val Asn Ala Tyr Leu Val Pro Thr Tyr Gly Trp Gln Ile Leu
                165                 170                 175

Phe Phe Ser Gly Ile Leu Ser Leu Ile Ala Ala Val Tyr Ile Ala Val
            180                 185                 190

Phe Val Pro Glu Ser Pro Ala Trp Leu Lys Ala Gln Ile Asn Lys Ser
        195                 200                 205

Gln Gly Lys Glu Ser Val Ser Lys Ala Glu Val Lys Ala Ala Thr Trp
    210                 215                 220

Thr Asp Leu Leu Lys Gly Ala Asn Leu Lys Thr Thr Leu Leu Ala Phe
225                 230                 235                 240

Gly Leu Cys Ala Ser Cys Leu Val Ser Tyr Trp Gly Ala Gly Ser Trp
                245                 250                 255

Ile Pro Ala Tyr Leu Ser Ala Glu Arg Gly Leu Asn Val Lys Asp Met
            260                 265                 270

Ser Gly Tyr Leu Met Ile Leu Asn Val Gly Gly Phe Ile Gly Tyr Tyr
        275                 280                 285

Val Tyr Gly Tyr Phe Ala Asp Lys Val Gly Arg Arg Ala Asn Phe Ile
    290                 295                 300

Phe Gly Ser Leu Ala Ser Ala Ala Val Met Leu Ile Trp Ile Asn Leu
305                 310                 315                 320

Ser Ser Pro Thr Ala Ile Leu Trp Met Ala Gly Val Phe Gly Phe Ile
                325                 330                 335

Thr Tyr Gly Tyr Trp Gly Pro Leu Ala Ala Phe Val Ser Glu Gln Phe
            340                 345                 350

Pro Thr Asn Val Arg Gly Ile Gly Thr Ala Phe Ala Tyr Ala Ser Gly
        355                 360                 365

Arg Met Met Ser Ala Leu Ala Pro Phe Leu Met Gly Gly Ile Ala Ser
    370                 375                 380

Lys Tyr Ser Leu Gly Phe Ala Leu Gly Leu Val Ser Val Ile Tyr Ala
385                 390                 395                 400

Ala Gly Ala Ile Phe Gly Tyr Phe Met Lys Glu Thr Lys Asp Ile Ile
                405                 410                 415

Ile Val Asp

<210> SEQ ID NO 30
<211> LENGTH: 1260
<212> TYPE: DNA
<213> ORGANISM: Desulfosporosinus youngiae

<400> SEQUENCE: 30
atggcggaat tatcctataa ccaaaaaata atagctgatc ctcttaagta taagtataag     60
gccttaaccg gtgccatatt gggttatatg ttcgatgctc aagactttat ggttctggcc    120
ctggttattc ctttgctggt aaaaacctgg ggcattagtt tagccagtgc cgggttaata    180
agtacagcga ctatctttgg cgcggcctta agcggctatc tttggggacc aatgatcgat    240
aaatttggac gcaagaagat gctgatcctg tgtctggcct ggtttggtat tttcaccttc    300
ttgtgtggat tcgcgacaaa ttatacgcaa ttaatcttat taagatttat agccggtata    360
gggctggggg gagaatgggt tattggtgcg gctttaatca gtgaattctt ccctcctgaa    420
caaagggctc gggctacttc ggcagtgcag agcggctggc cctgggcta tgctctggct     480
```

-continued

```
cttggcgtaa atgcctattt ggttccaacc tatggttggc agatcctttt ctttcagga    540 attctttctt tgattgcagc agtctatatc gctgtatttg ttccggagtc accagcctgg    600
ttaaaagccc aaatcaacaa aagtcaaggc aagaatctg tctccaaagc ggaggttaag    660
gcggcaacct ggactgatct gctcaaagga gccaacctga aaccaccctt attggctttc    720
ggactttgcg caagctgtct ggtctcttac tggggagcgg gatcgtggat tccggcctac    780 cttcggcag aacggggcct gaatgtaaaa gacatgagcg ttatttgat gattttaaat    840 gtgggggct ttatcggtta ttatgtttat ggatattttg cggataaagt cggacgtcgg    900
gcaaacttta tttttggatc actggcctcg gcggcagtta tgctgatctg atcaacctc    960 agcagcccaa cagctatctt gtggatggca ggggtatttg gttttataac ctacggctat   1020
tggggaccac tggcagcctt tgtttctgaa caatttccca ccaatgtgcg cgggatcgga   1080
acagcttttg cctatgccag cggcagaatg atgtccgcct agctcctttt tttgatgggt   1140
ggcattgcca gcaaatacag cctgggtttt gccttgggat tagtatccgt gatctatgcg   1200
gcaggtgcaa tcttcggata ctttatgaaa gaaacgaaag atatcattat agttgactag   1260
```

<210> SEQ ID NO 31
<211> LENGTH: 410
<212> TYPE: PRT
<213> ORGANISM: Klebsiella pneumoniae

<400> SEQUENCE: 31

```
Met His Gly Trp Thr Ser Arg Gln Arg Asn Ala Ala Ile Ala Ser Phe
1               5                   10                  15

Leu Ser Trp Thr Leu Asp Ala Phe Asp Phe Phe Leu Leu Val Phe Leu
            20                  25                  30

Leu Ser Asp Ile Ala His Ser Phe His Val Asp Leu Glu Glu Val Thr
        35                  40                  45

Leu Ala Ile Leu Leu Thr Leu Ala Val Arg Pro Val Gly Ala Leu Ile
    50                  55                  60

Phe Gly Arg Ala Ala Glu Lys Phe Gly Arg Lys Pro Ile Leu Met Leu
65                  70                  75                  80

Asn Ile Val Phe Phe Ser Ala Phe Glu Leu Leu Ser Ala Ala Ala Pro
                85                  90                  95

Ser Leu Met Leu Phe Phe Leu Leu Arg Val Leu Tyr Gly Val Ala Met
            100                 105                 110

Gly Gly Ile Trp Gly Val Ala Ser Ser Leu Ala Met Glu Thr Ile Pro
        115                 120                 125

Asp Arg Ser Arg Gly Leu Met Ser Gly Leu Phe Gln Ala Gly Tyr Pro
    130                 135                 140

Phe Gly Tyr Leu Leu Ala Ala Val Ala Tyr Gly Leu Phe Phe Glu Gln
145                 150                 155                 160

Leu Gly Trp Arg Gly Met Phe Val Ile Gly Ala Ala Pro Val Leu Leu
                165                 170                 175

Leu Pro Phe Ile Tyr Phe Cys Val Glu Glu Ser Pro Val Trp Gln Ala
            180                 185                 190

Ala Arg Gln Asn Lys Glu Ser Thr Ser Leu Leu Pro Val Leu Arg Ser
        195                 200                 205

His Trp Lys Leu Cys Leu Tyr Leu Val Val Leu Met Ala Ala Phe Asn
    210                 215                 220

Phe Phe Ser His Gly Thr Gln Asp Leu Tyr Pro Val Phe Leu Lys Val
225                 230                 235                 240
```

Gln His Gly Phe Glu Pro Lys Thr Val Ser Ile Ile Ala Val Cys Tyr
                245                 250                 255

Asn Ile Ala Ser Ile Ile Gly Gly Val Phe Phe Gly Ser Leu Ser Glu
            260                 265                 270

Lys Ile Gly Arg Arg Lys Ala Ile Met Ile Ala Ala Leu Leu Ala Leu
            275                 280                 285

Pro Val Ile Pro Leu Trp Ala Phe Ala Ser Gly Ser Leu Ala Leu Gly
        290                 295                 300

Ala Gly Ala Phe Leu Met Gln Phe Met Val Gln Gly Ala Trp Gly Val
305                 310                 315                 320

Ile Pro Thr Trp Leu Asn Glu Leu Val Pro Ala Asn Thr Arg Ala Val
                325                 330                 335

Leu Pro Gly Phe Val Tyr Gln Leu Gly Asn Leu Leu Ala Ser Val Asn
            340                 345                 350

Ala Thr Leu Gln Ala Ser Ile Ala Gln His His Gly His Asn Tyr Gly
            355                 360                 365

Leu Ala Met Ala Leu Val Ala Gly Thr Val Ala Ile Val Ile Thr Val
        370                 375                 380

Leu Thr Phe Phe Gly Arg Glu Gly Arg Val Ile Gln Ser Ala Gly Ala
385                 390                 395                 400

Gly His His Gln Pro Leu Ser Thr Ser Arg
                405                 410

<210> SEQ ID NO 32
<211> LENGTH: 1233
<212> TYPE: DNA
<213> ORGANISM: Klebsiella pneumoniae

<400> SEQUENCE: 32
atgcacggct ggacctcacg acagcgtaat gcggcgatag ccagtttttt aagctggacg     60
ctcgatgctt tcgactttt cctgttagtt ttttactga gcgatatcgc ccactcgttt     120
catgtcgacc ttgaggaggt caccctggcg attctgctga ctctggccgt gcggcccgtc    180
ggcgcgctaa ttttcggcag gcggcggag aagtttggtc gcaaaccaat cctgatgctc     240
aatattgtgt tcttctcggc ttttgagctg ctctccgccg ccgcgccgtc gttgatgctg    300
ttttcctgc tgcgggtgct gtacggcgtg gcgatgggcg ggatctgggg cgtgccctct    360
tcgctggcga tggagacgat ccccgaccgc tcgcgcggcc tgatgtccgg cctgttccag    420
gcgggatacc ccttcggcta tttgctggcg gccgtcgcct atgggctgtt ttttgaacaa    480
ctcggctggc gcgggatgtt tgtcattggc gccgcgccgg tgctgctgct gccgtttatc    540
tatttctgcg tcgaggagtc tccggtttgg caggcggcca gcagaataa agagagtacg     600
tccctgctgc cggtactgcg tagccactgg aagctgtgcc tgtacctggt ggtgttgatg    660
gcggctttca acttcttctc ccacgggacg caggatcttt acccggtctt tttgaaagtt    720
cagcacggct tcgagcctaa aacggtcagc atcatcgcgg tctgctataa catcgcctcg    780
atcattggtg gagtgttctt cggttcgctg tcggagaaga ttggccgacg caaagcgatt    840
atgatcgccg ccctgctggc gctgccggtc attccactgt gggctttcgc cagcggctcg    900
ctggcgctgg gggcgggggc gttcctgatg cagtttatgg tccaggggc ctgggggtg     960
atccccacct ggctcaatga actggtcccg gccaacaccc gggcggtgct gccggcttc    1020
gtctaccagc tgggtaattt gctggcttcg gtgaatgcca ctctccaggc atcaatcgcc   1080
cagcatcatg gcataacta cggcctggca atggccctgg tggccgggac ggtggcgatt   1140

-continued

```
gtcattaccg tcctgacctt ttttggtcgc gaaggccggg tgatccaatc cgcaggagcg      1200
ggacatcacc agccgctctc caccagccgt taa                                  1233
```

<210> SEQ ID NO 33
<211> LENGTH: 405
<212> TYPE: PRT
<213> ORGANISM: Escherichia coli

<400> SEQUENCE: 33

```
Met Ala Thr Ala Trp Tyr Lys Gln Val Asn Pro Pro Gln Arg Lys Ala
1               5                   10                  15

Leu Phe Ser Ala Trp Leu Gly Tyr Val Phe Asp Gly Phe Asp Phe Met
            20                  25                  30

Met Ile Phe Tyr Ile Leu His Ile Ile Lys Ala Asp Leu Gly Ile Thr
        35                  40                  45

Asp Ile Gln Ala Thr Leu Ile Gly Thr Val Ala Phe Ile Ala Arg Pro
    50                  55                  60

Ile Gly Gly Gly Phe Phe Gly Ala Met Ala Asp Lys Tyr Gly Arg Lys
65                  70                  75                  80

Pro Met Met Met Trp Ala Ile Phe Ile Tyr Ser Val Gly Thr Gly Leu
                85                  90                  95

Ser Gly Ile Ala Thr Asn Leu Tyr Met Leu Ala Val Cys Arg Phe Ile
            100                 105                 110

Val Gly Leu Gly Met Ser Gly Glu Tyr Ala Cys Ala Ser Thr Tyr Ala
        115                 120                 125

Val Glu Ser Trp Pro Lys Asn Leu Gln Ser Lys Ala Ser Ala Phe Leu
    130                 135                 140

Val Ser Gly Phe Ser Val Gly Asn Ile Ile Ala Ala Gln Ile Ile Pro
145                 150                 155                 160

Gln Phe Ala Glu Val Tyr Gly Trp Arg Asn Ser Phe Phe Ile Gly Leu
                165                 170                 175

Leu Pro Val Leu Leu Val Leu Trp Ile Arg Lys Ser Ala Pro Glu Ser
            180                 185                 190

Gln Glu Trp Ile Glu Asp Lys Tyr Lys Asp Lys Ser Thr Phe Leu Ser
        195                 200                 205

Val Phe Arg Lys Pro His Leu Ser Ile Ser Met Ile Val Phe Leu Val
    210                 215                 220

Cys Phe Cys Leu Phe Gly Ala Asn Trp Pro Ile Asn Gly Leu Leu Pro
225                 230                 235                 240

Ser Tyr Leu Ala Asp Asn Gly Val Asn Thr Val Val Ile Ser Thr Leu
                245                 250                 255

Met Thr Ile Ala Gly Leu Gly Thr Leu Thr Gly Thr Ile Phe Phe Gly
            260                 265                 270

Phe Val Gly Asp Lys Ile Gly Val Lys Lys Ala Phe Val Val Gly Leu
        275                 280                 285

Ile Thr Ser Phe Ile Phe Leu Cys Pro Leu Phe Phe Ile Ser Val Lys
    290                 295                 300

Asn Ser Ser Leu Ile Gly Leu Cys Leu Phe Gly Leu Met Phe Thr Asn
305                 310                 315                 320

Leu Gly Ile Ala Gly Leu Val Pro Lys Phe Ile Tyr Asp Tyr Phe Pro
                325                 330                 335

Thr Lys Leu Arg Gly Leu Gly Thr Gly Leu Ile Tyr Asn Leu Gly Ala
            340                 345                 350
```

Thr Gly Gly Met Ala Ala Pro Val Leu Ala Thr Tyr Ile Ser Gly Tyr
        355                 360                 365

Tyr Gly Leu Gly Val Ser Leu Phe Ile Val Thr Val Ala Phe Ser Ala
    370                 375                 380

Leu Leu Ile Leu Leu Val Gly Phe Asp Ile Pro Gly Lys Ile Tyr Lys
385                 390                 395                 400

Leu Ser Val Ala Lys
            405

<210> SEQ ID NO 34
<211> LENGTH: 1218
<212> TYPE: DNA
<213> ORGANISM: Escherichia coli

<400> SEQUENCE: 34

| | | | | |
|---|---|---|---|---|
| atggcaacag catggtataa acaagttaat ccaccacaac ggaaagctct tttttccgca | | | | 60 |
| tggcttggat atgtatttga tggctttgat tttatgatga tattttacat tcttcatatt | | | | 120 |
| ataaaagcag atcttggcat tacgatatt caggctactt taatagggac agtggccttc | | | | 180 |
| atagccagac ctattggagg tggttttttt ggtgccatgg ctgataaata tggtcgtaag | | | | 240 |
| ccaatgatga tgtgggcaat tttcatttac tcagtcggaa caggccttag cggtattgct | | | | 300 |
| acaaacttat atatgctcgc agtttgccgt tttattgttg cttagggat gtctggtgaa | | | | 360 |
| tatgcatgtg cttcaactta tgcggtagaa agttggccta aaaatcttca atctaaagct | | | | 420 |
| agtgctttt tggtaagtgg ttttttctgtt ggaaatatta ttgcggcaca aataatccct | | | | 480 |
| cagtttgctg aagtatatgg atggagaaac tcttttttta taggcctgtt accagtttta | | | | 540 |
| ctagttcttt ggatcagaaa aagtgctcca gaaagtcagg agtggattga agataaatat | | | | 600 |
| aaggataaat caacattttt gtctgtcttc agaaaaccac atctttcaat ctctatgatc | | | | 660 |
| gttttcctcg tctgtttttg tctatttggt gcaaactggc cgataaacgg actacttcct | | | | 720 |
| tcctacctgg cagataatgg agttaataca gtggtcattt caactctgat gacaatagca | | | | 780 |
| ggtttaggaa cactgacagg tacaatattt tttggttttg ttggtgataa gattggtgta | | | | 840 |
| aaaaaagcct ttgtagtcgg tctaataact tcatttattt tcctttgtcc tctttttttt | | | | 900 |
| atttctgtga aaaactcttc tcttatagga ttatgtctct ttggattaat gtttacaaat | | | | 960 |
| ttaggtattg cagggttggt tccaaaattt atatatgatt actttccaac aaaattaaga | | | | 1020 |
| ggattaggga ccggtcttat ttataactta ggggcaactg gaggaatggc cgcacctgta | | | | 1080 |
| ttagctacat acatttcagg atattatggc ttaggtgttt cattattcat tgttacggtt | | | | 1140 |
| gcattctctg ccttattaat tttgttagtt ggttttgata ttccaggtaa aatttataaa | | | | 1200 |
| ctatccgtgg ctaaatga | | | | 1218 |

<210> SEQ ID NO 35
<211> LENGTH: 405
<212> TYPE: PRT
<213> ORGANISM: Klebsiella pneumoniae

<400> SEQUENCE: 35

Met Ala Thr Ala Trp Tyr Lys Gln Val Asn Pro Pro Gln Arg Lys Ala
1               5                   10                  15

Leu Phe Ser Ala Trp Leu Gly Tyr Val Phe Asp Gly Phe Asp Phe Met
            20                  25                  30

Met Ile Phe Tyr Ile Leu His Ile Ile Lys Ala Asp Leu Gly Ile Thr
        35                  40                  45

-continued

```
Asp Ile Gln Ala Thr Leu Ile Gly Thr Val Ala Phe Ile Ala Arg Pro
 50                  55                  60
Ile Gly Gly Phe Phe Gly Ala Met Ala Asp Lys Tyr Gly Arg Lys
 65                  70                  75                  80
Pro Met Met Met Trp Ala Ile Phe Ile Tyr Ser Val Gly Thr Gly Leu
                     85                  90                  95
Ser Gly Ile Ala Thr Asn Leu Tyr Met Leu Ala Val Cys Arg Phe Ile
                100                 105                 110
Val Gly Leu Gly Met Ser Gly Glu Tyr Ala Cys Ala Ser Thr Tyr Ala
                115                 120                 125
Val Glu Ser Trp Pro Lys Asn Leu Gln Ser Lys Ala Ser Ala Phe Leu
130                 135                 140
Val Ser Gly Phe Ser Val Gly Asn Ile Ile Ala Ala Gln Ile Ile Pro
145                 150                 155                 160
Gln Phe Ala Glu Val Tyr Gly Trp Arg Asn Ser Phe Phe Ile Gly Leu
                165                 170                 175
Leu Pro Val Leu Leu Val Leu Trp Ile Arg Lys Ser Ala Pro Glu Ser
                180                 185                 190
Gln Glu Trp Ile Glu Asp Lys Tyr Lys Asp Lys Ser Thr Phe Leu Ser
                195                 200                 205
Val Phe Arg Lys Pro His Leu Ser Ile Ser Met Ile Val Phe Leu Val
210                 215                 220
Cys Phe Cys Leu Phe Gly Ala Asn Trp Pro Ile Asn Gly Leu Leu Pro
225                 230                 235                 240
Ser Tyr Leu Ala Asp Asn Gly Val Asn Thr Val Ile Ser Thr Leu
                245                 250                 255
Met Thr Ile Ala Gly Leu Gly Thr Leu Thr Gly Thr Ile Phe Phe Gly
                260                 265                 270
Phe Val Gly Asp Lys Ile Gly Val Lys Lys Ala Phe Val Val Gly Leu
                275                 280                 285
Ile Thr Ser Phe Ile Phe Leu Cys Pro Leu Phe Phe Ile Ser Val Lys
                290                 295                 300
Asn Ser Ser Leu Ile Gly Leu Cys Leu Phe Gly Leu Met Phe Thr Asn
305                 310                 315                 320
Leu Gly Ile Ala Gly Leu Val Pro Lys Phe Ile Tyr Asp Tyr Phe Pro
                325                 330                 335
Thr Lys Leu Arg Gly Leu Gly Thr Gly Leu Ile Tyr Asn Leu Gly Ala
                340                 345                 350
Thr Gly Gly Met Ala Ala Pro Val Leu Ala Thr Tyr Ile Ser Gly Tyr
                355                 360                 365
Tyr Gly Leu Gly Val Ser Leu Phe Ile Val Thr Val Ala Phe Ser Ala
                370                 375                 380
Leu Leu Ile Leu Leu Val Gly Phe Asp Ile Pro Gly Lys Ile Tyr Lys
385                 390                 395                 400
Leu Ser Val Ala Lys
                405
```

<210> SEQ ID NO 36
<211> LENGTH: 1218
<212> TYPE: DNA
<213> ORGANISM: Klebsiella pneumoniae

<400> SEQUENCE: 36
atggcaacag catggtataa acaagttaat ccaccacaac ggaaagctct tttttccgca    60

```
tggcttggat atgtatttga tggctttgat tttatgatga tattttacat tcttcatatt    120
ataaaagcag atcttggcat tacgatatt caggctactt taataggggac agtggccttc    180 atagccagac ctattggagg tggttttttt ggtgccatgg ctgataaata tggtcgtaag    240
ccaatgatga tgtgggcaat tttcatttac tcagtcggaa caggccttag cggtattgct    300
acaaacttat atatgctcgc agtttgccgt tttattgttg gcttagggat gtctggtgaa    360
tatgcatgtg cttcaactta tgcggtagaa agttggccta aaatcttca atctaaagct    420 agtgcttttt tggtaagtgg ttttttctgtt ggaaatatta ttgcggcaca ataatccct    480 cagtttgctg aagtatatgg atggagaaac tctttttta taggcctgtt accagtttta    540
ctagttcttt ggatcagaaa agtgctcca gaaagtcagg agtggattga agataaatat    600
aaggataaat caacatttt gtctgtcttc agaaaccac atctttcaat ctctatgatc       660
gttttcctcg tctgttttg tctatttggt gcaaactggc cgataaacgg actacttcct    720
tcctacctgg cagataatgg agttaataca gtggtcattt caactctgat gacaatagca    780
ggtttaggaa cactgacagg tacaatattt tttggttttg ttggtgataa gattggtgta    840
aaaaaagcct ttgtagtcgg tctaataact tcatttattt tcctttgtcc tcttttttt     900 atttctgtga aaaactcttc tcttatagga ttatgtctct ttggattaat gtttacaaat    960
ttaggtattg cagggttggt tccaaaattt atatatgatt acttttccaac aaaattaaga   1020 ggattaggga ccggtcttat ttataactta ggggcaactg gaggaatggc cgcacctgta    1080
ttagctacat acatttcagg atattatggc ttaggtgttt cattattcat tgttacggtt    1140
gcattctctg ccttattaat tttgttagtt ggttttgata ttccaggtaa aatttataaa    1200
ctatccgtgg ctaaatga                                                  1218
```

<210> SEQ ID NO 37
<211> LENGTH: 426
<212> TYPE: PRT
<213> ORGANISM: Salmonella enterica subsp. Enterica

<400> SEQUENCE: 37

```
Met Ile Ala Lys Phe Phe Pro Trp Tyr Ser Glu Ile Thr Arg Pro Gln
1               5                   10                  15

Lys Asn Ala Leu Phe Ser Ala Trp Leu Gly Tyr Val Phe Asp Gly Phe
            20                  25                  30

Asp Phe Met Leu Ile Phe Tyr Ile Met Tyr Leu Ile Lys Ala Asp Leu
        35                  40                  45

Gly Leu Thr Asp Met Glu Gly Ala Phe Leu Ala Thr Ala Ala Phe Ile
    50                  55                  60

Gly Arg Pro Phe Gly Gly Ala Leu Phe Gly Leu Leu Ala Asp Lys Phe
65                  70                  75                  80

Gly Arg Lys Pro Leu Met Met Trp Ser Ile Val Ala Tyr Ser Val Gly
                85                  90                  95

Thr Gly Leu Ser Gly Leu Ala Ser Gly Val Ile Met Leu Thr Leu Ser
            100                 105                 110

Arg Phe Ile Val Gly Met Gly Met Ala Gly Glu Tyr Ala Cys Ala Ser
        115                 120                 125

Thr Tyr Ala Val Glu Ser Trp Pro Lys His Leu Lys Ser Lys Ala Ser
    130                 135                 140

Ala Phe Leu Val Ser Gly Phe Gly Ile Gly Asn Ile Ile Ala Ala Tyr
145                 150                 155                 160

Phe Met Pro Ser Phe Ala Glu Ala Tyr Gly Trp Arg Ala Ala Phe Phe
```

```
                    165                 170                 175
Val Gly Leu Leu Pro Val Leu Val Ile Tyr Ile Arg Ala Arg Ala
                180                 185                 190

Pro Glu Ser Lys Glu Trp Glu Ala Lys Leu Ser Gly Leu Gly Lys
            195                 200                 205

His Ser Gln Ser Ala Trp Ser Val Phe Ser Leu Ser Met Lys Gly Leu
        210                 215                 220

Phe Asn Arg Ala Gln Phe Pro Leu Thr Leu Cys Val Phe Ile Val Leu
225                 230                 235                 240

Phe Ser Ile Phe Gly Ala Asn Trp Pro Ile Phe Gly Leu Leu Pro Thr
                245                 250                 255

Tyr Leu Ala Gly Glu Gly Phe Asp Thr Gly Val Val Ser Asn Leu Met
                260                 265                 270

Thr Ala Ala Ala Phe Gly Thr Val Leu Gly Asn Ile Val Trp Gly Leu
                275                 280                 285

Cys Ala Asp Arg Ile Gly Leu Lys Lys Thr Phe Ser Ile Gly Leu Leu
            290                 295                 300

Met Ser Phe Leu Phe Ile Phe Pro Leu Phe Arg Ile Pro Gln Asp Asn
305                 310                 315                 320

Tyr Leu Leu Leu Gly Ala Cys Leu Phe Gly Leu Met Ala Thr Asn Val
                325                 330                 335

Gly Val Gly Gly Leu Val Pro Lys Phe Leu Tyr Asp Tyr Phe Pro Leu
            340                 345                 350

Glu Val Arg Gly Leu Gly Thr Gly Leu Ile Tyr Asn Leu Ala Ala Thr
                355                 360                 365

Ser Gly Thr Phe Asn Ser Met Ala Ala Thr Trp Leu Gly Ile Thr Met
        370                 375                 380

Gly Leu Gly Val Ala Leu Thr Phe Ile Val Ala Phe Trp Thr Ala Thr
385                 390                 395                 400

Ile Leu Leu Ile Ile Gly Leu Ser Ile Pro Asp Arg Leu Lys Ala Arg
                405                 410                 415

Arg Glu Arg Phe Gln Ser Thr Lys Glu Phe
                420                 425

<210> SEQ ID NO 38
<211> LENGTH: 1281
<212> TYPE: DNA
<213> ORGANISM: Salmonella enterica subsp. Enterica

<400> SEQUENCE: 38
gtgatagcaa aattcttccc gtggtatagc gagataactc gtccacaaaa aaatgcttta      60
ttttcagcat ggctgggtta cgttttttgat ggcttcgact ttatgctgat tttctacatt    120
atgtatctga tcaaggctga cttaggattg acagatatgg agggcgcatt ccttgccaca    180
gcggccttta ttgggcgacc atttggcggg gcgctatttg gtctgctggc agataaattt    240
ggccgtaagc cgttaatgat gtggtcgata gttgcctatt ctgtaggtac agggttaagt    300
ggcctggctt ccggtgtaat tatgctgacg cttagtcgtt tcattgtcgg tatggggatg    360
gcgggggagt atgcttgcgc ttctacttat gccgtggaaa gttggccaaa gcatttaaaa    420
tctaaagcga gcgcatttct ggtttcaggt ttcggtattg taacatcat agcagcctat    480 tttatgccgt catttgccga agcgtatggt tggcgtgctg ctttttttgt cggtttgcta    540
cccgttcttt tagtaatcta catccggggcc agggctcctg aatctaaaga gtgggaagaa    600
gccaaactca gtggtctcgg aaagcactca caaagtgcct ggtcagtttt ctctttgtca    660
```

```
atgaaagggc tatttaatcg agctcaattt ccactgacat tatgtgtatt tattgttctg        720
ttctctattt tcggcgcaaa ctggccgatc tttggtctac tgcctacata tttggcggga        780
gagggctttg atacgggcgt ggtctctaat ttaatgacgg cggcggcatt cggcactgta        840
ttgggaaata tcgtttgggg tctgtgcgca gatagaattg gtttgaagaa aacgttcagc        900
attggtcttc tcatgtcctt tttattcatt ttcccgttat tcagaattcc gcaagataat        960
tatttactgc tgggcgcatg tttattcggt ttaatggcga ctaacgtagg tgttggcggg       1020
ctggttccca aatttctcta cgactacttt cctcttgagg ttcgtggttt gggtaccggg       1080
ctgatttaca atcttgctgc gacatcaggc acattcaatt caatggcggc gacctggctt       1140
ggaataacaa tgggactagg cgttgcgcta acgttcattg ttgctttctg gaccgcaaca       1200
attctactca ttattggctt atccattccg gataggctaa aagcacgtcg tgaaaggttt       1260
cagtcaacaa aagaattta a                                                  1281
```

<210> SEQ ID NO 39
<211> LENGTH: 496
<212> TYPE: PRT
<213> ORGANISM: Citrobacter freundii

<400> SEQUENCE: 39

```
Met Ser Thr Ser Thr Gln Ser Ile Pro Trp Tyr Arg His Leu Asn Arg
1               5                   10                  15

Ala Gln Trp Arg Ala Phe Ser Ala Ala Trp Leu Gly Tyr Leu Leu Asp
                20                  25                  30

Gly Phe Asp Phe Val Leu Ile Ala Leu Val Leu Thr Glu Val Gln Gly
            35                  40                  45

Glu Phe Gly Leu Thr Thr Val Gln Ala Ala Ser Leu Ile Ser Ala Ala
        50                  55                  60

Phe Ile Ser Arg Trp Phe Gly Gly Leu Met Leu Gly Ala Met Gly Asp
65                  70                  75                  80

Arg Tyr Gly Arg Arg Leu Ala Met Val Thr Ser Ile Ile Leu Phe Ser
                85                  90                  95

Val Gly Thr Leu Ala Cys Gly Phe Ala Pro Gly Tyr Thr Thr Met Phe
            100                 105                 110

Ile Ala Arg Leu Val Ile Gly Met Gly Met Ala Gly Glu Tyr Gly Ser
        115                 120                 125

Ser Ala Thr Tyr Val Ile Glu Ser Trp Pro Lys His Leu Arg Asn Lys
    130                 135                 140

Ala Ser Gly Phe Leu Ile Ser Gly Phe Ser Val Gly Ala Val Ile Ala
145                 150                 155                 160

Ala Gln Val Tyr Ser Leu Val Val Pro Val Trp Gly Trp Arg Ala Leu
                165                 170                 175

Phe Phe Ile Gly Ile Leu Pro Ile Ile Phe Ala Leu Trp Leu Arg Lys
            180                 185                 190

Asn Ile Pro Glu Ala Glu Asp Trp Lys Glu Lys His Glu Gly Lys Ala
        195                 200                 205

Pro Val Arg Thr Met Val Asp Ile Leu Tyr Arg Gly Glu His Arg Val
    210                 215                 220

Ile Asn Ile Leu Met Thr Leu Ala Ala Ala Thr Ala Leu Trp Phe Cys
225                 230                 235                 240

Phe Ala Gly Asp Leu Gln Asn Ala Ala Ile Val Ala Val Leu Gly Leu
                245                 250                 255
```

```
Ile Cys Ala Phe Ile Phe Ile Ser Phe Met Val Gln Ser Ser Gly Lys
                260                 265                 270

Arg Trp Pro Thr Gly Val Met Leu Met Val Val Leu Phe Ala Phe
            275                 280                 285

Leu Tyr Ser Trp Pro Ile Gln Ala Leu Leu Pro Thr Tyr Leu Lys Thr
        290                 295                 300

Glu Leu Leu Tyr Asp Pro Ser Thr Val Ala Arg Val Leu Phe Phe Ser
305                 310                 315                 320

Gly Phe Gly Ala Ala Val Gly Cys Cys Val Gly Phe Leu Gly Asp
                325                 330                 335

Trp Leu Gly Thr Arg Lys Ala Tyr Val Cys Ser Leu Leu Ala Ser Gln
                340                 345                 350

Leu Leu Ile Ile Pro Val Phe Ala Ile Gly Gly Ser Asn Val Trp Val
                355                 360                 365

Leu Gly Leu Leu Leu Phe Phe Gln Gln Met Leu Gly Gln Gly Ile Ser
                370                 375                 380

Gly Ile Leu Pro Lys Leu Ile Gly Gly Tyr Phe Asp Thr Asp Gln Arg
385                 390                 395                 400

Ala Ala Gly Leu Gly Phe Thr Tyr Asn Val Gly Ala Leu Gly Gly Ala
                405                 410                 415

Leu Ala Pro Ile Ile Gly Ala Leu Ile Ala Gln Arg Leu Asp Leu Gly
                420                 425                 430

Thr Ala Leu Gly Ser Leu Ser Phe Gly Leu Thr Phe Val Val Ile Leu
                435                 440                 445

Leu Ile Gly Leu Asp Met Pro Ser Arg Val Gln Arg Trp Leu Arg Pro
                450                 455                 460

Glu Ala Leu Arg Thr His Asp Ala Ile Asp Gly Arg Pro Phe Ser Gly
465                 470                 475                 480

Ala Val Pro Phe Gly Gly Asp Lys Ser Thr Met Val Lys Ser Lys Ser
                485                 490                 495

<210> SEQ ID NO 40
<211> LENGTH: 1491
<212> TYPE: DNA
<213> ORGANISM: Citrobacter freundii

<400> SEQUENCE: 40
atgagtactt ctacccagag catcccgtgg tatcgccatc tcaatcgggc acaatggcgg    60
gcattttccg ccgcctggct gggatatttg cttgatggtt tcgattttgt gttaatcgcc   120
ctggtgctga cagaagtgca gggcgaattc ggattgacga cggtgcaggc cgccagcctg   180
atctcggccg cctttatctc ccgttggttt ggcgggttaa tgctgggggc aatgggcgac   240
cgctacggac gccgcctggc aatggtcacc agcatcattc tgttctcggt gggaacgctg   300
gcctgcggtt tcgcgccggg ctacaccacc atgtttatcg cccgcctggt tatcggtatg   360
ggaatggcgg gtgagtacgg ctccagtgca acctatgtta ttgaaagttg gcctaaacac   420
ctgcgaaaca aagccagtgg tttcctgatt tcaggctttt ccgttggtgc cgtgatcgcc   480
gcccaggtct acagcctggt ggttccggtc tggggtggc gtgcgctgtt cttcatcggc   540
atcctgccaa ttatcttcgc cctctggctg cgtaaaaata ttccggaagc ggaagactgg   600
aaagagaaac acgaaggcaa agcgccagtg cgcacgatgg tggacattct ctaccggggc   660
gagcatcggg taattaatat tctgatgacg ctcgctgctg ccaccgcgct gtggttctgc   720
tttgcgggcg acctgcaaaa tgcggctatt gtggcggtcc tggggctgat atgcgcgttt   780
```

```
atcttcatta gctttatggt gcaaagcagc gggaaacgct ggccgacggg cgtcatgctg    840
atggtggttg tgctgtttgc cttcctgtac tcgtggccga ttcaggcgct gttgccaacc    900
tatctgaaaa ccgaactgct gtacgatcct tccacggtgg ccagggtgct cttctttagc    960
ggctttggtg cggcggtcgg ttgttgcgtc ggcggttttc ttggcgactg gctgggcacg   1020
cgtaaagcct atgtctgcag tctgctggcc tcgcagttgc tgattatacc ggtatttgcg   1080
ataggcggtt caaacgtctg ggtactgggt ttactgctgt ttttccagca aatgctcggc   1140
caggggatct ccgggatctt accaaaactg attggcggct atttcgatac cgatcagcgt   1200
gcggcgggac tgggcttcac ctataacgtg ggcgcactgg gcggggcgct ggcaccgatc   1260
atcggtgcgc tgattgccca acgtctggat ctgggtaccg cgctgggatc cctctctttc   1320
ggtctgacat ttgtagtgat cctgctgatt ggtcttgata tgccgtcccg tgtacagcgc   1380
tggctgcgtc ctgaagcgtt gcgtacgcat gatgccattg atggtcgacc gtttagcggt   1440
gccgtgccgt tcggtggtga caaaagcact atggtgaaat ccaaaagtta a            1491
```

<210> SEQ ID NO 41
<211> LENGTH: 451
<212> TYPE: PRT
<213> ORGANISM: Bacillus subtilis

<400> SEQUENCE: 41

```
Met Asn Thr Ile Phe Lys Gln Lys Asn Thr His Pro Phe Ser Asn Ala
1               5                   10                  15

Ala Asn Arg Leu Asp Arg Leu Pro Ile Ser Arg Val His Phe Gln Val
            20                  25                  30

Leu Thr Ala Leu Gly Ile Val Tyr Phe Phe Asp Leu Ala Asp Leu Phe
        35                  40                  45

Thr Leu Ser Asn Val Ala Pro Ala Leu Ile Glu His Trp Gly Ile Pro
    50                  55                  60

Leu Ser Thr Ile Ala Asn Val Thr Ala Ala Ser Phe Leu Gly Met Phe
65                  70                  75                  80

Leu Gly Ala Ser Leu Gly Gly Arg Leu Ser Asp Arg Ile Gly Arg Lys
                85                  90                  95

Lys Ala Leu Asn Leu Phe Val Phe Val Phe Ser Ile Ala Ser Leu Cys
            100                 105                 110

Asn Ala Ala Ala Trp Asp Ile Pro Ser Leu Met Thr Phe Arg Phe Leu
        115                 120                 125

Thr Gly Phe Gly Val Ala Ala Ala Met Val Ile Thr Asn Ser Tyr Leu
    130                 135                 140

Ala Glu Phe Phe Pro Ser Ser Val Arg Gly Lys Tyr Ile Ser Phe Cys
145                 150                 155                 160

Ala Met Ile Gly Leu Ile Gly Val Pro Ile Thr Asn Ile Val Ser Ala
                165                 170                 175

Phe Val Ile Pro Leu Gly Ser Trp Gly Trp Arg Leu Val Phe Val Trp
            180                 185                 190

Gly Ala Val Gly Leu Ile Tyr Phe Phe Ile His Arg Leu Glu Glu
        195                 200                 205

Ser Pro Arg Trp His Glu Asn Arg Gly Glu Tyr Ala Lys Ala Asp Ala
    210                 215                 220

Ile Leu Thr Arg Ile Glu Glu Gln Val Glu Lys Glu Lys Gly Pro Leu
225                 230                 235                 240

Pro Ala Ala Ser Gln Pro Lys Val Ser Glu Thr Val Lys Gln Asn Ala
                245                 250                 255
```

Gly Tyr Ala Gly Leu Leu Lys Gly Arg Asn Leu Lys Ile Thr Ile Val
            260                 265                 270

Leu Ser Ala Val Trp Ile Phe Glu Thr Gly Phe Tyr Gly Phe Ala
        275                 280                 285

Ser Trp Val Pro Ser Leu Leu Lys Ser Asn Gly Val Thr Met Glu Asn
    290                 295                 300

Thr Leu Trp Tyr Asn Val Leu His Ser Val Gly Ala Pro Leu Gly Ala
305                 310                 315                 320

Leu Leu Gly Ser Met Ile Ser Glu Arg Phe Gln Arg Lys Trp Ile Leu
                325                 330                 335

Ala Ala Ser Ala Phe Leu Thr Ala Ile Ala Gly Leu Leu Tyr Gly Met
            340                 345                 350

Thr Phe Ile Pro Ile Met Ile Ile Val Phe Gly Phe Ile Val Asn Ile
            355                 360                 365

Thr Glu Arg Val Phe Thr Ser Asn Leu Tyr Ala Tyr Thr Ser Glu Pro
        370                 375                 380

Tyr Pro Thr Glu Tyr Arg Ser Ser Gly Ser Gly Leu Ala Tyr Gly Leu
385                 390                 395                 400

Gly Arg Phe Ser Asn Ile Phe Gly Ser Leu Leu Val Gly Phe Ile Ala
                405                 410                 415

Val Gln Leu Gly Tyr Ile Ser Val Phe Leu Phe Ile Gly Gly Cys Trp
            420                 425                 430

Leu Ala Cys Ser Leu Leu Leu Ile Phe Phe Gly Pro Asn Thr Asn Ala
            435                 440                 445

Lys Gln Ile
    450

<210> SEQ ID NO 42
<211> LENGTH: 1356
<212> TYPE: DNA
<213> ORGANISM: Bacillus subtilis

<400> SEQUENCE: 42
atgaatacga tcttcaaaca aaagaataca catcctttct caaacgcagc gaatcgttta      60
gaccgccttc cgatttcacg cgttcatttc caagtgttaa ccgctctcgg cattgtttat     120
ttctttgatc tcgcagattt atttacccte agcaacgtag cgccggcact gatcgagcat     180
tggggcatcc cgctttcaac tattgctaac gtaacggccg cttcgttttt aggcatgttt     240
ttaggcgctt cactgggcgg acggctgtcc gatcgaatcg gccgcaaaaa agccttaaat     300
ctatttgtct ttgttttctc aatcgcatcg ctatgcaatg ctgcggcatg ggacattcca     360
tctttaatga cattccgttt cctcaccgga tttggcgttg cagccgccat ggtcattacg     420
aatagctatt tggcggaatt ttcccttca agtgtacgtg gaaaatatat ttctttttgt     480
gccatgattg gattgattgg ggttccgatc accaacattg tgtctgcctt tgtcattcct     540
cttggttcat ggggatggag ctagtatttg tatggggtg ccgtcggcct tatttatttt     600
ttcttcatcc accgtctgga agagtcacct cgctggcacg aaaatcgcgg ggaatatgcg     660
aaagccgatg cgatcctcac ccgaattgaa gaacaggttg aaaaggagaa aggcccgctt     720
ccggcagcat cccagcctaa agtaagcgaa actgttaagc agaatgcagg ttacgcaggc     780
ttattgaaag gcagaaacct caaaattacc atcgtattat ctgctgtatg gattttgaa     840
acgtttgggt tttacggatt tgcttcatgg gttccaagcc tgctaaaaag caatggcgta     900
accatggaaa atacattatg gtataacgta ttgcattccg tcggcgctcc acttggcgca     960

```
ctgctcggct ccatgatttc cgaaagattt caaagaaaat ggattttagc tgcgagtgcg    1020
tttctgacgg ccatcgccgg gctcttatat ggtatgactt ttattcccat catgatcatt    1080
gtatttggtt ttatcgtgaa tatcacagaa cgggtcttta cctcgaactt atacgcctat    1140
acatctgaac cttatccgac tgaataccgc tcgtctggca gcggtttagc ctatggtctt    1200
ggccgttttt caaacatttt tggctcattg cttgtcggat ttattgccgt tcagctcggc    1260
tatatcagcg tcttcttatt tattgggggc tgttggctcg catgctcctt gctgttaatc    1320
ttcttcggtc ctaatacgaa tgcaaaacag atttaa                              1356
```

<210> SEQ ID NO 43
<211> LENGTH: 543
<212> TYPE: PRT
<213> ORGANISM: Kluyveromyces lactis
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid

<400> SEQUENCE: 43

```
Met Ala Ala Glu Ser Ile Val Ser Arg Asp Glu Ser Ile Ala Ser Leu
1               5                   10                  15

Glu Lys Ala Glu Gly Arg Ile Thr Tyr Leu Lys Pro Gln Ser Arg Ile
            20                  25                  30

Thr Trp Ser Asp Ala Xaa Lys Tyr Leu Ala Thr Arg Ile Pro Thr Leu
        35                  40                  45

Phe Pro Thr Lys Ala Ser Ile Arg Glu Ala Arg Lys Glu Tyr Pro Ile
50                  55                  60

Asn Pro Phe Pro Ala Leu Arg Ser Met Asn Trp Leu Gln Thr Gln Tyr
65                  70                  75                  80

Phe Ile Val Gly Phe Leu Ala Trp Thr Trp Asp Ala Leu Asp Phe Phe
                85                  90                  95

Ala Val Ser Leu Asn Met Thr Asn Leu Ala Lys Asp Leu Asp Arg Pro
            100                 105                 110

Val Lys Asp Ile Ser His Ala Ile Thr Leu Val Leu Leu Leu Arg Val
        115                 120                 125

Ile Gly Ala Leu Ile Phe Gly Tyr Leu Gly Asp Arg Tyr Gly Arg Lys
    130                 135                 140

Tyr Ser Phe Val Leu Thr Met Ala Leu Ile Ile Val Ile Gln Ile Gly
145                 150                 155                 160

Thr Gly Phe Val Asn Ser Phe Ser Ala Phe Leu Gly Cys Arg Ala Ile
                165                 170                 175

Phe Gly Ile Ile Met Gly Ser Val Phe Gly Ser Ala Phe Leu Gly Cys
            180                 185                 190

Arg Ala Ile Phe Xaa Ile Ile Met Gly Ser Val Phe Gly Val Ala Ser
        195                 200                 205

Xaa Thr Ala Leu Glu Asn Ala Pro Asn Lys Ala Lys Ser Ile Leu Ser
```

```
Gly Ile Phe Gln Glu Gly Tyr Ala Phe Gly Xaa Leu Leu Gly Val Val
225                 230                 235                 240

Phe Gln Arg Ala Ile Val Asp Asn Ser Pro His Gly Trp Arg Ala Ile
            245                 250                 255

Phe Trp Phe Ser Ala Gly Pro Pro Val Leu Phe Ile Ala Trp Arg Leu
            260                 265                 270

Met Leu Pro Glu Ser Gln His Tyr Val Glu Arg Val Arg Leu Glu Lys
            275                 280                 285

Leu Glu Asn Asp Gly Lys Ser Gln Phe Trp Lys Asn Ala Lys Leu Ala
290                 295                 300

Cys Ser Gln Tyr Trp Leu Ser Met Ile Tyr Leu Val Leu Leu Met Ala
305                 310                 315                 320

Gly Phe Asn Phe Ser Ser His Gly Ser Gln Asp Leu Phe Pro Thr Met
            325                 330                 335

Leu Thr Ser Gln Tyr Gln Phe Ser Ala Asp Ala Ser Thr Val Thr Asn
            340                 345                 350

Ser Val Ala Asn Leu Gly Ala Ile Ala Gly Gly Ile Ile Val Ala His
            355                 360                 365

Ala Ser Ser Phe Phe Gly Arg Arg Phe Ser Ile Ile Val Cys Cys Ile
370                 375                 380

Gly Gly Gly Ala Met Leu Tyr Pro Trp Gly Phe Val Ala Asn Lys Ser
385                 390                 395                 400

Gly Ile Asn Ala Ser Val Phe Phe Leu Gln Phe Phe Val Gln Gly Ala
            405                 410                 415

Trp Gly Ile Val Pro Ile His Leu Thr Glu Leu Ala Pro Thr Glu Phe
            420                 425                 430

Arg Ala Leu Ile Thr Gly Val Ala Tyr Gln Leu Gly Asn Met Ile Ser
            435                 440                 445

Ser Ala Ser Ser Thr Ile Glu Ala Ser Ile Gly Glu Arg Phe Pro Leu
450                 455                 460

Glu Gly Arg Glu Asp Ala Tyr Asp Tyr Gly Lys Val Met Cys Ile Phe
465                 470                 475                 480

Met Gly Cys Val Phe Ala Tyr Leu Leu Ile Val Thr Val Leu Gly Pro
            485                 490                 495

Glu Asn Lys Gly Gly Glu Leu Arg Leu Ser Thr Thr Gly Thr Glu Gln
            500                 505                 510

Asp Asp Glu Glu Ser Gln Asn Asn Ile Ile Arg Arg Asn Cys Arg
            515                 520                 525

Gly Trp Thr Ser Phe Gly Ser Lys Phe Gln Ala Arg Asn Ser Thr
530                 535                 540
```

<210> SEQ ID NO 44
<211> LENGTH: 1632
<212> TYPE: DNA
<213> ORGANISM: Kluyveromyces lactis

<400> SEQUENCE: 44

```
atggctgcag aatcaatagt gtctcgcgat gaatccatcg cttcacttga aaaagcagaa      60
ggtagaatca catatttgaa accgcaatct aggatcacat ggagtgatgc taasaaatat     120
ttggctacaa gaataccyac tttgttccca acaaaagcat cgattagaga agcaaggaaa     180
gaataccctt aaatcctttt ccctgcctta cgttcgatga actggttgca acacaaatac     240
tttatcgttg ggttcttagc atggacttgg gatgcgttag atttctttgc cgtttcattg     300
```

```
aacatgacaa atttggccaa ggatctagac agacctgtaa aagatatttc tcatgccatt      360
actttggtgt tgctattaag ggtcatcggt gctcttatct ttggttattt gggtgacaga      420
tatggtagaa atactcatt tgttttaact atggctctca ttatcgttat tcaaatcggt       480
acagggttcg ttaattcttt ctctgctttc ttggggtgta gagctatctt tggtatcatt      540
atgggatctg tatttggttc tgctttcttg gggtgtagag ctatctttgk tatcattatg      600
ggatctgtat ttggtgttgc ttctkccact gccttggaaa atgctccaaa caaggctaag      660
tccatccttt ctggtatatt ccaagaaggt tatgctttcg gtwatttatt aggtgtcgtg      720
ttccaaagag ctattgttga taattctcca catggttgga gagctatatt ctggttcagt      780
gccgggcccc cagtgctttt cattgcttgg aggttgatgt tacctgaatc ccaacactat      840
gtcgaaagag tccgtttgga aaaattagaa aacgatggga agtctcaatt ctggaagaat      900
gctaagcttg cctgttctca atattggcta agtatgattt acttggttct tttaatggca      960
ggtttcaact tctcctccca tggttctcaa gatcttttcc caacaatgtt gacttctcaa     1020
taccaattct ccgctgatgc atcaactgtw acaaactctg ttgcaaacct tggtgccatc     1080
gctggtggta tcattgttgc ccatgcctcc tctttctttg gtcgtagatt ctctatcatt     1140
gtatgttgta ttggcggtgg tgctatgtta tacccatggg gttttgttgc taataaatct     1200
ggaattaatg cttcagtctt cttcttacaa ttcttcgtcc aaggtgcttg gggtattgtc     1260
ccaattcatt tgacggaatt agccccaacg gagttcagag ctttgatcac tggtgttgct     1320
taccaattgg gtaatatgat atctagtgcc tcctcaacta tcgaagcctc cattggtgaa     1380
agattcccac ttgaaggtag agaggacgct tatgattatg gtaaggtgat gtgtatcttc     1440
atgggatgcg tgttcgctta cttgttgatc gtaaccgttt tgggcccaga gaacaagggc     1500
ggtgagttga gattatccac tacgggtaca gaacaagacg atgaagaatc tcaaaataac     1560
aatatcattc gaagaaattg tcgcggctgg accagtttcg gatctaaatt tcaagcaaga     1620
aattcaacat aa                                                         1632
```

<210> SEQ ID NO 45
<211> LENGTH: 400
<212> TYPE: PRT
<213> ORGANISM: Bacillus subtilis

<400> SEQUENCE: 45

Met Gly Lys Gln Gln Pro Ile Ser Gln Arg Lys Leu Leu Gly Val Ala
1               5                   10                  15

Gly Leu Gly Trp Leu Phe Asp Ala Met Asp Val Gly Ile Leu Ser Phe
            20                  25                  30

Ile Ile Ala Ala Leu His Val Glu Trp Asn Leu Ser Pro Glu Glu Met
        35                  40                  45

Lys Trp Ile Gly Ser Val Asn Ser Ile Gly Met Ala Ala Gly Ala Phe
    50                  55                  60

Leu Phe Gly Leu Leu Ala Asp Arg Ile Gly Arg Lys Lys Val Phe Ile
65                  70                  75                  80

Ile Thr Leu Leu Cys Phe Ser Ile Gly Ser Gly Ile Ser Ala Phe Val
                85                  90                  95

Thr Ser Leu Ser Ala Phe Leu Ile Leu Arg Phe Val Ile Gly Met Gly
            100                 105                 110

Leu Gly Gly Glu Leu Pro Val Ala Ser Thr Leu Val Ser Glu Ala Val
        115                 120                 125

Val Pro Glu Lys Arg Gly Arg Val Ile Val Leu Leu Glu Ser Phe Trp
130                 135                 140

Ala Val Gly Trp Leu Ala Ala Ala Leu Ile Ser Tyr Phe Val Ile Pro
145                 150                 155                 160

Ser Phe Gly Trp Gln Ala Ala Leu Leu Leu Thr Ala Leu Thr Ala Phe
            165                 170                 175

Tyr Ala Leu Tyr Leu Arg Thr Ser Leu Pro Asp Ser Pro Lys Tyr Glu
            180                 185                 190

Ser Leu Ser Ala Lys Lys Arg Ser Met Trp Glu Asn Val Lys Ser Val
            195                 200                 205

Trp Ala Arg Gln Tyr Ile Arg Pro Thr Val Met Leu Ser Ile Val Trp
210                 215                 220

Phe Cys Val Val Phe Ser Tyr Tyr Gly Met Phe Leu Trp Leu Pro Ser
225                 230                 235                 240

Val Met Leu Leu Lys Gly Phe Ser Met Ile Gln Ser Phe Glu Tyr Val
            245                 250                 255

Leu Leu Met Thr Leu Ala Gln Leu Pro Gly Tyr Phe Ser Ala Ala Trp
            260                 265                 270

Leu Ile Glu Lys Ala Gly Arg Lys Trp Ile Leu Val Val Tyr Leu Ile
            275                 280                 285

Gly Thr Ala Gly Ser Ala Tyr Phe Phe Gly Thr Ala Asp Ser Leu Ser
            290                 295                 300

Leu Leu Leu Thr Ala Gly Val Leu Leu Ser Phe Asn Leu Gly Ala
305                 310                 315                 320

Trp Gly Val Leu Tyr Ala Tyr Thr Pro Glu Gln Tyr Pro Thr Ala Ile
            325                 330                 335

Arg Ala Thr Gly Ser Gly Thr Thr Ala Ala Phe Gly Arg Ile Gly Gly
            340                 345                 350

Ile Phe Gly Pro Leu Val Gly Thr Leu Ala Ala Arg His Ile Ser
            355                 360                 365

Phe Ser Val Ile Phe Ser Ile Phe Cys Ile Ala Ile Leu Leu Ala Val
            370                 375                 380

Ala Cys Ile Leu Ile Met Gly Lys Glu Thr Lys Gln Thr Glu Leu Glu
385                 390                 395                 400

<210> SEQ ID NO 46
<211> LENGTH: 1203
<212> TYPE: DNA
<213> ORGANISM: Bacillus subtilis

<400> SEQUENCE: 46
atgggaaaac aacagcctat atcccagcgt aaactgctgg gcgtcgccgg tttggggtgg      60
ctgtttgatg caatggatgt cggaatatta tcgtttatta tcgccgcgct ccatgtagag     120
tggaatctgt cgcccgaaga aatgaaatgg atcggaagcg tcaattccat cggcatggct     180
gcgggtgcgt ttttgtttgg tttgcttgct gatcgaatcg gccgcaaaaa agtgttcatc     240 atcaccccttt tatgctttc catcggaagc ggcatttccg cttttgtgac gagcttatcg     300
gcatttctaa tccttcgttt cgtgattggt atgggacttg gcggcgagct tccagtcgct     360
tcaacactcg tttcggaagc ggttgtgcct gaaaagcggg gcagagtgat gtgcttttg     420 gaaagctttt gggccgtggg ctggctcgca gcggccttga tttcttactt tgtgatacca     480
agcttcggct ggcaggctgc ccttctgtta actgcgctga ctgcttttta tgcgctgtac     540
ctgcggacga gtctacctga ttcgccgaaa tatgaatcgc tttctgccaa aaagaggtcg     600

-continued

```
atgtgggaga atgtaaaaag cgtctgggca agacagtata tacggccgac ggtgatgctg    660
tcgatcgttt ggttctgtgt ggtgttttct tattacggca tgttcctatg gctcccgagt    720
gtcatgctgc tgaaaggctt cagcatgatt caaagctttg aatatgtcct gctgatgacg    780
cttgctcagc tacctggcta tttctctgcc gcatggctga ttgaaaaagc gggccggaag    840
tggatactcg tcgtttactt gattggcaca gcaggaagcg cctatttctt cggaacggcg    900
gattccttaa gtcttctgct tacggctgga gtgctgttat cgttttcaa tctcggtgcg     960 tggggcgtgc tgtatgctta taccccggag caatacccga ctgcgattcg agcaacaggt   1020
tcaggaacga cagcagcgtt tggaagaatc ggcggcatct tcgggccttt gctcgtcgga   1080
accctggcag cccgtcatat ttcgttttcg gtcatctttt caatctttg cattgcaatc    1140 ttacttgcgg ttgcttgtat tttgattatg gggaagaaa cgaaacaaac tgagctagaa    1200
tag                                                                  1203
```

<210> SEQ ID NO 47
<211> LENGTH: 283
<212> TYPE: PRT
<213> ORGANISM: Saccharomyces cerevisiae

<400> SEQUENCE: 47

```
Met Ser Asp Lys Glu Gln Thr Ser Gly Asn Thr Asp Leu Glu Asn Ala
1               5                   10                  15

Pro Ala Gly Tyr Tyr Ser Ser His Asp Asn Asp Val Asn Gly Val Ala
            20                  25                  30

Glu Asp Glu Arg Pro Ser His Asp Ser Leu Gly Lys Ile Tyr Thr Gly
        35                  40                  45

Gly Asp Asn Asn Glu Tyr Ile Tyr Ile Gly Arg Gln Lys Phe Leu Lys
    50                  55                  60

Ser Asp Leu Tyr Gln Ala Phe Gly Gly Thr Leu Asn Pro Gly Leu Ala
65                  70                  75                  80

Pro Ala Pro Val His Lys Phe Ala Asn Pro Ala Pro Leu Gly Leu Ser
                85                  90                  95

Ala Phe Ala Leu Thr Thr Phe Val Leu Ser Met Phe Asn Ala Arg Ala
            100                 105                 110

Gln Gly Ile Thr Val Pro Asn Val Val Gly Cys Ala Met Phe Tyr
        115                 120                 125

Gly Gly Leu Val Gln Leu Ile Ala Gly Ile Trp Glu Ile Ala Leu Glu
    130                 135                 140

Asn Thr Phe Gly Gly Thr Ala Leu Cys Ser Tyr Gly Gly Phe Trp Leu
145                 150                 155                 160

Ser Phe Ala Ala Ile Tyr Ile Pro Trp Phe Gly Ile Leu Glu Ala Tyr
                165                 170                 175

Glu Asp Asn Glu Ser Asp Leu Asn Asn Ala Leu Gly Phe Tyr Leu Leu
            180                 185                 190

Gly Trp Ala Ile Phe Thr Phe Gly Leu Thr Val Cys Thr Met Lys Ser
        195                 200                 205

Thr Val Met Phe Phe Leu Leu Phe Leu Leu Ala Leu Thr Phe Leu
    210                 215                 220

Leu Leu Ser Ile Gly His Phe Ala Asn Arg Leu Gly Val Thr Arg Ala
225                 230                 235                 240

Gly Gly Val Leu Gly Val Val Ala Phe Ile Ala Trp Tyr Asn Ala
                245                 250                 255

Tyr Ala Gly Val Ala Thr Lys Gln Asn Ser Tyr Val Leu Ala Arg Pro
```

```
                    260              265              270
Phe Pro Leu Pro Ser Thr Glu Arg Val Ile Phe
            275              280

<210> SEQ ID NO 48
<211> LENGTH: 852
<212> TYPE: DNA
<213> ORGANISM: Saccharomyces cerevisiae

<400> SEQUENCE: 48
atgtctgaca aggaacaaac gagcggaaac acagatttgg agaatgcacc agcaggatac      60
tatagttccc atgataacga cgttaatggc gttgcagaag atgaacgtcc atctcatgat     120
tcgttgggca agatttacac tggaggtgat aacaatgaat atatctatat tgggcgtcaa     180
aagtttttga gagcgactt ataccaagcc tttggtggta ccttgaatcc agggttagct      240
cctgctccag tgcacaaatt tgctaatcct gcgcccttag gtctttcagc cttcgcgttg     300
acgacatttg tgctgtccat gttcaatgcg agagcgcaag ggatcactgt tcctaatgtt     360
gtcgtcggtt gtgctatgtt ttatggtggt ttggtgcaat tgattgctgg tatttgggag     420
atagctttgg aaaatacttt tggtggtacc gcattatgtt cttacggtgg gttttggttg     480
agtttcgctg caatttacat tccttggttt ggtatcttgg aagcttacga agacaatgaa     540
tctgatttga ataatgcttt aggattttat ttgttgggt gggccatctt tacgtttggt      600
ttaaccgttt gtaccatgaa atccactgtt atgttctttt tgttgttctt cttactagca     660
ttaactttcc tactgttgtc tattggtcac tttgctaata gacttggtgt cacaagagct     720
ggtggtgtcc tgggagttgt tgttgctttc attgcttggt acaacgcata tgcaggtgtt     780
gctacaaagc agaattcata tgtactggct cgtccattcc cattaccatc tactgaaagg     840
gtaatctttt aa                                                          852

<210> SEQ ID NO 49
<211> LENGTH: 428
<212> TYPE: PRT
<213> ORGANISM: Ralstonia pickettii

<400> SEQUENCE: 49

Met Trp Leu Lys Glu Thr Thr Gln Gly Glu Arg Lys Thr Leu Phe Ala
1               5                   10                  15

Ala Phe Val Gly Tyr Gly Val Asp Ala Phe Asp Tyr Met Ile Tyr Thr
            20                  25                  30

Phe Met Ile Pro Thr Phe Ile Leu Val Trp Gly Met Thr Lys Ala Glu
        35                  40                  45

Ala Gly Tyr Ile Ala Thr Gly Ala Leu Ile Ser Ser Ala Val Gly Gly
    50                  55                  60

Trp Leu Ala Gly Ile Leu Ala Asp Lys Tyr Gly Arg Val Arg Ile Leu
65                  70                  75                  80

Gln Leu Thr Val Leu Trp Phe Ser Phe Phe Thr Phe Leu Ser Gly Phe
                85                  90                  95

Thr Gln Ser Pro Glu Gln Leu Phe Val Thr Arg Met Leu Gln Gly Leu
            100                 105                 110

Gly Phe Gly Gly Glu Trp Ser Val Gly Ser Val Leu Ile Ala Glu Met
        115                 120                 125

Ile Arg Ala Arg His Arg Gly Lys Ala Val Gly Leu Val Gln Ser Ser
    130                 135                 140

Trp Ala Val Gly Trp Gly Leu Ser Ala Ile Ala Phe Trp Ala Val Tyr
```

```
                145                 150                 155                 160
        Ala Ala Phe Glu Gln Gln Tyr Ala Trp Arg Val Leu Phe Trp Ile Gly
                        165                 170                 175

Val Leu Pro Ala Leu Phe Ile Leu Tyr Ile Arg Arg Asn Ile Ser Glu
                        180                 185                 190

Pro Glu Val Tyr Gln Glu Thr Lys Ala Lys Leu Ala Arg Thr Gly Gln
                        195                 200                 205

Ser Asn Asn Phe Met Leu Ile Phe Lys Pro Gly Val Leu Arg Thr Thr
                    210                 215                 220

Val Leu Ala Ser Leu Leu Ala Thr Gly Met Gln Gly Ala Tyr Tyr Ser
        225                 230                 235                 240

Val Thr Thr Trp Leu Pro Thr Tyr Leu Lys Met Glu Arg Asn Leu Ser
                        245                 250                 255

Val Leu Asn Thr Ser Gly Tyr Leu Met Val Leu Ile Ala Gly Ser Phe
                        260                 265                 270

Ala Gly Tyr Leu Thr Ser Ala Trp Leu Ser Asp Arg Leu Gly Arg Arg
                        275                 280                 285

Arg Cys Phe Met Leu Phe Ala Val Ser Ala Ala Ile Leu Val Ile Cys
                        290                 295                 300

Tyr Thr Gln Leu Pro Ile Thr Asp Ala Ala Met Leu Leu Leu Gly Phe
        305                 310                 315                 320

Pro Leu Gly Phe Phe Leu Ser Gly Ile Phe Ser Gly Met Gly Ala Tyr
                        325                 330                 335

Leu Thr Glu Leu Tyr Pro Ser His Ile Arg Gly Ser Gly Gln Gly Phe
                        340                 345                 350

Ser Tyr Asn Phe Gly Arg Ala Val Gly Ser Val Phe Pro Ala Met Ile
                        355                 360                 365

Gly His Met Ser Ala Ser Met Ser Leu Gly Val Ala Ile Gly Tyr Leu
                        370                 375                 380

Ala Ala Gly Ala Tyr Gly Leu Val Ile Ile Ala Cys Leu Leu Leu Pro
        385                 390                 395                 400

Glu Thr Gln Gly Arg Glu Leu Leu Gly Glu Arg Glu Ala Gly Thr Glu
                        405                 410                 415

Gly Pro Ala Asp Ala Ala Thr Ser Arg Thr Val Ala
                        420                 425

<210> SEQ ID NO 50
<211> LENGTH: 1287
<212> TYPE: DNA
<213> ORGANISM: Ralstonia pickettii

<400> SEQUENCE: 50
atgtggctta aagaaacaac gcagggagag cgcaagacgc tctttgccgc cttcgtcggc      60
tacggggtcg atgcattcga ctacatgatc tacaccttca tgatccccac cttcatcctg     120
gtgtggggca tgaccaaggc cgaggccggc tatatcgcga cgggcgcgct catcagctcg     180
gccgtcggcg gctggctggc cggcatcctg ccgacaaat  atggccgcgt gcggatcctg     240
cagctgaccg tgctctggtt cagtttcttt accttcctga gcggattcac ccagtctccc     300
gagcaactgt tcgtgacccg catgctgcaa gggctggggt cggcggcga  atggtcggtc     360 ggttcggtgc tgatcgccga tgatccgt   gcccgccacc gcggcaaggc ggttggcctg     420
gtgcaaagca gctgggcagt cggctgggggc ctgtcggcga ttgccttctg gcggtctat     480 gccgcgttcg agcagcaata cgcatggcgc gtgctgttct ggatcggcgt gctgccggcg     540
```

```
ctctttatcc tctacatccg ccgcaatatc tccgaacccg aggtgtatca ggaaaccaag    600
gccaagctgg cccgcaccgg gcaaagcaat aacttcatgc tgatcttcaa gcccggcgtg    660
ctgcgcacca cggtgctggc cagcctgctg gcgaccggca tgcaaggtgc ctactattcg    720
gtgacgacct ggctgccgac ctatctcaag atggagcgca acctgtccgt gctcaatacc    780
agcggctacc tgatggtgct gatcgcaggc tccttcgccg gctatctgac cagcgcctgg    840
ctgtccgacc gctggggcg ccggcgttgc ttcatgctgt tcgcagtgag cgcagccatc    900
ctcgtgatct gctatacgca gctgccgatc accgacgcgg cgatgctgct gcttggcttc    960
cccttgggct tcttcctgtc tggcatcttt tcgggcatgg agcttacct gacggagctg    1020
tatccgagcc atatccgtgg ctccggacaa ggcttttcct acaacttcgg gcgcgcggtc    1080
ggctcggtgt ccccggccat gatcgggcat atgagcgcat cgatgtcgct gggcgtggcc    1140
atcggctatc tcgccgcggg cgcctatggg ttggtcatta tcgcgtgcct gctgttgccg    1200
gaaacacagg gacgcgaact actcggcgaa cgcgaggctg gcacggaagg accggctgac    1260
gcagcaactt cgcggacggt agcctga                                        1287
```

<210> SEQ ID NO 51
<211> LENGTH: 188
<212> TYPE: PRT
<213> ORGANISM: Klebsiella pneumoniae

<400> SEQUENCE: 51

```
Met Gly Asn Thr Lys Leu Ala Asn Pro Ala Pro Leu Gly Leu Met Gly
1               5                   10                  15
Phe Gly Met Thr Thr Ile Leu Leu Leu Ala Asn Ser Gly Leu Phe
            20                  25                  30
Ala Phe Asp Val Ala Ile Leu Ala Met Gly Ile Phe Tyr Gly Gly Ile
        35                  40                  45
Ala Gln Ile Phe Ala Gly Leu Leu Glu Tyr Lys Lys Gly Asn Thr Phe
    50                  55                  60
Gly Leu Thr Ala Phe Thr Ser Tyr Gly Ser Phe Trp Leu Thr Leu Val
65                  70                  75                  80
Ala Ile Leu Leu Met Pro Lys Met Gly Leu Ala Asp Ala Pro His Ala
                85                  90                  95
His Phe Leu Gly Met Tyr Leu Gly Leu Trp Gly Val Phe Thr Leu Phe
            100                 105                 110
Met Phe Phe Gly Thr Leu Lys Ala Ala Arg Met Leu Gln Phe Val Phe
        115                 120                 125
Leu Ser Leu Thr Val Leu Phe Ala Leu Leu Ala Ile Gly His Leu Ala
    130                 135                 140
Asp Asn Glu Gly Ile Val Lys Val Ala Gly Trp Val Gly Leu Ile Cys
145                 150                 155                 160
Gly Ala Ser Ala Ile Tyr Leu Ala Met Gly Glu Val Leu Asn Glu Gln
                165                 170                 175
Phe Gly Arg Thr Val Leu Pro Ile Gly Glu Pro Arg
            180                 185
```

<210> SEQ ID NO 52
<211> LENGTH: 567
<212> TYPE: DNA
<213> ORGANISM: Klebsiella pneumoniae

<400> SEQUENCE: 52

```
atgggcaaca ctaagttggc taatccggca ccgctgggcc ttatgggctt cggcatgacc    60
```

-continued

```
actattctgc ttaacctggc gaatagcggc ctgttcgcat tcgatgtagc tatcctggcg      120
atgggcattt tttacggcgg cattgcgcaa attttgccg gcctgctgga atacaaaaaa      180
ggcaacactt ttggcttaac cgcttttacc tcctacggca gcttctggct gacgctggtg      240
gcgattcttc tgatgccgaa aatgggcctg cagacgcgc cacacgcgca cttcctcggt      300
atgtacctcg gcctgtgggg cgtctttact ctgtttatgt tctttggcac cctgaaggca      360
gcccgcatgc tgcagtttgt cttcctgagc ctgaccgtac tgttcgcgct gctggcgatt      420
ggccatttgg ccgataacga aggcattgtg aaggtagccg ctgggtcgg cctgatttgt      480 ggcgccagcg ctatttacct ggcgatgggt gaagtgctga acgaacagtt cggccgcacc      540
gtgctgccga tcggcgaacc gcgctaa                                          567
```

<210> SEQ ID NO 53
<211> LENGTH: 188
<212> TYPE: PRT
<213> ORGANISM: Citrobacter sp.

<400> SEQUENCE: 53

```
Met Gly Asn Thr Lys Leu Ala Asn Pro Ala Pro Leu Gly Leu Met Gly
1               5                   10                  15

Phe Gly Met Thr Thr Ile Leu Leu Asn Leu His Asn Ala Gly Phe Phe
            20                  25                  30

Ala Leu Asp Val Ile Ile Leu Ala Met Gly Ile Phe Tyr Gly Gly Ile
        35                  40                  45

Ala Gln Ile Phe Ala Gly Leu Leu Glu Tyr Lys Lys Gly Asn Thr Phe
    50                  55                  60

Gly Leu Thr Ala Phe Thr Ser Tyr Gly Ser Phe Trp Leu Thr Leu Val
65                  70                  75                  80

Ala Ile Leu Leu Met Pro Lys Met Gly Leu Ala Asp Ala Thr Asn Gly
                85                  90                  95

Gln Phe Leu Gly Ala Tyr Leu Gly Leu Trp Gly Val Phe Thr Leu Phe
            100                 105                 110

Met Phe Ile Gly Thr Leu Lys Ala Ala Arg Met Leu Gln Phe Val Phe
        115                 120                 125

Leu Ser Leu Thr Val Leu Phe Ala Leu Leu Ala Val Gly Asn Ile Ala
    130                 135                 140

Gly Asn Glu Ala Ile Ile His Val Ala Gly Trp Val Gly Leu Val Cys
145                 150                 155                 160

Gly Ala Ser Ala Ile Tyr Leu Ala Met Gly Glu Val Leu Asn Glu Gln
                165                 170                 175

Phe Gly Arg Thr Ile Leu Pro Ile Gly Glu Ala His
            180                 185
```

<210> SEQ ID NO 54
<211> LENGTH: 567
<212> TYPE: DNA
<213> ORGANISM: Citrobacter sp.

<400> SEQUENCE: 54

```
atgggcaaca ctaagttggc taatccggca ccgctgggcc tgatgggctt ggcatgacc       60 accattctgc ttaacctgca caacgcgggt ttcttcgctc tggacgttat tattctggcg     120
atgggcattt tctacggcgg tatcgcgcaa attttgccg gactgctgga atataaaaaa     180
ggcaacacct tcggtttaac cgcctttacc tcctacggtt cgttctggct gacgctggtt     240
```

```
gcgatcctgc tgatgccgaa atgggcctg gcggatgcaa ccaatggtca gttcctgggc    300
gcttacctcg gtctgtgggg cgtgttcact ctgttcatgt tcatcggtac gctgaaagcg    360
gcgcgcatgc tgcagttcgt gttcctgagc ctgacagtgc tgttcgccct gctggccgtg    420
ggcaacattg cgggtaacga agcgatcatt cacgttgctg gctgggtagg cttagtgtgt    480
ggcgcaagcg ccatttacct ggcgatgggt gaagtgctga cgaacaatt tggccgtacc    540 atcctgccga ttggtgaagc gcactaa                                        567
```

```
<210> SEQ ID NO 55
<211> LENGTH: 380
<212> TYPE: PRT
<213> ORGANISM: Aspergillus oryzae

<400> SEQUENCE: 55

Met Leu Thr Pro Pro Lys Phe Glu Asp Glu Lys Gln Leu Gly Pro Val
 1               5                  10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
           100                 105                 110

Ser Arg Tyr Phe Gly Glu Glu Ser Asn Glu Ser Phe Gln Leu Ala Leu
       115                  120                 125

Glu Ala Leu Phe Trp Ile Tyr Cys Val Cys Thr Leu Leu Val Ala Ile
   130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
    210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Val Ile Arg Ser Pro
    290                 295                 300

Pro Glu Ala Phe His Leu Asn Trp Trp Ala Met Val Phe Pro Asn Thr
305                 310                 315                 320
```

```
Gly Phe Thr Leu Ala Thr Ile Thr Leu Gly Lys Ala Leu Asn Ser Asn
            325                 330                 335

Gly Val Lys Gly Val Gly Ser Ala Met Ser Ile Cys Ile Val Cys Met
        340                 345                 350

Tyr Ile Phe Val Phe Val Asn Asn Val Arg Ala Val Ile Arg Lys Asp
        355                 360                 365

Ile Met Tyr Pro Gly Lys Asp Glu Asp Val Ser Asp
        370                 375                 380

<210> SEQ ID NO 56
<211> LENGTH: 1143
<212> TYPE: DNA
<213> ORGANISM: Aspergillus oryzae

<400> SEQUENCE: 56
atgctgacac ctcccaagtt tgaggatgag aagcagctgg gccccgtggg tatccgggag      60
aggcttcgcc atttcacttg ggcctggtac acattaacga tgagtggagg agggctggcc     120
gtcctcatca tcagccagcc ctttgggttc gcgggattga gagagatcgg catcgctgtc     180
tatatcctca acctgatcct cttcgcccct gtctgctcta ccatggctat aaggttcatc     240
ctgcacggca accttctgga gtccctccgt catgaccgcg agggtctctt cttcccgacc     300
ttctggctct ccgtcgcaac catcatctgc ggcttgtctc gctacttcgg tgaagaatcg     360
aatgagtcct ccaactagc cctcgaagcc ctcttctgga tctactgcgt ctgcaccta      420 ctcgtcgcaa tcatccaata ctcgttcgtc ttctcatccc acaagtacgg ccttcaaacc     480
atgatgcctt catggatcct tccagccttc cccatcatgc tcagcggcac catcgcctcc     540
gtcatcggtg aacaacaacc cgctcgcgca gccctcccca tcatcggcgc cggcgtcacc     600
ttccagggcc tcggcttctc catcagcttc atgatgtacg cccactacat cggccgactg     660
atggagtccg gcctcccca cagcgaccac agaccaggca tgttcatctg cgtcggaccc     720
cccgccttca cagccctcgc cctcgtcggc atgagcaaag gcctccccga agacttcaag     780
ctgctccacg acgcccacgc cctggaagat ggccgcatca tcgagctgct ggccatctcc     840
gccggcgtct tcctctgggc cctgagtctc tggttcttct gcatcgccat gtcgccgtc      900 atccgctcgc cccccgaggc cttccacctc aactggtggg ccatggtctt ccccaacacc     960
ggcttcaccc tggccaccat caccctgggc aaggctctca cagtaacgg cgtgaagggc     1020 gtcggctccg ccatgtctat ctgcatcgtg tgcatgtaca tcttcgtctt tgtcaacaat     1080
gtccgcgccg ttatccggaa ggatatcatg tacccgggta agatgagga tgtatctgat     1140 tag                                                                  1143

<210> SEQ ID NO 57
<211> LENGTH: 438
<212> TYPE: PRT
<213> ORGANISM: Schizosaccharomyces pombe

<400> SEQUENCE: 57

Met Gly Glu Leu Lys Glu Ile Leu Lys Gln Arg Tyr His Glu Leu Leu
1               5                   10                  15

Asp Trp Asn Val Lys Ala Pro His Val Pro Leu Ser Gln Arg Leu Lys
            20                  25                  30

His Phe Thr Trp Ser Trp Phe Ala Cys Thr Met Ala Thr Gly Gly Val
        35                  40                  45

Gly Leu Ile Ile Gly Ser Phe Pro Phe Arg Phe Tyr Gly Leu Asn Thr
```

Ile Gly Lys Ile Val Tyr Ile Leu Gln Ile Phe Leu Phe Ser Leu Phe
65                  70                  75                  80

Gly Ser Cys Met Leu Phe Arg Phe Ile Lys Tyr Pro Ser Thr Ile Lys
                85                  90                  95

Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
        115                 120                 125

Asp Thr Gly Glu Trp Met Val Trp Val Ile Arg Ile Leu Tyr Tyr Ile
    130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
        195                 200                 205

Ile Leu Phe Gln Gly Leu Gly Phe Trp Val Tyr Leu Leu Phe Ala
    210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
        275                 280                 285

Met Ala Ile Phe Ile Trp Gly Leu Ala Ala Trp Cys Tyr Cys Leu Ala
    290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
            340                 345                 350

Phe Gly His Ile Ile Gly Val Ile Leu Cys Ile Gln Trp Ile Leu Leu
        355                 360                 365

Met Tyr Leu Met Val Arg Ala Phe Leu Val Asn Asp Leu Cys Tyr Pro
    370                 375                 380

Gly Lys Asp Glu Asp Ala His Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Asp Pro Pro Ser
            420                 425                 430

Ser Glu His Glu Ser Val
        435

<210> SEQ ID NO 58
<211> LENGTH: 1946
<212> TYPE: DNA
<213> ORGANISM: Schizosaccharomyces pombe

<400> SEQUENCE: 58

```
ttcatttttct ctcttggcca ctattttttt ttttaattcc cctttatctc tcgattcgac      60
atgggtgaac tcaaggaaat cttgaaacag aggtatcatg agttgcttga ctggaatgtc     120
aaagcccctc atgtccctct cagtcaacga ctgaagcatt tacatggtc ttggtttgca      180
tgtactatgg caactggtgg tgttggtttg attattggtt cttccccctt tcgattttat     240
ggtcttaata caattggcaa aattgtttat attcttcaaa tcttttttgtt ttctctcttt    300
ggatcatgca tgcttttttcg ctttattaaa tatccttcaa ctatcaagga ttcctggaac    360
catcatttgg aaaagctttt cattgctact tgtcttcttt caatatccac gttcatcgac     420
atgcttgcca tatacgccta tcctgatacc ggcgagtgga tggtgtgggt cattcgaatc     480
ctttattaca tttacgttgc agtatccttt atatactgcg taatggcttt ttttacaatt    540
ttcaacaacc atgtatatac cattgaaacc gcatctcctg cttggattct tcctattttc    600
cctcctatga tttgtggtgt cattgctggc gccgtcaatt ctacacaacc cgctcatcaa    660
ttaaaaaata tggttatctt tggtatcctc tttcaaggac ttggttttttg ggtttatctt   720
ttactgtttg ccgtcaatgt cttacggttt tttactgtag gcctggcaaa accccaagat    780
cgacctggta tgtttatgtt tgtcggtcca ccagcttctc caggtttggc cttaattaat    840
attgcgcgtg tgctatggg cagtcgccct tatattttg ttggcgccaa ctcatccgag      900
tatcttggtt ttgtttctac cttatggct attttttattt ggggtcttgc tgcttggtgt   960
tactgtctcg ccatggttag cttttttagcg ggcttttttca ctcgagcccc tctcaagttt 1020
gcttgtggat ggtttgcatt cattttcccc aacgtgggtt ttgttaattg taccattgag  1080
ataggtaaaa tgatagattc caaagctttc caaatgtttg acatatcat tggggtcatt   1140
ctttgtattc agtggatcct cctaatgtat ttaatggtcc gtgcgtttct cgtcaatgat  1200
ctttgctatc ctggcaaaga cgaagatgcc catcctccac caaaaccaaa tacaggtgtc  1260
cttaacccta ccttcccacc tgaaaaagca cctgcatctt tggaaaagt cgatacacat   1320
gtcacatcta ctggtggtga atcggatcct cctagtagtg aacatgaaag cgtttaagct  1380
tgtatgcttt tccttaattt ttctataaat ctgtgtgccc tgctcttaat accattatag  1440
attaatcatt ttgaatcatt ctgtatcttt attgtactac tggtactaat tttgcttaga  1500
cattttgct ccttcttctt cttttttgttt aaattataca taccaaaatt ttggactttg 1560
aataatggta attttggtt gtcgtagtgt taaatatgta tgcgtcttgc atatgaatca   1620
cgacgaagga atcaattaaa aaatcaatcc tgtacataat aaaattaagt ttatttattt   1680
cattttatcg gatttaatcg tctaaaattt atatcttggt catccaagct tatatctctt   1740
tctactctta tcagcagcac actttagtta tggttatttg aaaacttgtg tataaattcc   1800
tggttataga gaaatgagt ataagacaac aaaaaaaagc ctagtcggca tgcgacatgt    1860
ctcaaacata tctttggcgt attgatgagc atcttacaca ctcactatac gtaacaataa  1920
aattaagagg gatttcatga caaaag                                        1946
```

<210> SEQ ID NO 59
<211> LENGTH: 383
<212> TYPE: PRT
<213> ORGANISM: Pseudomonas sp.

<400> SEQUENCE: 59

```
Met Ile Cys Pro Asn Ser Ala Lys Pro Gly Ile Lys Pro Phe Ser Gln
1               5                   10                  15
```

```
Leu Gln His Pro Arg Glu Val Ile Arg Gln Phe Thr Pro Asn Trp Phe
            20                  25                  30

Ala Ala Thr Met Gly Thr Gly Val Leu Ala Leu Ala Leu Ala Gln Leu
        35                  40                  45

Pro Val Ala Ile Pro Gly Leu His Ala Val Ala Glu Gly Leu Trp Leu
 50                  55                  60

Phe Asn Ile Leu Leu Phe Thr Leu Phe Thr Phe Ala Tyr Ala Ala Arg
 65                  70                  75                  80

Trp Ile Leu Phe Phe Asp Glu Ala Arg Arg Ile Phe Gly His Ser Thr
                85                  90                  95

Val Ser Met Phe Gly Thr Ile Pro Met Gly Leu Ala Thr Ile Ile
                100                 105                 110

Asn Gly Phe Leu Val Phe Gly Leu Pro Arg Trp Gly Glu Gly Val Ile
                115                 120                 125

His Leu Ala Glu Val Leu Trp Trp Leu Asp Val Ala Met Ser Leu Ala
130                 135                 140

Cys Gly Val Leu Ile Pro Tyr Met Met Phe Thr Arg Gln Glu His Ser
145                 150                 155                 160

Ile Asp Gln Met Thr Ala Val Trp Leu Leu Pro Val Val Ala Ala Glu
                165                 170                 175

Val Ala Ala Ala Ser Gly Gly Leu Leu Ala Pro His Leu Ala Asp Ala
                180                 185                 190

His Ala Gln Leu Val Val Leu Thr Thr Ser Tyr Val Leu Trp Ala Phe
                195                 200                 205

Ser Leu Pro Val Ala Phe Ser Ile Leu Thr Ile Leu Leu Arg Met
210                 215                 220

Ala Leu His Lys Leu Pro His Glu Asn Met Ala Ala Ser Ser Trp Leu
225                 230                 235                 240

Ala Leu Gly Pro Ile Gly Thr Gly Ala Leu Gly Met Leu Leu Leu Gly
                245                 250                 255

Ser Asp Ala Pro Ala Ile Phe Ala Ala Asn Gly Leu Pro Gly Ile Gly
                260                 265                 270

Glu Ile Ala Ala Gly Leu Gly Leu Val Ala Gly Ile Thr Leu Trp Gly
                275                 280                 285

Phe Gly Leu Trp Trp Met Leu Met Ala Leu Leu Ile Thr Ala Arg Tyr
                290                 295                 300

Leu Arg Asp Gly Ile Pro Phe Asn Leu Gly Trp Trp Gly Phe Thr Phe
305                 310                 315                 320

Pro Leu Gly Val Tyr Ser Leu Ala Thr Leu Lys Leu Ala Ser Thr Leu
                325                 330                 335

Asn Leu Gly Phe Phe Ser Val Val Gly Cys Val Leu Val Ser Leu Leu
                340                 345                 350

Ala Val Met Trp Leu Ile Val Gly Lys Arg Thr Val Gln Gly Ala Trp
                355                 360                 365

Arg Gly Glu Leu Phe Val Ser Pro Cys Ile Ala Gly Leu Lys Gln
370                 375                 380

<210> SEQ ID NO 60
<211> LENGTH: 1143
<212> TYPE: DNA
<213> ORGANISM: Pseudomonas sp.

<400> SEQUENCE: 60
atgctgacac ctcccaagtt tgaggatgag aagcagctgg gccccgtggg tatccgggag    60
```

```
aggcttcgcc atttcacttg ggcctggtac acattaacga tgagtggagg agggctggcc    120
gtcctcatca tcagccagcc ctttgggttc cgcggattga gagagatcgg catcgctgtc    180
tatatcctca acctgatcct cttcgccctt gtctgctcta ccatggctat aaggttcatc    240
ctgcacggca accttctgga gtccctccgt catgaccgcg agggtctctt cttcccgacc    300
ttctggctct ccgtcgcaac catcatctgc ggcttgtctc gctacttcgg tgaagaatcg    360
aatgagtcct ccaactagc cctcgaagcc ctcttctgga tctactgcgt ctgcacctta    420
ctcgtcgcaa tcatccaata ctcgttcgtc ttctcatccc acaagtacgg ccttcaaacc    480
atgatgcctt catggatcct tccagccttc cccatcatgc tcagcggcac catcgcctcc    540
gtcatcggtg aacaacaacc cgctcgcgca gccctcccca tcatcggcgc cggcgtcacc    600
ttccagggcc tcggcttctc catcagcttc atgatgtacg cccactacat cggccgactg    660
atggagtccg gcctccccca cagcgaccac agaccaggca tgttcatctg cgtcggaccc    720
cccgccttca cagccctcgc cctcgtcggc atgagcaaag gctcccccga agacttcaag    780
ctgctccacg acgcccacgc cctggaagat ggccgcatca tcgagctgct ggccatctcc    840 gccgcgtct tcctctgggc cctgagtctc tggttcttct gcatcgccat gtcgccgtc    900 atccgctcgc ccccgaggc cttccacctc aactggtggg ccatggtctt ccccaacacc    960
ggcttcaccc tggccaccat caccctgggc aaggctctca acagtaacgg cgtgaagggc    1020
gtcggctccg ccatgtctat ctgcatcgtg tgcatgtaca tcttcgtctt tgtcaacaat    1080
gtccgcgccg ttatccggaa ggatatcatg tacccgggta agatgagga tgtatctgat    1140 tag                                                                  1143
```

<210> SEQ ID NO 61
<211> LENGTH: 386
<212> TYPE: PRT
<213> ORGANISM: Erwinia billingiae

<400> SEQUENCE: 61

```
Met Asn Asp Lys Ile Phe Thr Leu His Asn Gly Ala Arg Pro Leu Ser
1               5                   10                  15

Ala Leu Ser Ser Pro Lys Glu Ala Ile Arg Gln Phe Thr Pro Asn Trp
            20                  25                  30

Phe Ala Ala Thr Met Gly Thr Gly Ile Leu Ser Leu Ser Leu Ala Gln
        35                  40                  45

Phe Pro Trp Gln Val Pro Gly Leu Arg Leu Val Ala Glu Gly Leu Trp
    50                  55                  60

Met Phe Asn Ile Leu Leu Phe Ser Val Phe Ala Val Met Tyr Leu Ala
65                  70                  75                  80

Arg Trp Val Met Tyr Phe Gly Glu Ala Lys Arg Ile Phe Gly His Ser
                85                  90                  95

Thr Val Ser Met Phe Gly Thr Ile Pro Met Gly Met Ala Thr Ile
            100                 105                 110

Ile Asn Gly Leu Leu Ala Phe Gly Leu Pro Arg Trp Gly Ala Asp Val
        115                 120                 125

Ile Gln Val Ala His Ala Leu Trp Trp Leu Asp Val Ala Met Ser Leu
    130                 135                 140

Leu Cys Gly Val Cys Ile Pro Tyr Met Met Phe Thr Arg Gln Gln His
145                 150                 155                 160

Ser Ile Asp Gln Met Thr Ala Val Trp Leu Leu Pro Val Val Ala Ala
                165                 170                 175
```

```
Glu Val Ala Ala Val Ser Gly Gly Leu Leu Ala Pro His Ile Ala Ala
            180                 185                 190

Pro His Ala Gln Leu Gly Ile Ile Ile Thr Ser Tyr Val Leu Trp Ala
        195                 200                 205

Tyr Ser Val Pro Val Ala Leu Ser Ile Leu Ala Ile Leu Leu Arg
    210                 215                 220

Met Ala Leu His Lys Leu Pro His Glu Ser Met Ala Ala Ser Ser Trp
225                 230                 235                 240

Leu Ala Leu Gly Pro Ile Gly Thr Gly Ser Leu Gly Met Leu Val Ile
                245                 250                 255

Gly Gly Asp Ala Pro Gly Val Phe Ala Ala Gly Met Pro Glu Ile
            260                 265                 270

Gly His Ile Ala Gln Gly Val Gly Phe Val Ala Gly Ile Leu Phe Trp
        275                 280                 285

Gly Cys Gly Leu Trp Trp Met Leu Leu Ala Thr Leu Ile Thr Val Arg
    290                 295                 300

Tyr Phe Arg Glu Gly Ile Pro Phe Asn Leu Gly Trp Trp Gly Phe Thr
305                 310                 315                 320

Phe Pro Leu Gly Val Tyr Thr Val Ala Thr Leu Lys Leu Ser Thr Leu
                325                 330                 335

Ile Asp Leu Ala Phe Phe Lys Gly Phe Gly Ala Leu Leu Val Val Ile
            340                 345                 350

Leu Ala Ala Met Trp Leu Leu Val Ala Val Lys Thr Val Arg Gly Ala
        355                 360                 365

Trp Ser Gly Lys Leu Phe Val Ser Pro Cys Leu Ala Gly Leu Asp Arg
370                 375                 380

Lys Pro
385

<210> SEQ ID NO 62
<211> LENGTH: 1161
<212> TYPE: DNA
<213> ORGANISM: Erwinia billingiae

<400> SEQUENCE: 62
atgaacgata aaatattcac cctgcataac ggtgcgcgtc cgctgagcgc gctgagcagc      60
ccgaaagagg ccatacgaca gttcacgcct aactggttcg ccgcgaccat ggggaccggc     120
atcctgtcgc tgtctctggc gcagttcccc tggcaggttc cgggattgcg ccttgtcgcc     180
gaggggctct ggatgtttaa catcctcctg ttcagcgtct tgccgtgat gtatctggcc     240 cgctgggtga tgtacttcgg agaggcaaag cgcattttcg ccattcaac cgtgtccatg     300 ttcttcggca ccatcccgat gggcatggcg accatcatca atggcctgct ggcgttcggt     360
cttccgcgct ggggcgcaga cgttattcag gtggcacacg ccctgtggtg gctggacgtg     420
gcgatgtcgc tgctgtgcgg cgtgtgcatt ccctacatga tgtttacccg gcagcagcac     480
agtattgacc agatgactgc cgtctggtta ctgccggtcg tggcagccga ggtcgcggcg     540
gtcagcggcg gcctgctggc gccgcacatt gctgccccac acgcgcagct cggcatcatt     600
attaccagct acgtgctgtg gcgtactcc gtgccggtgg cgctgagcat cctgccatt      660 ctgctgctgc gtatggcgct gcacaagcta ccgcacgaaa gcatggcggc ctcaagctgg     720
ctggcgctgg gtccgattgg caccggctcg ctcggcatgc tggtcatcgg cggagatgcg     780
cccggggtgt tgccgcggc gggcatgccg gaaatcggtc acatcgcgca gggcgtgggg     840
```

```
ttcgttgccg gcattctctt ctggggctgc ggcctgtggt ggatgctgct ggccacgctg      900
ataaccgtgc gatacttccg tgaaggcatc ccgttcaacc ttggatggtg gggctttacc      960
ttcccgctgg gcgtgtacac cgtggccacg ctcaagctgt ctaccctgat tgacctcgca     1020
ttctttaaag gcttcggtgc gcttcttgtc gtcatactgg cggccatgtg gctgcttgtc     1080
gcggtgaaaa cagtgcgtgg ggcatggagc ggtaaactgt ttgtttctcc ctgtctggca     1140
ggcctggatc ggaagccgtg a                                               1161
```

<210> SEQ ID NO 63
<211> LENGTH: 433
<212> TYPE: PRT
<213> ORGANISM: Escherichia coli

<400> SEQUENCE: 63

```
Met Leu Val Val Glu Leu Ile Ile Val Leu Leu Ala Ile Phe Leu Gly
1               5                   10                  15

Ala Arg Leu Gly Gly Ile Gly Ile Gly Phe Ala Gly Gly Leu Gly Val
            20                  25                  30

Leu Val Leu Ala Ala Ile Gly Val Lys Pro Gly Asn Ile Pro Phe Asp
        35                  40                  45

Val Ile Ser Ile Ile Met Ala Val Ile Ala Ala Ile Ser Ala Met Gln
    50                  55                  60

Val Ala Gly Gly Leu Asp Tyr Leu Val His Gln Thr Glu Lys Leu Leu
65                  70                  75                  80

Arg Arg Asn Pro Lys Tyr Ile Thr Ile Leu Ala Pro Ile Val Thr Tyr
                85                  90                  95

Phe Leu Thr Ile Phe Ala Gly Thr Gly Asn Ile Ser Leu Ala Thr Leu
            100                 105                 110

Pro Val Ile Ala Glu Val Ala Lys Glu Gln Gly Val Lys Pro Cys Arg
        115                 120                 125

Pro Leu Ser Thr Ala Val Val Ser Ala Gln Ile Ala Ile Thr Ala Ser
    130                 135                 140

Pro Ile Ser Ala Ala Val Val Tyr Met Ser Ser Val Met Glu Gly His
145                 150                 155                 160

Gly Ile Ser Tyr Leu His Leu Leu Ser Val Val Ile Pro Ser Thr Leu
                165                 170                 175

Leu Ala Val Leu Val Met Ser Phe Leu Val Thr Met Leu Phe Asn Ser
            180                 185                 190

Lys Leu Ser Asp Asp Pro Ile Tyr Arg Lys Arg Leu Glu Glu Gly Leu
        195                 200                 205

Val Glu Leu Arg Gly Glu Lys Gln Ile Glu Ile Lys Ser Gly Ala Lys
    210                 215                 220

Thr Ser Val Trp Leu Phe Leu Leu Gly Val Gly Val Val Ile Tyr
225                 230                 235                 240

Ala Ile Ile Asn Ser Pro Ser Met Gly Leu Val Glu Lys Pro Leu Met
                245                 250                 255

Asn Thr Thr Asn Ala Ile Leu Ile Ile Met Leu Ser Val Ala Thr Leu
            260                 265                 270

Thr Thr Val Ile Cys Lys Val Asp Thr Asp Asn Ile Leu Asn Ser Ser
        275                 280                 285

Thr Phe Lys Ala Gly Met Ser Ala Cys Ile Cys Ile Leu Gly Val Ala
    290                 295                 300

Trp Leu Gly Asp Thr Phe Val Ser Asn Asn Ile Asp Trp Ile Lys Asp
305                 310                 315                 320
```

```
Thr Ala Gly Glu Val Ile Gln Gly His Pro Trp Leu Leu Ala Val Ile
                325                 330                 335

Phe Phe Phe Ala Ser Ala Leu Leu Tyr Ser Gln Ala Ala Thr Ala Lys
            340                 345                 350

Ala Leu Met Pro Met Ala Leu Ala Leu Asn Val Ser Pro Leu Thr Ala
        355                 360                 365

Val Ala Ser Phe Ala Ala Val Ser Gly Leu Phe Ile Leu Pro Thr Tyr
    370                 375                 380

Pro Thr Leu Val Ala Ala Val Gln Met Asp Asp Thr Gly Thr Thr Arg
385                 390                 395                 400

Ile Gly Lys Phe Val Phe Asn His Pro Phe Phe Ile Pro Gly Thr Leu
                405                 410                 415

Gly Val Ala Leu Ala Val Cys Phe Gly Phe Val Leu Gly Ser Phe Met
            420                 425                 430

Leu
```

```
<210> SEQ ID NO 64
<211> LENGTH: 1302
<212> TYPE: DNA
<213> ORGANISM: Escherichia coli

<400> SEQUENCE: 64
atgctagttg tagaactcat catagttttg ctggcgatct tcttgggcgc cagattgggg     60
ggaataggta ttggtttttgc aggcggattg ggggtgctgg ttcttgccgc tattggcgtt    120
aaacccggta acatcccgtt cgatgtcatc tccattatca tggcggttat cgccgctatt    180
tctgccatgc aggttgctgg cggtctggac tatctggttc atcagacaga aaagctgctg    240
cgccgtaacc cgaaatacat cacgatcctc gcaccgatcg tgacctattt cctgactatc    300
tttgctggta ctggcaacat ctctctggcg acactgccag ttatcgctga agttgcgaag    360
gaacaaggcg ttaaaccttg ccgtccgctg tctactgcag tggtatccgc gcagattgcg    420
atcaccgcat cgccaatctc agcggcagtg gtttacatgt cttccgtgat ggaaggtcat    480
ggcatcagct acctccatct gctctccgtg gtcatcccgt ccaccctgct ggcggttctg    540
gtgatgtcct tcctggtcac tatgctgttc aactccaaac tctctgacga tccgatttat    600
cgcaagcgtc tggaagaggg cctggttgaa ctgcgcggtg aaaagcagat gaaatcaaa    660
tccggtgcaa aaacgtccgt ctggctgttc ctgctgggcg tagttggcgt ggttatctat    720
gcaatcatca cagcccaag catgggtctg gttgaaaaac cgctgatgaa caccaccaac    780
gcaatcctga tcatcatgct cagcgttgca actctgacca ccgttatctg taaagtcgat    840
accgacaaca tcctcaactc cagcaccttc aaagcaggta tgagcgcctg tatttgtatc    900
ctgggtgttg cgtggctggg cgatactttc gtttccaaca acatcgactg gatcaaagat    960
accgctggtg aagtgattca gggtcatccg tggctgctgg ccgtcatctt cttctttgct   1020
tctgctctgc tgtactctca ggctgcaacc gcaaaagcac tgatgccgat ggctctggca   1080
ctgaacgttt caccgctgac cgctgttgct tcttttcgctg cggtgtctgg tctgttcatt   1140
ctgccgacct acccgacgct ggttgctgcg gtacagatgg atgacacggg tactacccgt   1200
atcggtaaat tcgtcttcaa ccatccgttc ttcatcccgg gtactctggg tgttgccctg   1260
gccgtttgct tcggcttcgt gctgggtagc ttcatgctgt aa                       1302
```

```
<210> SEQ ID NO 65
<211> LENGTH: 446
```

```
<212> TYPE: PRT
<213> ORGANISM: Escherichia coli

<400> SEQUENCE: 65

Met Leu Phe Thr Ile Gln Leu Ile Ile Leu Ile Cys Leu Phe Tyr
1               5                   10                  15

Gly Ala Arg Lys Gly Gly Ile Ala Leu Gly Leu Leu Gly Ile Gly
                20                  25                  30

Leu Val Ile Leu Val Phe Val Phe His Leu Gln Pro Gly Lys Pro Pro
            35                  40                  45

Val Asp Val Met Leu Val Ile Ile Ala Val Ala Ala Ser Ala Thr
    50                  55                  60

Leu Gln Ala Ser Gly Gly Leu Asp Val Met Leu Gln Ile Ala Glu Lys
65                  70                  75                  80

Leu Leu Arg Arg Asn Pro Lys Tyr Val Ser Ile Val Ala Pro Phe Val
                85                  90                  95

Thr Cys Thr Leu Thr Ile Leu Cys Gly Thr His Val Val Tyr Thr
                100                 105                 110

Ile Leu Pro Ile Ile Tyr Asp Val Ala Ile Lys Asn Asn Ile Arg Pro
            115                 120                 125

Glu Arg Pro Met Ala Ala Ser Ser Ile Gly Ala Gln Met Gly Ile Ile
    130                 135                 140

Ala Ser Pro Val Ser Val Ala Val Val Ser Leu Val Ala Met Leu Gly
145                 150                 155                 160

Asn Val Thr Phe Asp Gly Arg His Leu Glu Phe Leu Asp Leu Leu Ala
                165                 170                 175

Ile Thr Ile Pro Ser Thr Leu Ile Gly Ile Leu Ala Ile Gly Ile Phe
            180                 185                 190

Ser Trp Phe Arg Gly Lys Asp Leu Asp Lys Asp Glu Glu Phe Gln Lys
                195                 200                 205

Phe Ile Ser Val Pro Glu Asn Arg Glu Tyr Val Tyr Gly Asp Thr Ala
    210                 215                 220

Thr Leu Leu Asp Lys Lys Leu Pro Lys Ser Asn Trp Leu Ala Met Trp
225                 230                 235                 240

Ile Phe Leu Gly Ala Ile Ala Val Val Ala Leu Leu Gly Ala Asp Ser
                245                 250                 255

Asp Leu Arg Pro Ser Phe Gly Gly Lys Pro Leu Ser Met Val Leu Val
            260                 265                 270

Ile Gln Met Phe Met Leu Leu Thr Gly Ala Leu Ile Ile Ile Leu Thr
                275                 280                 285

Lys Thr Asn Pro Ala Ser Ile Ser Lys Asn Glu Val Phe Arg Ser Gly
    290                 295                 300

Met Ile Ala Ile Val Ala Val Tyr Gly Ile Ala Trp Met Ala Glu Thr
305                 310                 315                 320

Met Phe Gly Ala His Met Ser Glu Ile Gln Gly Val Leu Gly Glu Met
                325                 330                 335

Val Lys Glu Tyr Pro Trp Ala Tyr Ala Ile Val Leu Leu Val Ser
            340                 345                 350

Lys Phe Val Asn Ser Gln Ala Ala Leu Ala Ala Ile Val Pro Val
            355                 360                 365

Ala Leu Ala Ile Gly Val Asp Pro Ala Tyr Ile Val Ala Ser Ala Pro
    370                 375                 380

Ala Cys Tyr Gly Tyr Tyr Ile Leu Pro Thr Tyr Pro Ser Asp Leu Ala
385                 390                 395                 400
```

Ala Ile Gln Phe Asp Arg Ser Gly Thr Thr His Ile Gly Arg Phe Val
            405                 410                 415

Ile Asn His Ser Phe Ile Leu Pro Gly Leu Ile Gly Val Ser Val Ser
            420                 425                 430

Cys Val Phe Gly Trp Ile Phe Ala Ala Met Tyr Gly Phe Leu
            435                 440                 445

<210> SEQ ID NO 66
<211> LENGTH: 1341
<212> TYPE: DNA
<213> ORGANISM: Escherichia coli

<400> SEQUENCE: 66

```
atgttattta ctatccaact tatcataata ctgatatgtc tgttttatgg tgccagaaag      60
ggtggtatcg cgctgggttt attaggcggt atcggtctgg tcattctggt cttcgtcttc     120
caccttcagc caggtaaacc accagttgat gtcatgctgg ttatcattgc ggtggtggcg     180
gcatcggcga ccttgcaagc ttcgggcggt cttgatgtca tgctgcaaat tgccgagaag     240
ctgctgcgcc gcaacccgaa atatgtctca attgtcgcgc gtttgtgac ctgtacactg      300
accattcttt gcggtacggg tcatgtggtt tacaccattc tgccgatcat ctacgacgtc     360
gccattaaga caacatccg tccggaacgt ccgatggcgg caagttctat cggtgcacag      420
atggggatta tcgccagtcc ggtgtcggtt gcggtcgtgt ctctggttgc gatgctgggt     480
aatgtcacct tgatggtcg ccatcttgag ttcctcgatc tgctggcaat caccattcca      540
tcgacgttaa tcggtatcct ggcgatcggt atcttcagct ggttccgcgg taaagatctg     600
gataaagacg aagagttcca gaaattcatc tccgtaccgg aaaaccgtga gtatgtttac     660
ggtgataccg cgacgctgct ggataaaaaa ctgccgaaaa gcaactggct ggcaatgtgg     720
attttcctcg gggcaatcgc tgtagtcgcc cttcttggtg ctgattcgga cctgcgtcca     780
tccttcggcg gcaaaccgct gtcgatggta ctggttattc agatgtttat gctgctgacc     840
ggggcgctga ttattatcct gaccaaaacc aatcccgcgt ctatctcaaa aaacgaagtc     900
ttccgttccg gtatgatcgc catcgtggcg gtgtacggta tcgcatggat ggcagaaaacc    960
atgttcggtg cgcatatgtc tgaaattcag ggcgtactgg gtgaaatggt gaaagagtat   1020
ccgtgggcct atgccattgt tctgctgctg gtttccaagt ttgtaaactc tcaggctgcg   1080
gcgctggcgg cgattgttcc ggtcgcgctg gcgatcggcg ttgatccggc atacatcgtg   1140
gcttcagcac cggcttgcta cggttattac atcctgccga cttatccgag cgatctggca   1200
gcgattcagt ttgaccgttc cggcaccacc cacatcggtc gcttcgtcat caaccacagc   1260
tttattctgc cggggttgat tggtgtgagc gtatcgtgcg tcttcggctg gatcttcgcc   1320
gcgatgtacg ggttcttata a                                             1341
```

<210> SEQ ID NO 67
<211> LENGTH: 461
<212> TYPE: PRT
<213> ORGANISM: Escherichia coli

<400> SEQUENCE: 67

Met Leu Thr Phe Ile Glu Leu Leu Ile Gly Val Val Ile Val Gly
1               5                   10                  15

Val Ala Arg Tyr Ile Ile Lys Gly Tyr Ser Ala Thr Gly Val Leu Phe
            20                  25                  30

Val Gly Gly Leu Leu Leu Leu Ile Ile Ser Ala Ile Met Gly His Lys

```
            35                  40                  45
Val Leu Pro Ser Ser Gln Ala Ser Thr Gly Tyr Ser Ala Thr Asp Ile
 50                  55                  60

Val Glu Tyr Val Lys Ile Leu Leu Met Ser Arg Gly Gly Asp Leu Gly
 65                  70                  75                  80

Met Met Ile Met Met Leu Cys Gly Phe Ala Ala Tyr Met Thr His Ile
                     85                  90                  95

Gly Ala Asn Asp Met Val Val Lys Leu Ala Ser Lys Pro Leu Gln Tyr
                100                 105                 110

Ile Asn Ser Pro Tyr Leu Leu Met Ile Ala Ala Tyr Phe Val Ala Cys
                115                 120                 125

Leu Met Ser Leu Ala Val Ser Ser Ala Thr Gly Leu Gly Val Leu Leu
            130                 135                 140

Met Ala Thr Leu Phe Pro Val Met Val Asn Val Gly Ile Ser Arg Gly
145                 150                 155                 160

Ala Ala Ala Ala Ile Cys Ala Ser Pro Ala Ala Ile Ile Leu Ala Pro
                165                 170                 175

Thr Ser Gly Asp Val Val Leu Ala Ala Gln Ala Ser Glu Met Ser Leu
            180                 185                 190

Ile Asp Phe Ala Phe Lys Thr Thr Leu Pro Ile Ser Ile Ala Ala Ile
        195                 200                 205

Ile Gly Met Ala Ile Ala His Phe Phe Trp Gln Arg Tyr Leu Asp Lys
        210                 215                 220

Lys Glu His Ile Ser His Glu Met Leu Asp Val Ser Glu Ile Thr Thr
225                 230                 235                 240

Thr Ala Pro Ala Phe Tyr Ala Ile Leu Pro Phe Thr Pro Ile Ile Gly
                245                 250                 255

Val Leu Ile Phe Asp Gly Lys Trp Gly Pro Gln Leu His Ile Ile Thr
            260                 265                 270

Ile Leu Val Ile Cys Met Leu Ile Ala Ser Ile Leu Glu Phe Leu Arg
        275                 280                 285

Ser Phe Asn Thr Gln Lys Val Phe Ser Gly Leu Glu Val Ala Tyr Arg
    290                 295                 300

Gly Met Ala Asp Ala Phe Ala Asn Val Val Met Leu Leu Val Ala Ala
305                 310                 315                 320

Gly Val Phe Ala Gln Gly Leu Ser Thr Ile Gly Phe Ile Gln Ser Leu
                325                 330                 335

Ile Ser Ile Ala Thr Ser Phe Gly Ser Ala Ser Ile Ile Leu Met Leu
            340                 345                 350

Val Leu Val Ile Leu Thr Met Leu Ala Ala Val Thr Thr Gly Ser Gly
        355                 360                 365

Asn Ala Pro Phe Tyr Ala Phe Val Glu Met Ile Pro Lys Leu Ala His
        370                 375                 380

Ser Ser Gly Ile Asn Pro Ala Tyr Leu Thr Ile Pro Met Leu Gln Ala
385                 390                 395                 400

Ser Asn Leu Gly Arg Thr Leu Ser Pro Val Ser Gly Val Val Val Ala
                405                 410                 415

Val Ala Gly Met Ala Lys Ile Ser Pro Phe Glu Val Val Lys Arg Thr
            420                 425                 430

Ser Val Pro Val Leu Val Gly Leu Val Ile Val Ile Val Ala Thr Glu
        435                 440                 445

Leu Met Val Pro Gly Thr Ala Ala Ala Val Thr Gly Lys
450                 455                 460
```

```
<210> SEQ ID NO 68
<211> LENGTH: 1386
<212> TYPE: DNA
<213> ORGANISM: Escherichia coli

<400> SEQUENCE: 68
atgctgacat tcattgagct ccttattggg gttgtggtta ttgtgggtgt agctcgctac     60
atcattaaag ggtattccgc cactggtgtg ttatttgtcg gtggcctgtt attgctgatt    120
atcagtgcca ttatggggca aaagtgtta ccgtccagcc aggcttcaac aggctacagc    180
gccacggata tcgttgaata cgttaaaata ttactaatga gccgcggcgg cgacctcggc    240
atgatgatta tgatgctgtg tggatttgcc gcttacatga cccatatcgg cgcgaatgat    300
atggtggtca agctggcgtc aaaaccattg cagtatatta actcccctta cctgctgatg    360
attgccgcct attttgtcgc ctgtctgatg tctctggccg tctcttccgc aaccggtctg    420
ggtgttttgc tgatggcaac cctatttccg gtgatggtaa acgttggtat cagtcgtggc    480
gcagctgctg ccatttgtgc ctccccggcg gcgattattc tcgcaccgac ttcaggggat    540
gtggtgctgg cggcgcaagc ttccgaaatg tcgctgattg acttcgcctt caaaacgacg    600
ctgcctatct caattgctgc aattatcggc atggcgatcg cccacttctt ctggcaacgt    660
tatctggata aaaagagca catctctcat gaaatgttag atgtcagtga atcaccacc     720
actgctcctg cgttttatgc catttgccg ttcacgccga tcatcggtgt actgattttt    780
gacggtaaat ggggtccgca attacacatc atcactattc tggtgatttg tatgctgatt    840
gcctccattc tggagttcct ccgcagcttt aatacccaga aagttttctc tggtctggaa    900
gtggcttatc gcgggatggc agatgcgttt gctaacgtgg tgatgctgct ggttgccgct    960
ggggtattcg ctcaggggct tagcaccatc ggctttattc aaagtctgat ttctatcgct   1020
acctcgtttg gttcggcgag tatcatcctg atgctggtat tggtgattct gacaatgctg   1080
gcggcagtca cgaccggttc aggcaatgcg ccgttttatg cgtttgttga atgatcccg   1140
aaactggcgc actcttccgg cattaacccg gcgtatttga ctatcccgat gctgcaggcg   1200
tcaaaccttg gccgtaccct ttcgcccgtt tctggcgtag tcgttgcggt tgccgggatg   1260
gcgaagatct cgccgtttga agtcgtaaaa cgcacctcgg taccggtgct tgttggtttg   1320
gtgattgtta tcgttgctac agagctgatg gtgccaggaa cggcagcagc ggtcacaggc   1380
aagtaa                                                              1386

<210> SEQ ID NO 69
<211> LENGTH: 310
<212> TYPE: PRT
<213> ORGANISM: Escherichia coli

<400> SEQUENCE: 69

Met Lys Thr Leu Ile Arg Lys Phe Ser Arg Thr Ala Ile Thr Val Val
1               5                   10                  15

Leu Val Ile Leu Ala Phe Ile Ala Ile Phe Asn Ala Trp Val Tyr Tyr
            20                  25                  30

Thr Glu Ser Pro Trp Thr Arg Asp Ala Arg Phe Ser Ala Asp Val Val
        35                  40                  45

Ala Ile Ala Pro Asp Val Ser Gly Leu Ile Thr Gln Val Asn Val His
    50                  55                  60

Asp Asn Gln Leu Val Lys Lys Gly Gln Ile Leu Phe Thr Ile Asp Gln
65                  70                  75                  80
```

```
Pro Arg Tyr Gln Lys Ala Leu Glu Glu Ala Gln Ala Asp Val Ala Tyr
                85                  90                  95

Tyr Gln Val Leu Ala Gln Glu Lys Arg Gln Glu Ala Gly Arg Arg Asn
            100                 105                 110

Arg Leu Gly Val Gln Ala Met Ser Arg Glu Ile Asp Gln Ala Asn
        115                 120                 125

Asn Val Leu Gln Thr Val Leu His Gln Leu Ala Lys Ala Gln Ala Thr
130                 135                 140

Arg Asp Leu Ala Lys Leu Asp Leu Glu Arg Thr Val Ile Arg Ala Pro
145                 150                 155                 160

Ala Asp Gly Trp Val Thr Asn Leu Asn Val Tyr Thr Gly Glu Phe Ile
                165                 170                 175

Thr Arg Gly Ser Thr Ala Val Ala Leu Val Lys Gln Asn Ser Phe Tyr
            180                 185                 190

Val Leu Ala Tyr Met Glu Glu Thr Lys Leu Glu Gly Val Arg Pro Gly
        195                 200                 205

Tyr Arg Ala Glu Ile Thr Pro Leu Gly Ser Asn Lys Val Leu Lys Gly
    210                 215                 220

Thr Val Asp Ser Val Ala Ala Gly Val Thr Asn Ala Ser Ser Thr Arg
225                 230                 235                 240

Asp Asp Lys Gly Met Ala Thr Ile Asp Ser Asn Leu Glu Trp Val Arg
                245                 250                 255

Leu Ala Gln Arg Val Pro Val Arg Ile Arg Leu Asp Asn Gln Gln Glu
            260                 265                 270

Asn Ile Trp Pro Ala Gly Thr Thr Ala Thr Val Val Thr Gly Lys
        275                 280                 285

Gln Asp Arg Asp Glu Ser Gln Asp Ser Phe Phe Arg Lys Met Ala His
290                 295                 300

Arg Leu Arg Glu Phe Gly
305                 310

<210> SEQ ID NO 70
<211> LENGTH: 933
<212> TYPE: DNA
<213> ORGANISM: Escherichia coli

<400> SEQUENCE: 70
gtgaaaacac taataagaaa attctcccgt acggccatca cggtcgtatt agtcattctg      60
gccttcatcg caattttaa tgcctgggtc tattacaccg aatccccctg acgcgtgac      120 gcgcgcttta gcgctgacgt cgttgcgatc gcgccggacg tttctggact cattacccag      180
gtgaatgttc atgataacca gctggtgaaa aaaggacaga tactgttcac catcgaccag      240
ccgcgctatc aaaaggcgct tgaggaagcg caagccgatg ttgcttatta tcaggtactg      300
gcacaggaga aacgccagga ggccggacgt cgtaaccgtc tcggtgtgca ggcgatgtct      360
cgcgaagaga tcgaccaggc caacaacgta ctacaaacgg ttctgcatca gttagcgaaa      420
gcgcaggcga cccgcgatct ggcaaaactg gatcttgaac gcacggtgat ccgcgcgcca      480
gcagatggct gggtgaccaa cctcaacgtc tataccggtg agtttattac tcgaggatca      540
acggcggttg cgctggtgaa acagaactcc ttctatgtac tggcctatat ggaagaaact      600
aagctggaag gggtgcgtcc ggggtatcgt gcagagatca cgccgcttgg cagtaacaaa      660
gtgctgaaag gactgttgga tagtgttgcc gcagggtca ccaacgccag cagcacgcgt      720
gacgacaaag ggatggcgac tatagactct aaccttgaat gggtgcgtct tgcgcaacgt      780
```

```
gttccggttc gtattcgtct cgacaaccag caagagaaca tctggcctgc gggcaccact    840
gctacagtgg tggtcactgg caaacaagat cgcgacgaaa gccaggattc gttcttccgt    900
aaaatggccc atcgcctgcg tgagtttggt taa                                 933
```

<210> SEQ ID NO 71
<211> LENGTH: 655
<212> TYPE: PRT
<213> ORGANISM: Escherichia coli

<400> SEQUENCE: 71

```
Met Gly Ile Phe Ser Ile Ala Asn Gln His Ile Arg Phe Ala Val Lys
1               5                   10                  15

Leu Ala Thr Ala Ile Val Leu Ala Leu Phe Val Gly Phe His Phe Gln
            20                  25                  30

Leu Glu Thr Pro Arg Trp Ala Val Leu Thr Ala Ala Ile Val Ala Ala
        35                  40                  45

Gly Thr Ala Phe Ala Ala Gly Gly Glu Pro Tyr Ser Gly Ala Ile Arg
    50                  55                  60

Tyr Arg Gly Phe Leu Arg Ile Gly Thr Phe Ile Gly Cys Ile Ala
65                  70                  75                  80

Gly Leu Val Ile Ile Ile Ala Met Ile Arg Ala Pro Leu Leu Met Ile
                85                  90                  95

Leu Val Cys Cys Ile Trp Ala Gly Phe Cys Thr Trp Ile Ser Ser Leu
            100                 105                 110

Val Arg Ile Glu Asn Ser Tyr Ala Trp Gly Leu Ala Gly Tyr Thr Ala
        115                 120                 125

Leu Ile Ile Val Ile Thr Ile Gln Pro Glu Pro Leu Leu Thr Pro Gln
    130                 135                 140

Phe Ala Val Glu Arg Cys Ser Glu Ile Val Ile Gly Ile Val Cys Ala
145                 150                 155                 160

Ile Met Ala Asp Leu Leu Phe Ser Pro Arg Ser Ile Lys Gln Glu Val
                165                 170                 175

Asp Arg Glu Leu Glu Ser Leu Leu Val Ala Gln Tyr Gln Leu Met Gln
            180                 185                 190

Leu Cys Ile Lys His Gly Asp Gly Glu Val Val Asp Lys Ala Trp Gly
        195                 200                 205

Asp Leu Val Arg Arg Thr Thr Ala Leu Gln Gly Met Arg Ser Asn Leu
    210                 215                 220

Asn Met Glu Ser Ser Arg Trp Ala Arg Ala Asn Arg Arg Leu Lys Ala
225                 230                 235                 240

Ile Asn Thr Leu Ser Leu Thr Leu Ile Thr Gln Ser Cys Glu Thr Tyr
                245                 250                 255

Leu Ile Gln Asn Thr Arg Pro Glu Leu Ile Thr Asp Thr Phe Arg Glu
            260                 265                 270

Phe Phe Asp Thr Pro Val Glu Thr Ala Gln Asp Val His Lys Gln Leu
        275                 280                 285

Lys Arg Leu Arg Arg Val Ile Ala Trp Thr Gly Glu Arg Glu Thr Pro
    290                 295                 300

Val Thr Ile Tyr Ser Trp Val Ala Ala Ala Thr Arg Tyr Gln Leu Leu
305                 310                 315                 320

Lys Arg Gly Val Ile Ser Asn Thr Lys Ile Asn Ala Thr Glu Glu Glu
                325                 330                 335

Ile Leu Gln Gly Glu Pro Glu Val Lys Val Glu Ser Ala Glu Arg His
```

-continued

```
              340                 345                 350
His Ala Met Val Asn Phe Trp Arg Thr Thr Leu Ser Cys Ile Leu Gly
            355                 360                 365

Thr Leu Phe Trp Leu Trp Thr Gly Trp Thr Ser Gly Ser Gly Ala Met
        370                 375                 380

Val Met Ile Ala Val Val Thr Ser Leu Ala Met Arg Leu Pro Asn Pro
385                 390                 395                 400

Arg Met Val Ala Ile Asp Phe Ile Tyr Gly Thr Leu Ala Ala Leu Pro
                405                 410                 415

Leu Gly Leu Leu Tyr Phe Leu Val Ile Ile Pro Asn Thr Gln Gln Ser
            420                 425                 430

Met Leu Leu Leu Cys Ile Ser Leu Ala Val Leu Gly Phe Phe Leu Gly
        435                 440                 445

Ile Glu Val Gln Lys Arg Arg Leu Gly Ser Met Gly Ala Leu Ala Ser
    450                 455                 460

Thr Ile Asn Ile Ile Val Leu Asp Asn Pro Met Thr Phe His Phe Ser
465                 470                 475                 480

Gln Phe Leu Asp Ser Ala Leu Gly Gln Ile Val Gly Cys Val Leu Ala
                485                 490                 495

Phe Thr Val Ile Leu Leu Val Arg Asp Lys Ser Arg Asp Arg Thr Gly
            500                 505                 510

Arg Val Leu Leu Asn Gln Phe Val Ser Ala Val Ser Ala Met Thr
        515                 520                 525

Thr Asn Val Ala Arg Arg Lys Glu Asn His Leu Pro Ala Leu Tyr Gln
    530                 535                 540

Gln Leu Phe Leu Leu Met Asn Lys Phe Pro Gly Asp Leu Pro Lys Phe
545                 550                 555                 560

Arg Leu Ala Leu Thr Met Ile Ile Ala His Gln Arg Leu Arg Asp Ala
                565                 570                 575

Pro Ile Pro Val Asn Glu Asp Leu Ser Ala Phe His Arg Gln Met Arg
            580                 585                 590

Arg Thr Ala Asp His Val Ile Ser Ala Arg Ser Asp Lys Arg Arg
        595                 600                 605

Arg Tyr Phe Gly Gln Leu Leu Glu Glu Leu Glu Ile Tyr Gln Glu Lys
    610                 615                 620

Leu Arg Ile Trp Gln Ala Pro Pro Gln Val Thr Glu Pro Val Asn Arg
625                 630                 635                 640

Leu Ala Gly Met Leu His Lys Tyr Gln His Ala Leu Thr Asp Ser
                645                 650                 655

<210> SEQ ID NO 72
<211> LENGTH: 1968
<212> TYPE: DNA
<213> ORGANISM: Escherichia coli

<400> SEQUENCE: 72
atgggtattt tctccattgc taaccaacat attcgctttg cggtaaaact ggcgaccgcc      60
attgtactgg cgctgtttgt tggctttcac ttccagctgg aaacgccacg ctgggcggta     120
ctgacagcgg cgattgttgc cgccggtacg gcctttgctg cggaggtga accgtattct     180 ggcgctattc gctatcgtgg cttttttgcgc atcatcggca catttattgg ctgtattgcc     240
ggactggtga tcatcattgc gatgatccgc gcaccattat tgatgattct ggtgtgctgt     300
atctgggccg gttttttgtac ctggatatcc tcgctggtac gaatagaaaa ctcgtatgcg     360
```

```
tgggggctgg ccggttatac cgcgctgatc attgtgatca ccattcagcc ggaaccattg    420
cttacgccgc agtttgccgt cgaacgttgt agcgagatcg ttatcggtat tgtgtgtgcg    480
attatggcgg atttgctctt ttctccgcga tcgatcaaac aagaagtgga tcgagagctg    540
gaaagtttgc tggtcgcgca atatcaatta atgcaactct gtatcaagca tggcgatggt    600
gaagttgtcg ataaagcctg gggcgacctg gtgcgacgca ccacggcgct acaaggcatg    660
cgcagcaacc tgaatatgga atcttcccgc tgggcgcggg ccaatcgacg tttaaaagcg    720
atcaatacgc tatcgctgac gctgattacc caatcctgcg aaacttatct tattcagaat    780
acgcgcccgg aattgatcac tgatactttc cgcgaatttt ttgacacgcc ggtagaaacc    840
gcgcaggacg tccacaagca gctcaaacgc ctgcggagag ttatcgcctg gaccggggaa    900
cgggaaacgc ctgtcaccat ttatagctgg gtcgcggcgg caacgcgtta tcagcttctc    960
aagcgcggcg ttatcagtaa cacaaaaatc aacgccaccg aagaagagat cctgcaaggc   1020
gaaccggaag taaaagtaga gtcagccgaa cgtcatcatg caatggttaa cttctggcga   1080
accacacttt cctgcattct gggcacgctt ttctggctgt ggacgggctg gacttccggc   1140
agtggtgcaa tggtgatgat tgcggtagtg acgtcactgg caatgcgttt gccgaatcca   1200
cgcatggtgc cgatcgactt tatctacggg acgctgccg cgctgccgtt agggctgctc   1260
tacttttgg tgattatccc taatacccaa cagagcatgt tgctgctgtg cattagcctg   1320
gcagtgctgg gattcttcct cggtatagaa gtacagaaac ggcgactggg ctcgatgggg   1380
gcactggcca gcaccataaa tattatcgtg ctggataacc cgatgacttt ccatttcagt   1440
cagtttctcg acagcgcatt agggcaaatc gtcggctgtg tgctcgcgtt caccgttatt   1500
ttgctggtgc gggataaatc gcgcgacagg accggacgtg tactgcttaa tcagtttgtt   1560
tctgccgctg tttccgcgat gactaccaat gtggcacgtc gtaaagaaa ccacctcccg   1620
gcactttatc agcagctgtt tttgctgatg aataagttcc aggggatttt gccgaaattt   1680
cgcctggcgc tgacgatgat tatcgcgcac cagcgcctgc gtgatgcacc gatcccggtt   1740
aacgaggatt tatcggcgtt tcaccgacaa atgcgccgca cagcagacca tgtgatatct   1800
gcccgtagcg atgataaacg tcgtcggtac tttggccagt tgctgaaga actggaaatc   1860
taccaggaaa agctacgcat ctggcaagcg ccaccgcagg tgacggaacc ggtaaatcgg   1920
ctggcgggga tgctccataa gtatcaacat gcgttgaccg atagttaa               1968
```

<210> SEQ ID NO 73
<211> LENGTH: 151
<212> TYPE: PRT
<213> ORGANISM: Escherichia coli

<400> SEQUENCE: 73

```
Met Ala Glu Ser Thr Val Thr Ala Asp Ser Lys Leu Thr Ser Ser Asp
1               5                   10                  15

Thr Arg Arg Arg Ile Trp Ala Ile Val Gly Ala Ser Ser Gly Asn Leu
            20                  25                  30

Val Glu Trp Phe Asp Phe Tyr Val Tyr Ser Phe Cys Ser Leu Tyr Phe
        35                  40                  45

Ala His Ile Phe Phe Pro Ser Gly Asn Thr Thr Gln Leu Leu Gln
    50                  55                  60

Thr Ala Gly Val Phe Ala Ala Gly Phe Leu Met Arg Pro Ile Gly Gly
65                  70                  75                  80

Trp Leu Phe Gly Arg Ile Ala Asp Lys His Gly Arg Lys Lys Ser Met
                85                  90                  95
```

Leu Leu Ser Val Cys Met Met Cys Phe Gly Ser Leu Val Ile Ala Cys
            100                 105                 110

Leu Pro Gly Tyr Glu Thr Ile Gly Thr Trp Ala Pro Ala Leu Leu Leu
        115                 120                 125

Leu Ala Arg Leu Phe Gln Gly Leu Ser Val Gly Gly Glu Tyr Gly Thr
    130                 135                 140

Ser Ala Thr Tyr Met Ser Glu
145                 150

<210> SEQ ID NO 74
<211> LENGTH: 1299
<212> TYPE: DNA
<213> ORGANISM: Escherichia coli

<400> SEQUENCE: 74

```
atggctgaaa gtactgtaac ggcagacagc aaactgacaa gtagtgatac tcgtcgccgc      60
atttgggcga ttgtgggggc ctcttcaggt aatctggtcg agtggttcga tttctatgtc     120
tactcgttct gttcactcta ctttgcccac atcttcttcc cttccgggaa cacgacgact     180
caactactac aaacagcagg tgttttttgct gcgggattcc tgatgcgccc aataggcggt     240
tggctatttg ccgcatagc cgataaacat ggtcgcaaaa atcgatgct gttatcggtg       300
tgtatgatgt gtttcggatc gctggttatc gcctgcctcc caggttatga actataggt      360
acgtgggctc cggcattatt gcttctcgct cgtttatttc agggattatc tgttggcgga     420
gaatatggca ccagcgccac ctatatgagt gaagttgccg ttgaagggcg caaaggtttt     480
tacgcatcat ttcagtatgt gacgttgatc ggcggacaac tgctagccct actggttgtc     540
gtggttttac aacacaccat ggaagacgct gcactcagag agtggggatg gcgtattcct     600
ttcgcgttag gagctgtgtt agctgttgtg gcgttgtggt tacgtcgtca gttagatgaa     660
acttcgcaac aagaaacgcg cgcttttaaaa gaagctggat ctctgaaagg atattatggcgc    720
aatcgccgtg cattcatcat ggttctcggt tttaccgctg cgggctccct ttgtttctat     780
accttcacta cttatatgca gaagtatctg gtaaatactg cgggaatgca tgccaacgtg     840
gcgagtggca ttatgactgc cgcattgttt gtattcatgc ttattcaacc actcattggc     900
gcgctgtcgg ataagattgg tcgccgtacc tcaatgttat gtttcggttc gctggcagcc     960
atttttaccg ttcctattct ctcagcattg caaaacgttt cctcgcctta tgccgctttt   1020
ggtctggtga tgtgtgccct gctgatagtg agttttata catcaatcag tggaatactg    1080
aaggctgaga tgttcccggc acaggttcgc gcattaggcg ttggtctgtc atatgcggtc   1140
gctaatgcta tatttggtgg ttcggcggag tacgtagcgt tgtcgctgaa atcaatagga   1200
atggaaacag ccttcttctg gtatgtgacc ttgatggccg tggtggcgtt tctggtttct   1260
ttgatgctac atcgcaaagg gaaggggatg cgtctttag                         1299
```

<210> SEQ ID NO 75
<211> LENGTH: 161
<212> TYPE: PRT
<213> ORGANISM: Escherichia coli

<400> SEQUENCE: 75

Met Asn Leu Trp Gln Gln Asn Tyr Asp Pro Ala Gly Asn Ile Trp Leu
1               5                   10                  15

Ser Ser Leu Ile Ala Ser Leu Pro Ile Leu Phe Phe Phe Ala Leu
            20                  25                  30

```
Ile Lys Leu Lys Leu Lys Gly Tyr Val Ala Ala Ser Trp Thr Val Ala
            35                  40                  45
Ile Ala Leu Ala Val Ala Leu Leu Phe Tyr Lys Met Pro Val Ala Asn
 50                  55                  60
Ala Leu Ala Ser Val Val Tyr Gly Phe Phe Tyr Gly Leu Trp Pro Ile
 65                  70                  75                  80
Ala Trp Ile Ile Ile Ala Ala Val Phe Val Tyr Lys Ile Ser Val Lys
                 85                  90                  95
Thr Gly Gln Phe Asp Ile Ile Arg Ser Ser Ile Leu Ser Ile Thr Pro
                100                 105                 110
Asp Gln Arg Leu Gln Met Leu Ile Val Gly Phe Cys Phe Gly Ala Phe
            115                 120                 125
Leu Glu Gly Ala Ala Gly Phe Gly Ala Pro Val Ala Ile Thr Ala Ala
        130                 135                 140
Leu Leu Val Gly Leu Gly Phe Lys Pro Leu Tyr Ala Ala Gly Leu Cys
145                 150                 155                 160

Leu

<210> SEQ ID NO 76
<211> LENGTH: 1656
<212> TYPE: DNA
<213> ORGANISM: Escherichia coli

<400> SEQUENCE: 76
atgaatctct ggcaacaaaa ctacgatccc gccgggaata tctggctttc cagtctgata      60
gcatcgcttc ccatcctgtt tttcttcttt gcgctgatta agctcaaact gaaaggatac     120
gtcgccgcct cgtggacggt ggcaatcgcc cttgccgtgg ctttgctgtt ctataaaatg     180
ccggtcgcta acgcgctggc ctcggtggtt tatggtttct tctacgggtt gtggcccatc     240
gcgtggatca ttattgcagc ggtgttcgtc tataagatct cggtgaaaac cgggcagttt     300
gacatcattc gctcgtctat tctttcgata ccccctgacc agcgtctgca aatgctgatc     360
gtcggtttct gtttcggcgc gttccttgaa ggagccgcag gctttggcgc accggtagca     420
attaccgccg cattgctggt cggcctgggt tttaaaccgc tgtacgccgc cgggctgtgc     480
ctgattgtta acaccgcgcc agtggcattt ggtgcgatgg gcattccaat cctggttgcc     540
ggacaggtaa caggtatcga cagctttgag attggtcaga tggtggggcg gcagctaccg     600
tttatgacca ttatcgtgct gttctggatc atggcgatta tggacggctg cgcggtatc      660
aaagagacgt ggcctgcggt cgtggttgcg ggcggctcgt ttgccatcgc tcagtacctt     720
agctctaact tcattgggcc ggagctgccg gacattatct cttcgctggt atcactgctc     780
tgcctgacgc tgttcctcaa cgctggcag ccagtgcgtg tattccgttt ggtgatttg      840
ggggcgtcac aggttgatat gacgctggcc cacaccggtt acactgcggg tcaggtgtta     900
cgtgcctgga caccgttcct gttcctgaca gctaccgtaa cactgtggag tatcccgccg     960
tttaaagccc tgttcgcatc gggtggcgcg ctgtatgagt gggtgatcaa tattccggtg    1020
ccgtacctcg ataaactggt tgcccgtatg ccgccagtgg tcagcgaggc tacagcctat    1080
gccgccgtgt ttaagtttga ctggttctct gccaccggca ccgccattct gtttgctgca    1140
ctgctctcga ttgtctggct gaagatgaaa ccgtctgacg ctatcagcac cttcggcagc    1200
acgctgaaag aactggctct gcccatctac tccatcggta tggtgctggc attcgccttt    1260
atttcgaact attccggact gtcatcaaca ctggcgctgg cactggcgca caccggtcat    1320
gcattcacct tcttctcgcc gttcctcggc tggctggggg tattcctgac cgggtcggat    1380
```

-continued

```
acctcatcta acgccctgtt cgccgcgctg caagccaccg cagcacaaca aattggcgtc    1440
tctgatctgt tgctggttgc cgccaatacc accggtggcg tcaccggtaa gatgatctcc    1500
ccgcaatcta tcgctatcgc ctgtgcggcg gtaggcctgg tgggcaaaga gtctgatttg    1560
ttccgcttta ctgtcaaaca cagcctgatc ttcacctgta tagtgggcgt gatcaccacg    1620
cttcaggctt atgtcttaac gtggatgatt ccttaa                              1656
```

<210> SEQ ID NO 77
<211> LENGTH: 156
<212> TYPE: PRT
<213> ORGANISM: Escherichia coli

<400> SEQUENCE: 77

Met Val Thr Trp Thr Gln Met Tyr Met Pro Met Gly Gly Leu Gly Leu
1               5                   10                  15

Ser Ala Leu Val Ala Leu Ile Pro Ile Ile Phe Phe Val Ala Leu
            20                  25                  30

Ala Val Leu Arg Leu Lys Gly His Val Ala Gly Ala Ile Thr Leu Ile
        35                  40                  45

Leu Ser Ile Leu Ile Ala Ile Phe Ala Phe Lys Met Pro Ile Asp Met
    50                  55                  60

Ala Phe Ala Ala Ala Gly Tyr Gly Phe Ile Tyr Gly Leu Trp Pro Ile
65                  70                  75                  80

Ala Trp Ile Ile Val Ala Ala Val Phe Leu Tyr Lys Leu Thr Val Ala
                85                  90                  95

Ser Gly Gln Phe Asp Ile Ile Arg Ser Ser Val Ile Ser Ile Thr Asp
            100                 105                 110

Asp Gln Arg Leu Gln Val Leu Leu Ile Gly Phe Ser Phe Gly Ala Leu
        115                 120                 125

Leu Glu Gly Ala Ala Gly Phe Gly Ala Pro Val Ala Ile Thr Gly Ala
    130                 135                 140

Leu Leu Val Gly Leu Gly Phe Lys Pro Leu Tyr Ala
145                 150                 155

<210> SEQ ID NO 78
<211> LENGTH: 1683
<212> TYPE: DNA
<213> ORGANISM: Escherichia coli

<400> SEQUENCE: 78

```
atggttacct ggacccaaat gtatatgccg atgggaggac tggggctatc cgctctggtc     60
gccctgatcc cgataatatt cttcttcgtt gcactcgcgg tattacgtct gaaaggacat    120
gtcgctggag caataaccct tatattatct atcctgattg caatattcgc ctttaaaatg    180
ccgattgata tggcatttgc tgctgcgggc tatggcttta tttatggatt atggccaata    240
gcgtggatta ttgtcgcggc ggtgttcctg tataaattaa ccgttgccag cgggcagttc    300
gatattatcc gcagctcggt tatctccatc accgacgatc agcgtttgca ggtgttactg    360
attggtttct cctttggtgc gttgctggaa ggagcggctg gctttggtgc gccggtggcg    420
attaccggtg cgctgctggt gggcctgggc ttcaaaccgt atacgcggc ggggctgtgt    480 ctgattgcca atactgcgcc ggtggcgttt ggtgcgttgg gcgtgccgat tctggtcgcc    540
ggtcaggtaa cgggaatcga tccgttccac attggcgcaa tggcgggacg tcagttaccg    600
ttcctgtcgg ttcttgtgcc gttctggctg gtagcaatga tggacggctg gaaaggggtg    660
```

```
aaagagacgt ggccagcggc gctggttgct gggggaagct tcgctgtcac tcagttcttt    720
acctctaact atattggtcc ggaactgccg gatattactt cggcgctggt gagtatcgtc    780
tcactcgctt tattccttaa agtctggcgg ccgaaaaata ccgaaacggc aatcagcatg    840
ggacaatccg caggtgcgat ggtggtaaat aagccatctt ctggcggtcc cgtgccttca    900
gaatatagtc tggggcaaat cattcgagcg tggtcaccgt ttttaatctt aacggtgctg    960
gtcaccatct ggaccatgaa gccgtttaaa gcgttatttg ctccgggcgg cgcgttttat   1020
tcactggtga ttaatttcca gatccctcat ttgcatcaac aagtgttgaa agcggcaccc   1080
attgtcgccc aaccaacgcc aatggatgcg gtgtttaaat cgacccccct ctcggctggc   1140
ggcaccgcta tttttattgc ggcgattatc tctatcttca tcctcggtgt ggggatcaag   1200
aaaggtattg gcgtctttgc cgaaacgcta attagcttga agtggccgat actgtcgatt   1260
ggcatggtgc tggcgttcgc cttcgtcacc aactattctg gcatgtccac cacgctggcg   1320
ctggtactgg caggtacagg cgtgatgttc ccgttcttct caccgtttct cggctggctg   1380
ggcgtattcc ttaccggctc ggacacctcc tctaacgccc tgtttggttc actgcaatcg   1440
accacggcgc agcaaatcaa cgtctctgac accctgctgg tggcagcaaa caccagcggc   1500
ggcgtaactg gcaagatgat ctccccgcaa tctatcgccg tggcctgcgc cgcgacgggc   1560
atggtgggcc gagaatctga actgttccgc tacaccgtga agcacagtct gattttgcc    1620
agcgttatcg gcattatcac cctgctgcag gcgtatgtgt taccgggat gttagtctcg    1680
taa                                                                  1683

<210> SEQ ID NO 79
<211> LENGTH: 150
<212> TYPE: PRT
<213> ORGANISM: Escherichia coli

<400> SEQUENCE: 79

Met Lys Arg Val Leu Thr Ala Leu Ala Ala Thr Leu Pro Phe Ala Ala
1               5                   10                  15

Asn Ala Ala Asp Ala Ile Ser Gly Ala Val Glu Arg Gln Pro Thr Asn
            20                  25                  30

Trp Gln Ala Ile Ile Met Phe Leu Ile Phe Val Val Phe Thr Leu Gly
        35                  40                  45

Ile Thr Tyr Trp Ala Ser Lys Arg Val Arg Ser Arg Ser Asp Tyr Tyr
    50                  55                  60

Thr Ala Gly Gly Asn Ile Thr Gly Phe Gln Asn Gly Leu Ala Ile Ala
65                  70                  75                  80

Gly Asp Tyr Met Ser Ala Ala Ser Phe Leu Gly Ile Ser Ala Leu Val
                85                  90                  95

Phe Thr Ser Gly Tyr Asp Gly Leu Ile Tyr Ser Leu Gly Phe Leu Val
            100                 105                 110

Gly Trp Pro Ile Ile Leu Phe Leu Ile Ala Glu Arg Leu Arg Asn Leu
        115                 120                 125

Gly Arg Tyr Thr Phe Ala Asp Val Ala Ser Tyr Arg Leu Lys Gln Gly
    130                 135                 140

Pro Ile Arg Ile Leu Ser
145                 150

<210> SEQ ID NO 80
<211> LENGTH: 1650
<212> TYPE: DNA
<213> ORGANISM: Escherichia coli
```

<400> SEQUENCE: 80

```
atgaaaagag ttctgacggc gcttgccgcc acactcccttt tcgcagctaa cgccgcggat    60
gctattagcg gggccgtaga gcgccagcca acgaactggc aggcgattat tatgttcctg   120
attttcgtcg tgtttacgct cggcattacc tactgggcat caaaacgcgt acgttctcgt   180
agcgactact acaccgcagg cggcaatatc actggcttcc agaacgggct ggcgattgcc   240
ggggactata tgtccgccgc ctcattcttg gggatctccg cgctggtgtt tacctccggc   300
tatgacggct taatttactc gctgggcttc ctggtgggct ggccgatcat tttgttcctg   360
attgccgaac gtctgcgtaa cctggggcgc tacacctttg ccgatgtggc ctcttaccgt   420
ctgaaacaag gccgattcg tattctttcg gcctgtggtt ctctggtggt ggtggcgctt   480
taccttatcg cccagatggt gggcgcaggt aaactgatcg agctgctgtt tggccttaac   540
tatcacattg cggtggtgct ggtcggcgtg ctgatgatga tgtacgtcct gttcggcggc   600
atgctggcga ccacctgggt gcaaattatc aaagccgtgc tgttgctgtt cggtgccagc   660
tttatggcct ttatggtgat gaaacacgtc ggctttagct tcaacaatct gttcagtgaa   720
gcgatggcg tacaccccgaa aggtgtcgac atcatgaagc cgggcgggct ggtgaaagat   780
ccgatctccg cgctctctct gggtctggga ctgatgtttg gtacggcggg cttgccgcac   840
attctgatgc gcttctttac agtcagcgat gcccgcgaag cacgtaagag cgtgttctac   900
gccaccgggt ttatgggcta cttctatatt ctgacctta ttatcggctt cggcgcgatc   960
atgctggttg gtgcgaatcc ggaatataaa gacgcggcgg ccatctgat tggtggtaac  1020
aacatggcgg ccgttcacct ggcgaatgca gtgggcggca acctgttcct cggttttatt  1080
tcagcggttg ctttcgccac tatcctcgcg gtggttgcgg tctgacgct ggcgggcgca  1140
tccgcggttt cgcatgactt gtacgctaac gtcttcaaaa aaggcgcgac cgaacgtgaa  1200
gagctgcggg tatcaaaaat caccgtactg atcctcggcg tgattgcgat tatcctcggc  1260
gtgctgtttg agaatcagaa catcgccttt atggtggggc tggcgtttgc catcgcggcg  1320
agctgtaact tcccgatcat tctgctttct atgtactggt cgaaactgac cacgcgtggc  1380
gcgatgatgg gtggctggct ggggctgatt accgcagtag tactgatgat cctcggcccg  1440
acgatttggg tacagatcct tggtcacgaa aaagccatct tcccgtatga ataccccggcg  1500
ctgttctcta tcaccgtggc attcctcggc atctggttct tctcggcaac cgataactca  1560
gcggaaggcg cgcgtgagcg tgaactgttc cgcgcgcagt ttatccgctc ccagaccggc  1620
tttggcgttg agcaaggccg cgcgcattaa                                    1650
```

<210> SEQ ID NO 81
<211> LENGTH: 152
<212> TYPE: PRT
<213> ORGANISM: Escherichia coli

<400> SEQUENCE: 81

```
Met Asp Arg Phe Pro Arg Ser Asp Ser Ile Val Gln Pro Arg Ala Gly
1               5                   10                  15

Leu Gln Thr Tyr Met Ala Gln Val Tyr Gly Trp Met Thr Val Gly Leu
            20                  25                  30

Leu Leu Thr Ala Phe Val Ala Trp Tyr Ala Ala Asn Ser Ala Ala Val
        35                  40                  45

Met Glu Leu Leu Phe Thr Asn Arg Val Phe Leu Ile Gly Leu Ile Ile
    50                  55                  60
```

```
Ala Gln Leu Ala Leu Val Ile Val Leu Ser Ala Met Ile Gln Lys Leu
 65                  70                  75                  80

Ser Ala Gly Val Thr Thr Met Leu Phe Met Tyr Ser Ala Leu Thr
                 85                  90                  95

Gly Leu Thr Leu Ser Ser Ile Phe Ile Val Tyr Thr Ala Ala Ser Ile
            100                 105                 110

Ala Ser Thr Phe Val Val Thr Ala Gly Met Phe Gly Ala Met Ser Leu
            115                 120                 125

Tyr Gly Tyr Thr Thr Lys Arg Asp Leu Ser Gly Phe Gly Asn Met Leu
            130                 135                 140

Phe Met Ala Leu Ile Gly Ile Val
145                 150
```

<210> SEQ ID NO 82
<211> LENGTH: 705
<212> TYPE: DNA
<213> ORGANISM: Escherichia coli

<400> SEQUENCE: 82

```
atggacagat tcccacgttc tgattcaatc gtacaacccc gggctggctt gcaaacttat    60
atggctcaag tctatggctg gatgaccgtt ggcttgttgc tgaccgcatt tgttgcctgg   120
tatgcggcta attccgcggc cgtgatggag ctgttgttca ctaaccgtgt cttttaatc   180
ggtctgatca tcgcgcaatt agcattggtt attgtgttat cagcgatgat tcaaaagctg   240
agcgcaggtg taacgacgat gctctttatg ctttattcgg cgctgacggg tcttacgctt   300
tccagtatat tcattgtcta taccgctgct tctatcgcca gtactttcgt cgttactgcc   360
gggatgttcg gcgcaatgag cctgtacggt tacaccacga agcgcgattt aagtggcttt   420
ggcaatatgc tgtttatggc gttaatcggc attgtgctgg catcgctggt caacttctgg   480
ttgaaaagcg aagcattgat gtgggcagtt acctacatcg gcgtgattgt ctttgtcgga   540
ttgacggcgt atgacacgca gaaactgaaa aatatgggtg agcagattga tacccgcgac   600
acgtcgaacc tgcgcaaata ttccattctt ggcgcgttaa ccttgtatct ggacttcatc   660
aacctgttcc tgatgttgtt gcggatcttc ggcaaccgcc gttaa             705
```

<210> SEQ ID NO 83
<211> LENGTH: 155
<212> TYPE: PRT
<213> ORGANISM: Escherichia coli

<400> SEQUENCE: 83

```
Met Ala Ile Ser Thr Pro Met Leu Val Thr Phe Cys Val Tyr Ile Phe
1               5                  10                  15

Gly Met Ile Leu Ile Gly Phe Ile Ala Trp Arg Ser Thr Lys Asn Phe
                20                  25                  30

Asp Asp Tyr Ile Leu Gly Gly Arg Ser Leu Gly Pro Phe Val Thr Ala
            35                  40                  45

Leu Ser Ala Gly Ala Ser Asp Met Ser Gly Trp Leu Met Gly Leu
 50                  55                  60

Pro Gly Ala Val Phe Leu Ser Gly Ile Ser Glu Ser Trp Ile Ala Ile
65                  70                  75                  80

Gly Leu Thr Leu Gly Ala Trp Ile Asn Trp Lys Leu Val Ala Gly Arg
                85                  90                  95

Leu Arg Val His Thr Glu Tyr Asn Asn Asn Ala Leu Thr Leu Pro Asp
            100                 105                 110
```

Tyr Phe Thr Gly Arg Phe Glu Asp Lys Ser Arg Ile Leu Arg Ile Ile
            115                 120                 125

Ser Ala Leu Val Ile Leu Leu Phe Phe Thr Ile Tyr Cys Ala Ser Gly
    130                 135                 140

Ile Val Ala Gly Ala Arg Leu Phe Glu Ser Thr
145                 150                 155

<210> SEQ ID NO 84
<211> LENGTH: 1509
<212> TYPE: DNA
<213> ORGANISM: Escherichia coli

<400> SEQUENCE: 84

| | |
|---|---:|
| atggctatta gcacaccgat gttggtgaca ttttgtgtct atatctttgg catgatattg | 60 |
| attgggttta tcgcctggcg atcaacgaaa aactttgacg actatattct gggcggtcgt | 120 |
| agtcttgggc cattcgtgac ggcattatcg gcgggtgcgt cggatatgag cggctggctg | 180 |
| ttaatggggt tgccgggcgc tgttttctt tccgggattt ccgaaagctg gatcgccatt | 240 |
| ggcctgacat taggcgcgtg gattaactgg aagctggtgg ccgggcggtt gcgtgtgcat | 300 |
| accgaataca caataacgc cttaacactg ccgattatt tcaccgggcg ctttgaagat | 360 |
| aaaagccgca ttttgcgcat tatctctgcg ctggttattt tgctgttctt caccatttat | 420 |
| tgcgcttcgg gcattgtggc aggcgcgcgt ctgtttgaaa gtacctttgg catgagctac | 480 |
| gaaacggctc tgtgggcggg cgctgcggcg acgatccttt acacctttat tggcggtttc | 540 |
| ctcgcggtga gctggactga cactgtacag gccagcctga tgattttgc cctgatcctg | 600 |
| acgccggtta tcgtcattat cagtgtcggt ggctttggtg actcgctgga agtgatcaaa | 660 |
| caaaagagca tcgaaaacgt tgatatgctc aaaggtctga actttgttgc cattatctca | 720 |
| ctgatgggtt ggggctgggg ttacttcggg cagccgcaca ttctggcgcg ttttatggcg | 780 |
| gcggattctc accacagcat tgtccatgcg cgtcgtatta gtatgacctg gatgatcctc | 840 |
| tgcctggcag gggcggtggc tgtcggcttc tttgggattg cttactttaa cgatcatccg | 900 |
| gcgttggctg gtgcggtaaa tcagaacgcc gagcgtgtgt ttatcgaact ggcgcaaatt | 960 |
| ctgtttaacc cgtggattgc cgggattctg ctgtcggcaa ttctggcggc ggtaatgtca | 1020 |
| accttaagtt gccagctgct ggtgtgctcc agtgcgatta ccgaagattt gtacaaagcg | 1080 |
| tttctgcgta acatgccag ccagaaagag ctggtgtggg tagggcgtgt gatggtgctg | 1140 |
| gtggtggcgc tggtggcgat tgcgctggcg gcaaacccgg aaaaccgcgt gctgggctta | 1200 |
| gtgagctacg cgtgggcagg ctttggcgcg cgtttggtc cagtggtgct gttctcggtg | 1260 |
| atgtggtcac gcatgacgcg taacggtgcg ctggcgggga tgatcatcgg tgcgctgacg | 1320 |
| gttatcgtct ggaaacagtt cggctggctg ggactgtacg aaattattcc gggctttatc | 1380 |
| ttcggcagta ttgggattgt agtgtttagt ttgctgggta aagcgccgtc agcggcgatg | 1440 |
| caaaaacgct tgccgaggc cgatgcgcac tatcattcgg ctccgccgtc acggttgcag | 1500 |
| gaaagctaa | 1509 |

<210> SEQ ID NO 85
<211> LENGTH: 150
<212> TYPE: PRT
<213> ORGANISM: Escherichia coli

<400> SEQUENCE: 85

Met Gln Leu Glu Val Ile Leu Pro Leu Val Ala Tyr Leu Val Val Val
1               5                   10                  15

```
Phe Gly Ile Ser Val Tyr Ala Met Arg Lys Arg Ser Thr Gly Thr Phe
         20                  25                  30

Leu Asn Glu Tyr Phe Leu Gly Ser Arg Ser Met Gly Gly Ile Val Leu
         35                  40                  45

Ala Met Thr Leu Thr Ala Thr Tyr Ile Ser Ala Ser Ser Phe Ile Gly
 50                  55                  60

Gly Pro Gly Ala Ala Tyr Lys Tyr Gly Leu Gly Trp Val Leu Leu Ala
 65                  70                  75                  80

Met Ile Gln Leu Pro Ala Val Trp Leu Ser Leu Gly Ile Leu Gly Lys
             85                  90                  95

Lys Phe Ala Ile Leu Ala Arg Arg Tyr Asn Ala Val Thr Leu Asn Asp
             100                 105                 110

Met Leu Phe Ala Arg Tyr Gln Ser Arg Leu Leu Val Trp Leu Ala Ser
             115                 120                 125

Leu Ser Leu Leu Val Ala Phe Val Gly Ala Met Thr Val Gln Phe Ile
 130                 135                 140

Gly Gly Ala Arg Leu Leu
145                 150

<210> SEQ ID NO 86
<211> LENGTH: 1452
<212> TYPE: DNA
<213> ORGANISM: Escherichia coli

<400> SEQUENCE: 86
atgcagcttg aagtaattct accgctggtc gcctatctgg tggtggtgtt cggtatctcg      60
gtttatgcga tgcgtaaacg gagcaccggc accttcctta atgagtattt cctcggcagc     120
cgctctatgg gcgtattgt gctggcgatg acgctcaccg cgacctatat cagtgccagt      180
tcgtttatcg gcgggccagg agctgcttat aaatacgggc tgggctgggt attgctggcg     240
atgattcagc ttcctgcagt ctggctttca ctcggtattc tcggcaagaa gtttgcgatt     300
cttgcgcgcc gctacaatgc agtgacgctg aacgatatgc tgtttgcccg ctaccagagt     360
cgtcttctgg tgtggctggc gagttttagt ttgctggttg cgttcgttgg tgcgatgacc     420
gtgcagttta tcggcggtgc gcgcctgctg aaaccgcgg cgggtattcc ttatgaaacc      480
gggctgctga ttttggtat cagcattgcg ttatataccg cctttggtgg ctttcgcgcc      540
agcgtgctga cgacaccat gcaagggctt gtgatgctga ttggcaccgt gtgctgctt      600 attggcgtag tacatgccgc tggcggctta agtaacgcag tacagacctt gcaaaccatc      660
gatccgcaac tggttacgcc acaaggcgct gacgatattc tgtcgcctgc ctttatgacg      720
tcgttctggg tactggtgtg ttttggcgtg attggcctgc cgcatactgc ggtgcgctgt      780
atctcttata agacagcaa agccgtacat cgggggatca tcatcggtac gattgtggtc      840
gcaattctga tgttcggtat gcacctggcc ggagcgttag tcgggcggt gatcccgat      900 ctcaccgtac cggacctggt gatcccaacg ttaatggtaa aagtgctgcc accgtttgct      960
gccgggatct tcctggctgc accgatggct gcgatcatgt cgacaattaa cgcccaactg     1020
ctgcaaagtt ccgctacgat cattaaagat ctctatctga atatccgtcc ggatcaaatg     1080
caaaacgaga cgcgtctgaa gcggatgtcg gcggtaatta cgttagttct cggcgcgttg     1140
ctgctgcttg ccgcctggaa gccgccagaa atgatcatct ggctgaattt gttggccttc     1200
ggtgggctga agccgttttt cctgtggccg ctggtgctgg gtctttactg gaacgcgcc      1260 aacgccaaag gcgcgctaag tgcgatgatc gttggcggcg tgctgtatgc cgtactcgcg     1320
```

```
acgctgaata ttcagtacct gggcttccac cctatcgtgc cctcgttact actaagtttg    1380
ctggctttcc tggtcggaaa ccgtttcggt acatccgtcc cgcaagctac cgttttgact    1440
actgataaat aa                                                        1452
```

<210> SEQ ID NO 87
<211> LENGTH: 140
<212> TYPE: PRT
<213> ORGANISM: Escherichia coli

<400> SEQUENCE: 87

```
Met Gly Asn Thr Lys Leu Ala Asn Pro Ala Pro Leu Gly Leu Met Gly
1               5                   10                  15

Phe Gly Met Thr Thr Ile Leu Leu Asn Leu His Asn Val Gly Tyr Phe
            20                  25                  30

Ala Leu Asp Gly Ile Ile Leu Ala Met Gly Ile Phe Tyr Gly Gly Ile
        35                  40                  45

Ala Gln Ile Phe Ala Gly Leu Leu Glu Tyr Lys Lys Gly Asn Thr Phe
    50                  55                  60

Gly Leu Thr Ala Phe Thr Ser Tyr Gly Ser Phe Trp Leu Thr Leu Val
65                  70                  75                  80

Ala Ile Leu Leu Met Pro Lys Leu Gly Leu Thr Asp Ala Pro Asn Ala
                85                  90                  95

Gln Phe Leu Gly Val Tyr Leu Gly Leu Trp Gly Val Phe Thr Leu Phe
            100                 105                 110

Met Phe Phe Gly Thr Leu Lys Gly Ala Arg Val Leu Gln Phe Val Phe
        115                 120                 125

Phe Ser Leu Thr Val Leu Phe Ala Leu Leu Ala Ile
    130                 135                 140
```

<210> SEQ ID NO 88
<211> LENGTH: 567
<212> TYPE: DNA
<213> ORGANISM: Escherichia coli

<400> SEQUENCE: 88

```
atgggcaaca ctaagttggc taatccggca ccgctgggcc tgatgggctt cggcatgacc     60
accattctgc ttaacctgca caacgtgggt tatttcgctc tggacggtat tattcttgcc    120
atgggcattt tctacggcgg catcgcgcaa attttgctg gtctgctgga gtacaaaaaa    180
ggcaacactt tcggtttaac cgcattcacc tcttacggtt cttttctggct gacgctggtt    240 gcgattctgc tgatgccgaa actgggtctg accgatgcgc aaatgcaca gttccttggt    300 gtctacctgg gtctgtgggg cgtatttacg ctgtttatgt tcttcggcac gctgaaaggc    360
gcacgcgttc tgcaattcgt tttctttagc ctgaccgtgc tgtttgccct gctggcgatc    420
ggtaacattg ccgtaacgc cgcaatcatc cactttgccg gctggattgg gctgatctgc    480
ggtgccagcg caatctatct ggcgatgggt gaagtactga acgagcagtt tggtcgcacc    540
gttctgccga ttggtgaatc ccactaa                                       567
```

<210> SEQ ID NO 89
<211> LENGTH: 144
<212> TYPE: PRT
<213> ORGANISM: Escherichia coli

<400> SEQUENCE: 89

Met Ile Gly Arg Ile Ser Arg Phe Met Thr Arg Phe Val Ser Arg Trp

```
 1               5                   10                  15
Leu Pro Asp Pro Leu Ile Phe Ala Met Leu Leu Thr Leu Leu Thr Phe
            20                  25                  30

Val Ile Ala Leu Trp Leu Thr Pro Gln Thr Pro Ile Ser Met Val Lys
            35                  40                  45

Met Trp Gly Asp Gly Phe Trp Asn Leu Leu Ala Phe Gly Met Gln Met
        50                  55                  60

Ala Leu Ile Ile Val Thr Gly His Ala Leu Ala Ser Ser Ala Pro Val
65                  70                  75                  80

Lys Ser Leu Leu Arg Thr Ala Ala Ser Ala Ala Lys Thr Pro Val Gln
                85                  90                  95

Gly Val Met Leu Val Thr Phe Phe Gly Ser Val Ala Cys Val Ile Asn
            100                 105                 110

Trp Gly Phe Gly Leu Val Val Gly Ala Met Phe Ala Arg Glu Val Ala
            115                 120                 125

Arg Arg Val Pro Gly Ser Asp Tyr Pro Leu Leu Ile Ala Cys Ala Tyr
        130                 135                 140
```

<210> SEQ ID NO 90
<211> LENGTH: 1323
<212> TYPE: DNA
<213> ORGANISM: Escherichia coli

<400> SEQUENCE: 90

```
atgattggtc gcatatcgcg ttttatgacg cgttttgtca gccggtggct tcccgatcca    60
ctgatctttg ccatgttgct gacattgcta acattcgtga tcgcgctttg gttaacacca   120
caaacgccga tcagcatggt gaaaatgtgg ggtgacggtt tctggaactt gctggcgttt   180
ggtatgcaga tggcgcttat catcgttacc ggtcatgccc ttgccagctc tgctccggtg   240
aaaagtttgc tgcgtactgc cgcctccgcc gcaaagacgc ccgtacaggg cgtcatgctg   300
gtcactttct tcggttcagt cgcttgtgtc atcaactggg gatttggttt ggttgtcggc   360
gcaatgtttg cccgtgaagt cgcccggcga gtccccggtt ctgattatcc gttgctcatt   420
gcctgcgcct acattggttt ctcacctgg gtggcggct tctctggatc aatgcctctg    480
ttggctgcaa caccgggcaa cccggttgag catatcgccg gctgatccc ggtgggcgat    540
actctgttca gtggttttaa catttcatc actgtggcgt tgattgtggt gatgccattt    600
atcacccgca tgatgatgcc aaaaccgtct gacgtggtga tatcgatcc aaaactactc    660
atggaagagg ctgattttca aaagcagcta ccgaaagatg ccccaccatc cgagcgactg    720
gaagaaagcc gcattctgac gttgatcatc ggcgcactcg gtatcgctta ccttgcgatg    780
tacttcagcg aacatggctt caacatcacc atcaataccg tcaacctgat gtttatgatt    840
gcgggtctgc tgctacataa aacgccaatg gcttatatgc gtgctatcag cgcggcagca    900
cgcagtactg ccggtattct ggtgcaattc cccttctacg ctgggatcca actgatgatg    960
gagcattccg gtctgggcgg actcattacc gaattcttca tcaatgttgc gaacaaagac   1020
accttcccgg taatgaccct ttttagttct gcactgatta acttcgccgt tccgtctggc   1080
ggcggtcact gggttattca gggaccttc gtgatacccg cagcccaggc gctgggcgct   1140
gatctcggta atcggtaat ggcgatcgcc tacggcgagc aatggatgaa catggcacaa   1200
ccattctggg cgctgccagc actggcaatc gccggactcg gtgtccgcga catcatgggc   1260
tactgcatca ctgccctgct cttctccggt gtcattttcg tcattggttt aacgctgttc   1320
tga                                                                 1323
```

<210> SEQ ID NO 91
<211> LENGTH: 166
<212> TYPE: PRT
<213> ORGANISM: Escherichia coli

<400> SEQUENCE: 91

Met His Ser Gln Ile Trp Val Val Ser Thr Leu Leu Ile Ser Ile Val
1               5                   10                  15

Leu Ile Val Leu Thr Ile Val Lys Phe Lys Phe His Pro Phe Leu Ala
            20                  25                  30

Leu Leu Leu Ala Ser Phe Phe Val Gly Thr Met Gly Met Gly Met Gly Pro
        35                  40                  45

Leu Asp Met Val Asn Ala Ile Glu Ser Gly Ile Gly Gly Thr Leu Gly
    50                  55                  60

Phe Leu Ala Ala Val Ile Gly Leu Gly Thr Ile Leu Gly Lys Met Met
65                  70                  75                  80

Glu Val Ser Gly Ala Ala Glu Arg Ile Gly Leu Thr Leu Gln Arg Cys
                85                  90                  95

Arg Trp Leu Ser Val Asp Val Ile Met Val Leu Val Gly Leu Ile Cys
            100                 105                 110

Gly Ile Thr Leu Phe Val Glu Val Gly Val Val Leu Leu Ile Pro Leu
        115                 120                 125

Ala Phe Ser Ile Ala Lys Lys Thr Asn Thr Ser Leu Leu Lys Leu Ala
    130                 135                 140

Ile Pro Leu Cys Thr Ala Leu Met Ala Val His Cys Val Val Pro Pro
145                 150                 155                 160

His Pro Ala Ala Leu Tyr
                165

<210> SEQ ID NO 92
<211> LENGTH: 1338
<212> TYPE: DNA
<213> ORGANISM: Escherichia coli

<400> SEQUENCE: 92
atgcactctc aaatctgggt tgtgagcacg ctgcttatca gcatcgtgtt aattgtactg      60
accatcgtga agttcaaatt ccacccgttt ctggcgctgt tgctggccag cttcttcgtg     120
ggaacgatga tgggcatggg gccactggat atggtaaatg ctattgaaag tggaattggc     180
ggaacgctgg ggttcctcgc agcggttatc ggccttggca cgatactggg aaaaatgatg     240
gaagtatccg gggccgcaga agaattggt ctgacacttc aacgctgccg ctggctttca     300
gttgatgtca ttatggtgct ggttggcctg atttgtggca tcacgctgtt tgttgaagtg     360
ggcgtcgtgc tattgattcc tctggctttt tcaattgcca aaaaaaccaa tacctcatta     420
ttaaagcttg ccattccgct atgtaccgca ttgatggcag tgcactgcgt ggttcctcca     480
catccggctg ctttatatgt tgccaataag ctgggcgcag atatcggttc ggtgatcgtc     540
tacggtttgc tggttgggct gatggcatca ctgatcggtg cccactttt ccttaaattt     600 ctgggtcaac gactgccctt taaacctgta cccacagagt ttgcagatct caaagttcgc     660
gatgaaaaaa cactaccgtc attaggcgca acgttattca ccatactgct acccattgcg     720
ctgatgttgg ttaaaacgat tgccgaattg aatatggcgc gtgagagtgg tttgtatatc     780
ttggttgagt ttattggcaa ccctatcact gccatgttta tcgccgtgtt tgtcgcctat     840
tatgtgttgg gtatacgcca gcatatgagc atggggacga tgctcacaca tacggaaaat     900

```
ggcttcggtt ctattgctaa tattttgctg attatcgggg ccggaggcgc attcaacgcc    960
attttaaaaa gcagcagtct cgctgatacg ctggcagtta ttctctccaa tatgcatatg   1020
cacccgattc ttctggcctg gttagtggct cttattctgc atgcggcagt gggctccgct   1080
accgtggcaa tgatggggc aacggcaatt gttgcaccca tgctgccgct gtatcccgac   1140
atcagcccgg aaattattgc gattgctatc ggttcaggtg caattggctg cactatcgtt   1200
acggactcgc ttttctggct agtgaagcaa tattgcggcg ctacgctcaa tgaaacattt   1260
aaatactata cgacagcgac atttatcgct tcagtcgtcg ctctggcggg cacattcctg   1320
ctgtcattta tcatctaa                                                 1338
```

<210> SEQ ID NO 93
<211> LENGTH: 151
<212> TYPE: PRT
<213> ORGANISM: Escherichia coli

<400> SEQUENCE: 93

```
Met Glu Ser Tyr Ser Gln Asn Ser Asn Lys Leu Asp Phe Gln His Glu
1               5                   10                  15

Ala Arg Ile Leu Asn Gly Ile Trp Leu Ile Thr Ala Leu Gly Leu Val
            20                  25                  30

Ala Thr Ala Gly Leu Ala Trp Gly Ala Lys Tyr Ile Glu Ile Thr Ala
        35                  40                  45

Thr Lys Tyr Asp Ser Pro Pro Met Tyr Val Ala Ile Gly Leu Leu Leu
    50                  55                  60

Leu Cys Met Tyr Gly Leu Ser Lys Asp Ile Asn Lys Ile Asn Ala Ala
65                  70                  75                  80

Ile Ala Gly Val Ile Tyr Leu Phe Leu Leu Ser Leu Val Ala Ile Val
                85                  90                  95

Val Ala Ser Leu Val Pro Val Tyr Ala Ile Ile Ile Val Phe Ser Thr
            100                 105                 110

Ala Gly Ala Met Phe Leu Ile Ser Met Leu Ala Gly Leu Leu Phe Asn
        115                 120                 125

Val Asp Pro Gly Ser His Arg Phe Ile Ile Met Met Thr Leu Thr Gly
    130                 135                 140

Leu Ala Leu Val Ile Ile Val
145                 150
```

<210> SEQ ID NO 94
<211> LENGTH: 714
<212> TYPE: DNA
<213> ORGANISM: Escherichia coli

<400> SEQUENCE: 94

```
atggaatcat actcgcaaaa cagcaataaa ttagattttc agcacgaggc caggatatta    60
aacggtatat ggctcattac cgctttaggt ttggtggcaa ccgcaggact agcctgggga   120
gctaagtata tcgaaattac ggcaaccaaa tatgattcac caccaatgta tgtcgccata   180
gggttattat actttgtat gtatggctta agtaaggata tcaacaagat aaatgccgcc   240
atcgcgggcg taatatatct gtttttactc tctttggtgg cgattgtcgt tgcaagttta   300
gttcctgtat atgccattat catcgtgttc agcactgcgg gcgcgatgtt tttaatcagt   360
atgctggccg gttattatt taatgttgat cctggttctc accgttttat cattatgatg   420
acgttgacag ggttggccct ggtaatcatc gtgaatgcgg cattaatgag tgaacggccc   480
```

```
atttggataa taagttgctt aatgattgtg ttatggtcag gcattatctc gcatggacga    540
aataagctcc ttgaattggc ggggaaatgc catagtgaag agttgtggag tccggttcgt    600
tgcgctttta caggtgcatt aacactctat tactatttta tcggcttctt tgggatactt    660
gccgcgatag ctataacgct tgtctggcaa aggcatacgc gtttttttca ttag           714
```

<210> SEQ ID NO 95
<211> LENGTH: 369
<212> TYPE: PRT
<213> ORGANISM: Escherichia coli

<400> SEQUENCE: 95

```
Met Lys Ser Arg Ala Ala Val Ala Phe Ala Pro Gly Lys Pro Leu Glu
  1               5                  10                  15

Ile Val Glu Ile Asp Val Ala Pro Pro Lys Lys Gly Glu Val Leu Ile
             20                  25                  30

Lys Val Thr His Thr Gly Val Cys His Thr Asp Ala Phe Thr Leu Ser
         35                  40                  45

Gly Asp Asp Pro Glu Gly Val Phe Pro Val Val Leu Gly His Glu Gly
     50                  55                  60

Ala Gly Val Val Val Glu Val Gly Glu Gly Val Thr Ser Val Lys Pro
 65                  70                  75                  80

Gly Asp His Val Ile Pro Leu Tyr Thr Ala Glu Cys Gly Glu Cys Glu
                 85                  90                  95

Phe Cys Arg Ser Gly Lys Thr Asn Leu Cys Val Ala Val Arg Glu Thr
            100                 105                 110

Gln Gly Lys Gly Leu Met Pro Asp Gly Thr Thr Arg Phe Ser Tyr Asn
        115                 120                 125

Gly Gln Pro Leu Tyr His Tyr Met Gly Cys Ser Thr Phe Ser Glu Tyr
    130                 135                 140

Thr Val Val Ala Glu Val Ser Leu Ala Lys Ile Asn Pro Glu Ala Asn
145                 150                 155                 160

His Glu His Val Cys Leu Leu Gly Cys Gly Val Thr Thr Gly Ile Gly
                165                 170                 175

Ala Val His Asn Thr Ala Lys Val Gln Pro Gly Asp Ser Val Ala Val
            180                 185                 190

Phe Gly Leu Gly Ala Ile Gly Leu Ala Val Val Gln Gly Ala Arg Gln
        195                 200                 205

Ala Lys Ala Gly Arg Ile Ile Ala Ile Asp Thr Asn Pro Lys Lys Phe
    210                 215                 220

Asp Leu Ala Arg Arg Phe Gly Ala Thr Asp Cys Ile Asn Pro Asn Asp
225                 230                 235                 240

Tyr Asp Lys Pro Ile Lys Asp Val Leu Leu Asp Ile Asn Lys Trp Gly
                245                 250                 255

Ile Asp His Thr Phe Glu Cys Ile Gly Asn Val Asn Val Met Arg Ala
            260                 265                 270

Ala Leu Glu Ser Ala His Arg Gly Trp Gly Gln Ser Val Ile Ile Gly
        275                 280                 285

Val Ala Val Ala Gly Gln Glu Ile Ser Thr Arg Pro Phe Gln Leu Val
    290                 295                 300

Thr Gly Arg Val Trp Lys Gly Ser Ala Phe Gly Gly Val Lys Gly Arg
305                 310                 315                 320

Ser Gln Leu Pro Gly Met Val Glu Asp Ala Met Lys Gly Asp Ile Asp
                325                 330                 335
```

Leu Glu Pro Phe Val Thr His Thr Met Ser Leu Asp Glu Ile Asn Asp
                340                 345                 350

Ala Phe Asp Leu Met His Glu Gly Lys Ser Ile Arg Thr Val Ile Arg
            355                 360                 365

Tyr

<210> SEQ ID NO 96
<211> LENGTH: 336
<212> TYPE: PRT
<213> ORGANISM: Escherichia coli

<400> SEQUENCE: 96

Met Lys Ala Ala Val Val Thr Lys Asp His His Val Asp Val Thr Tyr
 1               5                  10                  15

Lys Thr Leu Arg Ser Leu Lys His Gly Glu Ala Leu Leu Lys Met Glu
             20                  25                  30

Cys Cys Gly Val Cys His Thr Asp Leu His Val Lys Asn Gly Asp Phe
         35                  40                  45

Gly Asp Lys Thr Gly Val Ile Leu Gly His Glu Gly Ile Gly Val Val
     50                  55                  60

Ala Glu Val Gly Pro Gly Val Thr Ser Leu Lys Pro Gly Asp Arg Ala
 65                  70                  75                  80

Ser Val Ala Trp Phe Tyr Glu Gly Cys Gly His Cys Glu Tyr Cys Asn
                 85                  90                  95

Ser Gly Asn Glu Thr Leu Cys Arg Ser Val Lys Asn Ala Gly Tyr Ser
            100                 105                 110

Val Asp Gly Gly Met Ala Glu Cys Ile Val Val Ala Asp Tyr Ala
        115                 120                 125

Val Lys Val Pro Asp Gly Leu Asp Ser Ala Ala Ser Ser Ile Thr
    130                 135                 140

Cys Ala Gly Val Thr Thr Tyr Lys Ala Val Lys Leu Ser Lys Ile Arg
145                 150                 155                 160

Pro Gly Gln Trp Ile Ala Ile Tyr Gly Leu Gly Gly Leu Gly Asn Leu
                165                 170                 175

Ala Leu Gln Tyr Ala Lys Asn Val Phe Asn Ala Lys Val Ile Ala Ile
            180                 185                 190

Asp Val Asn Asp Glu Gln Leu Lys Leu Ala Thr Glu Met Gly Ala Asp
        195                 200                 205

Leu Ala Ile Asn Ser His Thr Glu Asp Ala Ala Lys Ile Val Gln Glu
    210                 215                 220

Lys Thr Gly Gly Ala His Ala Ala Val Val Thr Ala Val Ala Lys Ala
225                 230                 235                 240

Ala Phe Asn Ser Ala Val Asp Ala Val Arg Ala Gly Gly Arg Val Val
                245                 250                 255

Ala Val Gly Leu Pro Pro Glu Ser Met Ser Leu Asp Ile Pro Arg Leu
            260                 265                 270

Val Leu Asp Gly Ile Glu Val Val Gly Ser Leu Val Gly Thr Arg Gln
        275                 280                 285

Asp Leu Thr Glu Ala Phe Gln Phe Ala Ala Glu Gly Lys Val Val Pro
    290                 295                 300

Lys Val Ala Leu Arg Pro Leu Ala Asp Ile Asn Thr Ile Phe Thr Glu
305                 310                 315                 320

Met Glu Glu Gly Lys Ile Arg Gly Arg Met Val Ile Asp Phe Arg His
                325                 330                 335

```
<210> SEQ ID NO 97
<211> LENGTH: 383
<212> TYPE: PRT
<213> ORGANISM: Escherichia coli

<400> SEQUENCE: 97

Met Ala Ala Ser Thr Phe Phe Ile Pro Ser Val Asn Val Ile Gly Ala
1               5                   10                  15

Asp Ser Leu Thr Asp Ala Met Asn Met Met Ala Asp Tyr Gly Phe Thr
            20                  25                  30

Arg Thr Leu Ile Val Thr Asp Asn Met Leu Thr Lys Leu Gly Met Ala
        35                  40                  45

Gly Asp Val Gln Lys Ala Leu Glu Glu Arg Asn Ile Phe Ser Val Ile
    50                  55                  60

Tyr Asp Gly Thr Gln Pro Asn Pro Thr Thr Glu Asn Val Ala Ala Gly
65                  70                  75                  80

Leu Lys Leu Leu Lys Glu Asn Asn Cys Asp Ser Val Ile Ser Leu Gly
                85                  90                  95

Gly Gly Ser Pro His Asp Cys Ala Lys Gly Ile Ala Leu Val Ala Ala
            100                 105                 110

Asn Gly Gly Asp Ile Arg Asp Tyr Glu Gly Val Asp Arg Ser Ala Lys
        115                 120                 125

Pro Gln Leu Pro Met Ile Ala Ile Asn Thr Thr Ala Gly Thr Ala Ser
    130                 135                 140

Glu Met Thr Arg Phe Cys Ile Ile Thr Asp Glu Ala Arg His Ile Lys
145                 150                 155                 160

Met Ala Ile Val Asp Lys His Val Thr Pro Leu Leu Ser Val Asn Asp
                165                 170                 175

Ser Ser Leu Met Ile Gly Met Pro Lys Ser Leu Thr Ala Ala Thr Gly
            180                 185                 190

Met Asp Ala Leu Thr His Ala Ile Glu Ala Tyr Val Ser Ile Ala Ala
        195                 200                 205

Thr Pro Ile Thr Asp Ala Cys Ala Leu Lys Ala Val Thr Met Ile Ala
    210                 215                 220

Glu Asn Leu Pro Leu Ala Val Glu Asp Gly Ser Asn Ala Lys Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Phe
            260                 265                 270

Tyr Asn Leu Pro His Gly Val Cys Asn Ala Val Leu Leu Pro His Val
        275                 280                 285

Gln Val Phe Asn Ser Lys Val Ala Ala Ala Arg Leu Arg Asp Cys Ala
    290                 295                 300

Ala Ala Met Gly Val Asn Val Thr Gly Lys Asn Asp Ala Glu Gly Ala
305                 310                 315                 320

Glu Ala Cys Ile Asn Ala Ile Arg Glu Leu Ala Lys Lys Val Asp Ile
                325                 330                 335

Pro Ala Gly Leu Arg Asp Leu Asn Val Lys Glu Glu Asp Phe Ala Val
            340                 345                 350

Leu Ala Thr Asn Ala Leu Lys Asp Ala Cys Gly Phe Thr Asn Pro Ile
        355                 360                 365

Gln Ala Thr His Glu Glu Ile Val Ala Ile Tyr Arg Ala Ala Met
    370                 375                 380
```

<210> SEQ ID NO 98
<211> LENGTH: 395
<212> TYPE: PRT
<213> ORGANISM: Escherichia coli

<400> SEQUENCE: 98

```
Met Gln Asn Glu Leu Gln Thr Ala Leu Phe Gln Ala Phe Asp Thr Leu
1               5                   10                  15

Asn Leu Gln Arg Val Lys Thr Phe Ser Val Pro Val Thr Leu Cys
            20                  25                  30

Gly Pro Gly Ser Val Ser Ser Cys Gly Gln Gln Ala Gln Thr Arg Gly
            35                  40                  45

Leu Lys His Leu Phe Val Met Ala Asp Ser Phe Leu His Gln Ala Gly
        50                  55                  60

Met Thr Ala Gly Leu Thr Arg Ser Leu Thr Val Lys Gly Ile Ala Met
65                  70                  75                  80

Thr Leu Trp Pro Cys Pro Val Gly Glu Pro Cys Ile Thr Asp Val Cys
                85                  90                  95

Ala Ala Val Ala Gln Leu Arg Glu Ser Gly Cys Asp Gly Val Ile Ala
            100                 105                 110

Phe Gly Gly Gly Ser Val Leu Asp Ala Ala Lys Ala Val Thr Leu Leu
        115                 120                 125

Val Thr Asn Pro Asp Ser Thr Leu Ala Glu Met Ser Glu Thr Ser Val
130                 135                 140

Leu Gln Pro Arg Leu Pro Leu Ile Ala Ile Pro Thr Thr Ala Gly Thr
145                 150                 155                 160

Gly Ser Glu Thr Thr Asn Val Thr Val Ile Ile Asp Ala Val Ser Gly
                165                 170                 175

Arg Lys Gln Val Leu Ala His Ala Ser Leu Met Pro Asp Val Ala Ile
            180                 185                 190

Leu Asp Ala Ala Leu Thr Glu Gly Val Pro Ser His Val Thr Ala Met
        195                 200                 205

Thr Gly Ile Asp Ala Leu Thr His Ala Ile Glu Ala Tyr Ser Ala Leu
210                 215                 220

Asn Ala Thr Pro Phe Thr Asp Ser Leu Ala Ile Gly Ala Ile Ala Met
225                 230                 235                 240

Ile Gly Lys Ser Leu Pro Lys Ala Val Gly Tyr Gly His Asp Leu Ala
                245                 250                 255

Ala Arg Glu Ser Met Leu Leu Ala Ser Cys Met Ala Gly Met Ala Phe
            260                 265                 270

Ser Ser Ala Gly Leu Gly Leu Cys His Ala Met Ala His Gln Pro Gly
        275                 280                 285

Ala Ala Leu His Ile Pro His Gly Leu Ala Asn Ala Met Leu Leu Pro
290                 295                 300

Thr Val Met Glu Phe Asn Arg Met Val Cys Arg Glu Arg Phe Ser Gln
305                 310                 315                 320

Ile Gly Arg Ala Leu Arg Thr Lys Ser Asp Asp Arg Asp Ala Ile
                325                 330                 335

Asn Ala Val Ser Glu Leu Ile Ala Glu Val Gly Ile Gly Lys Arg Leu
            340                 345                 350

Gly Asp Val Gly Ala Thr Ser Ala His Tyr Gly Ala Trp Ala Gln Ala
        355                 360                 365

Ala Leu Glu Asp Ile Cys Leu Arg Ser Asn Pro Arg Thr Ala Ser Leu
```

370                 375                 380
Glu Gln Ile Val Gly Leu Tyr Ala Ala Ala Gln
385                 390                 395

<210> SEQ ID NO 99
<211> LENGTH: 387
<212> TYPE: PRT
<213> ORGANISM: Escherichia coli

<400> SEQUENCE: 99

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

```
Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
    370                 375                 380

Ala Ala Arg
385

<210> SEQ ID NO 100
<211> LENGTH: 284
<212> TYPE: PRT
<213> ORGANISM: Escherichia coli

<400> SEQUENCE: 100

Met Gln Gln Lys Met Ile Gln Phe Ser Gly Asp Val Ser Leu Pro Ala
1               5                   10                  15

Val Gly Gln Gly Thr Trp Tyr Met Gly Glu Asp Ala Ser Gln Arg Lys
            20                  25                  30

Thr Glu Val Ala Ala Leu Arg Ala Gly Ile Glu Leu Gly Leu Thr Leu
        35                  40                  45

Ile Asp Thr Ala Glu Met Tyr Ala Asp Gly Gly Ala Glu Lys Val Val
50                  55                  60

Gly Glu Ala Leu Thr Gly Leu Arg Glu Lys Val Phe Leu Val Ser Lys
65                  70                  75                  80

Val Tyr Pro Trp Asn Ala Gly Gly Gln Lys Ala Ile Asn Ala Cys Glu
                85                  90                  95

Ala Ser Leu Arg Arg Leu Asn Thr Asp Tyr Leu Asp Leu Tyr Leu Leu
            100                 105                 110

His Trp Ser Gly Ser Phe Ala Phe Glu Glu Thr Val Ala Ala Met Glu
        115                 120                 125

Lys Leu Ile Ala Gln Gly Lys Ile Arg Arg Trp Gly Val Ser Asn Leu
130                 135                 140

Asp Tyr Ala Asp Met Gln Glu Leu Trp Gln Leu Pro Gly Gly Asn Gln
145                 150                 155                 160

Cys Ala Thr Asn Gln Val Leu Tyr His Leu Gly Ser Arg Gly Ile Glu
                165                 170                 175

Tyr Asp Leu Leu Pro Trp Cys Gln Gln Gln Met Pro Val Met Ala
            180                 185                 190

Tyr Ser Pro Leu Ala Gln Ala Gly Arg Leu Arg Asn Gly Leu Leu Lys
        195                 200                 205

Asn Ala Val Val Asn Glu Ile Ala His Ala His Asn Ile Ser Ala Ala
210                 215                 220

Gln Val Leu Leu Ala Trp Val Ile Ser His Gln Gly Val Met Ala Ile
225                 230                 235                 240

Pro Lys Ala Ala Thr Ile Ala His Val Gln Gln Asn Ala Ala Val Leu
                245                 250                 255

Glu Val Glu Leu Ser Ser Ala Glu Leu Ala Met Leu Asp Lys Ala Tyr
            260                 265                 270

Pro Ala Pro Lys Gly Lys Thr Ala Leu Asp Met Val
        275                 280

<210> SEQ ID NO 101
<211> LENGTH: 298
<212> TYPE: PRT
<213> ORGANISM: Escherichia coli

<400> SEQUENCE: 101
```

```
Met Val Gln Arg Ile Thr Ile Ala Pro Gln Gly Pro Glu Phe Ser Arg
1               5                   10                  15

Phe Val Met Gly Tyr Trp Arg Leu Met Asp Trp Asn Met Ser Ala Arg
            20                  25                  30

Gln Leu Val Ser Phe Ile Glu Glu His Leu Asp Leu Gly Val Thr Thr
        35                  40                  45

Val Asp His Ala Asp Ile Tyr Gly Gly Tyr Gln Cys Glu Ala Ala Phe
50                  55                  60

Gly Glu Ala Leu Lys Leu Ala Pro His Leu Glu Arg Met Glu Ile
65                  70                  75                  80

Val Ser Lys Cys Gly Ile Ala Thr Thr Ala Arg Glu Glu Asn Val Ile
                85                  90                  95

Gly His Tyr Ile Thr Asp Arg Asp His Ile Ile Lys Ser Ala Glu Gln
            100                 105                 110

Ser Leu Ile Asn Leu Ala Thr Asp His Leu Asp Leu Leu Ile His
        115                 120                 125

Arg Pro Asp Pro Leu Met Asp Ala Asp Glu Val Ala Asp Ala Phe Lys
    130                 135                 140

His Leu His Gln Ser Gly Lys Val Arg His Phe Gly Val Ser Asn Phe
145                 150                 155                 160

Thr Pro Ala Gln Phe Ala Leu Leu Gln Ser Arg Leu Pro Phe Thr Leu
                165                 170                 175

Ala Thr Asn Gln Val Glu Ile Ser Pro Val His Gln Pro Leu Leu Leu
            180                 185                 190

Asp Gly Thr Leu Asp Gln Leu Gln Gln Leu Arg Val Arg Pro Met Ala
        195                 200                 205

Trp Ser Cys Leu Gly Gly Gly Arg Leu Phe Asn Asp Asp Tyr Phe Gln
    210                 215                 220

Pro Leu Arg Asp Glu Leu Ala Val Val Ala Glu Glu Leu Asn Ala Gly
225                 230                 235                 240

Ser Ile Glu Gln Val Val Tyr Ala Trp Val Leu Arg Leu Pro Ser Gln
                245                 250                 255

Pro Leu Pro Ile Ile Gly Ser Gly Lys Ile Glu Arg Val Arg Ala Ala
            260                 265                 270

Val Glu Ala Glu Thr Leu Lys Met Thr Arg Gln Gln Trp Phe Arg Ile
        275                 280                 285

Arg Lys Ala Ala Leu Gly Tyr Asp Val Pro
    290                 295

<210> SEQ ID NO 102
<211> LENGTH: 122
<212> TYPE: PRT
<213> ORGANISM: Escherichia coli

<400> SEQUENCE: 102

Met Trp Leu Leu Asp Gln Trp Ala Glu Arg His Ile Ala Glu Ala Gln
1               5                   10                  15

Ala Lys Gly Glu Phe Asp Asn Leu Ala Gly Ser Gly Glu Pro Leu Ile
            20                  25                  30

Leu Asp Asp Asp Ser His Val Pro Pro Glu Leu Arg Ala Gly Tyr Arg
        35                  40                  45

Leu Leu Lys Asn Ala Gly Cys Leu Pro Pro Glu Leu Glu Gln Arg Arg
    50                  55                  60

Glu Ala Ile Gln Leu Leu Asp Ile Leu Lys Gly Ile Arg His Asp Asp
65                  70                  75                  80
```

```
Pro Gln Tyr Gln Glu Val Ser Arg Arg Leu Ser Leu Glu Leu Lys
                85                  90                  95

Leu Arg Gln Ala Gly Leu Ser Thr Asp Phe Leu Arg Gly Asp Tyr Ala
            100                 105                 110

Asp Lys Leu Leu Asp Lys Ile Asn Asp Asn
        115                 120
```

<210> SEQ ID NO 103
<211> LENGTH: 412
<212> TYPE: PRT
<213> ORGANISM: Escherichia coli

<400> SEQUENCE: 103

```
Met Lys Ala Leu Thr Tyr His Gly Pro His Val Gln Val Glu Asn
1               5                   10                  15

Val Pro Asp Pro Gly Val Glu Gln Ala Asp Ile Ile Leu Arg Ile
                20                  25                  30

Thr Ala Thr Ala Ile Cys Gly Ser Asp Leu His Leu Tyr Arg Gly Lys
            35                  40                  45

Ile Pro Gln Val Lys His Gly Asp Ile Phe Gly His Glu Phe Met Gly
        50                  55                  60

Glu Val Val Glu Thr Gly Lys Asp Val Lys Asn Leu Gln Lys Gly Asp
65                  70                  75                  80

Arg Val Val Ile Pro Phe Val Ile Ala Cys Gly Asp Cys Phe Phe Cys
                85                  90                  95

Arg Leu Gln Gln Tyr Ala Ala Cys Glu Asn Thr Asn Ala Gly Lys Gly
            100                 105                 110

Ala Ala Leu Asn Lys Lys Gln Ile Pro Ala Pro Ala Ala Leu Phe Gly
        115                 120                 125

Tyr Ser His Leu Tyr Gly Gly Val Pro Gly Gly Gln Ala Glu Tyr Val
    130                 135                 140

Arg Val Pro Lys Gly Asn Val Gly Pro Phe Lys Val Pro Pro Leu Leu
145                 150                 155                 160

Ser Asp Asp Lys Ala Leu Phe Leu Ser Asp Ile Leu Pro Thr Ala Trp
                165                 170                 175

Gln Ala Ala Lys Asn Ala Gln Ile Gln Gln Gly Ser Ser Val Ala Val
            180                 185                 190

Tyr Gly Ala Gly Pro Val Gly Leu Leu Thr Ile Ala Cys Ala Arg Leu
        195                 200                 205

Leu Gly Ala Glu Gln Ile Phe Val Val Asp His His Pro Tyr Arg Leu
    210                 215                 220

His Phe Ala Ala Asp Arg Tyr Gly Ala Ile Pro Ile Asn Phe Asp Glu
225                 230                 235                 240

Asp Ser Asp Pro Ala Gln Ser Ile Ile Glu Gln Thr Ala Gly His Arg
                245                 250                 255

Gly Val Asp Ala Val Ile Asp Ala Val Gly Phe Glu Ala Lys Gly Ser
            260                 265                 270

Thr Thr Glu Thr Val Leu Thr Asn Leu Lys Leu Glu Gly Ser Ser Gly
        275                 280                 285

Lys Ala Leu Arg Gln Cys Ile Ala Ala Val Arg Arg Gly Gly Ile Val
    290                 295                 300

Ser Val Pro Gly Val Tyr Ala Gly Phe Ile His Gly Phe Leu Phe Gly
305                 310                 315                 320

Asp Ala Phe Asp Lys Gly Leu Ser Phe Lys Met Gly Gln Thr His Val
```

```
                325                 330                 335
His Ala Trp Leu Gly Glu Leu Leu Pro Leu Ile Glu Lys Gly Leu Leu
            340                 345                 350

Lys Pro Glu Glu Ile Val Thr His Tyr Met Pro Phe Glu Glu Ala Ala
            355                 360                 365

Arg Gly Tyr Glu Ile Phe Glu Lys Arg Glu Glu Cys Arg Lys Val
            370                 375                 380

Ile Leu Val Pro Gly Ala Gln Ser Ala Glu Ala Ala Gln Lys Ala Val
385                 390                 395                 400

Ser Gly Leu Val Asn Ala Met Pro Gly Gly Thr Ile
            405                 410

<210> SEQ ID NO 104
<211> LENGTH: 362
<212> TYPE: PRT
<213> ORGANISM: Escherichia coli

<400> SEQUENCE: 104

Met Pro His Asn Pro Ile Arg Val Val Gly Pro Ala Asn Tyr Phe
1               5                   10                  15

Ser His Pro Gly Ser Phe Asn His Leu His Asp Phe Phe Thr Asp Glu
            20                  25                  30

Gln Leu Ser Arg Ala Val Trp Ile Tyr Gly Lys Arg Ala Ile Ala Ala
        35                  40                  45

Ala Gln Thr Lys Leu Pro Pro Ala Phe Gly Leu Pro Gly Ala Lys His
    50                  55                  60

Ile Leu Phe Arg Gly His Cys Ser Glu Ser Asp Val Gln Gln Leu Ala
65                  70                  75                  80

Ala Glu Ser Gly Asp Asp Arg Ser Val Val Ile Gly Val Gly Gly Gly
                85                  90                  95

Ala Leu Leu Asp Thr Ala Lys Ala Leu Ala Arg Arg Leu Gly Leu Pro
            100                 105                 110

Phe Val Ala Val Pro Thr Ile Ala Ala Thr Cys Ala Ala Trp Thr Pro
            115                 120                 125

Leu Ser Val Trp Tyr Asn Asp Ala Gly Gln Ala Leu His Tyr Glu Ile
        130                 135                 140

Phe Asp Asp Ala Asn Phe Met Val Leu Val Glu Pro Glu Ile Ile Leu
145                 150                 155                 160

Asn Ala Pro Gln Gln Tyr Leu Leu Ala Gly Ile Gly Asp Thr Leu Ala
                165                 170                 175

Lys Trp Tyr Glu Ala Val Val Leu Ala Pro Gln Pro Glu Thr Leu Pro
            180                 185                 190

Leu Thr Val Arg Leu Gly Ile Asn Asn Ala Gln Ala Ile Arg Asp Val
        195                 200                 205

Leu Leu Asn Ser Ser Glu Gln Ala Leu Ser Asp Gln Gln Asn Gln Gln
    210                 215                 220

Leu Thr Gln Ser Phe Cys Asp Val Val Asp Ala Ile Ile Ala Gly Gly
225                 230                 235                 240

Gly Met Val Gly Gly Leu Gly Asp Arg Phe Thr Arg Val Ala Ala Ala
                245                 250                 255

His Ala Val His Asn Gly Leu Thr Val Leu Pro Gln Thr Glu Lys Phe
            260                 265                 270

Leu His Gly Thr Lys Val Ala Tyr Gly Ile Leu Val Gln Ser Ala Leu
        275                 280                 285
```

```
Leu Gly Gln Asp Asp Val Leu Ala Gln Leu Thr Gly Ala Tyr Gln Arg
        290                 295                 300

Phe His Leu Pro Thr Thr Leu Ala Glu Leu Glu Val Asp Ile Asn Asn
305                 310                 315                 320

Gln Ala Glu Ile Asp Lys Val Ile Ala His Thr Leu Arg Pro Val Glu
                    325                 330                 335

Ser Ile His Tyr Leu Pro Val Thr Leu Thr Pro Asp Thr Leu Arg Ala
                340                 345                 350

Ala Phe Lys Lys Val Glu Ser Phe Lys Ala
                355                 360

<210> SEQ ID NO 105
<211> LENGTH: 347
<212> TYPE: PRT
<213> ORGANISM: Escherichia coli

<400> SEQUENCE: 105

Met Lys Asn Ser Lys Ala Ile Leu Gln Val Pro Gly Thr Met Lys Ile
1               5                   10                  15

Ile Ser Ala Glu Ile Pro Val Pro Lys Glu Asp Glu Val Leu Ile Lys
                20                  25                  30

Val Glu Tyr Val Gly Ile Cys Gly Ser Asp Val His Gly Phe Glu Ser
            35                  40                  45

Gly Pro Phe Ile Pro Pro Lys Asp Pro Asn Gln Glu Ile Gly Leu Gly
        50                  55                  60

His Glu Cys Ala Gly Thr Val Ala Val Gly Ser Arg Val Arg Lys
65                  70                  75                  80

Phe Lys Pro Gly Asp Arg Val Asn Ile Glu Pro Gly Val Pro Cys Gly
                85                  90                  95

His Cys Arg Tyr Cys Leu Glu Gly Lys Tyr Asn Ile Cys Pro Asp Val
            100                 105                 110

Asp Phe Met Ala Thr Gln Pro Asn Tyr Arg Gly Ala Leu Thr His Tyr
        115                 120                 125

Leu Cys His Pro Glu Ser Phe Thr Tyr Lys Leu Pro Asp Asn Met Asp
130                 135                 140

Thr Met Glu Gly Ala Leu Val Glu Pro Ala Ala Val Gly Met His Ala
145                 150                 155                 160

Ala Met Leu Ala Asp Val Lys Pro Gly Lys Lys Ile Ile Leu Gly
                165                 170                 175

Ala Gly Cys Ile Gly Leu Met Thr Leu Gln Ala Cys Lys Cys Leu Gly
            180                 185                 190

Ala Thr Glu Ile Ala Val Val Asp Val Leu Glu Lys Arg Leu Ala Met
        195                 200                 205

Ala Glu Gln Leu Gly Ala Thr Val Val Ile Asn Gly Ala Lys Glu Asp
    210                 215                 220

Thr Ile Ala Arg Cys Gln Gln Phe Thr Glu Asp Met Gly Ala Asp Ile
225                 230                 235                 240

Val Phe Glu Thr Ala Gly Ser Ala Val Thr Val Lys Gln Ala Pro Tyr
                245                 250                 255

Leu Val Met Arg Gly Gly Lys Ile Met Ile Val Gly Thr Val Pro Gly
            260                 265                 270

Asp Ser Ala Ile Asn Phe Leu Lys Ile Asn Arg Glu Val Thr Ile Gln
        275                 280                 285

Thr Val Phe Arg Tyr Ala Asn Arg Tyr Pro Val Thr Ile Glu Ala Ile
    290                 295                 300
```

-continued

Ser Ser Gly Arg Phe Asp Val Lys Ser Met Val Thr His Ile Tyr Asp
305                 310                 315                 320

Tyr Arg Asp Val Gln Gln Ala Phe Glu Glu Ser Val Asn Asn Lys Arg
                325                 330                 335

Asp Ile Ile Lys Gly Val Ile Lys Ile Ser Asp
            340                 345

<210> SEQ ID NO 106
<211> LENGTH: 358
<212> TYPE: PRT
<213> ORGANISM: Escherichia coli

<400> SEQUENCE: 106

Met Lys Ala Leu Ala Arg Phe Gly Lys Ala Phe Gly Gly Tyr Lys Met
1               5                   10                  15

Ile Asp Val Pro Gln Pro Met Cys Gly Pro Glu Asp Val Val Ile Glu
            20                  25                  30

Ile Lys Ala Ala Ala Ile Cys Gly Ala Asp Met Lys His Tyr Asn Val
        35                  40                  45

Asp Ser Gly Ser Asp Glu Phe Asn Ser Ile Arg Gly His Glu Phe Ala
    50                  55                  60

Gly Cys Ile Ala Gln Val Gly Glu Lys Val Lys Asp Trp Lys Val Gly
65                  70                  75                  80

Gln Arg Val Val Ser Asp Asn Ser Gly His Val Cys Gly Val Cys Pro
                85                  90                  95

Ala Cys Glu Gln Gly Asp Phe Leu Cys Cys Thr Glu Lys Val Asn Leu
            100                 105                 110

Gly Leu Asp Asn Asn Thr Trp Gly Gly Phe Ser Lys Tyr Cys Leu
        115                 120                 125

Val Pro Gly Glu Ile Leu Lys Ile His Arg His Ala Leu Trp Glu Ile
130                 135                 140

Pro Asp Gly Val Asp Tyr Glu Asp Ala Ala Val Leu Asp Pro Ile Cys
145                 150                 155                 160

Asn Ala Tyr Lys Ser Ile Ala Gln Gln Ser Lys Phe Leu Pro Gly Gln
                165                 170                 175

Asp Val Val Ile Gly Thr Gly Pro Leu Gly Leu Phe Ser Val Gln
            180                 185                 190

Met Ala Arg Ile Met Gly Ala Val Asn Ile Val Val Gly Leu Gln
        195                 200                 205

Glu Asp Val Ala Val Arg Phe Pro Val Ala Lys Glu Leu Gly Ala Thr
210                 215                 220

Ala Val Val Asn Gly Ser Thr Glu Asp Val Val Ala Arg Cys Gln Gln
225                 230                 235                 240

Ile Cys Gly Lys Asp Asn Leu Gly Leu Val Ile Glu Cys Ser Gly Ala
                245                 250                 255

Asn Ile Ala Leu Lys Gln Ala Ile Glu Met Leu Arg Pro Asn Gly Glu
            260                 265                 270

Val Val Arg Val Gly Met Gly Phe Lys Pro Leu Asp Phe Ser Ile Asn
        275                 280                 285

Asp Ile Thr Ala Trp Asn Lys Ser Ile Gly His Met Ala Tyr Asp
    290                 295                 300

Ser Thr Ser Trp Arg Asn Ala Ile Arg Leu Leu Ala Ser Gly Ala Ile
305                 310                 315                 320

Lys Val Lys Pro Met Ile Thr His Arg Ile Gly Leu Ser Gln Trp Arg

```
                        325                 330                 335

Glu Gly Phe Asp Ala Met Val Asp Lys Thr Ala Ile Lys Val Ile Met
            340                 345                 350

Thr Tyr Asp Phe Asp Glu
        355

<210> SEQ ID NO 107
<211> LENGTH: 390
<212> TYPE: PRT
<213> ORGANISM: Clostridium acetobutylicum

<400> SEQUENCE: 107

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335
```

```
Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
            355                 360                 365

Gly Thr Ile Gly Asn Leu Arg Pro Val Asn Ala Ser Glu Val Leu Gln
            370                 375                 380

Ile Phe Lys Lys Ser Val
385             390

<210> SEQ ID NO 108
<211> LENGTH: 389
<212> TYPE: PRT
<213> ORGANISM: Clostridium acetobutylicum

<400> SEQUENCE: 108

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
            35                  40                  45

Asp Arg Ala Thr Ala Ile Leu Lys Glu Asn Asn Ile Ala Phe Tyr Glu
        50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
            115                 120                 125

Lys Val Leu Pro Ile Ala Ser Ile Leu Thr Leu Ser Ala Thr Gly Ser
        130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
            195                 200                 205

Gly Ala Tyr Val Gln Asp Gly Ile Ala Glu Ala Ile Leu Arg Thr Cys
        210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
            275                 280                 285

Thr Pro Asn Trp Met Glu Tyr Ile Leu Asn Asp Asp Thr Leu His Lys
        290                 295                 300

Phe Val Ser Tyr Gly Ile Asn Val Trp Gly Ile Asp Lys Asn Lys Asp
305                 310                 315                 320
```

Asn Tyr Glu Ile Ala Arg Glu Ala Ile Lys Asn Thr Arg Glu Tyr Phe
            325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
            355                 360                 365

Thr Ile Gly Ser Leu Arg Pro Ile Asn Ala Glu Asp Val Leu Glu Ile
            370                 375                 380

Phe Lys Lys Ser Tyr
385

<210> SEQ ID NO 109
<211> LENGTH: 386
<212> TYPE: PRT
<213> ORGANISM: Clostridium acetobutylicum

<400> SEQUENCE: 109

Met Tyr Asn Phe Asp Phe Phe Asn Pro Thr His Ile Val Phe Gly Lys
1               5                   10                  15

Asp Arg Leu Asn Glu Leu Asp Asn Leu Val Pro Arg Asp Ala Lys Val
            20                  25                  30

Leu Val Leu Tyr Gly Gly Gly Ser Val Lys Lys Phe Gly Thr Leu Glu
        35                  40                  45

Lys Val Ile Asn Gly Leu Gly Asn Arg Gln Val Ile Glu Phe Gly Gly
    50                  55                  60

Ile Glu Pro Asn Pro Gln Phe Thr Thr Leu Met Lys Ala Val Asp Ile
65                  70                  75                  80

Val Lys Lys Glu Asn Ile Asp Phe Leu Leu Ala Val Gly Gly Gly Ser
                85                  90                  95

Val Met Asp Gly Thr Lys Phe Val Ala Leu Ala Ala Tyr Tyr Glu Gly
            100                 105                 110

Asp Asn Ala Ala Glu Ile Leu Tyr Ser Arg Glu Lys Ala Ala Ala Ile
            115                 120                 125

Asn Lys Ala Val Pro Leu Gly Thr Val Val Thr Leu Pro Ala Thr Gly
        130                 135                 140

Ser Glu Met Asn Asn Gly Gly Val Ile Ser Tyr Glu His Gly Lys Tyr
145                 150                 155                 160

Gly Phe Gly Ser Lys Leu Val Phe Pro Lys Phe Ser Val Leu Asp Pro
                165                 170                 175

Thr Leu Thr Tyr Thr Leu Pro Glu Ser Gln Val Ala Asn Gly Val Ala
            180                 185                 190

Asp Thr Phe Val His Val Leu Glu Gln Tyr Ala Thr Phe Lys Ala Glu
            195                 200                 205

Gly Arg Phe Gln Asp Arg Thr Ala Glu Gly Ile Leu Gln Thr Leu Ile
        210                 215                 220

Glu Ile Gly Arg Lys Thr Ile Asp Asn Pro Thr Asp Tyr Asp Thr Arg
225                 230                 235                 240

Ala Asn Leu Val Trp Cys Ala Thr Met Ala Leu Asn Gly Leu Ile Gly
                245                 250                 255

Ala Gly Val Pro Gln Asp Trp Ser Thr His Met Ile Gly His Glu Leu
            260                 265                 270

Thr Ala Met Phe Gly Ile Asp His Gly Lys Thr Leu Ala Ile Ile Leu
            275                 280                 285

Pro Ser Ile Trp Asn Val Met Arg Glu Gln Lys Lys Gly Lys Ile Leu

```
            290                 295                 300
Gln Tyr Ala Glu Arg Val Leu Gly Ile Thr Glu Gly Asp Asp Ser
305                 310                 315                 320

Arg Ile Asp Leu Ala Ile Leu Arg Thr Arg Glu Phe Phe Glu Ser Leu
                325                 330                 335

Gly Ile Lys Thr His Leu Ser Glu Tyr Gly Val Thr Ala Asp Lys Ile
                340                 345                 350

Asp Asp Ile Val Asn Ala Leu Asp Lys His Gly Met Lys Ala Leu Ser
                355                 360                 365

Glu Thr Gly Ala Ile Thr Leu Glu Val Ser Arg Lys Ile Leu Glu Gly
                370                 375                 380

Ala Met
385

<210> SEQ ID NO 110
<211> LENGTH: 348
<212> TYPE: PRT
<213> ORGANISM: Saccharomyces cerevisiae

<400> SEQUENCE: 110

Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
                20                  25                  30

Glu Leu Leu Ile Asn Val Lys Tyr Ser Gly Val Cys His Thr Asp Leu
            35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
                100                 105                 110

Pro His Ala Asp Leu Ser Gly Tyr Thr His Asp Gly Ser Phe Gln Gln
            115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
    195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270
```

```
Ala Gly Ala Lys Cys Cys Ser Asp Val Phe Asn Gln Val Lys Ser
            275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345
```

<210> SEQ ID NO 111
<211> LENGTH: 348
<212> TYPE: PRT
<213> ORGANISM: Saccharomyces cerevisiae

<400> SEQUENCE: 111

```
Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205

Glu Leu Phe Thr Ser Leu Gly Gly Glu Val Phe Ile Asp Phe Thr Lys
    210                 215                 220

Glu Lys Asp Ile Val Ser Ala Val Val Lys Ala Thr Asn Gly Gly Ala
225                 230                 235                 240

His Gly Ile Ile Asn Val Ser Val Ser Glu Ala Ala Ile Glu Ala Ser
                245                 250                 255

Thr Arg Tyr Cys Arg Ala Asn Gly Thr Val Val Leu Val Gly Leu Pro
            260                 265                 270

Ala Gly Ala Lys Cys Ser Ser Asp Val Phe Asn His Val Lys Ser
        275                 280                 285

Ile Ser Ile Val Gly Ser Tyr Val Gly Asn Arg Ala Asp Thr Arg Glu
    290                 295                 300
```

```
Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
                325                 330                 335

Gln Ile Ala Gly Arg Tyr Val Val Asp Thr Ser Lys
            340                 345

<210> SEQ ID NO 112
<211> LENGTH: 375
<212> TYPE: PRT
<213> ORGANISM: Saccharomyces cerevisiae

<400> SEQUENCE: 112

Met Leu Arg Thr Ser Thr Leu Phe Thr Arg Val Gln Pro Ser Leu
1               5                   10                  15

Phe Ser Arg Asn Ile Leu Arg Leu Gln Ser Thr Ala Ala Ile Pro Lys
                20                  25                  30

Thr Gln Lys Gly Val Ile Phe Tyr Glu Asn Lys Gly Lys Leu His Tyr
            35                  40                  45

Lys Asp Ile Pro Val Pro Glu Pro Lys Pro Asn Glu Ile Leu Ile Asn
50                  55                  60

Val Lys Tyr Ser Gly Val Cys His Thr Asp Leu His Ala Trp His Gly
65                  70                  75                  80

Asp Trp Pro Leu Pro Val Lys Leu Pro Leu Val Gly Gly His Glu Gly
                85                  90                  95

Ala Gly Val Val Val Lys Leu Gly Ser Asn Val Lys Gly Trp Lys Val
            100                 105                 110

Gly Asp Leu Ala Gly Ile Lys Trp Leu Asn Gly Ser Cys Met Thr Cys
        115                 120                 125

Glu Phe Cys Glu Ser Gly His Glu Ser Asn Cys Pro Asp Ala Asp Leu
130                 135                 140

Ser Gly Tyr Thr His Asp Gly Ser Phe Gln Gln Phe Ala Thr Ala Asp
145                 150                 155                 160

Ala Ile Gln Ala Ala Lys Ile Gln Gln Gly Thr Asp Leu Ala Glu Val
                165                 170                 175

Ala Pro Ile Leu Cys Ala Gly Val Thr Val Tyr Lys Ala Leu Lys Glu
            180                 185                 190

Ala Asp Leu Lys Ala Gly Asp Trp Val Ala Ile Ser Gly Ala Ala Gly
        195                 200                 205

Gly Leu Gly Ser Leu Ala Val Gln Tyr Ala Thr Ala Met Gly Tyr Arg
    210                 215                 220

Val Leu Gly Ile Asp Ala Gly Glu Glu Lys Glu Lys Leu Phe Lys Lys
225                 230                 235                 240

Leu Gly Gly Glu Val Phe Ile Asp Phe Thr Lys Thr Lys Asn Met Val
                245                 250                 255

Ser Asp Ile Gln Glu Ala Thr Lys Gly Gly Pro His Gly Val Ile Asn
            260                 265                 270

Val Ser Val Ser Glu Ala Ala Ile Ser Leu Ser Thr Glu Tyr Val Arg
        275                 280                 285

Pro Cys Gly Thr Val Val Leu Val Gly Leu Pro Ala Asn Ala Tyr Val
    290                 295                 300

Lys Ser Glu Val Phe Ser His Val Val Lys Ser Ile Asn Ile Lys Gly
305                 310                 315                 320

Ser Tyr Val Gly Asn Arg Ala Asp Thr Arg Glu Ala Leu Asp Phe Phe
```

```
                    325                 330                 335
Ser Arg Gly Leu Ile Lys Ser Pro Ile Lys Ile Val Gly Leu Ser Glu
                340                 345                 350

Leu Pro Lys Val Tyr Asp Leu Met Glu Lys Gly Lys Ile Leu Gly Arg
                355                 360                 365

Tyr Val Val Asp Thr Ser Lys
    370                 375

<210> SEQ ID NO 113
<211> LENGTH: 382
<212> TYPE: PRT
<213> ORGANISM: Saccharomyces cerevisiae

<400> SEQUENCE: 113

Met Ser Ser Val Thr Gly Phe Tyr Ile Pro Pro Ile Ser Phe Phe Gly
1               5                   10                  15

Glu Gly Ala Leu Glu Glu Thr Ala Asp Tyr Ile Lys Asn Lys Asp Tyr
                20                  25                  30

Lys Lys Ala Leu Ile Val Thr Asp Pro Gly Ile Ala Ala Ile Gly Leu
                35                  40                  45

Ser Gly Arg Val Gln Lys Met Leu Glu Glu Arg Asp Leu Asn Val Ala
            50                  55                  60

Ile Tyr Asp Lys Thr Gln Pro Asn Pro Asn Ile Ala Asn Val Thr Ala
65                  70                  75                  80

Gly Leu Lys Val Leu Lys Glu Gln Asn Ser Glu Ile Val Val Ser Ile
                85                  90                  95

Gly Gly Gly Ser Ala His Asp Asn Ala Lys Ala Ile Ala Leu Leu Ala
                100                 105                 110

Thr Asn Gly Gly Glu Ile Gly Asp Tyr Glu Gly Val Asn Gln Ser Lys
            115                 120                 125

Lys Ala Ala Leu Pro Leu Phe Ala Ile Asn Thr Thr Ala Gly Thr Ala
            130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
            195                 200                 205

Ser Asn Pro Ile Thr Asp Ala Cys Ala Leu Lys Gly Ile Asp Leu Ile
    210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
                260                 265                 270

Phe Tyr His Leu Pro His Gly Val Cys Asn Ala Val Leu Leu Pro His
            275                 280                 285

Val Gln Glu Ala Asn Met Gln Cys Pro Lys Ala Lys Lys Arg Leu Gly
            290                 295                 300

Glu Ile Ala Leu His Phe Gly Ala Ser Gln Glu Asp Pro Glu Glu Thr
305                 310                 315                 320
```

Ile Lys Ala Leu His Val Leu Asn Arg Thr Met Asn Ile Pro Arg Asn
            325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
            355                 360                 365

Lys Glu Gln Val Val Ala Ile Ile Lys Lys Ala Tyr Glu Tyr
            370                 375             380

<210> SEQ ID NO 114
<211> LENGTH: 331
<212> TYPE: PRT
<213> ORGANISM: Bacillus subtilis

<400> SEQUENCE: 114

Met Glu Tyr Thr Ser Ile Ala Asp Thr Gly Ile Glu Ala Ser Arg Ile
1               5                   10                  15

Gly Leu Gly Thr Trp Ala Ile Gly Gly Thr Met Trp Gly Gly Thr Asp
            20                  25                  30

Glu Lys Thr Ser Ile Glu Thr Ile Arg Ala Ala Leu Asp Gln Gly Ile
            35                  40                  45

Thr Leu Ile Asp Thr Ala Pro Ala Tyr Gly Phe Gly Gln Ser Glu Glu
    50                  55                  60

Ile Val Gly Lys Ala Ile Lys Glu Tyr Gly Lys Arg Asp Gln Val Ile
65                  70                  75                  80

Leu Ala Thr Lys Thr Ala Leu Asp Trp Lys Asn Asn Gln Leu Phe Arg
                85                  90                  95

His Ala Asn Arg Ala Arg Ile Val Glu Glu Val Glu Asn Ser Leu Lys
            100                 105                 110

Arg Leu Gln Thr Asp Tyr Ile Asp Leu Tyr Gln Val His Trp Pro Asp
            115                 120                 125

Pro Leu Val Pro Ile Glu Glu Thr Ala Glu Val Met Lys Glu Leu Tyr
            130                 135                 140

Asp Ala Gly Lys Ile Arg Ala Ile Gly Val Ser Asn Phe Ser Ile Glu
145                 150                 155                 160

Gln Met Asp Thr Phe Arg Ala Val Ala Pro Leu His Thr Ile Gln Pro
                165                 170                 175

Pro Tyr Asn Leu Phe Glu Arg Glu Met Glu Glu Ser Val Leu Pro Tyr
            180                 185                 190

Ala Lys Asp Asn Lys Ile Thr Thr Leu Leu Tyr Gly Ser Leu Cys Arg
            195                 200                 205

Gly Leu Leu Thr Gly Lys Met Thr Glu Glu Tyr Thr Phe Glu Gly Asp
    210                 215                 220

Asp Leu Arg Asn His Asp Pro Lys Phe Gln Lys Pro Arg Phe Lys Glu
225                 230                 235                 240

Tyr Leu Ser Ala Val Asn Gln Leu Asp Lys Leu Ala Lys Thr Arg Tyr
                245                 250                 255

Gly Lys Ser Val Ile His Leu Ala Val Arg Trp Ile Leu Asp Gln Pro
            260                 265                 270

Gly Ala Asp Ile Ala Leu Trp Gly Ala Arg Lys Pro Gly Gln Leu Glu
    275                 280                 285

Ala Leu Ser Glu Ile Thr Gly Trp Thr Leu Asn Ser Glu Asp Gln Lys
            290                 295                 300

Asp Ile Asn Thr Ile Leu Glu Asn Thr Ile Ser Asp Pro Val Gly Pro
305                 310                 315                 320

Glu Phe Met Ala Pro Pro Thr Arg Glu Glu Ile
                325                 330

<210> SEQ ID NO 115
<211> LENGTH: 332
<212> TYPE: PRT
<213> ORGANISM: Gluconobacter oxydans

<400> SEQUENCE: 115

Met Ala Ser Asp Thr Ile Arg Ile Pro Gly Ile Asp Thr Pro Leu Ser
1               5                   10                  15

Arg Val Ala Leu Gly Thr Trp Ala Ile Gly Gly Trp Met Trp Gly Gly
            20                  25                  30

Pro Asp Asp Asn Gly Val Arg Thr Ile His Ala Ala Leu Asp Glu
        35                  40                  45

Gly Ile Asn Leu Ile Asp Thr Ala Pro Val Tyr Gly Phe Gly His Ser
    50                  55                  60

Glu Glu Ile Val Gly Arg Ala Leu Ala Gly Lys Pro Asn Lys Ala His
65                  70                  75                  80

Val Ala Thr Lys Leu Gly Leu His Trp Val Gly Glu Asp Glu Lys Asn
                85                  90                  95

Met Lys Val Phe Arg Asp Ser Arg Pro Ala Arg Ile Arg Lys Glu Val
            100                 105                 110

Glu Asp Ser Leu Arg Arg Leu Arg Val Glu Thr Ile Asp Leu Glu Gln
        115                 120                 125

Ile His Trp Pro Asp Asp Lys Thr Pro Ile Asp Glu Ser Ala Arg Glu
    130                 135                 140

Leu Gln Lys Leu His Gln Asp Gly Lys Ile Arg Ala Leu Gly Val Ser
145                 150                 155                 160

Asn Phe Ser Pro Glu Gln Met Asp Ile Phe Arg Glu Val Ala Pro Leu
                165                 170                 175

Ala Thr Ile Gln Pro Pro Leu Asn Leu Phe Glu Arg Thr Ile Glu Lys
            180                 185                 190

Asp Ile Leu Pro Tyr Ala Glu Lys His Asn Ala Val Val Leu Ala Tyr
        195                 200                 205

Gly Ala Leu Cys Arg Gly Leu Leu Thr Gly Lys Met Asn Arg Asp Thr
    210                 215                 220

Thr Phe Pro Lys Asp Asp Leu Arg Ser Asn Asp Pro Lys Phe Gln Lys
225                 230                 235                 240

Pro Asn Phe Glu Lys Tyr Leu Ala Ala Met Asp Glu Phe Glu Lys Leu
                245                 250                 255

Ala Glu Lys Arg Gly Lys Ser Val Met Ala Phe Ala Val Arg Trp Val
            260                 265                 270

Leu Asp Gln Gly Pro Val Ile Ala Leu Trp Gly Ala Arg Lys Pro Gly
        275                 280                 285

Gln Val Ser Gly Val Lys Asp Val Phe Gly Trp Ser Leu Thr Asp Glu
    290                 295                 300

Glu Lys Lys Ala Val Asp Asp Ile Leu Ala Arg His Val Pro Asn Pro
305                 310                 315                 320

Ile Asp Pro Thr Phe Met Ala Pro Pro Ala Arg Asp
                325                 330

<210> SEQ ID NO 116
<211> LENGTH: 339
<212> TYPE: PRT

<213> ORGANISM: Escherichia coli

<400> SEQUENCE: 116

```
Met Ser Met Ile Lys Ser Tyr Ala Ala Lys Glu Ala Gly Gly Glu Leu
1               5                   10                  15
Glu Val Tyr Glu Tyr Asp Pro Gly Glu Leu Arg Pro Gln Asp Val Glu
            20                  25                  30
Val Gln Val Asp Tyr Cys Gly Ile Cys His Ser Asp Leu Ser Met Ile
        35                  40                  45
Asp Asn Glu Trp Gly Phe Ser Gln Tyr Pro Leu Val Ala Gly His Glu
    50                  55                  60
Val Ile Gly Arg Val Val Ala Leu Gly Ser Ala Ala Gln Asp Lys Gly
65                  70                  75                  80
Leu Gln Val Gly Gln Arg Val Gly Ile Gly Trp Thr Ala Arg Ser Cys
                85                  90                  95
Gly His Cys Asp Ala Cys Ile Ser Gly Asn Gln Ile Asn Cys Glu Gln
            100                 105                 110
Gly Ala Val Pro Thr Ile Met Asn Arg Gly Gly Phe Ala Glu Lys Leu
        115                 120                 125
Arg Ala Asp Trp Gln Trp Val Ile Pro Leu Pro Glu Asn Ile Asp Ile
    130                 135                 140
Glu Ser Ala Gly Pro Leu Leu Cys Gly Gly Ile Thr Val Phe Lys Pro
145                 150                 155                 160
Leu Leu Met His His Ile Thr Ala Thr Ser Arg Val Gly Val Ile Gly
                165                 170                 175
Ile Gly Gly Leu Gly His Ile Ala Ile Lys Leu Leu His Ala Met Gly
            180                 185                 190
Cys Glu Val Thr Ala Phe Ser Ser Asn Pro Ala Lys Glu Gln Glu Val
        195                 200                 205
Leu Ala Met Gly Ala Asp Lys Val Val Asn Ser Arg Asp Pro Gln Ala
    210                 215                 220
Leu Lys Ala Leu Ala Gly Gln Phe Asp Leu Ile Ile Asn Thr Val Asn
225                 230                 235                 240
Val Ser Leu Asp Trp Gln Pro Tyr Phe Glu Ala Leu Thr Tyr Gly Gly
                245                 250                 255
Asn Phe His Thr Val Gly Ala Val Leu Thr Pro Leu Ser Val Pro Ala
            260                 265                 270
Phe Thr Leu Ile Ala Gly Asp Arg Ser Val Ser Gly Ser Ala Thr Gly
        275                 280                 285
Thr Pro Tyr Glu Leu Arg Lys Leu Met Arg Phe Ala Ala Arg Ser Lys
    290                 295                 300
Val Ala Pro Thr Thr Glu Leu Phe Pro Met Ser Lys Ile Asn Asp Ala
305                 310                 315                 320
Ile Gln His Val Arg Asp Gly Lys Ala Arg Tyr Arg Val Val Leu Lys
                325                 330                 335
Ala Asp Phe
```

<210> SEQ ID NO 117
<211> LENGTH: 315
<212> TYPE: PRT
<213> ORGANISM: Arabidopsis thaliana

<400> SEQUENCE: 117

```
Met Ala Asn Ala Ile Thr Phe Phe Lys Leu Asn Thr Gly Ala Lys Phe
1               5                   10                  15
```

```
Pro Ser Val Gly Leu Gly Thr Trp Gln Ala Ser Pro Gly Leu Val Gly
            20                  25                  30

Asp Ala Val Ala Ala Val Lys Ile Gly Tyr Arg His Ile Asp Cys
            35                  40                  45

Ala Gln Ile Tyr Gly Asn Glu Lys Glu Ile Gly Ala Val Leu Lys Lys
 50                  55                  60

Leu Phe Glu Asp Arg Val Val Lys Arg Glu Asp Leu Phe Ile Thr Ser
 65                  70                  75                  80

Lys Leu Trp Cys Thr Asp His Asp Pro Gln Asp Val Pro Glu Ala Leu
                85                  90                  95

Asn Arg Thr Leu Lys Asp Leu Gln Leu Glu Tyr Val Asp Leu Tyr Leu
            100                 105                 110

Ile His Trp Pro Ala Arg Ile Lys Lys Gly Ser Val Gly Ile Lys Pro
            115                 120                 125

Glu Asn Leu Leu Pro Val Asp Ile Pro Ser Thr Trp Lys Ala Met Glu
130                 135                 140

Ala Leu Tyr Asp Ser Gly Lys Ala Arg Ala Ile Gly Val Ser Asn Phe
145                 150                 155                 160

Ser Thr Lys Lys Leu Ala Asp Leu Leu Glu Leu Ala Arg Val Pro Pro
                165                 170                 175

Ala Val Asn Gln Val Glu Cys His Pro Ser Trp Arg Gln Thr Lys Leu
            180                 185                 190

Gln Glu Phe Cys Lys Ser Lys Gly Val His Leu Ser Ala Tyr Ser Pro
            195                 200                 205

Leu Gly Ser Pro Gly Thr Thr Trp Leu Lys Ser Asp Val Leu Lys Asn
            210                 215                 220

Pro Ile Leu Asn Met Val Ala Glu Lys Leu Gly Lys Ser Pro Ala Gln
225                 230                 235                 240

Val Ala Leu Arg Trp Gly Leu Gln Met Gly His Ser Val Leu Pro Lys
                245                 250                 255

Ser Thr Asn Glu Gly Arg Ile Lys Glu Asn Phe Asn Val Phe Asp Trp
            260                 265                 270

Ser Ile Pro Asp Tyr Met Phe Ala Lys Phe Ala Glu Ile Glu Gln Ala
            275                 280                 285

Arg Leu Val Thr Gly Ser Phe Leu Val His Glu Thr Leu Ser Pro Tyr
290                 295                 300

Lys Ser Ile Glu Glu Leu Trp Asp Gly Glu Ile
305                 310                 315

<210> SEQ ID NO 118
<211> LENGTH: 284
<212> TYPE: PRT
<213> ORGANISM: Leishmania donovani

<400> SEQUENCE: 118

Met Ala Asp Val Gly Lys Ala Met Val Thr Leu Ser Asn Gly Val Gln
 1                   5                  10                  15

Met Pro Gln Leu Gly Leu Gly Val Trp Gln Ser Pro Ala Gly Glu Val
            20                  25                  30

Thr Ala Asn Ala Val Lys Trp Ala Leu Cys Ala Gly Tyr Arg His Ile
            35                  40                  45

Asp Thr Ala Ala Ile Tyr Lys Asn Glu Glu Ser Val Gly Ala Gly Leu
 50                  55                  60

Arg Ala Ser Gly Val Pro Arg Glu Asp Val Phe Ile Thr Thr Lys Leu
```

```
                65                  70                  75                  80
Trp Asn Thr Glu Gln Gly Tyr Glu Ser Thr Leu Ala Ala Phe Glu Glu
                    85                  90                  95

Ser Arg Gln Lys Leu Gly Val Asp Tyr Ile Asp Leu Tyr Leu Ile His
                100                 105                 110

Trp Pro Arg Gly Lys Asp Ile Val Ser Lys Glu Gly Lys Lys Tyr Leu
                115                 120                 125

Asp Ser Trp Arg Ala Phe Glu Gln Leu Tyr Lys Asp Lys Lys Val Arg
            130                 135                 140

Ala Ile Gly Val Ser Asn Phe His Ile His His Leu Glu Asp Val Leu
145                 150                 155                 160

Ala Met Cys Thr Val Thr Pro Met Val Asn Gln Val Glu Leu His Pro
                165                 170                 175

Leu Asn Asn Gln Ala Glu Leu Arg Ala Phe Cys Asp Ala Lys Gln Ile
                180                 185                 190

Lys Val Glu Ala Trp Ser Pro Leu Gly Gln Gly Lys Leu Leu Ser Asn
                195                 200                 205

Pro Ile Leu Ala Ala Ile Gly Ala Lys Tyr Asn Lys Thr Ala Ala Gln
            210                 215                 220

Val Ile Leu Arg Trp Asn Ile Gln Lys Asn Leu Ile Thr Ile Pro Lys
225                 230                 235                 240

Ser Val His Lys Glu Arg Ile Glu Glu Asn Ala Asp Val Phe Asn Phe
                245                 250                 255

Glu Leu Asp Ala Glu Asp Val Met Ser Ile Asp Ala Leu Asn Thr Asn
                260                 265                 270

Ser Arg Tyr Gly Pro Asp Pro Asp Glu Ala Gln Phe
                275                 280

<210> SEQ ID NO 119
<211> LENGTH: 349
<212> TYPE: PRT
<213> ORGANISM: Escherichia coli

<400> SEQUENCE: 119

Met Lys Ile Lys Ala Val Gly Ala Tyr Ser Ala Lys Gln Pro Leu Glu
1               5                   10                  15

Pro Met Asp Ile Thr Arg Arg Glu Pro Gly Pro Asn Asp Val Lys Ile
                20                  25                  30

Glu Ile Ala Tyr Cys Gly Val Cys His Ser Asp Leu His Gln Val Arg
            35                  40                  45

Ser Glu Trp Ala Gly Thr Val Tyr Pro Cys Val Pro Gly His Glu Ile
        50                  55                  60

Val Gly Arg Val Val Ala Val Gly Asp Gln Val Glu Lys Tyr Ala Pro
65                  70                  75                  80

Gly Asp Leu Val Gly Val Gly Cys Ile Val Asp Ser Cys Lys His Cys
                85                  90                  95

Glu Glu Cys Glu Asp Gly Leu Glu Asn Tyr Cys Asp His Met Thr Gly
                100                 105                 110

Thr Tyr Asn Ser Pro Thr Pro Asp Glu Pro Gly His Thr Leu Gly Gly
                115                 120                 125

Tyr Ser Gln Gln Ile Val Val His Glu Arg Tyr Val Leu Arg Ile Arg
            130                 135                 140

His Pro Gln Glu Gln Leu Ala Ala Val Ala Pro Leu Leu Cys Ala Gly
145                 150                 155                 160
```

```
Ile Thr Thr Tyr Ser Pro Leu Arg His Trp Gln Ala Gly Pro Gly Lys
            165                 170                 175

Lys Val Gly Val Val Gly Ile Gly Gly Leu Gly His Met Gly Ile Lys
        180                 185                 190

Leu Ala His Ala Met Gly Ala His Val Val Ala Phe Thr Thr Ser Glu
        195                 200                 205

Ala Lys Arg Glu Ala Ala Lys Ala Leu Gly Ala Asp Glu Val Val Asn
        210                 215                 220

Ser Arg Asn Ala Asp Glu Met Ala Ala His Leu Lys Ser Phe Asp Phe
225                 230                 235                 240

Ile Leu Asn Thr Val Ala Ala Pro His Asn Leu Asp Asp Phe Thr Thr
            245                 250                 255

Leu Leu Lys Arg Asp Gly Thr Met Thr Leu Val Gly Ala Pro Ala Thr
        260                 265                 270

Pro His Lys Ser Pro Glu Val Phe Asn Leu Ile Met Lys Arg Arg Ala
        275                 280                 285

Ile Ala Gly Ser Met Ile Gly Gly Ile Pro Glu Thr Gln Glu Met Leu
        290                 295                 300

Asp Phe Cys Ala Glu His Gly Ile Val Ala Asp Ile Glu Met Ile Arg
305                 310                 315                 320

Ala Asp Gln Ile Asn Glu Ala Tyr Glu Arg Met Leu Arg Gly Asp Val
                325                 330                 335

Lys Tyr Arg Phe Val Ile Asp Asn Arg Thr Leu Thr Asp
            340                 345

<210> SEQ ID NO 120
<211> LENGTH: 346
<212> TYPE: PRT
<213> ORGANISM: Escherichia coli

<400> SEQUENCE: 120

Met Gln Tyr His Arg Ile Pro His Ser Ser Leu Glu Val Ser Thr Leu
1               5                   10                  15

Gly Leu Gly Thr Met Thr Phe Gly Glu Gln Asn Ser Glu Ala Asp Ala
            20                  25                  30

His Ala Gln Leu Asp Tyr Ala Val Ala Gln Gly Ile Asn Leu Ile Asp
        35                  40                  45

Val Ala Glu Met Tyr Pro Val Pro Pro Arg Pro Glu Thr Gln Gly Leu
    50                  55                  60

Thr Glu Thr Tyr Val Gly Asn Trp Leu Ala Lys His Gly Ser Arg Glu
65              70                  75                  80

Lys Leu Ile Ile Ala Ser Lys Val Ser Gly Pro Ser Arg Asn Asn Asp
            85                  90                  95

Lys Gly Ile Arg Pro Asp Gln Ala Leu Asp Arg Lys Asn Ile Arg Glu
        100                 105                 110

Ala Leu His Asp Ser Leu Lys Arg Leu Gln Thr Asp Tyr Leu Asp Leu
    115                 120                 125

Tyr Gln Val His Trp Pro Gln Arg Pro Thr Asn Cys Phe Gly Lys Leu
    130                 135                 140

Gly Tyr Ser Trp Thr Asp Ser Ala Pro Val Ser Leu Leu Asp Thr
145                 150                 155                 160

Leu Asp Ala Leu Ala Glu Tyr Gln Arg Ala Gly Lys Ile Arg Tyr Ile
                165                 170                 175

Gly Val Ser Asn Glu Thr Ala Phe Gly Val Met Arg Tyr Leu His Leu
            180                 185                 190
```

```
Ala Asp Lys His Asp Leu Pro Arg Ile Val Thr Ile Gln Asn Pro Tyr
            195                 200                 205

Ser Leu Leu Asn Arg Ser Phe Glu Val Gly Leu Ala Glu Val Ser Gln
    210                 215                 220

Tyr Glu Gly Val Glu Leu Leu Ala Tyr Ser Cys Leu Gly Phe Gly Thr
225                 230                 235                 240

Leu Thr Gly Lys Tyr Leu Asn Gly Ala Lys Pro Ala Gly Ala Arg Asn
                245                 250                 255

Thr Leu Phe Ser Arg Phe Thr Arg Tyr Ser Gly Glu Gln Thr Gln Lys
                260                 265                 270

Ala Val Ala Ala Tyr Val Asp Ile Ala Arg Arg His Gly Leu Asp Pro
            275                 280                 285

Ala Gln Met Ala Leu Ala Phe Val Arg Arg Gln Pro Phe Val Ala Ser
        290                 295                 300

Thr Leu Leu Gly Ala Thr Thr Met Asp Gln Leu Lys Thr Asn Ile Glu
305                 310                 315                 320

Ser Leu His Leu Glu Leu Ser Glu Asp Val Leu Ala Glu Ile Glu Ala
                325                 330                 335

Val His Gln Val Tyr Thr Tyr Pro Ala Pro
            340                 345

<210> SEQ ID NO 121
<211> LENGTH: 399
<212> TYPE: PRT
<213> ORGANISM: Thermoanaerobacter ethaolicus

<400> SEQUENCE: 121

Met Trp Glu Thr Lys Ile Asn Pro Asn Lys Val Phe Glu Leu Arg Cys
1               5                   10                  15

Lys Asn Thr Thr Tyr Phe Gly Ile Gly Ser Ile Lys Lys Ile Lys Asp
            20                  25                  30

Ile Leu Glu Val Leu Lys Asn Lys Gly Ile Asn Asn Val Ile Leu Val
        35                  40                  45

Thr Gly Lys Gly Ser Tyr Lys Ala Ser Gly Ala Trp Asp Val Val Lys
    50                  55                  60

Pro Ala Leu Glu Thr Leu Gly Phe Lys Tyr Ser Leu Tyr Asp Lys Val
65                  70                  75                  80

Gly Pro Asn Pro Thr Val Asp Met Ile Asp Glu Ala Ala Lys Ile Gly
                85                  90                  95

Arg Glu Thr Gly Ala Lys Ala Val Ile Gly Ile Gly Gly Ser Pro
            100                 105                 110

Ile Asp Thr Ala Lys Ser Val Ala Val Leu Leu Glu Tyr Thr Asp Lys
        115                 120                 125

Asn Ala Arg Glu Leu Tyr Glu Gln Lys Phe Ile Pro Glu Lys Ala Ala
    130                 135                 140

Pro Ile Ile Ala Ile Asn Leu Thr His Gly Thr Gly Thr Glu Val Asp
145                 150                 155                 160

Arg Phe Ala Val Ala Thr Ile Pro Glu Lys Asn Tyr Lys Pro Ala Ile
                165                 170                 175

Ala Tyr Asp Cys Leu Tyr Pro Met Tyr Ala Ile Asp Asp Pro Ser Leu
            180                 185                 190

Met Thr Lys Leu Asp Lys Lys Gln Thr Ile Ala Val Thr Ile Asp Ala
        195                 200                 205

Leu Asn His Val Thr Glu Ala Ala Thr Thr Leu Val Ala Ser Pro Tyr
```

```
        210                 215                 220
Ser Val Leu Met Ala Lys Glu Thr Val Arg Leu Ile Val Arg Tyr Leu
225                 230                 235                 240

Pro Ala Ala Val Asn Asp Pro Glu Asn Leu Val Ala Arg Tyr Tyr Leu
                245                 250                 255

Leu Tyr Ala Ser Ala Leu Ala Gly Ile Ser Phe Asp Asn Gly Leu Leu
            260                 265                 270

His Leu Thr His Ala Leu Glu His Pro Leu Ser Ala Val Lys Pro Glu
        275                 280                 285

Ile Ala His Gly Leu Gly Leu Gly Ala Ile Leu Pro Ala Val Val Lys
    290                 295                 300

Ala Ile Tyr Pro Ser Val Ala Glu Val Leu Ala Glu Val Tyr Ser Pro
305                 310                 315                 320

Ile Val Pro Gly Leu Lys Gly Leu Pro Ala Glu Ala Glu Tyr Val Ala
                325                 330                 335

Lys Lys Val Glu Glu Trp Leu Phe Lys Val Gly Cys Thr Gln Lys Leu
            340                 345                 350

Ser Asp Phe Gly Phe Thr Lys Glu Asp Ile Pro Thr Leu Val Arg Leu
        355                 360                 365

Ala Lys Thr Thr Pro Ser Leu Asp Gly Leu Leu Ser Asn Ala Pro Val
    370                 375                 380

Glu Ala Thr Glu Ala Val Ile Ala Lys Ile Tyr Glu Glu Ser Phe
385                 390                 395

<210> SEQ ID NO 122
<211> LENGTH: 346
<212> TYPE: PRT
<213> ORGANISM: Bacillus subtilis

<400> SEQUENCE: 122

Met Lys Ala Ala Arg Trp His Asn Gln Lys Asp Ile Arg Ile Glu His
1               5                   10                  15

Ile Glu Glu Pro Lys Thr Glu Pro Gly Lys Val Lys Ile Lys Val Lys
            20                  25                  30

Trp Cys Gly Ile Cys Gly Ser Asp Leu His Glu Tyr Leu Gly Gly Pro
        35                  40                  45

Ile Phe Ile Pro Val Asp Lys Pro His Pro Leu Thr Asn Glu Thr Ala
    50                  55                  60

Pro Val Thr Met Gly His Glu Phe Ser Gly Glu Val Val Glu Val Gly
65                  70                  75                  80

Glu Gly Val Glu Asn Tyr Lys Val Gly Asp Arg Val Val Glu Pro
                85                  90                  95

Ile Phe Ala Thr His Gly His Gln Gly Ala Tyr Asn Leu Asp Glu Gln
            100                 105                 110

Met Gly Phe Leu Gly Leu Ala Gly Gly Gly Gly Phe Ser Glu Tyr
        115                 120                 125

Val Ser Val Asp Glu Glu Leu Leu Phe Lys Leu Pro Asp Glu Leu Ser
    130                 135                 140

Tyr Glu Gln Gly Ala Leu Val Glu Pro Ser Ala Val Ala Leu Tyr Ala
145                 150                 155                 160

Val Arg Ser Ser Lys Leu Lys Ala Gly Asp Lys Ala Ala Val Phe Gly
                165                 170                 175

Cys Gly Pro Ile Gly Leu Leu Val Ile Glu Ala Leu Lys Ala Ala Gly
            180                 185                 190
```

```
Ala Thr Asp Ile Tyr Ala Val Glu Leu Ser Pro Glu Arg Gln Gln Lys
            195                 200                 205

Ala Glu Glu Leu Gly Ala Ile Ile Val Asp Pro Ser Lys Thr Asp Asp
210                 215                 220

Val Val Ala Glu Ile Ala Glu Arg Thr Gly Gly Val Asp Val Ala
225                 230                 235                 240

Phe Glu Val Thr Gly Val Pro Val Val Leu Arg Gln Ala Ile Gln Ser
                245                 250                 255

Thr Thr Ile Ala Gly Glu Thr Val Ile Val Ser Ile Trp Glu Lys Gly
            260                 265                 270

Ala Glu Ile His Pro Asn Asp Ile Val Ile Lys Glu Arg Thr Val Lys
            275                 280                 285

Gly Ile Ile Gly Tyr Arg Asp Ile Phe Pro Ala Val Leu Ser Leu Met
            290                 295                 300

Lys Glu Gly Tyr Phe Ser Ala Asp Lys Leu Val Thr Lys Lys Ile Val
305                 310                 315                 320

Leu Asp Asp Leu Ile Glu Glu Gly Phe Gly Ala Leu Ile Lys Glu Lys
                325                 330                 335

Ser Gln Val Lys Ile Leu Val Arg Pro Asn
            340                 345

<210> SEQ ID NO 123
<211> LENGTH: 382
<212> TYPE: PRT
<213> ORGANISM: Saccharomyces cerevisiae

<400> SEQUENCE: 123

Met Arg Ala Leu Ala Tyr Phe Lys Lys Gly Asp Ile His Phe Thr Asn
1               5                   10                  15

Asp Ile Pro Arg Pro Glu Ile Gln Thr Asp Asp Glu Val Ile Ile Asp
                20                  25                  30

Val Ser Trp Cys Gly Ile Cys Gly Ser Asp Leu His Glu Tyr Leu Asp
            35                  40                  45

Gly Pro Ile Phe Met Pro Lys Asp Gly Glu Cys His Lys Leu Ser Asn
        50                  55                  60

Ala Ala Leu Pro Leu Ala Met Gly His Glu Met Ser Gly Ile Val Ser
65                  70                  75                  80

Lys Val Gly Pro Lys Val Thr Lys Val Lys Val Gly Asp His Val Val
                85                  90                  95

Val Asp Ala Ala Ser Ser Cys Ala Asp Leu His Cys Trp Pro His Ser
            100                 105                 110

Lys Phe Tyr Asn Ser Lys Pro Cys Asp Ala Cys Gln Arg Gly Ser Glu
        115                 120                 125

Asn Leu Cys Thr His Ala Gly Phe Val Gly Leu Gly Val Ile Ser Gly
130                 135                 140

Gly Phe Ala Glu Gln Val Val Val Ser Gln His His Ile Ile Pro Val
145                 150                 155                 160

Pro Lys Glu Ile Pro Leu Asp Val Ala Ala Leu Val Glu Pro Leu Ser
                165                 170                 175

Val Thr Trp His Ala Val Lys Ile Ser Gly Phe Lys Lys Gly Ser Ser
            180                 185                 190

Ala Leu Val Leu Gly Ala Gly Pro Ile Gly Leu Cys Thr Ile Leu Val
        195                 200                 205

Leu Lys Gly Met Gly Ala Ser Lys Ile Val Val Ser Glu Ile Ala Glu
210                 215                 220
```

```
Arg Arg Ile Glu Met Ala Lys Lys Leu Gly Val Glu Val Phe Asn Pro
225                 230                 235                 240

Ser Lys His Gly His Lys Ser Ile Glu Ile Leu Arg Gly Leu Thr Lys
            245                 250                 255

Ser His Asp Gly Phe Asp Tyr Ser Tyr Asp Cys Ser Gly Ile Gln Val
            260                 265                 270

Thr Phe Glu Thr Ser Leu Lys Ala Leu Thr Phe Lys Gly Thr Ala Thr
            275                 280                 285

Asn Ile Ala Val Trp Gly Pro Lys Pro Val Pro Phe Gln Pro Met Asp
            290                 295                 300

Val Thr Leu Gln Glu Lys Val Met Thr Gly Ser Ile Gly Tyr Val Val
305                 310                 315                 320

Glu Asp Phe Glu Glu Val Val Arg Ala Ile His Asn Gly Asp Ile Ala
                325                 330                 335

Met Glu Asp Cys Lys Gln Leu Ile Thr Gly Lys Gln Arg Ile Glu Asp
                340                 345                 350

Gly Trp Glu Lys Gly Phe Gln Glu Leu Met Asp His Lys Glu Ser Asn
            355                 360                 365

Val Lys Ile Leu Leu Thr Pro Asn Asn His Gly Glu Met Lys
    370                 375                 380
```

<210> SEQ ID NO 124
<211> LENGTH: 258
<212> TYPE: PRT
<213> ORGANISM: Corynebacterium glutamicum

<400> SEQUENCE: 124

```
Met Ser Lys Val Ala Met Val Thr Gly Gly Ala Gln Gly Ile Gly Arg
1               5                   10                  15

Gly Ile Ser Glu Lys Leu Ala Ala Asp Gly Phe Asp Ile Ala Val Ala
            20                  25                  30

Asp Leu Pro Gln Gln Glu Glu Gln Ala Ala Glu Thr Ile Lys Leu Ile
        35                  40                  45

Glu Ala Ala Gly Gln Lys Ala Val Phe Val Gly Leu Asp Val Thr Asp
50                  55                  60

Lys Ala Asn Phe Asp Ser Ala Ile Asp Glu Ala Ala Glu Lys Leu Gly
65                  70                  75                  80

Gly Phe Asp Val Leu Val Asn Asn Ala Gly Ile Ala Gln Ile Lys Pro
                85                  90                  95

Leu Leu Glu Val Thr Glu Glu Asp Leu Lys Gln Ile Tyr Ser Val Asn
            100                 105                 110

Val Phe Ser Val Phe Phe Gly Ile Gln Ala Ala Ser Arg Lys Phe Asp
        115                 120                 125

Glu Leu Gly Val Lys Gly Lys Ile Ile Asn Ala Ala Ser Ile Ala Ala
130                 135                 140

Ile Gln Gly Phe Pro Ile Leu Ser Ala Tyr Ser Thr Thr Lys Phe Ala
145                 150                 155                 160

Val Arg Gly Leu Thr Gln Ala Ala Ala Gln Glu Leu Ala Pro Lys Gly
                165                 170                 175

His Thr Val Asn Ala Tyr Ala Pro Gly Ile Val Gly Thr Gly Met Trp
            180                 185                 190

Glu Gln Ile Asp Ala Glu Leu Ser Lys Ile Asn Gly Lys Pro Ile Gly
        195                 200                 205

Glu Asn Phe Lys Glu Tyr Ser Ser Ser Ile Ala Leu Gly Arg Pro Ser
```

```
                210                 215                 220
Val Pro Glu Asp Val Ala Gly Leu Val Ser Phe Leu Ala Ser Glu Asn
225                 230                 235                 240

Ser Asn Tyr Ile Thr Gly Gln Val Met Leu Val Asp Gly Gly Met Leu
                245                 250                 255

Tyr Asn

<210> SEQ ID NO 125
<211> LENGTH: 256
<212> TYPE: PRT
<213> ORGANISM: Klebsiella pneumoniae

<400> SEQUENCE: 125

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
                20                  25                  30

Asp Tyr Asn Asp Ala Thr Ala Lys Ala Val Ala Ser Glu Ile Asn Gln
            35                  40                  45

Ala Gly Gly Arg Ala Met Ala Val Lys Val Asp Val Ser Asp Arg Asp
        50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255

<210> SEQ ID NO 126
<211> LENGTH: 251
<212> TYPE: PRT
<213> ORGANISM: Serratia marcescens

<400> SEQUENCE: 126

Met Arg Phe Asp Asn Lys Val Val Val Ile Thr Gly Ala Gly Thr Gly
1               5                   10                  15

Met Gly Glu Ala Ala Ala Arg Arg Phe Ser Ala Glu Gly Ala Ile Val
                20                  25                  30
```

```
Val Leu Ala Asp Trp Ala Lys Glu Ala Val Asp Lys Val Ala Ser
         35                  40                  45

Leu Pro Lys Gly Arg Ala Met Ala Val His Ile Asp Val Ser Asp His
 50                  55                  60

Val Ala Val Glu Lys Met Met Asn Glu Val Ala Glu Lys Leu Gly Arg
 65                  70                  75                  80

Ile Asp Val Leu Leu Asn Asn Ala Gly Val His Val Ala Gly Ser Val
                 85                  90                  95

Leu Glu Thr Ser Val Asp Asp Trp Arg Arg Ile Ala Gly Val Asp Ile
            100                 105                 110

Asp Gly Val Val Phe Cys Ser Lys Phe Ala Leu Pro His Leu Leu Lys
        115                 120                 125

Thr Lys Gly Cys Ile Val Asn Thr Ala Ser Val Ser Gly Leu Gly Gly
    130                 135                 140

Asp Trp Gly Ala Ala Tyr Tyr Cys Ala Ala Lys Gly Ala Val Val Asn
145                 150                 155                 160

Leu Thr Arg Ala Met Ala Leu Asp His Gly Asp Gly Val Arg Ile
                165                 170                 175

Asn Ser Val Cys Pro Ser Leu Val Lys Thr Asn Met Thr Asn Gly Trp
            180                 185                 190

Pro Gln Glu Ile Arg Asp Lys Phe Asn Glu Arg Ile Ala Leu Gly Arg
        195                 200                 205

Ala Ala Glu Pro Glu Glu Val Ala Ala Val Met Ala Phe Leu Ala Ser
    210                 215                 220

Asp Asp Ala Ser Phe Ile Asn Gly Ala Asn Ile Pro Val Asp Gly Gly
225                 230                 235                 240

Ala Thr Ala Ser Asp Gly Gln Gln Asn Ile Val
                245                 250

<210> SEQ ID NO 127
<211> LENGTH: 367
<212> TYPE: PRT
<213> ORGANISM: Escherichia coli

<400> SEQUENCE: 127

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
                20                  25                  30

Leu Val Val Gly Asp Lys Phe Val Leu Gly Phe Ala Gln Ser Thr Val
         35                  40                  45

Glu Lys Ser Phe Lys Asp Ala Gly Leu Val Val Glu Ile Ala Pro Phe
 50                  55                  60

Gly Gly Glu Cys Ser Gln Asn Glu Ile Asp Arg Leu Arg Gly Ile Ala
 65                  70                  75                  80

Glu Thr Ala Gln Cys Gly Ala Ile Leu Gly Ile Gly Gly Gly Lys Thr
                 85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
```

```
            145                 150                 155                 160
Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 128
<211> LENGTH: 258
<212> TYPE: PRT
<213> ORGANISM: Corynebacterium glutamicum

<400> SEQUENCE: 128

Met Ser Lys Val Ala Met Val Thr Gly Gly Ala Gln Gly Ile Gly Arg
1               5                   10                  15

Gly Ile Ser Glu Lys Leu Ala Ala Asp Gly Phe Asp Ile Ala Val Ala
            20                  25                  30

Asp Leu Pro Gln Gln Glu Gln Ala Ala Glu Thr Ile Lys Leu Ile
        35                  40                  45

Glu Ala Ala Asp Gln Lys Ala Val Phe Val Gly Leu Asp Val Thr Asp
    50                  55                  60

Lys Ala Asn Phe Asp Ser Ala Ile Asp Glu Ala Glu Lys Leu Gly
65                  70                  75                  80

Gly Phe Asp Val Leu Val Asn Asn Ala Gly Ile Ala Gln Ile Lys Pro
                85                  90                  95

Leu Leu Glu Val Thr Glu Glu Asp Leu Lys Gln Ile Tyr Ser Val Asn
            100                 105                 110

Val Phe Ser Val Phe Phe Gly Ile Gln Ala Ala Ser Arg Lys Phe Asp
        115                 120                 125

Glu Leu Gly Val Lys Gly Lys Ile Ile Asn Ala Ala Ser Ile Ala Ala
    130                 135                 140

Ile Gln Gly Phe Pro Ile Leu Ser Ala Tyr Ser Thr Thr Lys Phe Ala
145                 150                 155                 160
```

Val Arg Gly Leu Thr Gln Ala Ala Gln Glu Leu Ala Pro Lys Gly
            165                 170                 175

His Thr Val Asn Ala Tyr Ala Pro Gly Ile Val Gly Thr Gly Met Trp
        180                 185                 190

Glu Gln Ile Asp Ala Glu Leu Ser Lys Ile Asn Gly Lys Pro Ile Gly
            195                 200                 205

Glu Asn Phe Lys Glu Tyr Ser Ser Ser Ile Ala Leu Gly Arg Pro Ser
        210                 215                 220

Val Pro Glu Asp Val Ala Gly Leu Val Ser Phe Leu Ala Ser Glu Asn
225                 230                 235                 240

Ser Asn Tyr Val Thr Gly Gln Val Met Leu Val Asp Gly Gly Met Leu
            245                 250                 255

Tyr Asn

<210> SEQ ID NO 129
<211> LENGTH: 318
<212> TYPE: PRT
<213> ORGANISM: Hypocrea jecorina

<400> SEQUENCE: 129

Met Ala Ser Lys Thr Tyr Thr Leu Asn Thr Gly Ala Lys Ile Pro Ala
1               5                   10                  15

Val Gly Phe Gly Thr Phe Ala Asn Glu Gly Ala Lys Gly Glu Thr Tyr
            20                  25                  30

Ala Ala Val Thr Lys Ala Leu Asp Val Gly Tyr Arg His Leu Asp Cys
        35                  40                  45

Ala Trp Phe Tyr His Asn Glu Asp Glu Val Gly Asp Ala Val Arg Asp
    50                  55                  60

Phe Leu Ala Arg Arg Pro Asp Val Lys Arg Glu Asp Leu Phe Ile Cys
65                  70                  75                  80

Thr Lys Val Trp Asn His Leu His Glu Pro Glu Asp Val Lys Trp Ser
            85                  90                  95

Ala Lys Asn Ser Cys Glu Asn Leu Lys Val Asp Tyr Ile Asp Leu Phe
        100                 105                 110

Leu Val His Trp Pro Ile Ala Ala Glu Lys Asn Ser Asp Arg Ser Val
    115                 120                 125

Lys Leu Gly Pro Asp Gly Lys Tyr Val Ile Asn Gln Ala Leu Thr Glu
130                 135                 140

Asn Pro Glu Pro Thr Trp Arg Ala Met Glu Glu Leu Val Glu Ser Gly
145                 150                 155                 160

Leu Val Lys Ala Ile Gly Val Ser Asn Trp Thr Ile Pro Gly Leu Lys
            165                 170                 175

Lys Leu Leu Gln Ile Ala Lys Ile Lys Pro Ala Val Asn Gln Ile Glu
        180                 185                 190

Ile His Pro Phe Leu Pro Asn Glu Glu Leu Val Ala Phe Cys Phe Glu
    195                 200                 205

Asn Gly Ile Leu Pro Glu Ala Tyr Ser Pro Leu Gly Ser Gln Asn Gln
        210                 215                 220

Val Pro Ser Thr Gly Glu Arg Val Arg Asp Asn Pro Thr Leu Lys Ala
225                 230                 235                 240

Val Ala Glu Arg Ser Gly Tyr Ser Leu Ala Gln Ile Leu Leu Ala Trp
            245                 250                 255

Gly Leu Lys Arg Gly Tyr Val Val Leu Pro Lys Ser Ser Thr Pro Ser
        260                 265                 270

```
Arg Ile Glu Ser Asn Phe Asn Ile Pro Glu Leu Ser Asp Glu Asp Phe
            275                 280                 285

Glu Ala Ile Gln Gln Val Ala Lys Gly Arg His Thr Arg Phe Val Asn
            290                 295                 300

Met Lys Asp Thr Phe Gly Tyr Asn Val Trp Pro Glu Glu Glu
305                 310                 315

<210> SEQ ID NO 130
<211> LENGTH: 385
<212> TYPE: PRT
<213> ORGANISM: Clostridium butyricum

<400> SEQUENCE: 130

Met Arg Met Tyr Asp Tyr Leu Val Pro Ser Val Asn Phe Met Gly Ala
1               5                   10                  15

Asn Ser Val Ser Val Val Gly Glu Arg Cys Lys Ile Leu Gly Gly Lys
            20                  25                  30

Lys Ala Leu Ile Val Thr Asp Lys Phe Leu Lys Asp Met Glu Gly Gly
        35                  40                  45

Ala Val Glu Leu Thr Val Lys Tyr Leu Lys Glu Ala Gly Leu Asp Val
    50                  55                  60

Val Tyr Tyr Asp Gly Val Glu Pro Asn Pro Lys Asp Val Asn Val Ile
65                  70                  75                  80

Glu Gly Leu Lys Ile Phe Lys Glu Glu Asn Cys Asp Met Ile Val Thr
                85                  90                  95

Val Gly Gly Gly Ser Ser His Asp Cys Gly Lys Gly Ile Gly Ile Ala
            100                 105                 110

Ala Thr His Glu Gly Asp Leu Tyr Asp Tyr Ala Gly Ile Glu Thr Leu
        115                 120                 125

Val Asn Pro Leu Pro Pro Ile Val Ala Val Asn Thr Thr Ala Gly Thr
    130                 135                 140

Ala Ser Glu Leu Thr Arg His Cys Val Leu Thr Asn Thr Lys Lys Lys
145                 150                 155                 160

Ile Lys Phe Val Ile Val Ser Trp Arg Asn Leu Pro Leu Val Ser Ile
                165                 170                 175

Asn Asp Pro Met Leu Met Val Lys Lys Pro Ala Gly Leu Thr Ala Ala
            180                 185                 190

Thr Gly Met Asp Ala Leu Thr His Ala Ile Glu Ala Tyr Val Ser Lys
        195                 200                 205

Asp Ala Asn Pro Val Thr Asp Ala Ser Ala Ile Gln Ala Ile Lys Leu
    210                 215                 220

Ile Ser Gln Asn Leu Arg Gln Ala Val Ala Leu Gly Glu Asn Leu Glu
225                 230                 235                 240

Ala Arg Glu Asn Met Ala Tyr Ala Ser Leu Leu Ala Gly Met Ala Phe
                245                 250                 255

Asn Asn Ala Asn Leu Gly Tyr Val His Ala Met Ala His Gln Leu Gly
            260                 265                 270

Gly Leu Tyr Asp Met Pro His Gly Val Ala Asn Ala Met Leu Leu Pro
        275                 280                 285

His Val Glu Arg Tyr Asn Met Leu Ser Asn Pro Lys Lys Phe Ala Asp
    290                 295                 300

Ile Ala Glu Phe Met Gly Glu Asn Ile Ser Gly Leu Ser Val Met Glu
305                 310                 315                 320

Ala Ala Glu Lys Ala Ile Asn Ala Met Phe Arg Leu Ser Glu Asp Val
                325                 330                 335
```

```
Gly Ile Pro Lys Ser Leu Lys Glu Met Gly Val Lys Gln Glu Asp Phe
            340                 345                 350

Glu His Met Ala Glu Leu Ala Leu Leu Asp Gly Asn Ala Phe Ser Asn
            355                 360                 365

Pro Arg Lys Gly Asn Ala Lys Asp Ile Ile Asn Ile Phe Lys Ala Ala
            370                 375                 380

Tyr
385

<210> SEQ ID NO 131
<211> LENGTH: 387
<212> TYPE: PRT
<213> ORGANISM: Citrobacter freundii

<400> SEQUENCE: 131

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Lys Leu Leu Gly
            20                  25                  30

Gly Lys Lys Ala Leu Leu Val Thr Asp Lys Gly Leu Arg Ala Ile Lys
        35                  40                  45

Asp Gly Ala Val Asp Lys Thr Leu Thr His Leu Arg Glu Ala Gly Ile
 50                  55                  60

Asp Val Val Phe Asp Gly Val Glu Pro Asn Pro Lys Asp Thr Asn
65                  70                  75                  80

Val Arg Asp Gly Leu Glu Val Phe Arg Lys Glu His Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Ser Tyr Ala Gly Ile Glu
        115                 120                 125

Thr Leu Thr Asn Pro Leu Pro Pro Ile Val Ala Val Asn Thr Thr Ala
130                 135                 140

Gly Thr Ala Ser Glu Val Thr Arg His Cys Val Leu Thr Asn Thr Lys
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Leu Gly Lys Pro Ala Pro Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Ile Gln Ala Ile
    210                 215                 220

Arg Leu Ile Ala Arg Asn Leu Arg Gln Ala Val Ala Leu Gly Ser Asn
225                 230                 235                 240

Leu Lys Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
            260                 265                 270

Leu Gly Gly Leu Tyr Asp Met Pro His Gly Val Ala Asn Ala Val Leu
        275                 280                 285

Leu Pro His Val Ala Arg Tyr Asn Leu Ile Ala Asn Pro Glu Lys Phe
    290                 295                 300

Ala Asp Ile Ala Glu Phe Met Gly Glu Asn Thr Asp Gly Leu Ser Thr
```

```
            305                 310                 315                 320
Met Asp Ala Ala Glu Leu Ala Ile His Ala Ile Ala Arg Leu Ser Ala
                325                 330                 335

Asp Ile Gly Ile Pro Gln His Leu Arg Asp Leu Gly Val Lys Glu Ala
                340                 345                 350

Asp Phe Pro Tyr Met Ala Glu Met Ala Leu Lys Asp Gly Asn Ala Phe
                355                 360                 365

Ser Asn Pro Arg Lys Gly Asn Glu Lys Glu Ile Ala Glu Ile Phe Arg
                370                 375                 380

Gln Ala Phe
385

<210> SEQ ID NO 132
<211> LENGTH: 387
<212> TYPE: PRT
<213> ORGANISM: klebsiella pneumonia

<400> SEQUENCE: 132

Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
                20                  25                  30

Gly Lys Lys Ala Leu Leu Val Thr Asp Lys Gly Leu Arg Ala Ile Lys
            35                  40                  45

Asp Gly Ala Val Asp Lys Thr Leu His Tyr Leu Arg Glu Ala Gly Ile
        50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
                100                 105                 110

Ile Ala Ala Thr His Glu Gly Asp Leu Tyr Gln Tyr Ala Gly Ile Glu
            115                 120                 125

Thr Leu Thr Asn Pro Leu Pro Pro Ile Val Ala Val Asn Thr Thr Ala
        130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
                180                 185                 190

Ala Ala Thr Gly Met Asp Ala Leu Thr His Ala Val Glu Ala Tyr Ile
            195                 200                 205

Ser Lys Asp Ala Asn Pro Val Thr Asp Ala Ala Met Gln Ala Ile
        210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255

Ala Phe Asn Asn Ala Asn Leu Gly Tyr Val His Ala Met Ala His Gln
                260                 265                 270

Leu Gly Gly Leu Tyr Asp Met Pro His Gly Val Ala Asn Ala Val Leu
            275                 280                 285
```

Leu Pro His Val Ala Arg Tyr Asn Leu Ile Ala Asn Pro Glu Lys Phe
290                 295                 300

Ala Asp Ile Ala Glu Leu Met Gly Glu Asn Ile Thr Gly Leu Ser Thr
305                 310                 315                 320

Leu Asp Ala Ala Glu Lys Ala Ile Ala Ala Ile Thr Arg Leu Ser Met
            325                 330                 335

Asp Ile Gly Ile Pro Gln His Leu Arg Asp Leu Gly Val Lys Glu Ala
                340                 345                 350

Asp Phe Pro Tyr Met Ala Glu Met Ala Leu Lys Asp Gly Asn Ala Phe
            355                 360                 365

Ser Asn Pro Arg Lys Gly Asn Glu Gln Glu Ile Ala Ala Ile Phe Arg
370                 375                 380

Gln Ala Phe
385

<210> SEQ ID NO 133
<211> LENGTH: 22
<212> TYPE: PRT
<213> ORGANISM: Rhodoccus erythropolis

<400> SEQUENCE: 133

Met Lys Thr Lys Ala Ala Val Leu Phe Glu Thr His Lys Pro Phe Glu
1               5                   10                  15

Ile Val Glu Leu Glu Leu
            20

<210> SEQ ID NO 134
<211> LENGTH: 371
<212> TYPE: PRT
<213> ORGANISM: Amycolatopsis methanolica

<400> SEQUENCE: 134

Met Lys Thr Lys Ala Ala Val Leu His Ser Ala Gly Lys Pro Phe Glu
1               5                   10                  15

Ile Glu Glu Leu Glu Leu Asp Gly Pro Arg Glu Gly Glu Val Leu Ile
            20                  25                  30

Lys Tyr Thr Ala Ala Gly Leu Cys His Ser Asp Leu His Leu Ile Asp
            35                  40                  45

Asn Asp Leu Val Pro Arg Phe Pro Ile Val Gly Gly His Glu Gly Ala
50                  55                  60

Gly Val Ile Glu Asp Val Gly Pro Gly Val Thr Lys Val Lys Pro Gly
65                  70                  75                  80

Asp His Val Val Cys Ser Phe Ile Pro Asn Cys Gly Thr Cys Arg Tyr
                85                  90                  95

Cys Ala Thr Gly Arg Ser Asn Leu Cys Asp Met Gly Ala Thr Ile Leu
            100                 105                 110

Asp Gly Gly Met Pro Asp Gly Ser Phe Arg Phe His Arg Gly Gly Thr
        115                 120                 125

Asp Tyr Gly Ala Met Cys Met Leu Gly Thr Phe Ser Glu Arg Ala Thr
    130                 135                 140

Ile Ser Gln His Ser Val Val Lys Val Asp Asp Trp Leu Pro Leu Glu
145                 150                 155                 160

Thr Ala Val Leu Val Gly Cys Gly Val Pro Thr Gly Trp Ala Ser Ala
                165                 170                 175

Asn Tyr Ala Gly Gly Val Arg Ala Gly Asp Thr Cys Val Val Tyr Gly
            180                 185                 190

```
Ile Gly Gly Ile Gly Ile Asn Ala Val Gln Gly Ala Ala His Ala Gly
            195                 200                 205

Ala Ala Asn Val Ile Ala Val Asp Pro Val Ala Phe Lys Arg Glu Lys
210                 215                 220

Ala Leu Glu Leu Gly Ala Thr His Ala Phe Ala Ser Ala Asp Glu Ala
225                 230                 235                 240

Ala Ala Lys Val Ala Glu Leu Thr Trp Gly Gln Met Ala Asp Gln Ala
            245                 250                 255

Leu Ile Thr Val Gly Thr Val Val Glu Gln Val Val Thr Asp Ala Phe
                260                 265                 270

Asn Val Ile Gly Lys Gly Gly Thr Val Val Ile Thr Gly Leu Ala Asn
            275                 280                 285

Pro Glu Lys Leu Thr Val His Leu Ser Gly Gly Val Met Thr Leu Phe
290                 295                 300

Glu Lys Thr Val Lys Gly Thr Leu Phe Gly Ser Ala Asn Pro Gln Tyr
305                 310                 315                 320

Asp Ile Val Arg Leu Leu Arg Leu Tyr Gln Ala Gly His Val Lys Leu
                325                 330                 335

Asp Glu Leu Val Thr Lys Arg Tyr Ser Leu Glu Glu Val Asn Glu Gly
            340                 345                 350

Tyr Gln Asp Leu Arg Asp Gly Lys Asn Ile Arg Gly Val Ile Met His
                355                 360                 365

Ser Ala Asp
    370

<210> SEQ ID NO 135
<211> LENGTH: 382
<212> TYPE: PRT
<213> ORGANISM: Escherichia coli

<400> SEQUENCE: 135

Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
            20                  25                  30

Ala Leu Ile Val Thr Asp Lys Thr Leu Val Gln Cys Gly Val Val Ala
        35                  40                  45

Lys Val Thr Asp Lys Met Asp Ala Ala Gly Leu Ala Trp Ala Ile Tyr
50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
            85                  90                  95

Gly Ser Pro Gln Asp Thr Cys Lys Ala Ile Gly Ile Ile Ser Asn Asn
        100                 105                 110

Pro Glu Phe Ala Asp Val Arg Ser Leu Glu Gly Leu Ser Pro Thr Asn
    115                 120                 125

Lys Pro Ser Val Pro Ile Leu Ala Ile Pro Thr Thr Ala Gly Thr Ala
130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190
```

Gly Val Asp Ala Leu Thr His Ala Ile Glu Gly Tyr Ile Thr Arg Gly
            195                 200                 205

Ala Trp Ala Leu Thr Asp Ala Leu His Ile Lys Ala Ile Glu Ile Ile
210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
        275                 280                 285

Arg Tyr Asn Ala Asp Phe Thr Gly Glu Lys Tyr Arg Asp Ile Ala Arg
    290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Glu Asp Ile Pro Ala Leu
            340                 345                 350

Ala Gln Ala Ala Leu Asp Asp Val Cys Thr Gly Gly Asn Pro Arg Glu
        355                 360                 365

Ala Thr Leu Glu Asp Ile Val Glu Leu Tyr His Thr Ala Trp
    370                 375                 380

<210> SEQ ID NO 136
<211> LENGTH: 312
<212> TYPE: PRT
<213> ORGANISM: Escherichia coli

<400> SEQUENCE: 136

Met Asp Ile Ile Phe Tyr His Pro Thr Phe Asp Thr Gln Trp Trp Ile
1               5                   10                  15

Glu Ala Leu Arg Lys Ala Ile Pro Gln Ala Arg Val Arg Ala Trp Lys
            20                  25                  30

Ser Gly Asp Asn Asp Ser Ala Asp Tyr Ala Leu Val Trp His Pro Pro
        35                  40                  45

Val Glu Met Leu Ala Gly Arg Asp Leu Lys Ala Val Phe Ala Leu Gly
    50                  55                  60

Ala Gly Val Asp Ser Ile Leu Ser Lys Leu Gln Ala His Pro Glu Met
65                  70                  75                  80

Leu Asn Pro Ser Val Pro Leu Phe Arg Leu Glu Asp Thr Gly Met Gly
                85                  90                  95

Glu Gln Met Gln Glu Tyr Ala Val Ser Gln Val Leu His Trp Phe Arg
            100                 105                 110

Arg Phe Asp Asp Tyr Arg Ile Gln Gln Asn Ser Ser Trp Gln Pro
        115                 120                 125

Leu Pro Glu Tyr His Arg Glu Asp Phe Thr Ile Gly Ile Leu Gly Ala
    130                 135                 140

Gly Val Leu Gly Ser Lys Val Ala Gln Ser Leu Gln Thr Trp Arg Phe
145                 150                 155                 160

Pro Leu Arg Cys Trp Ser Arg Thr Arg Lys Ser Trp Pro Gly Val Gln
                165                 170                 175

Ser Phe Ala Gly Arg Glu Glu Leu Ser Ala Phe Leu Ser Gln Cys Arg

```
            180                 185                 190
Val Leu Ile Asn Leu Leu Pro Asn Thr Pro Glu Thr Val Gly Ile Ile
            195                 200                 205

Asn Gln Gln Leu Leu Glu Lys Leu Pro Asp Gly Ala Tyr Leu Leu Asn
            210                 215                 220

Leu Ala Arg Gly Val His Val Val Glu Asp Leu Leu Ala Ala Leu
225                 230                 235                 240

Asp Ser Gly Lys Val Lys Gly Ala Met Leu Asp Val Phe Asn Arg Glu
                    245                 250                 255

Pro Leu Pro Pro Glu Ser Pro Leu Trp Gln His Pro Arg Val Thr Ile
            260                 265                 270

Thr Pro His Val Ala Ala Ile Thr Arg Pro Ala Glu Ala Val Glu Tyr
            275                 280                 285

Ile Ser Arg Thr Ile Ala Gln Leu Glu Lys Gly Glu Arg Val Cys Gly
            290                 295                 300

Gln Val Asp Arg Ala Arg Gly Tyr
305                 310

<210> SEQ ID NO 137
<211> LENGTH: 324
<212> TYPE: PRT
<213> ORGANISM: Escherichia coli

<400> SEQUENCE: 137

Met Lys Pro Ser Val Ile Leu Tyr Lys Ala Leu Pro Asp Asp Leu Leu
1               5                   10                  15

Gln Arg Leu Gln Glu His Phe Thr Val His Gln Val Ala Asn Leu Ser
            20                  25                  30

Pro Gln Thr Val Glu Gln Asn Ala Ala Ile Phe Ala Glu Ala Glu Gly
        35                  40                  45

Leu Leu Gly Ser Asn Glu Asn Val Asn Ala Ala Leu Leu Glu Lys Met
50                  55                  60

Pro Lys Leu Arg Ala Thr Ser Thr Ile Ser Val Gly Tyr Asp Asn Phe
65                  70                  75                  80

Asp Val Asp Ala Leu Thr Ala Arg Lys Ile Leu Leu Met His Thr Pro
                85                  90                  95

Thr Val Leu Thr Glu Thr Val Ala Asp Thr Leu Met Ala Leu Val Leu
            100                 105                 110

Ser Thr Ala Arg Arg Val Val Glu Val Ala Glu Arg Val Lys Ala Gly
            115                 120                 125

Glu Trp Thr Ala Ser Ile Gly Pro Asp Trp Tyr Gly Thr Asp Val His
130                 135                 140

His Lys Thr Leu Gly Ile Val Gly Met Gly Arg Ile Gly Met Ala Leu
145                 150                 155                 160

Ala Gln Arg Ala His Phe Gly Phe Asn Met Pro Ile Leu Tyr Asn Ala
                165                 170                 175

Arg Arg His His Lys Glu Ala Glu Glu Arg Phe Asn Ala Arg Tyr Cys
            180                 185                 190

Asp Leu Asp Thr Leu Leu Gln Glu Ser Asp Phe Val Cys Leu Ile Leu
            195                 200                 205

Pro Leu Thr Asp Glu Thr His His Leu Phe Gly Ala Glu Gln Phe Ala
        210                 215                 220

Lys Met Lys Ser Ser Ala Ile Phe Ile Asn Ala Gly Arg Gly Pro Val
225                 230                 235                 240
```

Val Asp Glu Asn Ala Leu Ile Ala Ala Leu Gln Lys Gly Glu Ile His
            245                 250                 255

Ala Ala Gly Leu Asp Val Phe Glu Gln Glu Pro Leu Ser Val Asp Ser
        260                 265                 270

Pro Leu Leu Ser Met Ala Asn Val Val Ala Val Pro His Ile Gly Ser
            275                 280                 285

Ala Thr His Glu Thr Arg Tyr Gly Met Ala Ala Cys Ala Val Asp Asn
        290                 295                 300

Leu Ile Asp Ala Leu Gln Gly Lys Val Glu Lys Asn Cys Val Asn Pro
305                 310                 315                 320

His Val Ala Asp

<210> SEQ ID NO 138
<211> LENGTH: 275
<212> TYPE: PRT
<213> ORGANISM: Escherichia coli

<400> SEQUENCE: 138

Met Ala Asn Pro Thr Val Ile Lys Leu Gln Asp Gly Asn Val Met Pro
1               5                   10                  15

Gln Leu Gly Leu Gly Val Trp Gln Ala Ser Asn Glu Glu Val Ile Thr
            20                  25                  30

Ala Ile Gln Lys Ala Leu Glu Val Gly Tyr Arg Ser Ile Asp Thr Ala
        35                  40                  45

Ala Ala Tyr Lys Asn Glu Glu Gly Val Gly Lys Ala Leu Lys Asn Ala
    50                  55                  60

Ser Val Asn Arg Glu Glu Leu Phe Ile Thr Thr Lys Leu Trp Asn Asp
65                  70                  75                  80

Asp His Lys Arg Pro Arg Glu Ala Leu Leu Asp Ser Leu Lys Lys Leu
                85                  90                  95

Gln Leu Asp Tyr Ile Asp Leu Tyr Leu Met His Trp Pro Val Pro Ala
            100                 105                 110

Ile Asp His Tyr Val Glu Ala Trp Lys Gly Met Ile Glu Leu Gln Lys
        115                 120                 125

Glu Gly Leu Ile Lys Ser Ile Gly Val Cys Asn Phe Gln Ile His His
    130                 135                 140

Leu Gln Arg Leu Ile Asp Glu Thr Gly Val Thr Pro Val Ile Asn Gln
145                 150                 155                 160

Ile Glu Leu His Pro Leu Met Gln Gln Arg Gln Leu His Ala Trp Asn
                165                 170                 175

Ala Thr His Lys Ile Gln Thr Glu Ser Trp Ser Pro Leu Ala Gln Gly
            180                 185                 190

Gly Lys Gly Val Phe Asp Gln Lys Val Ile Arg Asp Leu Ala Asp Lys
        195                 200                 205

Tyr Gly Lys Thr Pro Ala Gln Ile Val Ile Arg Trp His Leu Asp Ser
    210                 215                 220

Gly Leu Val Val Ile Pro Lys Ser Val Thr Pro Ser Arg Ile Ala Glu
225                 230                 235                 240

Asn Phe Asp Val Trp Asp Phe Arg Leu Asp Lys Asp Glu Leu Gly Glu
                245                 250                 255

Ile Ala Lys Leu Asp Gln Gly Lys Arg Leu Gly Pro Asp Pro Asp Gln
            260                 265                 270

Phe Gly Gly
        275

<210> SEQ ID NO 139
<211> LENGTH: 267
<212> TYPE: PRT
<213> ORGANISM: Escherichia coli

<400> SEQUENCE: 139

Met Ala Ile Pro Ala Phe Gly Leu Gly Thr Phe Arg Leu Lys Asp Asp
1               5                   10                  15

Val Val Ile Ser Ser Val Ile Thr Ala Leu Glu Leu Gly Tyr Arg Ala
            20                  25                  30

Ile Asp Thr Ala Gln Ile Tyr Asp Asn Glu Ala Ala Val Gly Gln Ala
        35                  40                  45

Ile Ala Glu Ser Gly Val Pro Arg His Glu Leu Tyr Ile Thr Thr Lys
50                  55                  60

Ile Trp Ile Glu Asn Leu Ser Lys Asp Lys Leu Ile Pro Ser Leu Lys
65                  70                  75                  80

Glu Ser Leu Gln Lys Leu Arg Thr Asp Tyr Val Asp Leu Thr Leu Ile
                85                  90                  95

His Trp Pro Ser Pro Asn Asp Glu Val Ser Val Glu Glu Phe Met Gln
            100                 105                 110

Ala Leu Leu Glu Ala Lys Lys Gln Gly Leu Thr Arg Glu Ile Gly Ile
        115                 120                 125

Ser Asn Phe Thr Ile Pro Leu Met Glu Lys Ala Ile Ala Ala Val Gly
130                 135                 140

Ala Glu Asn Ile Ala Thr Asn Gln Ile Glu Leu Ser Pro Tyr Leu Gln
145                 150                 155                 160

Asn Arg Lys Val Val Ala Trp Ala Lys Gln His Gly Ile His Ile Thr
                165                 170                 175

Ser Tyr Met Thr Leu Ala Tyr Gly Lys Ala Leu Lys Asp Glu Val Ile
            180                 185                 190

Ala Arg Ile Ala Ala Lys His Asn Ala Thr Pro Ala Gln Val Ile Leu
        195                 200                 205

Ala Trp Ala Met Gly Glu Gly Tyr Ser Val Ile Pro Ser Ser Thr Lys
210                 215                 220

Arg Lys Asn Leu Glu Ser Asn Leu Lys Ala Gln Asn Leu Gln Leu Asp
225                 230                 235                 240

Ala Glu Asp Lys Lys Ala Ile Ala Ala Leu Asp Cys Asn Asp Arg Leu
                245                 250                 255

Val Ser Pro Glu Gly Leu Ala Pro Glu Trp Asp
            260                 265

<210> SEQ ID NO 140
<211> LENGTH: 495
<212> TYPE: PRT
<213> ORGANISM: Escherichia coli

<400> SEQUENCE: 140

Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
50                  55                  60

```
Ala Ala Arg Gly Val Phe Glu Arg Gly Asp Trp Ser Leu Ser Ser Pro
 65                  70                  75                  80

Ala Lys Arg Lys Ala Val Leu Asn Lys Leu Ala Asp Leu Met Glu Ala
                 85                  90                  95

His Ala Glu Glu Leu Ala Leu Leu Glu Thr Leu Asp Thr Gly Lys Pro
            100                 105                 110

Ile Arg His Ser Leu Arg Asp Asp Ile Pro Gly Ala Ala Arg Ala Ile
            115                 120                 125

Arg Trp Tyr Ala Glu Ala Ile Asp Lys Val Tyr Gly Glu Val Ala Thr
130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
            195                 200                 205

Glu Ala Gly Leu Pro Asp Gly Val Leu Asn Val Thr Gly Phe Gly
210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Gly Lys Ser
            260                 265                 270

Ala Asn Ile Val Phe Ala Asp Cys Pro Asp Leu Gln Gln Ala Ala Ser
            275                 280                 285

Ala Thr Ala Ala Gly Ile Phe Tyr Asn Gln Gly Gln Val Cys Ile Ala
            290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335

Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
            355                 360                 365

Asp Gly Arg Asn Ala Gly Leu Ala Ala Ala Ile Gly Pro Thr Ile Phe
370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
                405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
            435                 440                 445

Val Phe Val Asn Asn Tyr Asn Asp Gly Asp Met Thr Val Pro Phe Gly
            450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
```

<210> SEQ ID NO 141
<211> LENGTH: 496
<212> TYPE: PRT
<213> ORGANISM: Klebsiella pneumoniae

<400> SEQUENCE: 141

| | | | | | | | | | | | | | | |
|---|---|---|---|---|---|---|---|---|---|---|---|---|---|---|
| Met | Met | Asn | Phe | Gln | His | Leu | Ala | Tyr | Trp | Gln | Glu | Lys | Ala | Lys | Asn |
| 1 | | | | 5 | | | | | 10 | | | | | 15 | |
| Leu | Ala | Ile | Glu | Thr | Arg | Leu | Phe | Ile | Asn | Gly | Glu | Tyr | Cys | Ala | Ala |
| | | | 20 | | | | | 25 | | | | | 30 | | |
| Ala | Asp | Asn | Thr | Thr | Phe | Glu | Thr | Ile | Asp | Pro | Ala | Ala | Gln | Gln | Thr |
| | | | 35 | | | | | 40 | | | | | 45 | | |
| Leu | Ala | Gln | Val | Ala | Arg | Gly | Lys | Lys | Ala | Asp | Val | Glu | Arg | Ala | Val |
| | | 50 | | | | | 55 | | | | | 60 | | | |
| Lys | Ala | Ala | Arg | Gln | Ala | Phe | Asp | Asn | Gly | Asp | Trp | Ser | Gln | Ala | Ser |
| 65 | | | | | 70 | | | | | 75 | | | | | 80 |
| Pro | Ala | Gln | Arg | Lys | Ala | Ile | Leu | Thr | Arg | Phe | Ala | Asn | Leu | Met | Glu |
| | | | | 85 | | | | | 90 | | | | | 95 | |
| Ala | His | Arg | Glu | Glu | Leu | Ala | Leu | Leu | Glu | Thr | Leu | Asp | Thr | Gly | Lys |
| | | | 100 | | | | | 105 | | | | | 110 | | |
| Pro | Ile | Arg | His | Ser | Leu | Arg | Asp | Asp | Ile | Pro | Gly | Ala | Ala | Arg | Ala |
| | | | 115 | | | | | 120 | | | | | 125 | | |
| Ile | Arg | Trp | Tyr | Ala | Glu | Ala | Leu | Asp | Lys | Val | Tyr | Gly | Glu | Val | Ala |
| | | 130 | | | | | 135 | | | | | 140 | | | |
| Pro | Thr | Gly | Ser | Asn | Glu | Leu | Ala | Met | Ile | Val | Arg | Glu | Pro | Ile | Gly |
| 145 | | | | | 150 | | | | | 155 | | | | | 160 |
| Val | Ile | Ala | Ala | Val | Val | Pro | Trp | Asn | Phe | Pro | Leu | Leu | Leu | Ala | Cys |
| | | | | 165 | | | | | 170 | | | | | 175 | |
| Trp | Lys | Leu | Gly | Pro | Ala | Leu | Ala | Ala | Gly | Asn | Ser | Val | Ile | Leu | Lys |
| | | | 180 | | | | | 185 | | | | | 190 | | |
| Pro | Ser | Glu | Lys | Ser | Pro | Leu | Thr | Ala | Leu | Arg | Leu | Ala | Gly | Leu | Ala |
| | | | 195 | | | | | 200 | | | | | 205 | | |
| Lys | Glu | Ala | Gly | Leu | Pro | Asp | Gly | Val | Leu | Asn | Val | Val | Ser | Gly | Phe |
| | | 210 | | | | | 215 | | | | | 220 | | | |
| Gly | His | Glu | Ala | Gly | Gln | Ala | Leu | Ala | Leu | His | Pro | Asp | Val | Glu | Val |
| 225 | | | | | 230 | | | | | 235 | | | | | 240 |
| Ile | Thr | Phe | Thr | Gly | Ser | Thr | Arg | Thr | Gly | Lys | Gln | Leu | Leu | Lys | Asp |
| | | | | 245 | | | | | 250 | | | | | 255 | |
| Ala | Gly | Asp | Ser | Asn | Met | Lys | Arg | Val | Trp | Leu | Glu | Ala | Gly | Gly | Lys |
| | | | 260 | | | | | 265 | | | | | 270 | | |
| Ser | Ala | Asn | Ile | Val | Phe | Ala | Asp | Cys | Pro | Asp | Leu | Gln | Gln | Ala | Val |
| | | | 275 | | | | | 280 | | | | | 285 | | |
| Arg | Ala | Thr | Ala | Gly | Gly | Ile | Phe | Tyr | Asn | Gln | Gly | Gln | Val | Cys | Ile |
| | | 290 | | | | | 295 | | | | | 300 | | | |
| Ala | Gly | Thr | Arg | Leu | Leu | Leu | Glu | Glu | Ser | Ile | Ala | Asp | Glu | Phe | Leu |
| 305 | | | | | 310 | | | | | 315 | | | | | 320 |
| Ala | Arg | Leu | Lys | Ala | Glu | Ala | Gln | His | Trp | Gln | Pro | Gly | Asn | Pro | Leu |
| | | | | 325 | | | | | 330 | | | | | 335 | |
| Asp | Pro | Asp | Thr | Thr | Met | Gly | Met | Leu | Ile | Asp | Asn | Thr | His | Ala | Asp |
| | | | 340 | | | | | 345 | | | | | 350 | | |
| Asn | Val | His | Ser | Phe | Ile | Arg | Gly | Gly | Glu | Ser | Gln | Ser | Thr | Leu | Phe |
| | | | 355 | | | | | 360 | | | | | 365 | | |

```
Leu Asp Gly Arg Lys Asn Pro Trp Pro Ala Ala Val Gly Pro Thr Ile
    370                 375                 380

Phe Val Asp Val Asp Pro Ala Ser Thr Leu Ser Arg Glu Glu Ile Phe
385                 390                 395                 400

Gly Pro Val Leu Val Thr Arg Phe Lys Ser Glu Glu Ala Leu
                405                 410                 415

Lys Leu Ala Asn Asp Ser Asp Tyr Gly Leu Gly Ala Ala Val Trp Thr
                420                 425                 430

Arg Asp Leu Ser Arg Ala His Arg Met Ser Arg Arg Leu Lys Ala Gly
                435                 440                 445

Ser Val Phe Val Asn Asn Tyr Asn Asp Gly Asp Met Thr Val Pro Phe
450                 455                 460

Gly Gly Tyr Lys Gln Ser Gly Asn Gly Arg Asp Lys Ser Leu His Ala
465                 470                 475                 480

Leu Glu Lys Phe Thr Glu Leu Lys Thr Ile Trp Ile Ala Leu Glu Ser
                485                 490                 495

<210> SEQ ID NO 142
<211> LENGTH: 519
<212> TYPE: PRT
<213> ORGANISM: Saccharomyces cerevisiae

<400> SEQUENCE: 142

Met Phe Ser Arg Ser Thr Leu Cys Leu Lys Thr Ser Ala Ser Ser Ile
1               5                   10                  15

Gly Arg Leu Gln Leu Arg Tyr Phe Ser His Leu Pro Met Thr Val Pro
                20                  25                  30

Ile Lys Leu Pro Asn Gly Leu Glu Tyr Glu Gln Pro Thr Gly Leu Phe
                35                  40                  45

Ile Asn Asn Lys Phe Val Pro Ser Lys Gln Asn Lys Thr Phe Glu Val
            50                  55                  60

Ile Asn Pro Ser Thr Glu Glu Ile Cys His Ile Tyr Glu Gly Arg
65              70                  75                  80

Glu Asp Asp Val Glu Glu Ala Val Gln Ala Ala Asp Arg Ala Phe Ser
                85                  90                  95

Asn Gly Ser Trp Asn Gly Ile Asp Pro Ile Asp Arg Gly Lys Ala Leu
                100                 105                 110

Tyr Arg Leu Ala Glu Leu Ile Glu Gln Asp Lys Asp Val Ile Ala Ser
                115                 120                 125

Ile Glu Thr Leu Asp Asn Gly Lys Ala Ile Ser Ser Ser Arg Gly Asp
                130                 135                 140

Val Asp Leu Val Ile Asn Tyr Leu Lys Ser Ser Ala Gly Phe Ala Asp
145                 150                 155                 160

Lys Ile Asp Gly Arg Met Ile Asp Thr Gly Arg Thr His Phe Ser Tyr
                165                 170                 175

Thr Lys Arg Gln Pro Leu Gly Val Cys Gly Gln Ile Ile Pro Trp Asn
                180                 185                 190

Phe Pro Leu Leu Met Trp Ala Trp Lys Ile Ala Pro Ala Leu Val Thr
                195                 200                 205

Gly Asn Thr Val Val Leu Lys Thr Ala Glu Ser Thr Pro Leu Ser Ala
                210                 215                 220

Leu Tyr Val Ser Lys Tyr Ile Pro Gln Ala Gly Ile Pro Pro Gly Val
225                 230                 235                 240

Ile Asn Ile Val Ser Gly Phe Gly Lys Ile Val Gly Glu Ala Ile Thr
                245                 250                 255
```

```
Asn His Pro Lys Ile Lys Lys Val Ala Phe Thr Gly Ser Thr Ala Thr
            260                 265                 270

Gly Arg His Ile Tyr Gln Ser Ala Ala Ala Gly Leu Lys Lys Val Thr
        275                 280                 285

Leu Glu Leu Gly Gly Lys Ser Pro Asn Ile Val Phe Ala Asp Ala Glu
290                 295                 300

Leu Lys Lys Ala Val Gln Asn Ile Ile Leu Gly Ile Tyr Tyr Asn Ser
305                 310                 315                 320

Gly Glu Val Cys Cys Ala Gly Ser Arg Val Tyr Val Glu Glu Ser Ile
                325                 330                 335

Tyr Asp Lys Phe Ile Glu Glu Phe Lys Ala Ala Ser Glu Ser Ile Lys
                340                 345                 350

Val Gly Asp Pro Phe Asp Glu Ser Thr Phe Gln Gly Ala Gln Thr Ser
                355                 360                 365

Gln Met Gln Leu Asn Lys Ile Leu Lys Tyr Val Asp Ile Gly Lys Asn
    370                 375                 380

Glu Gly Ala Thr Leu Ile Thr Gly Gly Glu Arg Leu Gly Ser Lys Gly
385                 390                 395                 400

Tyr Phe Ile Lys Pro Thr Val Phe Gly Asp Val Lys Glu Asp Met Arg
                405                 410                 415

Ile Val Lys Glu Glu Ile Phe Gly Pro Val Val Thr Val Thr Lys Phe
                420                 425                 430

Lys Ser Ala Asp Glu Val Ile Asn Met Ala Asn Asp Ser Glu Tyr Gly
                435                 440                 445

Leu Ala Ala Gly Ile His Thr Ser Asn Ile Asn Thr Ala Leu Lys Val
            450                 455                 460

Ala Asp Arg Val Asn Ala Gly Thr Val Trp Ile Asn Thr Tyr Asn Asp
465                 470                 475                 480

Phe His His Ala Val Pro Phe Gly Gly Phe Asn Ala Ser Gly Leu Gly
                485                 490                 495

Arg Glu Met Ser Val Asp Ala Leu Gln Asn Tyr Leu Gln Val Lys Ala
                500                 505                 510

Val Arg Ala Lys Leu Asp Glu
        515

<210> SEQ ID NO 143
<211> LENGTH: 520
<212> TYPE: PRT
<213> ORGANISM: Saccharomyces cerevisiae

<400> SEQUENCE: 143

Met Leu Ser Arg Thr Arg Ala Ala Ala Pro Asn Ser Arg Ile Phe Thr
1               5                   10                  15

Arg Ser Leu Leu Arg Leu Tyr Ser Gln Ala Pro Leu Arg Val Pro Ile
            20                  25                  30

Thr Leu Pro Asn Gly Phe Thr Tyr Glu Gln Pro Thr Gly Leu Phe Ile
        35                  40                  45

Asn Gly Glu Phe Val Ala Ser Lys Gln Lys Thr Phe Asp Val Ile
    50                  55                  60

Asn Pro Ser Asn Glu Glu Lys Ile Thr Thr Val Tyr Lys Ala Met Glu
65                  70                  75                  80

Asp Asp Val Asp Glu Ala Val Ala Ala Ala Lys Lys Ala Phe Glu Thr
                85                  90                  95

Lys Trp Ser Ile Val Glu Pro Glu Val Arg Ala Lys Ala Leu Phe Asn
```

```
              100                 105                 110
Leu Ala Asp Leu Val Glu Lys His Gln Glu Thr Leu Ala Ala Ile Glu
            115                 120                 125

Ser Met Asp Asn Gly Lys Ser Leu Phe Cys Ala Arg Gly Asp Val Ala
            130                 135                 140

Leu Val Ser Lys Tyr Leu Arg Ser Cys Gly Gly Trp Ala Asp Lys Ile
145                 150                 155                 160

Tyr Gly Asn Val Ile Asp Thr Gly Lys Asn His Phe Thr Tyr Ser Ile
                165                 170                 175

Lys Glu Pro Leu Gly Val Cys Gly Gln Ile Ile Pro Trp Asn Phe Pro
            180                 185                 190

Leu Leu Met Trp Ser Trp Lys Ile Gly Pro Ala Leu Ala Thr Gly Asn
            195                 200                 205

Thr Val Val Leu Lys Pro Ala Glu Thr Thr Pro Leu Ser Ala Leu Phe
        210                 215                 220

Ala Ser Gln Leu Cys Gln Glu Ala Gly Ile Pro Ala Gly Val Val Asn
225                 230                 235                 240

Ile Leu Pro Gly Ser Gly Arg Val Val Gly Glu Arg Leu Ser Ala His
                245                 250                 255

Pro Asp Val Lys Lys Ile Ala Phe Thr Gly Ser Thr Ala Thr Gly Arg
            260                 265                 270

His Ile Met Lys Val Ala Ala Asp Thr Val Lys Lys Val Thr Leu Glu
            275                 280                 285

Leu Gly Gly Lys Ser Pro Asn Ile Val Phe Ala Asp Ala Asp Leu Asp
        290                 295                 300

Lys Ala Val Lys Asn Ile Ala Phe Gly Ile Phe Tyr Asn Ser Gly Glu
305                 310                 315                 320

Val Cys Cys Ala Gly Ser Arg Ile Tyr Ile Gln Asp Thr Val Tyr Glu
                325                 330                 335

Glu Val Leu Gln Lys Leu Lys Asp Tyr Thr Glu Ser Leu Lys Val Gly
            340                 345                 350

Asp Pro Phe Asp Glu Glu Val Phe Gln Gly Ala Gln Thr Ser Asp Lys
            355                 360                 365

Gln Leu His Lys Ile Leu Asp Tyr Val Asp Val Ala Lys Ser Glu Gly
        370                 375                 380

Ala Arg Leu Val Thr Gly Gly Ala Arg His Gly Ser Lys Gly Tyr Phe
385                 390                 395                 400

Val Lys Pro Thr Val Phe Ala Asp Val Lys Glu Asp Met Arg Ile Val
                405                 410                 415

Lys Glu Glu Val Phe Gly Pro Ile Val Thr Val Ser Lys Phe Ser Thr
            420                 425                 430

Val Asp Glu Val Ile Ala Met Ala Asn Asp Ser Gln Tyr Gly Leu Ala
            435                 440                 445

Ala Gly Ile His Thr Asn Asp Ile Asn Lys Ala Val Asp Val Ser Lys
        450                 455                 460

Arg Val Lys Ala Gly Thr Val Trp Ile Asn Thr Tyr Asn Asn Phe His
465                 470                 475                 480

Gln Asn Val Pro Phe Gly Gly Phe Gly Gln Ser Gly Ile Gly Arg Glu
                485                 490                 495

Met Gly Glu Ala Ala Leu Ser Asn Tyr Thr Gln Thr Lys Ser Val Arg
            500                 505                 510

Ile Ala Ile Asp Lys Pro Ile Arg
            515                 520
```

<210> SEQ ID NO 144
<211> LENGTH: 462
<212> TYPE: PRT
<213> ORGANISM: Escherichia coli

<400> SEQUENCE: 144

Met Thr Ile Thr Pro Ala Thr His Ala Ile Ser Ile Asn Pro Ala Thr
1               5                   10                  15

Gly Glu Gln Leu Ser Val Leu Pro Trp Ala Gly Ala Asp Asp Ile Glu
            20                  25                  30

Asn Ala Leu Gln Leu Ala Ala Gly Phe Arg Asp Trp Arg Glu Thr
        35                  40                  45

Asn Ile Asp Tyr Arg Ala Glu Lys Leu Arg Asp Ile Gly Lys Ala Leu
    50                  55                  60

Arg Ala Arg Ser Glu Glu Met Ala Gln Met Ile Thr Arg Glu Met Gly
65                  70                  75                  80

Lys Pro Ile Asn Gln Ala Arg Ala Glu Val Ala Lys Ser Ala Asn Leu
                85                  90                  95

Cys Asp Trp Tyr Ala Glu His Gly Pro Ala Met Leu Lys Ala Glu Pro
            100                 105                 110

Thr Leu Val Glu Asn Gln Gln Ala Val Ile Glu Tyr Arg Pro Leu Gly
        115                 120                 125

Thr Ile Leu Ala Ile Met Pro Trp Asn Phe Pro Leu Trp Gln Val Met
    130                 135                 140

Arg Gly Ala Val Pro Ile Ile Leu Ala Gly Asn Gly Tyr Leu Leu Lys
145                 150                 155                 160

His Ala Pro Asn Val Met Gly Cys Ala Gln Leu Ile Ala Gln Val Phe
                165                 170                 175

Lys Asp Ala Gly Ile Pro Gln Gly Val Tyr Gly Trp Leu Asn Ala Asp
            180                 185                 190

Asn Asp Gly Val Ser Gln Met Ile Lys Asp Ser Arg Ile Ala Ala Val
        195                 200                 205

Thr Val Thr Gly Ser Val Arg Ala Gly Ala Ala Ile Gly Ala Gln Ala
    210                 215                 220

Gly Ala Ala Leu Lys Lys Cys Val Leu Glu Leu Gly Gly Ser Asp Pro
225                 230                 235                 240

Phe Ile Val Leu Asn Asp Ala Asp Leu Glu Leu Ala Val Lys Ala Ala
                245                 250                 255

Val Ala Gly Arg Tyr Gln Asn Thr Gly Gln Val Cys Ala Ala Ala Lys
            260                 265                 270

Arg Phe Ile Ile Glu Glu Gly Ile Ala Ser Ala Phe Thr Glu Arg Phe
        275                 280                 285

Val Ala Ala Ala Ala Leu Lys Met Gly Asp Pro Arg Asp Glu Glu
    290                 295                 300

Asn Ala Leu Gly Pro Met Ala Arg Phe Asp Leu Arg Asp Glu Leu His
305                 310                 315                 320

His Gln Val Glu Lys Thr Leu Ala Gln Gly Ala Arg Leu Leu Leu Gly
                325                 330                 335

Gly Glu Lys Met Ala Gly Ala Gly Asn Tyr Tyr Pro Pro Thr Val Leu
            340                 345                 350

Ala Asn Val Thr Pro Glu Met Thr Ala Phe Arg Glu Glu Met Phe Gly
        355                 360                 365

Pro Val Ala Ala Ile Thr Ile Ala Lys Asp Ala Glu His Ala Leu Glu

```
            370                 375                 380
Leu Ala Asn Asp Ser Glu Phe Gly Leu Ser Ala Thr Ile Phe Thr Thr
385                 390                 395                 400

Asp Glu Thr Gln Ala Arg Gln Met Ala Ala Arg Leu Glu Cys Gly Gly
                405                 410                 415

Val Phe Ile Asn Gly Tyr Cys Ala Ser Asp Ala Arg Val Ala Phe Gly
                420                 425                 430

Gly Val Lys Lys Ser Gly Phe Gly Arg Glu Leu Ser His Phe Gly Leu
                435                 440                 445

His Glu Phe Cys Asn Ile Gln Thr Val Trp Lys Asp Arg Ile
                450                 455                 460
```

<210> SEQ ID NO 145
<211> LENGTH: 482
<212> TYPE: PRT
<213> ORGANISM: Escherichia coli

<400> SEQUENCE: 145

```
Met Lys Leu Asn Asp Ser Asn Leu Phe Arg Gln Gln Ala Leu Ile Asn
1               5                   10                  15

Gly Glu Trp Leu Asp Ala Asn Asn Gly Glu Ala Ile Asp Val Thr Asn
                20                  25                  30

Pro Ala Asn Gly Asp Lys Leu Gly Ser Val Pro Lys Met Gly Ala Asp
                35                  40                  45

Glu Thr Arg Ala Ala Ile Asp Ala Ala Asn Arg Ala Leu Pro Ala Trp
50                  55                  60

Arg Ala Leu Thr Ala Lys Glu Arg Ala Thr Ile Leu Arg Asn Trp Phe
65                  70                  75                  80

Asn Leu Met Met Glu His Gln Asp Asp Leu Ala Arg Leu Met Thr Leu
                85                  90                  95

Glu Gln Gly Lys Pro Leu Ala Glu Ala Lys Gly Glu Ile Ser Tyr Ala
                100                 105                 110

Ala Ser Phe Ile Glu Trp Phe Ala Glu Glu Gly Lys Arg Ile Tyr Gly
                115                 120                 125

Asp Thr Ile Pro Gly His Gln Ala Asp Lys Arg Leu Ile Val Ile Lys
                130                 135                 140

Gln Pro Ile Gly Val Thr Ala Ala Ile Thr Pro Trp Asn Phe Pro Ala
145                 150                 155                 160

Ala Met Ile Thr Arg Lys Ala Gly Pro Ala Leu Ala Ala Gly Cys Thr
                165                 170                 175

Met Val Leu Lys Pro Ala Ser Gln Thr Pro Phe Ser Ala Leu Ala Leu
                180                 185                 190

Ala Glu Leu Ala Ile Arg Ala Gly Val Pro Ala Gly Val Phe Asn Val
                195                 200                 205

Val Thr Gly Ser Ala Gly Ala Val Gly Asn Glu Leu Thr Ser Asn Pro
                210                 215                 220

Leu Val Arg Lys Leu Ser Phe Thr Gly Ser Thr Glu Ile Gly Arg Gln
225                 230                 235                 240

Leu Met Glu Gln Cys Ala Lys Asp Ile Lys Lys Val Ser Leu Glu Leu
                245                 250                 255

Gly Gly Asn Ala Pro Phe Ile Val Phe Asp Asp Ala Asp Leu Asp Lys
                260                 265                 270

Ala Val Glu Gly Ala Leu Ala Ser Lys Phe Arg Asn Ala Gly Gln Thr
                275                 280                 285
```

```
Cys Val Cys Ala Asn Arg Leu Tyr Val Gln Asp Gly Val Tyr Asp Arg
    290                 295                 300

Phe Ala Glu Lys Leu Gln Gln Ala Val Ser Lys Leu His Ile Gly Asp
305                 310                 315                 320

Gly Leu Asp Asn Gly Val Thr Ile Gly Pro Leu Ile Asp Glu Lys Ala
                325                 330                 335

Val Ala Lys Val Glu Glu His Ile Ala Asp Ala Leu Glu Lys Gly Ala
            340                 345                 350

Arg Val Val Cys Gly Gly Lys Ala His Glu Arg Gly Gly Asn Phe Phe
        355                 360                 365

Gln Pro Thr Ile Leu Val Asp Val Pro Ala Asn Ala Lys Val Ser Lys
370                 375                 380

Glu Glu Thr Phe Gly Pro Leu Ala Pro Leu Phe Arg Phe Lys Asp Glu
385                 390                 395                 400

Ala Asp Val Ile Ala Gln Ala Asn Asp Thr Glu Phe Gly Leu Ala Ala
                405                 410                 415

Tyr Phe Tyr Ala Arg Asp Leu Ser Arg Val Phe Arg Val Gly Glu Ala
            420                 425                 430

Leu Glu Tyr Gly Ile Val Gly Ile Asn Thr Gly Ile Ile Ser Asn Glu
        435                 440                 445

Val Ala Pro Phe Gly Gly Ile Lys Ala Ser Gly Leu Gly Arg Glu Gly
450                 455                 460

Ser Lys Tyr Gly Ile Glu Asp Tyr Leu Glu Ile Lys Tyr Met Cys Ile
465                 470                 475                 480

Gly Leu

<210> SEQ ID NO 146
<211> LENGTH: 474
<212> TYPE: PRT
<213> ORGANISM: Escherichia coli

<400> SEQUENCE: 146

Met Gln His Lys Leu Leu Ile Asn Gly Glu Leu Val Ser Gly Glu Gly
1               5                   10                  15

Glu Lys Gln Pro Val Tyr Asn Pro Ala Thr Gly Asp Val Leu Leu Glu
            20                  25                  30

Ile Ala Glu Ala Ser Ala Glu Gln Val Asp Ala Val Arg Ala Ala
        35                  40                  45

Asp Ala Ala Phe Ala Glu Trp Gly Gln Thr Thr Pro Lys Val Arg Ala
    50                  55                  60

Glu Cys Leu Leu Lys Leu Ala Asp Val Ile Glu Asn Gly Gln Val
65                  70                  75                  80

Phe Ala Glu Leu Glu Ser Arg Asn Cys Gly Lys Pro Leu His Ser Ala
                85                  90                  95

Phe Asn Asp Glu Ile Pro Ala Ile Val Asp Val Phe Arg Phe Phe Ala
            100                 105                 110

Gly Ala Ala Arg Cys Leu Asn Gly Leu Ala Ala Gly Glu Tyr Leu Glu
        115                 120                 125

Gly His Thr Ser Met Ile Arg Arg Asp Pro Leu Gly Val Val Ala Ser
    130                 135                 140

Ile Ala Pro Trp Asn Tyr Pro Leu Met Met Ala Ala Trp Lys Leu Ala
145                 150                 155                 160

Pro Ala Leu Ala Ala Gly Asn Cys Val Val Leu Lys Pro Ser Glu Ile
                165                 170                 175
```

```
Thr Pro Leu Thr Ala Leu Lys Leu Ala Glu Leu Ala Lys Asp Ile Phe
            180                 185                 190

Pro Ala Gly Val Ile Asn Ile Leu Phe Gly Arg Gly Lys Thr Val Gly
        195                 200                 205

Asp Pro Leu Thr Gly His Pro Lys Val Arg Met Val Ser Leu Thr Gly
    210                 215                 220

Ser Ile Ala Thr Gly Glu His Ile Ile Ser His Thr Ala Ser Ser Ile
225                 230                 235                 240

Lys Arg Thr His Met Glu Leu Gly Gly Lys Ala Pro Val Ile Val Phe
                245                 250                 255

Asp Asp Ala Asp Ile Glu Ala Val Val Glu Gly Val Arg Thr Phe Gly
            260                 265                 270

Tyr Tyr Asn Ala Gly Gln Asp Cys Thr Ala Ala Cys Arg Ile Tyr Ala
        275                 280                 285

Gln Lys Gly Ile Tyr Asp Thr Leu Val Glu Lys Leu Gly Ala Ala Val
    290                 295                 300

Ala Thr Leu Lys Ser Gly Ala Pro Asp Asp Glu Ser Thr Glu Leu Gly
305                 310                 315                 320

Pro Leu Ser Ser Leu Ala His Leu Glu Arg Val Gly Lys Ala Val Glu
                325                 330                 335

Glu Ala Lys Ala Thr Gly His Ile Lys Val Ile Thr Gly Gly Glu Lys
            340                 345                 350

Arg Lys Gly Asn Gly Tyr Tyr Tyr Ala Pro Thr Leu Leu Ala Gly Ala
        355                 360                 365

Leu Gln Asp Asp Ala Ile Val Gln Lys Glu Val Phe Gly Pro Val Val
    370                 375                 380

Ser Val Thr Pro Phe Asp Asn Glu Glu Gln Val Val Asn Trp Ala Asn
385                 390                 395                 400

Asp Ser Gln Tyr Gly Leu Ala Ser Ser Val Trp Thr Lys Asp Val Gly
                405                 410                 415

Arg Ala His Arg Val Ser Ala Arg Leu Gln Tyr Gly Cys Thr Trp Val
            420                 425                 430

Asn Thr His Phe Met Leu Val Ser Glu Met Pro His Gly Gly Gln Lys
        435                 440                 445

Leu Ser Gly Tyr Gly Lys Asp Met Ser Leu Tyr Gly Leu Glu Asp Tyr
    450                 455                 460

Thr Val Val Arg His Val Met Val Lys His
465                 470

<210> SEQ ID NO 147
<211> LENGTH: 480
<212> TYPE: PRT
<213> ORGANISM: Pseudomonas putida

<400> SEQUENCE: 147

Met Gln Leu Lys Asp Ala Gln Leu Phe Arg Gln Gln Ala Tyr Ile Asn
1               5                   10                  15

Gly Glu Trp Leu Asp Ala Asp Asn Gly Gln Thr Ile Lys Val Thr Asn
                20                  25                  30

Pro Ala Thr Gly Glu Val Ile Gly Thr Val Pro Lys Met Gly Thr Ala
            35                  40                  45

Glu Thr Arg Arg Ala Ile Glu Ala Ala Asp Lys Ala Leu Pro Ala Trp
        50                  55                  60

Arg Ala Leu Thr Ala Lys Glu Arg Ser Ala Lys Leu Arg Arg Trp Phe
65                  70                  75                  80
```

Glu Leu Met Ile Glu Asn Gln Asp Asp Leu Ala Arg Leu Met Thr Thr
                85                  90                  95

Glu Gln Gly Lys Pro Leu Ala Glu Ala Lys Gly Glu Ile Ala Tyr Ala
            100                 105                 110

Ala Ser Phe Ile Glu Trp Phe Ala Glu Ala Lys Arg Ile Tyr Gly
        115                 120                 125

Asp Thr Ile Pro Gly His Gln Pro Asp Lys Arg Leu Ile Val Ile Lys
    130                 135                 140

Gln Pro Ile Gly Val Thr Ala Ala Ile Thr Pro Trp Asn Phe Pro Ala
145                 150                 155                 160

Ala Met Ile Thr Arg Lys Ala Gly Pro Ala Leu Ala Ala Gly Cys Thr
                165                 170                 175

Met Val Leu Lys Pro Ala Ser Gln Thr Pro Tyr Ser Ala Leu Ala Leu
            180                 185                 190

Val Glu Leu Ala His Arg Ala Gly Ile Pro Ala Gly Val Leu Ser Val
        195                 200                 205

Val Thr Gly Ser Ala Gly Glu Val Gly Gly Glu Leu Thr Gly Asn Ser
    210                 215                 220

Leu Val Arg Lys Leu Ser Phe Thr Gly Ser Thr Glu Ile Gly Arg Gln
225                 230                 235                 240

Leu Met Glu Glu Cys Ala Lys Asp Ile Lys Lys Val Ser Leu Glu Leu
                245                 250                 255

Gly Gly Asn Ala Pro Phe Ile Val Phe Asp Asp Ala Asp Leu Asp Lys
            260                 265                 270

Ala Val Glu Gly Ala Ile Ile Ser Lys Tyr Arg Asn Asn Gly Gln Thr
        275                 280                 285

Cys Val Cys Ala Asn Arg Ile Tyr Val Gln Asp Gly Val Tyr Asp Ala
    290                 295                 300

Phe Ala Glu Lys Leu Ala Ala Ala Val Ala Lys Leu Lys Ile Gly Asn
305                 310                 315                 320

Gly Leu Glu Glu Gly Thr Thr Thr Gly Pro Leu Ile Asp Gly Lys Ala
                325                 330                 335

Val Ala Lys Val Gln Glu His Ile Glu Asp Ala Val Ser Lys Gly Ala
            340                 345                 350

Lys Val Leu Ser Gly Gly Lys Leu Ile Glu Gly Asn Phe Phe Glu Pro
        355                 360                 365

Thr Ile Leu Val Asp Val Pro Lys Thr Ala Ala Val Ala Lys Glu Glu
    370                 375                 380

Thr Phe Gly Pro Leu Ala Pro Leu Phe Arg Phe Lys Asp Glu Ala Glu
385                 390                 395                 400

Val Ile Ala Met Ser Asn Asp Thr Glu Phe Gly Leu Ala Ser Tyr Phe
                405                 410                 415

Tyr Ala Arg Asp Met Ser Arg Val Phe Arg Val Ala Glu Ala Leu Glu
            420                 425                 430

Tyr Gly Met Val Gly Ile Asn Thr Gly Leu Ile Ser Asn Glu Val Ala
        435                 440                 445

Pro Phe Gly Gly Ile Lys Ala Ser Gly Leu Gly Arg Glu Gly Ser Lys
    450                 455                 460

Tyr Gly Ile Glu Asp Tyr Leu Glu Ile Lys Tyr Leu Cys Ile Ser Val
465                 470                 475                 480

<210> SEQ ID NO 148
<211> LENGTH: 479

<212> TYPE: PRT
<213> ORGANISM: Escherichia coli

<400> SEQUENCE: 148

```
Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
                85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
        115                 120                 125

Ser Asp Arg Pro Gly Glu Asn Ile Leu Leu Phe Lys Arg Ala Leu Gly
130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Ala Leu Glu Arg
                325                 330                 335

Val Glu Gln Lys Val Ala Arg Ala Val Glu Glu Gly Ala Arg Val Ala
            340                 345                 350

Phe Gly Gly Lys Ala Val Glu Gly Lys Gly Tyr Tyr Tyr Pro Pro Thr
        355                 360                 365

Leu Leu Leu Asp Val Arg Gln Glu Met Ser Ile Met His Glu Glu Thr
370                 375                 380

Phe Gly Pro Val Leu Pro Val Val Ala Phe Asp Thr Leu Glu Asp Ala
385                 390                 395                 400
```

```
Ile Ser Met Ala Asn Asp Ser Asp Tyr Gly Leu Thr Ser Ser Ile Tyr
            405                 410                 415

Thr Gln Asn Leu Asn Val Ala Met Lys Ala Ile Lys Gly Leu Lys Phe
        420                 425                 430

Gly Glu Thr Tyr Ile Asn Arg Glu Asn Phe Glu Ala Met Gln Gly Phe
        435                 440                 445

His Ala Gly Trp Arg Lys Ser Gly Ile Gly Gly Ala Asp Gly Lys His
    450                 455                 460

Gly Leu His Glu Tyr Leu Gln Thr Gln Val Val Tyr Leu Gln Ser
465                 470                 475

<210> SEQ ID NO 149
<211> LENGTH: 512
<212> TYPE: PRT
<213> ORGANISM: Escherichia coli

<400> SEQUENCE: 149

Met Thr Asn Asn Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
            20                  25                  30

Trp Val Ala Pro Ala Asp Gly Glu Tyr Tyr Gln Asn Leu Thr Pro Val
        35                  40                  45

Thr Gly Gln Leu Leu Cys Glu Val Ala Ser Ser Gly Lys Arg Asp Ile
    50                  55                  60

Asp Leu Ala Leu Asp Ala Ala His Lys Val Lys Asp Lys Trp Ala His
65                  70                  75                  80

Thr Ser Val Gln Asp Arg Ala Ala Ile Leu Phe Lys Ile Ala Asp Arg
                85                  90                  95

Met Glu Gln Asn Leu Glu Leu Leu Ala Thr Ala Glu Thr Trp Asp Asn
            100                 105                 110

Gly Lys Pro Ile Arg Glu Thr Ser Ala Ala Asp Val Pro Leu Ala Ile
        115                 120                 125

Asp His Phe Arg Tyr Phe Ala Ser Cys Ile Arg Ala Gln Glu Gly Gly
    130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Leu Met Glu
        195                 200                 205

Ile Val Gly Asp Leu Leu Pro Pro Gly Val Val Asn Val Val Asn Gly
    210                 215                 220

Ala Gly Gly Val Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                245                 250                 255

Tyr Ala Thr Gln Asn Ile Ile Pro Val Thr Leu Glu Leu Gly Gly Lys
            260                 265                 270

Ser Pro Asn Ile Phe Phe Ala Asp Val Met Asp Glu Glu Asp Ala Phe
        275                 280                 285

Phe Asp Lys Ala Leu Glu Gly Phe Ala Leu Phe Ala Phe Asn Gln Gly
```

```
                  290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
                325                 330                 335

Gly Asn Pro Leu Asp Ser Val Thr Gln Met Gly Ala Gln Val Ser His
            340                 345                 350

Gly Gln Leu Glu Thr Ile Leu Asn Tyr Ile Asp Ile Gly Lys Lys Glu
        355                 360                 365

Gly Ala Asp Val Leu Thr Gly Gly Arg Arg Lys Leu Leu Glu Gly Glu
    370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Glu Ile Phe Gly Pro Val Leu Ala Val
                405                 410                 415

Thr Thr Phe Lys Thr Met Glu Glu Ala Leu Glu Leu Ala Asn Asp Thr
            420                 425                 430

Gln Tyr Gly Leu Gly Ala Gly Val Trp Ser Arg Asn Gly Asn Leu Ala
        435                 440                 445

Tyr Lys Met Gly Arg Gly Ile Gln Ala Gly Arg Val Trp Thr Asn Cys
    450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
                485                 490                 495

Thr Lys Cys Leu Leu Val Ser Tyr Ser Asp Lys Pro Leu Gly Leu Phe
            500                 505                 510

<210> SEQ ID NO 150
<211> LENGTH: 463
<212> TYPE: PRT
<213> ORGANISM: Methanocaldococcus jannaschii

<400> SEQUENCE: 150

Met Phe Ile Asp Gly Lys Trp Ile Asn Arg Glu Asp Met Asp Val Ile
1               5                   10                  15

Asn Pro Tyr Ser Leu Glu Val Ile Lys Lys Ile Pro Ala Leu Ser Arg
            20                  25                  30

Glu Glu Ala Lys Glu Ala Ile Asp Thr Ala Glu Lys Tyr Lys Glu Val
        35                  40                  45

Met Lys Asn Leu Pro Ile Thr Lys Arg Tyr Asn Ile Leu Met Asn Ile
    50                  55                  60

Ala Lys Gln Ile Lys Glu Lys Lys Glu Glu Leu Ala Lys Ile Leu Ala
65                  70                  75                  80

Ile Asp Ala Gly Lys Pro Ile Lys Gln Ala Arg Val Glu Val Glu Arg
                85                  90                  95

Ser Ile Gly Thr Phe Lys Leu Ala Ala Phe Tyr Val Lys Glu His Arg
            100                 105                 110

Asp Glu Val Ile Pro Ser Asp Asp Arg Leu Ile Phe Thr Arg Arg Glu
        115                 120                 125

Pro Val Gly Ile Val Gly Ala Ile Thr Pro Phe Asn Phe Pro Leu Asn
    130                 135                 140

Leu Ser Ala His Lys Ile Ala Pro Ala Ile Ala Thr Gly Asn Val Ile
145                 150                 155                 160
```

Val His His Pro Ser Ser Lys Ala Pro Leu Val Cys Ile Glu Leu Ala
            165                 170                 175

Lys Ile Ile Glu Asn Ala Leu Lys Lys Tyr Asn Val Pro Leu Gly Val
        180                 185                 190

Tyr Asn Leu Leu Thr Gly Ala Gly Glu Val Val Gly Asp Glu Ile Val
        195                 200                 205

Val Asn Glu Lys Val Asn Met Ile Ser Phe Thr Gly Ser Ser Lys Val
    210                 215                 220

Gly Glu Leu Ile Thr Lys Lys Ala Gly Phe Lys Lys Ile Ala Leu Glu
225                 230                 235                 240

Leu Gly Gly Val Asn Pro Asn Ile Val Leu Lys Asp Ala Asp Leu Asn
                245                 250                 255

Lys Ala Val Asn Ala Leu Ile Lys Gly Ser Phe Ile Tyr Ala Gly Gln
            260                 265                 270

Val Cys Ile Ser Val Gly Met Ile Leu Val Asp Glu Ser Ile Ala Asp
        275                 280                 285

Lys Phe Ile Glu Met Phe Val Asn Lys Ala Lys Val Leu Asn Val Gly
            290                 295                 300

Asn Pro Leu Asp Glu Lys Thr Asp Val Gly Pro Leu Ile Ser Val Glu
305                 310                 315                 320

His Ala Glu Trp Val Glu Lys Val Glu Lys Ala Ile Asp Glu Gly
                325                 330                 335

Gly Lys Leu Leu Leu Gly Gly Lys Arg Asp Lys Ala Leu Phe Tyr Pro
                340                 345                 350

Thr Ile Leu Glu Val Asp Arg Asp Asn Ile Leu Cys Lys Thr Glu Thr
                355                 360                 365

Phe Ala Pro Val Ile Pro Ile Ile Arg Thr Asn Glu Glu Met Ile
370                 375                 380

Asp Ile Ala Asn Ser Thr Glu Tyr Gly Leu His Ser Ala Ile Phe Thr
385                 390                 395                 400

Asn Asp Ile Asn Lys Ser Leu Lys Phe Ala Glu Asn Leu Glu Phe Gly
                405                 410                 415

Gly Val Val Ile Asn Asp Ser Ser Leu Phe Arg Gln Asp Asn Met Pro
            420                 425                 430

Phe Gly Gly Val Lys Lys Ser Gly Leu Gly Arg Glu Gly Val Lys Tyr
                435                 440                 445

Ala Met Glu Glu Met Ser Asn Ile Lys Thr Ile Ile Ile Ser Lys
        450                 455                 460

<210> SEQ ID NO 151
<211> LENGTH: 488
<212> TYPE: PRT
<213> ORGANISM: Bacillus licheniformis

<400> SEQUENCE: 151

Met Ser Val Ala Ala Glu Ser Lys Thr Tyr Phe Asn Phe Ile Asn Gly
1               5                   10                  15

Arg Trp Val Lys Ala Glu Ser Gly Gly Met Glu Gln Ser Leu Asn Pro
            20                  25                  30

Ala Asp Thr Arg Asp Ile Val Gly Leu Val Gln Lys Ser Ser Ile Glu
        35                  40                  45

Asp Val Asp Arg Ala Val Glu Ala Ala Lys Gln Ala Lys Lys Ala Trp
    50                  55                  60

Arg Lys Leu Ser Gly Ala Glu Arg Gly Gln Phe Leu Tyr Lys Ala Ala
65                  70                  75                  80

-continued

```
Asp Ile Met Glu Gln Arg Leu Asp Glu Ile Ala Glu Cys Ala Thr Arg
                85                  90                  95

Glu Met Gly Lys Thr Leu Pro Glu Ala Lys Gly Glu Thr Ala Arg Gly
            100                 105                 110

Ile Ala Ile Leu Arg Tyr Tyr Ala Gly Glu Gly Leu Arg Lys Thr Gly
        115                 120                 125

Asp Val Ile Pro Ser Thr Asp Ser Ser Ala Phe Met Tyr Thr Asp Arg
    130                 135                 140

Val Pro Leu Gly Val Val Gly Val Ile Ser Pro Trp Asn Phe Pro Val
145                 150                 155                 160

Ala Ile Pro Ile Trp Lys Met Ala Pro Ala Leu Ile Tyr Gly Asn Thr
                165                 170                 175

Val Val Ile Lys Pro Ala Thr Glu Thr Ala Val Thr Cys Leu Lys Val
            180                 185                 190

Ile Ser Cys Phe Glu Glu Ala Gly Ile Pro Ser Gly Val Val Asn Ala
        195                 200                 205

Val Thr Gly Pro Gly Ser Ser Ala Gly Gln Arg Leu Ala Glu His Pro
    210                 215                 220

Asp Val Asn Gly Ile Thr Phe Thr Gly Ser Asn Gln Thr Gly Lys Ile
225                 230                 235                 240

Ile Gly Arg Thr Ala Phe Glu Arg Gly Ala Lys Tyr Gln Leu Glu Met
                245                 250                 255

Gly Gly Lys Asn Pro Val Ile Val Ala Asp Asp Ala Asp Leu Asp Ile
            260                 265                 270

Ala Val Glu Ala Val Ile Ser Gly Ala Phe Arg Ser Thr Gly Gln Lys
        275                 280                 285

Cys Thr Ala Thr Ser Arg Val Ile Val Leu Asn Gly Val Tyr Asp Arg
    290                 295                 300

Phe Lys Glu Lys Leu Leu Gln Gln Thr Lys Glu Ile Thr Ile Gly Asp
305                 310                 315                 320

Ser Leu Lys Glu Asp Val Trp Met Gly Pro Ile Ala Asn Lys Gln Gln
                325                 330                 335

Leu Asp Asn Cys Leu Ser Tyr Ile Ala Lys Gly Lys Gln Glu Gly Ala
            340                 345                 350

Asp Leu Ile Phe Gly Gly Glu Arg Leu Ala Asp Gly Lys Tyr Glu Asn
        355                 360                 365

Gly Tyr Tyr Ile Arg Pro Ala Ile Phe Asp Asn Val Thr Ser Gly Met
    370                 375                 380

Thr Ile Ala Gln Glu Glu Ile Phe Gly Pro Val Ile Ala Leu Ile Lys
385                 390                 395                 400

Ala Asp Thr Leu Glu Glu Ala Leu Glu Thr Ala Asn Asp Val Lys Phe
                405                 410                 415

Gly Leu Ser Ala Ser Ile Phe Thr Gln Asn Ile Arg Arg Met Leu Ser
            420                 425                 430

Phe Thr Asp Glu Ile Glu Ala Gly Leu Ile Arg Val Asn Ala Glu Ser
        435                 440                 445

Ala Gly Val Glu Leu Gln Ala Pro Phe Gly Gly Val Lys Gln Ser Ser
    450                 455                 460

Ser His Ser Arg Glu Gln Gly Glu Ala Ala Lys Glu Phe Phe Thr Ala
465                 470                 475                 480

Val Lys Thr Val Phe Val Lys Pro
                485
```

<210> SEQ ID NO 152
<211> LENGTH: 491
<212> TYPE: PRT
<213> ORGANISM: Pseudomonas sp.

<400> SEQUENCE: 152

| | | | | | | | | | | | | | | |
|---|---|---|---|---|---|---|---|---|---|---|---|---|---|---|
| Met | Lys | Gln | Tyr | Arg | Asn | Phe | Val | Asp | Gly | Lys | Trp | Val | Glu | Ser | Ser |
| 1 | | | | 5 | | | | | 10 | | | | | 15 | |
| Lys | Thr | Phe | Gln | Asp | Val | Thr | Pro | Ile | Asp | Gly | Ser | Val | Ala | Val |
| | | | 20 | | | | | 25 | | | | | 30 | |
| Val | His | Glu | Ala | Asp | Arg | Asp | Leu | Val | Asp | Ala | Val | Lys | Ala | Gly |
| | | 35 | | | | | 40 | | | | | 45 | | |
| His | Arg | Ala | Leu | Glu | Gly | Glu | Trp | Gly | Arg | Thr | Thr | Ala | Ala | Gln | Arg |
| | 50 | | | | | 55 | | | | | 60 | | | | |
| Val | Asp | Trp | Leu | Arg | Arg | Ile | Ala | Asn | Glu | Met | Glu | Arg | Arg | Gln | Gln |
| 65 | | | | | 70 | | | | | 75 | | | | | 80 |
| Asp | Phe | Leu | Asp | Ala | Glu | Met | Ala | Asp | Thr | Gly | Lys | Pro | Leu | Ser | Met |
| | | | | 85 | | | | | 90 | | | | | 95 | |
| Ala | Ala | Thr | Ile | Asp | Ile | Pro | Arg | Gly | Ile | Ala | Asn | Phe | Arg | Asn | Phe |
| | | | 100 | | | | | 105 | | | | | 110 | | |
| Ala | Asp | Ile | Leu | Ala | Thr | Ala | Pro | Val | Asp | Ser | His | Arg | Leu | Asp | Leu |
| | | | 115 | | | | | 120 | | | | | 125 | | |
| Pro | Asp | Gly | Ala | Tyr | Ala | Leu | Asn | Tyr | Ala | Ala | Arg | Lys | Pro | Leu | Gly |
| | 130 | | | | | 135 | | | | | 140 | | | | |
| Val | Val | Gly | Val | Ile | Ser | Pro | Trp | Asn | Leu | Pro | Leu | Leu | Leu | Thr |
| 145 | | | | | 150 | | | | | 155 | | | | | 160 |
| Trp | Lys | Val | Ala | Pro | Ala | Leu | Ala | Cys | Gly | Asn | Ala | Val | Val | Lys |
| | | | | 165 | | | | | 170 | | | | | 175 | |
| Pro | Ser | Glu | Asp | Thr | Pro | Gly | Thr | Ala | Thr | Leu | Leu | Ala | Glu | Val | Met |
| | | | 180 | | | | | 185 | | | | | 190 | | |
| Glu | Ala | Val | Gly | Ile | Pro | Pro | Gly | Val | Phe | Asn | Leu | Val | His | Gly | Phe |
| | | | 195 | | | | | 200 | | | | | 205 | | |
| Gly | Pro | Asn | Ser | Ala | Gly | Glu | Phe | Ile | Ser | Gln | His | Pro | Asp | Ile | Ser |
| | 210 | | | | | 215 | | | | | 220 | | | | |
| Ala | Ile | Thr | Phe | Thr | Gly | Glu | Ser | Lys | Thr | Gly | Ser | Thr | Ile | Met | Arg |
| 225 | | | | | 230 | | | | | 235 | | | | | 240 |
| Ala | Ala | Ala | Glu | Gly | Val | Lys | Pro | Val | Ser | Phe | Glu | Leu | Gly | Gly | Lys |
| | | | | 245 | | | | | 250 | | | | | 255 | |
| Asn | Ala | Ala | Val | Ile | Phe | Ala | Asp | Cys | Asp | Phe | Glu | Lys | Met | Leu | Asp |
| | | | 260 | | | | | 265 | | | | | 270 | | |
| Gly | Met | Met | Arg | Ala | Leu | Phe | Leu | Asn | Ser | Gly | Gln | Val | Cys | Leu | Cys |
| | | 275 | | | | | 280 | | | | | 285 | | | |
| Ser | Glu | Arg | Val | Tyr | Val | Glu | Arg | Pro | Ile | Phe | Asp | Arg | Phe | Cys | Val |
| | 290 | | | | | 295 | | | | | 300 | | | | |
| Ala | Leu | Ala | Glu | Arg | Ile | Lys | Ala | Leu | Lys | Val | Asp | Trp | Pro | His | Glu |
| 305 | | | | | 310 | | | | | 315 | | | | | 320 |
| Thr | Asp | Thr | Gln | Met | Gly | Pro | Leu | Ile | Ser | Ser | Lys | His | Arg | Asp | Lys |
| | | | | 325 | | | | | 330 | | | | | 335 | |
| Val | Leu | Ser | Tyr | Phe | Glu | Leu | Ala | Arg | Gln | Glu | Gly | Ala | Thr | Phe | Leu |
| | | | 340 | | | | | 345 | | | | | 350 | | |
| Ala | Gly | Gly | Gly | Val | Pro | Arg | Phe | Gly | Asp | Glu | Arg | Asp | Asn | Gly | Ala |
| | | 355 | | | | | 360 | | | | | 365 | | | |
| Trp | Val | Glu | Pro | Thr | Val | Ile | Ala | Gly | Leu | Ser | Asp | Asp | Ala | Arg | Val |
| | 370 | | | | | 375 | | | | | 380 | | | | |

-continued

Val Arg Glu Ile Phe Gly Pro Ile Cys His Val Thr Pro Phe Asp
385                 390                 395                 400

Ser Glu Ser Glu Val Ile Arg Arg Ala Asn Asp Thr Arg Tyr Gly Leu
            405                 410                 415

Ala Ala Thr Ile Trp Thr Thr Asn Leu Ser Arg Ala His Arg Val Ser
        420                 425                 430

Glu Leu Met Arg Val Gly Ile Ser Trp Val Asn Thr Trp Phe Leu Arg
            435                 440                 445

Asp Leu Arg Thr Pro Phe Gly Gly Ala Gly Leu Ser Gly Ile Gly Arg
        450                 455                 460

Glu Gly Gly Met His Ser Leu Asn Phe Tyr Ser Glu Leu Thr Asn Val
465                 470                 475                 480

Cys Val Arg Ile Asp Lys Glu Ser Pro Asp Val
            485                 490

<210> SEQ ID NO 153
<211> LENGTH: 499
<212> TYPE: PRT
<213> ORGANISM: Escherichia coli

<400> SEQUENCE: 153

Met Thr Glu Pro His Val Ala Val Leu Ser Gln Val Gln Gln Phe Leu
1               5                   10                  15

Asp Arg Gln His Gly Leu Tyr Ile Asp Gly Arg Pro Gly Pro Ala Gln
            20                  25                  30

Ser Glu Lys Arg Leu Ala Ile Phe Asp Pro Ala Thr Gly Gln Glu Ile
        35                  40                  45

Ala Ser Thr Ala Asp Ala Asn Glu Ala Asp Val Asp Asn Ala Val Met
    50                  55                  60

Ser Ala Trp Arg Ala Phe Val Ser Arg Arg Trp Ala Gly Arg Leu Pro
65                  70                  75                  80

Ala Glu Arg Glu Arg Ile Leu Leu Arg Phe Ala Asp Leu Val Glu Gln
                85                  90                  95

His Ser Glu Glu Leu Ala Gln Leu Glu Thr Leu Glu Gln Gly Lys Ser
            100                 105                 110

Ile Ala Ile Ser Arg Ala Phe Glu Val Gly Cys Thr Leu Asn Trp Met
        115                 120                 125

Arg Tyr Thr Ala Gly Leu Thr Thr Lys Ile Ala Gly Lys Thr Leu Asp
    130                 135                 140

Leu Ser Ile Pro Leu Pro Gln Gly Ala Arg Tyr Gln Ala Trp Thr Arg
145                 150                 155                 160

Lys Glu Pro Val Gly Val Val Ala Gly Ile Val Pro Trp Asn Phe Pro
                165                 170                 175

Leu Met Ile Gly Met Trp Lys Val Met Pro Ala Leu Ala Ala Gly Cys
            180                 185                 190

Ser Ile Val Ile Lys Pro Ser Glu Thr Thr Pro Leu Thr Met Leu Arg
        195                 200                 205

Val Ala Glu Leu Ala Ser Glu Ala Gly Ile Pro Asp Gly Val Phe Asn
    210                 215                 220

Val Val Thr Gly Ser Gly Ala Val Cys Gly Ala Ala Leu Thr Ser His
225                 230                 235                 240

Pro His Val Ala Lys Ile Ser Phe Thr Gly Ser Thr Ala Thr Gly Lys
                245                 250                 255

Gly Ile Ala Arg Thr Ala Ala Asp His Leu Thr Arg Val Thr Leu Glu

```
            260                 265                 270
Leu Gly Gly Lys Asn Pro Ala Ile Val Leu Lys Asp Ala Asp Pro Gln
            275                 280                 285
Trp Val Ile Glu Gly Leu Met Thr Gly Ser Phe Leu Asn Gln Gly Gln
            290                 295                 300
Val Cys Ala Ala Ser Ser Arg Ile Tyr Ile Glu Ala Pro Leu Phe Asp
305                 310                 315                 320
Thr Leu Val Ser Gly Phe Glu Gln Ala Val Lys Ser Leu Gln Val Gly
                    325                 330                 335
Pro Gly Met Ser Pro Val Ala Gln Ile Asn Pro Leu Val Ser Arg Ala
                    340                 345                 350
His Cys Asp Lys Val Cys Ser Phe Leu Asp Asp Ala Gln Ala Gln Gln
                    355                 360                 365
Ala Glu Leu Ile Arg Gly Ser Asn Gly Pro Ala Gly Glu Gly Tyr Tyr
                    370                 375                 380
Val Ala Pro Thr Leu Val Val Asn Pro Asp Ala Lys Leu Arg Leu Thr
385                 390                 395                 400
Arg Glu Glu Val Phe Gly Pro Val Val Asn Leu Val Arg Val Ala Asp
                    405                 410                 415
Gly Glu Glu Ala Leu Gln Leu Ala Asn Asp Thr Glu Tyr Gly Leu Thr
                    420                 425                 430
Ala Ser Val Trp Thr Gln Asn Leu Ser Gln Ala Leu Glu Tyr Ser Asp
                    435                 440                 445
Arg Leu Gln Ala Gly Thr Val Trp Val Asn Ser His Thr Leu Ile Asp
                    450                 455                 460
Ala Asn Leu Pro Phe Gly Gly Met Lys Gln Ser Gly Thr Gly Arg Asp
465                 470                 475                 480
Phe Gly Pro Asp Trp Leu Asp Gly Trp Cys Glu Thr Lys Ser Val Cys
                    485                 490                 495
Val Arg Tyr

<210> SEQ ID NO 154
<211> LENGTH: 492
<212> TYPE: PRT
<213> ORGANISM: Escherichia coli

<400> SEQUENCE: 154

Met Thr Leu Trp Ile Asn Gly Asp Trp Ile Thr Gly Gln Gly Ala Ser
1               5                   10                  15
Arg Val Lys Arg Asn Pro Val Ser Gly Glu Val Leu Trp Gln Gly Asn
            20                  25                  30
Asp Ala Asp Ala Ala Gln Val Glu Gln Ala Cys Arg Ala Ala Arg Ala
            35                  40                  45
Ala Phe Pro Arg Trp Ala Arg Leu Ser Phe Ala Glu Arg His Ala Val
        50                  55                  60
Val Glu Arg Phe Ala Ala Leu Leu Glu Ser Asn Lys Ala Glu Leu Thr
65                  70                  75                  80
Ala Ile Ile Ala Arg Glu Thr Gly Lys Pro Arg Trp Glu Ala Ala Thr
                85                  90                  95
Glu Val Thr Ala Met Ile Asn Lys Ile Ala Ile Ser Ile Lys Ala Tyr
            100                 105                 110
His Val Arg Thr Gly Glu Gln Arg Ser Glu Met Pro Asp Gly Ala Ala
            115                 120                 125
Ser Leu Arg His Arg Pro His Gly Val Leu Ala Val Phe Gly Pro Tyr
```

```
                    130                 135                 140
Asn Phe Pro Gly His Leu Pro Asn Gly His Ile Val Pro Ala Leu Leu
145                 150                 155                 160

Ala Gly Asn Thr Ile Ile Phe Lys Pro Ser Glu Leu Thr Pro Trp Ser
                165                 170                 175

Gly Glu Ala Val Met Arg Leu Trp Gln Gln Ala Gly Leu Pro Pro Gly
            180                 185                 190

Val Leu Asn Leu Val Gln Gly Gly Arg Glu Thr Gly Gln Ala Leu Ser
        195                 200                 205

Ala Leu Glu Asp Leu Asp Gly Leu Leu Phe Thr Gly Ser Ala Asn Thr
    210                 215                 220

Gly Tyr Gln Leu His Arg Gln Leu Ser Gly Gln Pro Glu Lys Ile Leu
225                 230                 235                 240

Ala Leu Glu Met Gly Gly Asn Asn Pro Leu Ile Ile Asp Glu Val Ala
                245                 250                 255

Asp Ile Asp Ala Ala Val His Leu Thr Ile Gln Ser Ala Phe Val Thr
            260                 265                 270

Ala Gly Gln Arg Cys Thr Cys Ala Arg Arg Leu Leu Leu Lys Ser Gly
        275                 280                 285

Ala Gln Gly Asp Ala Phe Leu Ala Arg Leu Val Ala Val Ser Gln Arg
    290                 295                 300

Leu Thr Pro Gly Asn Trp Asp Asp Glu Pro Gln Pro Phe Ile Gly Gly
305                 310                 315                 320

Leu Ile Ser Glu Gln Ala Ala Gln Gln Val Val Thr Ala Trp Gln Gln
                325                 330                 335

Leu Glu Ala Met Gly Gly Arg Pro Leu Leu Ala Pro Arg Leu Leu Gln
            340                 345                 350

Ala Gly Thr Ser Leu Leu Thr Pro Gly Ile Ile Glu Met Thr Gly Val
        355                 360                 365

Ala Gly Val Pro Asp Glu Glu Val Phe Gly Pro Leu Leu Arg Val Trp
    370                 375                 380

Arg Tyr Asp Thr Phe Asp Glu Ala Ile Arg Met Ala Asn Asn Thr Arg
385                 390                 395                 400

Phe Gly Leu Ser Cys Gly Leu Val Ser Pro Glu Arg Glu Lys Phe Asp
                405                 410                 415

Gln Leu Leu Leu Glu Ala Arg Ala Gly Ile Val Asn Trp Asn Lys Pro
            420                 425                 430

Leu Thr Gly Ala Ala Ser Thr Ala Pro Phe Gly Gly Ile Gly Ala Ser
        435                 440                 445

Gly Asn His Arg Pro Ser Ala Trp Tyr Ala Asp Tyr Cys Ala Trp
    450                 455                 460

Pro Met Ala Ser Leu Glu Ser Asp Ser Leu Thr Leu Pro Ala Thr Leu
465                 470                 475                 480

Asn Pro Gly Leu Asp Phe Ser Asp Glu Val Val Arg
                485                 490

<210> SEQ ID NO 155
<211> LENGTH: 1358
<212> TYPE: PRT
<213> ORGANISM: Zea mays (Maize)

<400> SEQUENCE: 155

Met Gly Lys Glu Ala Gly Ala Ala Glu Ser Ser Thr Val Val Leu Ala
1               5                   10                  15
```

```
Val Asn Gly Lys Arg Tyr Glu Ala Ala Gly Val Ala Pro Ser Thr Ser
         20                  25                  30

Leu Leu Glu Phe Leu Arg Thr Gln Thr Pro Val Arg Gly Pro Lys Leu
         35                  40                  45

Gly Cys Gly Glu Gly Gly Cys Gly Ala Cys Val Val Leu Val Ser Lys
         50                  55                  60

Tyr Asp Pro Ala Thr Asp Glu Val Thr Glu Phe Ser Ala Ser Ser Cys
65                   70                  75                  80

Leu Thr Leu Leu His Ser Val Asp Arg Cys Ser Val Thr Thr Ser Glu
                 85                  90                  95

Gly Ile Gly Asn Thr Arg Asp Gly Tyr His Pro Val Gln Gln Arg Leu
                100                 105                 110

Ser Gly Phe His Ala Ser Gln Cys Gly Phe Cys Thr Pro Gly Met Cys
                115                 120                 125

Met Ser Ile Phe Ser Ala Leu Val Lys Ala Asp Asn Lys Ser Asp Arg
        130                 135                 140

Pro Asp Pro Pro Ala Gly Phe Ser Lys Ile Thr Thr Ser Glu Ala Glu
145                 150                 155                 160

Lys Ala Val Ser Gly Asn Leu Cys Arg Cys Thr Gly Tyr Arg Pro Ile
                165                 170                 175

Val Asp Thr Cys Lys Ser Phe Ala Ser Asp Val Asp Leu Glu Asp Leu
                180                 185                 190

Gly Leu Asn Cys Phe Trp Lys Lys Gly Glu Glu Pro Ala Glu Val Ser
                195                 200                 205

Arg Leu Pro Gly Tyr Asn Ser Gly Ala Val Cys Thr Phe Pro Glu Phe
        210                 215                 220

Leu Lys Ser Glu Ile Lys Ser Thr Met Lys Gln Val Asn Asp Val Pro
225                 230                 235                 240

Ile Ala Ala Ser Gly Asp Gly Trp Tyr His Pro Lys Ser Ile Glu Glu
                245                 250                 255

Leu His Arg Leu Phe Asp Ser Ser Trp Phe Asp Ser Ser Val Lys
        260                 265                 270

Ile Val Ala Ser Asn Thr Gly Ser Gly Val Tyr Lys Asp Gln Asp Leu
                275                 280                 285

Tyr Asp Lys Tyr Ile Asp Ile Lys Gly Ile Pro Glu Leu Ser Val Ile
        290                 295                 300

Asn Lys Asn Asp Lys Ala Ile Glu Leu Gly Ser Val Val Ser Ile Ser
305                 310                 315                 320

Lys Ala Ile Glu Val Leu Ser Asp Gly Asn Leu Val Phe Arg Lys Ile
                325                 330                 335

Ala Asp His Leu Asn Lys Val Ala Ser Pro Phe Val Arg Asn Thr Ala
                340                 345                 350

Thr Ile Gly Gly Asn Ile Met Met Ala Gln Arg Leu Pro Phe Glu Ser
        355                 360                 365

Asp Val Ala Thr Val Leu Leu Ala Ala Gly Ser Thr Val Thr Val Gln
        370                 375                 380

Val Ala Ser Lys Arg Leu Cys Phe Thr Leu Glu Glu Phe Leu Glu Gln
385                 390                 395                 400

Pro Pro Cys Asp Ser Arg Thr Leu Leu Ser Ile Phe Ile Pro Glu
                405                 410                 415

Trp Gly Ser Asp Tyr Val Thr Phe Glu Thr Phe Arg Ala Ala Pro Arg
        420                 425                 430

Pro Phe Gly Asn Ala Val Ser Tyr Val Asn Ser Ala Phe Leu Ala Arg
```

-continued

```
            435                 440                 445
Thr Ser Gly Ser Leu Leu Ile Glu Asp Ile Cys Leu Ala Phe Gly Ala
450                 455                 460
Tyr Gly Val Asp His Ala Ile Arg Ala Lys Lys Val Glu Asp Phe Leu
465                 470                 475                 480
Lys Gly Lys Ser Leu Ser Ser Phe Val Ile Leu Glu Ala Ile Lys Leu
                485                 490                 495
Leu Lys Asp Thr Val Ser Pro Ser Glu Gly Thr Thr His His Glu Tyr
                500                 505                 510
Arg Val Ser Leu Ala Val Ser Phe Leu Phe Ser Phe Leu Ser Ser Leu
                515                 520                 525
Ala Asn Ser Ser Ser Ala Pro Ser Asn Ile Asp Thr Pro Asn Gly Ser
530                 535                 540
Tyr Thr His Glu Thr Gly Ser Asn Val Asp Ser Pro Glu Arg His Ile
545                 550                 555                 560
Lys Val Asp Ser Asn Asp Leu Pro Ile Arg Ser Arg Gln Glu Met Val
                565                 570                 575
Phe Ser Asp Glu Tyr Lys Pro Val Gly Lys Pro Ile Lys Lys Val Gly
                580                 585                 590
Ala Glu Ile Gln Ala Ser Gly Glu Ala Val Tyr Val Asp Asp Ile Pro
                595                 600                 605
Ala Pro Lys Asp Cys Leu Tyr Gly Ala Phe Ile Tyr Ser Thr His Pro
                610                 615                 620
His Ala His Val Arg Ser Ile Asn Phe Lys Ser Ser Leu Ala Ser Gln
625                 630                 635                 640
Lys Val Ile Thr Val Ile Thr Ala Lys Asp Ile Pro Ser Gly Gly Glu
                645                 650                 655
Asn Ile Gly Ser Ser Phe Leu Met Gln Gly Glu Ala Leu Phe Ala Asp
                660                 665                 670
Pro Ile Ala Glu Phe Ala Gly Gln Asn Ile Gly Val Val Ile Ala Glu
                675                 680                 685
Thr Gln Arg Tyr Ala Asn Met Ala Ala Lys Gln Ala Val Val Glu Tyr
                690                 695                 700
Ser Thr Glu Asn Leu Gln Pro Pro Ile Leu Thr Ile Glu Asp Ala Ile
705                 710                 715                 720
Gln Arg Asn Ser Tyr Ile Gln Ile Pro Pro Phe Leu Ala Pro Lys Pro
                725                 730                 735
Val Gly Asp Tyr Asn Lys Gly Met Ala Glu Ala Asp His Lys Ile Leu
                740                 745                 750
Ser Ala Glu Val Lys Leu Glu Ser Gln Tyr Tyr Phe Tyr Met Glu Thr
                755                 760                 765
Gln Ala Ala Leu Ala Ile Pro Asp Glu Asp Asn Cys Ile Thr Ile Tyr
                770                 775                 780
Ser Ser Thr Gln Met Pro Glu Leu Thr Gln Asn Leu Ile Ala Arg Cys
785                 790                 795                 800
Leu Gly Ile Pro Phe His Asn Val Arg Val Ile Ser Arg Arg Val Gly
                805                 810                 815
Gly Gly Phe Gly Gly Lys Ala Met Lys Ala Thr His Thr Ala Cys Ala
                820                 825                 830
Cys Ala Leu Ala Ala Phe Lys Leu Arg Arg Pro Val Arg Met Tyr Leu
                835                 840                 845
Asp Arg Lys Thr Asp Met Ile Met Ala Gly Gly Arg His Pro Met Lys
850                 855                 860
```

```
Ala Lys Tyr Ser Val Gly Phe Lys Ser Asp Gly Lys Ile Thr Ala Leu
865                 870                 875                 880

His Leu Asp Leu Gly Ile Asn Ala Gly Ile Ser Pro Asp Val Ser Pro
            885                 890                 895

Leu Met Pro Arg Ala Ile Ile Gly Ala Leu Lys Lys Tyr Asn Trp Gly
                900                 905                 910

Thr Leu Glu Phe Asp Thr Lys Val Cys Lys Thr Asn Val Ser Ser Lys
        915                 920                 925

Ser Ala Met Arg Ala Pro Gly Asp Val Gln Gly Ser Phe Ile Ala Glu
930                 935                 940

Ala Ile Ile Glu His Val Ala Ser Ala Leu Ala Leu Asp Thr Asn Thr
945                 950                 955                 960

Val Arg Arg Lys Asn Leu His Asp Phe Glu Ser Leu Glu Val Phe Tyr
            965                 970                 975

Gly Glu Ser Ala Gly Glu Ala Ser Thr Tyr Ser Leu Val Ser Met Phe
                980                 985                 990

Asp Lys Leu Ala Leu Ser Pro Glu Tyr Gln His Arg Ala Ala Met Ile
        995                 1000                1005

Glu Gln Phe Asn Ser Ser Asn Lys Trp Lys Lys Arg Gly Ile Ser
1010                1015                1020

Cys Val Pro Ala Thr Tyr Glu Val Asn Leu Arg Pro Thr Pro Gly
1025                1030                1035

Lys Val Ser Ile Met Asn Asp Gly Ser Ile Ala Val Glu Val Gly
1040                1045                1050

Gly Ile Glu Ile Gly Gln Gly Leu Trp Thr Lys Val Lys Gln Met
1055                1060                1065

Thr Ala Phe Gly Leu Gly Gln Leu Cys Pro Asp Gly Gly Glu Cys
1070                1075                1080

Leu Leu Asp Lys Val Arg Val Ile Gln Ala Asp Thr Leu Ser Leu
1085                1090                1095

Ile Gln Gly Gly Met Thr Ala Gly Ser Thr Thr Ser Glu Thr Ser
1100                1105                1110

Cys Glu Thr Val Arg Gln Ser Cys Val Ala Leu Val Glu Lys Leu
1115                1120                1125

Asn Pro Ile Lys Glu Ser Leu Glu Ala Lys Ser Asn Thr Val Glu
1130                1135                1140

Trp Ser Ala Leu Ile Ala Gln Ala Ser Met Ala Ser Val Asn Leu
1145                1150                1155

Ser Ala Gln Pro Tyr Trp Thr Pro Asp Pro Ser Phe Lys Ser Tyr
1160                1165                1170

Leu Asn Tyr Gly Ala Gly Thr Ser Glu Val Glu Val Asp Ile Leu
1175                1180                1185

Thr Gly Ala Thr Thr Ile Leu Arg Ser Asp Leu Val Tyr Asp Cys
1190                1195                1200

Gly Gln Ser Leu Asn Pro Ala Val Asp Leu Gly Gln Ile Glu Gly
1205                1210                1215

Cys Phe Val Gln Gly Ile Gly Phe Phe Thr Asn Glu Asp Tyr Lys
1220                1225                1230

Thr Asn Ser Asp Gly Leu Val Ile His Asp Gly Thr Trp Thr Tyr
1235                1240                1245

Lys Ile Pro Thr Val Asp Asn Ile Pro Lys Glu Phe Asn Val Glu
1250                1255                1260
```

| Met | Phe | Asn | Ser | Ala | Pro | Asp | Lys | Lys | Arg | Val | Leu | Ser | Ser | Lys |
|---|---|---|---|---|---|---|---|---|---|---|---|---|---|---|
| 1265 | | | | | 1270 | | | | | 1275 | | | | |

| Ala | Ser | Gly | Glu | Pro | Pro | Leu | Val | Leu | Ala | Thr | Ser | Val | His | Cys |
|---|---|---|---|---|---|---|---|---|---|---|---|---|---|---|
| 1280 | | | | | 1285 | | | | | 1290 | | | | |

| Ala | Met | Arg | Glu | Ala | Ile | Arg | Ala | Ala | Arg | Lys | Glu | Phe | Ser | Val |
|---|---|---|---|---|---|---|---|---|---|---|---|---|---|---|
| 1295 | | | | | 1300 | | | | | 1305 | | | | |

| Ser | Thr | Ser | Pro | Ala | Lys | Ser | Ala | Val | Thr | Phe | Gln | Met | Asp | Val |
|---|---|---|---|---|---|---|---|---|---|---|---|---|---|---|
| 1310 | | | | | 1315 | | | | | 1320 | | | | |

| Pro | Ala | Thr | Met | Pro | Val | Val | Lys | Glu | Leu | Cys | Gly | Leu | Asp | Val |
|---|---|---|---|---|---|---|---|---|---|---|---|---|---|---|
| 1325 | | | | | 1330 | | | | | 1335 | | | | |

| Val | Glu | Arg | Tyr | Leu | Glu | Asn | Val | Ser | Ala | Ala | Ser | Ala | Gly | Pro |
|---|---|---|---|---|---|---|---|---|---|---|---|---|---|---|
| 1340 | | | | | 1345 | | | | | 1350 | | | | |

| Asn | Thr | Ala | Lys | Ala |
|---|---|---|---|---|
| 1355 | | | | |

<210> SEQ ID NO 156
<211> LENGTH: 747
<212> TYPE: DNA
<213> ORGANISM: Caulobacter crescentus

<400> SEQUENCE: 156

```
atgtcctcag ccatctatcc cagcctgaag gcaagcgcg tcgtcatcac cggcggcggc      60
tcgggcatcg gggccggcct caccgccggc ttcgcccgtc agggcgcgga ggtgatcttc    120
ctcgacatcg ccgacgagga ctccagggct ctttgaggcc agctggccgg ctcgccgatc    180
ccgccggtct acaagcgctg cgacctgatg aacctcgagg cgatcaaggc ggtcttcgcc    240
gagatcggcg acgtcgacgt gctggtcaac aacgccggca atgacgaccg ccacaagctg    300
gccgacgtga ccggcgccta ttgggacgag cggatcaacg tcaacctgcg ccacatgctg    360
ttctgcaccc aggccgtcgc gccgggcatg aagaagcgtg gcggcggggc ggtgatcaac    420
ttcggttcga tcagctggca cctggggctt gaggacctcg tcctctacga aaccgccaag    480
gccggcatcg aaggcatgac ccgcgcgctg gcccgggagc tgggtcccga cgacatccgc    540
gtcacctgcg tggtgccggg caacgtcaag accaagcgcc aggagaagtg gtacacgccc    600
gaaggcgagg cccagatcgt ggcggcccaa tgcctgaagg ccgcatcgt cccggagaac    660
gtcgccgcgc tggtgctgtt cctggcctcg gatgacgcgt cgctctgcac cggccacgaa    720
tactggatcg acgccggctg gcgttga                                       747
```

<210> SEQ ID NO 157
<211> LENGTH: 870
<212> TYPE: DNA
<213> ORGANISM: Caulobacter crescentus

<400> SEQUENCE: 157

```
atgaccgctc aagtcacttg cgtatgggat ctgaaggcca cgttgggcga aggcccgatc      60
tggcatggcg acaccctgtg gttcgtcgac atcaagcagc gtaaaatcca aactaccac     120
cccgccaccg gcgagcgctt cagcttcgac gcgccggatc aggtgacctt cctcgcgccg    180
atcgtcggcg cgaccggctt tgtcgtcggt ctgaagaccg ggattcaccg cttccacccg    240
gccacgggct tcagcctgct gctcgaggtc gaggacgcgg cgctgaacaa cgccccaac    300
gacgccacgg tcgacgcgca aggccgtctg tggttcggca ccatgcacga cggggaagag    360
aacaatagcg gctcgctcta tcggatggac ctcaccggcg tcgcccggat ggaccgcgac    420
atctgcatca ccaacggccc gtgcgtctcg cccgacggca agaccttcta ccacaccgac    480
```

```
accctggaaa agacgatcta cgccttcgac ctggccgagg acggcctgct gtcgaacaag      540
cgcgtcttcg tgcagttcgc cctgggcgac gatgtctatc cggacggttc ggtcgtcgat      600
tccgaaggct atctgtggac cgccctgtgg ggcggtttcg gcgcggtccg cttctcgccg      660
caaggcgacg ccgtgacgcg catcgaactg cccgccccca acgtcaccaa gccctgcttc      720
ggcgggcctg acctgaagac cctctatttc accaccgccc gcaagggcct gagcgacgag      780
accctggccc agtacccgct ggccggcggt gtgttcgccg ttccggtcga tgtggccggc      840
caaccccagc atgaggtccg ccttgtctaa                                       870
```

<210> SEQ ID NO 158
<211> LENGTH: 1968
<212> TYPE: DNA
<213> ORGANISM: Escherichia coli

<400> SEQUENCE: 158

```
atgtctgttc gcaatatttt tgctgacgag agccacgata tttacaccgt cagaacgcac       60
gccgatggcc cggacggcga actcccatta accgcagaga tgcttatcaa ccgcccgagc      120
ggggatctgt tcggtatgac catgaatgcc ggaatgggtt ggtctccgga cgagctggat      180
cgggacggta ttttactgct cagtacactc ggtggcttac gcggcgcaga cggtaaaccc      240
gtggcgctgg cgttgcacca ggggcattac gaactgggaca tccagatgaa agcggcggcc      300
gaggttatta aagccaacca tgccctgccc tatgccgtgt acgtctccga tccttgtgac      360
gggcgtactc agggtacaac ggggatgttt gattcgctac cataccgaaa tgacgcatcg      420
atggtaatgc gccgccttat tcgctctctg cccgacgcga aagcagttat tggtgtggcg      480
agttgcgata aggggcttcc ggccaccatg atggcactcg ccgcgcagca acatcgca      540 accgtgctgt tccccggcgg cgcgacgctg cccgcaaagg atggagaaga caacggcaag      600
gtgcaaacca ttggcgcacg cttcgccaat ggcgaattat ctctacagga cgcacgccgt      660
gcgggctgta aagcctgtgc ctcttccggc ggcggctgtc aatttttggg cactgccggg      720
acatctcagg tggtggccga aggattggga ctggcaatcc cacattcagc cctggcccct      780
tccggtgagc ctgtgtggcg ggagatcgcc agagcttccg cgcgagctgc gctgaacctg      840
agtcaaaaag gcatcaccac ccgggaaatt ctcaccgata aagcgataga gaatgcgatg      900
acggtccatg ccgcgttcgg tggttcaaca aacctgctgt acacatccc ggcaattgct      960 caccaggcag gttgccatat cccgaccgtt gatgactgga tccgcatcaa caagcgcgtg     1020
ccccgactgg tgagcgtact gcctaatggc ccggtttatc atccaacggt caatgccttt     1080
atggcaggtg gtgtgccgga agtcatgttg catctgcgca gcctcggatt gttgcatgaa     1140
gacgttatga cggttaccgg cagcacgctg aaagaaaacc tcgactggtg ggagcactcc     1200
gaacggcgtc agcggttcaa gcaactcctg ctcgatcagg aacaaatcaa cgctgacgaa     1260
gtgatcatgt ctccgcagca agcaaaagcg cgcggattaa cctcaactat caccttcccg     1320
gtgggcaata ttgcgccaga aggttcggtg atcaaatcca ccgccattga cccctcgatg     1380
attgatgagc aaggtatcta ttaccataaa ggtgtggcga aggtttatct gtccgagaaa     1440
agtgcgattt acgatatcaa acatgacaag atcaaggcgg cgatattct ggtcattatt     1500 ggcgttggac cttcaggtac agggatggaa gaaacctacc aggttaccag tgccctgaag     1560
catctgtcat acgtaagca tgtttcgtta atcaccgatg cacgtttctc gggcgttttct     1620 actgcgcgt gcatcggcca tgtggggcca gaagcgctgg ccgagggccc catcggtaaa     1680
ttacgcaccg gggatttaat tgaaattaaa attgattgtc gcgagcttca cggcgaagtc     1740
```

```
aatttcctcg gaacccgtag cgatgaacaa ttaccttcac aggaggaggc aactgcaata      1800
ttaaatgcca gacccagcca tcaggattta cttcccgatc ctgaattgcc agatgatacc      1860
cggctatggg caatgcttca ggccgtgagt ggtgggacat ggaccggttg tatttatgat      1920
gtaaacaaaa ttggcgcggc tttgcgcgat tttatgaata aaaactga                   1968
```

<210> SEQ ID NO 159
<211> LENGTH: 1383
<212> TYPE: DNA
<213> ORGANISM: Escherichia coli

<400> SEQUENCE: 159

```
atgacgcaat taaccatgaa agacaaaatt ggctacgggc tgggagacac cgcctgcggc        60
ttcgtctggc aggccacgat gttcctgctg gcctatttct acaccgacgt cttcggcctg       120
tcggcgggga ttatgggcac gctgtttttg gtctcccgcg tgctcgacgc cgtcaccgac       180
ccgctgatgg ggctgctggt agaccgcacc cgcacgcggc acggccagtt ccgcccgttc       240
ctgctgtggg gggccatccc gttcggcatc gtctgcgtgc tgaccttcta cacgccggac       300
ttctccgcac agggcaagat catctacgcc tgcgtgacct acattctcct gaccctggtc       360
tacaccttcg ttaacgtgcc gtactgcgcc atgccgggcg tcatcaccgc cgacccgaaa       420
gagcgtcacg ccctgcagtc ctggcgcttc ttcctggcgg cggcgggctc gctcgctatc       480
agcggcatcg cgctgccgct ggtgagcatc atcggcaaag gggacgagca ggtgggctac       540
ttcggcgcca tgtgcgtgct ggggctgagc ggcgtggtgc tgctctacgt ctgcttcttc       600
acgaccaaag agcgctacac ctttgaggtg cagccgggct cgtcggtggc gaaagacctt       660
aagctgctgc tgggcaacag ccagtggcgc atcatgtgcg cgttcaagat gatggcgacc       720
tgctccaacg tggtgcgcgg cggggcgacg ctctacttcg tgaaatacgt gatggatcac       780
ccggagttgg cgacccagtt tttactttac ggcagcctcg ccaccatgtt cggctcgctt       840
tgctcctcac gcctgctggg ccgcttcgac cgcgtcaccg ccttcaagtg gatcatcgtc       900
gcctactcgc tgatcagcct gctgattttc gtcaccccgg cggagcacat cgcgctcatt       960
tttgccctca acatcctgtt cctgttcgtc tttaatacca ccacgccgct gcagtggctg      1020
atggcttctg acgtggtgga ctacgaggag agccgcagcg tcgccgcct cgacgggctg      1080 gtgttctcca cctacctgtt cagcctgaag attggcctgg cgattggcgg ggcggtggtg      1140
ggctggatcc tggcgtacgt caactattcc gccagcagca gcgtgcagcc ggttgaggtg      1200
ctcaccacca tcaaaattct gttctgcgtg gtgccggtgg tgctctacgc gggcatgttc      1260
atcatgctgt cgctctacaa gctcaccgat gcccgcgtgg aggccatcag ccggcagctg      1320
attaagcacc gcgcggcgca gggcgaggcc gttcccgacg ccgcgacagc cgcatcccat      1380
taa                                                                   1383
```

<210> SEQ ID NO 160
<211> LENGTH: 1041
<212> TYPE: DNA
<213> ORGANISM: Escherichia coli

<400> SEQUENCE: 160

```
atgcagaaca tcatccgaaa aggaggaact atgaaggctg cagttgttac gaaggatcat        60
catgttgacg ttacgtataa aactgcgcgc tcactgaaac atggcgaagc cctgctgaaa       120
atggagtgtt gtggtgtatg tcataccgat cttcatgtta gaatggcga ttttggtgac       180
```

| | |
|---|---|
| aaaaccggcg taattctggg ccatgaaggc atcggtgtgg tggcagaagt gggtccaggt | 240 |
| gtcacctcat taaaaccagg cgatcgtgcc agcgtggcgt ggttctacga aggatgcggt | 300 |
| cattgcgaat actgtaacag tggtaacgaa acgctctgcc gttcagttaa aaatgccgga | 360 |
| tacagcgttg atggcgggat ggcggaagag tgcatcgtgg tcgccgatta cgcggtaaaa | 420 |
| gtgccagatg gtctggactc ggcggcggcc agcagcatta cctgtgcggg agtcaccacc | 480 |
| tacaaagccg ttaagctgtc aaaaattcgt ccagggcagt ggattgctat ctacggtctt | 540 |
| ggcggtctgg gtaacctcgc cctgcaatac gcgaagaatg tctttaacgc caaagtgatc | 600 |
| gccattgatg tcaatgatga gcagttaaaa ctggcaaccg aaatgggcgc agatttagcg | 660 |
| attaactcac acaccgaaga cgccgccaaa attgtgcagg agaaaactgg tggcgctcac | 720 |
| gctgcggtgg taacagcggt agctaaagct gcgtttaact cggcagttga tgctgtccgt | 780 |
| gcaggcggtc gtgttgtggc tgtcggtcta ccgccggagt ctatgagcct ggatatccca | 840 |
| cgtcttgtgc tggatggtat tgaagtggtc ggttcgctgg tcggcacgcg ccaggattta | 900 |
| actgaagcct tccagtttgc cgccgaaggt aaagtggtgc cgaaagtcgc cctgcgtccg | 960 |
| ttagcggaca tcaacaccat ctttactgag atggaagaag gcaaaatccg tggccgcatg | 1020 |
| gtgattgatt ccgtcacta a | 1041 |

<210> SEQ ID NO 161
<211> LENGTH: 1164
<212> TYPE: DNA
<213> ORGANISM: Escherichia coli

<400> SEQUENCE: 161

| | |
|---|---|
| atgaacaact ttaatctgca caccccaacc cgcattctgt ttggtaaagg cgcaatcgct | 60 |
| ggtttacgcg aacaaattcc tcacgatgct cgcgtattga ttacctacgg cggcggcagc | 120 |
| gtgaaaaaaa ccggcgttct cgatcaagtt ctggatgccc tgaaaggcat ggacgtgctg | 180 |
| gaatttggcg gtattgagcc aaaccccggct tatgaaacgc tgatgaacgc cgtgaaactg | 240 |
| gttcgcgaac agaaagtgac tttcctgctg gcggttggcg gcggttctgt actggacggc | 300 |
| accaaattta tcgccgcagc ggctaactat ccggaaaata tcgatccgtg gcacattctg | 360 |
| caaacgggcg gtaaagagat taaaagcgcc atcccgatgg gctgtgtgct gacgctgcca | 420 |
| gcaaccggtt cagaatccaa cgcaggcgcg gtgatctccc gtaaaaccac aggcgacaag | 480 |
| caggcgttcc attctgccca tgttcagccg gtatttgccg tgctcgatcc ggtttatacc | 540 |
| tacacccctgc cgccgcgtca ggtggctaac ggcgtagtgg acgcctttgt acacaccgtg | 600 |
| gaacagtatg ttaccaaacc ggttgatgcc aaaattcagg accgtttcgc agaaggcatt | 660 |
| ttgctgacgc taatcgaaga tggtccgaaa gccctgaaag agccagaaaa ctacgatgtg | 720 |
| cgcgccaacg tcatgtgggc ggcgactcag gcgctgaacg gtttgattgg cgctggcgta | 780 |
| ccgcaggact gggcaacgca tatgctgggc cacgaactga ctgcgatgca cggtctggat | 840 |
| cacgcgcaaa cactggctat cgtcctgcct gcactgtgga atgaaaaacg cgataccaag | 900 |
| cgcgctaagc tgctgcaata tgctgaacgc gtctggaaca tcactgaagg ttccgatgat | 960 |
| gagcgtattg acgccgcgat tgccgcaacc cgcaatttct ttgagcaatt aggcgtgccg | 1020 |
| acccacctct ccgactacgg tctggacggc agctccatcc cggctttgct gaaaaaactg | 1080 |
| gaagagcacg gcatgaccca actgggcgaa aatcatgaca ttacgttgga tgtcagccgc | 1140 |
| cgtatatacg aagccgcccg ctaa | 1164 |

<210> SEQ ID NO 162
<211> LENGTH: 1587
<212> TYPE: DNA
<213> ORGANISM: Pseudomonas putida

<400> SEQUENCE: 162

| | | | | | | |
|---|---|---|---|---|---|---|
| atggcttcgg | tacacggcac | cacatacgaa | ctcttgcgac | gtcaaggcat | cgatacggtc | 60 |
| ttcggcaatc | ctggctcgaa | cgagctcccg | tttttgaagg | actttccaga | ggactttcga | 120 |
| tacatcctgg | ctttgcagga | agcgtgtgtg | gtgggcattg | cagacggcta | tgcgcaagcc | 180 |
| agtcggaagc | cggctttcat | taacctgcat | tctgctgctg | gtaccggcaa | tgctatgggt | 240 |
| gcactcagta | acgcctggaa | ctcacattcc | ccgctgatcg | tcactgccgg | ccagcagacc | 300 |
| agggcgatga | ttggcgttga | agctctgctg | accaacgtcg | atgccgccaa | cctgccacga | 360 |
| ccacttgtca | aatggagcta | cgagcccgca | agcgcagcag | aagtccctca | tgcgatgagc | 420 |
| agggctatcc | atatggcaag | catggcgcca | caaggccctg | tctatctttc | ggtgccatat | 480 |
| gacgattggg | ataaggatgc | tgatcctcag | tcccaccacc | ttttgatcg | ccatgtcagt | 540 |
| tcatcagtac | gcctgaacga | ccaggatctc | gatattctgg | tgaaagctct | caacagcgca | 600 |
| tccaacccgg | cgatcgtcct | gggcccggac | gtcgacgcag | caaatgcgaa | cgcagactgc | 660 |
| gtcatgttgg | ccgaacgcct | caaagctccg | gtttgggttg | cgccatccgc | tccacgctgc | 720 |
| ccattcccta | cccgtcatcc | ttgcttccgt | ggattgatgc | cagctggcat | cgcagcgatt | 780 |
| tctcagctgc | tcgaaggtca | cgatgtggtt | ttggtaatcg | gcgctccagt | gttccgttac | 840 |
| caccaatacg | acccaggtca | atatctcaaa | cctggcacgc | gattgatttc | ggtgacctgc | 900 |
| gacccgctcg | aagctgcacg | cgcgccaatg | ggcgatgcga | tcgtggcaga | cattggtgcg | 960 |
| atggctagcg | ctcttgccaa | cttggttgaa | gagagcagcc | gccagctccc | aactgcagct | 1020 |
| ccggaacccg | cgaaggttga | ccaagacgct | ggccgacttc | acccagagac | agtgttcgac | 1080 |
| acactgaacg | acatggcccc | ggagaatgcg | atttacctga | cgagtcgac | ttcaacgacc | 1140 |
| gcccaaatgt | ggcagcgcct | gaacatgcgc | aaccctggta | gctactactt | ctgtgcagct | 1200 |
| ggcggactgg | gcttcgccct | gcctgcagca | attggcgttc | aactcgcaga | acccgagcga | 1260 |
| caagtcatcg | ccgtcattgg | cgacggatcg | gcgaactaca | gcattagtgc | gttgtggact | 1320 |
| gcagctcagt | acaacatccc | cactatcttc | gtgatcatga | acaacggcac | ctacggtgcg | 1380 |
| ttgcgatggt | ttgccggcgt | tctcgaagca | gaaaacgttc | tgggctgga | tgtgccaggg | 1440 |
| atcgacttcc | gcgcactcgc | caagggctat | ggtgtccaag | cgctgaaagc | cgacaacctt | 1500 |
| gagcagctca | agggttcgct | acaagaagcg | ctttctgcca | aaggcccggt | acttatcgaa | 1560 |
| gtaagcaccg | taagcccggt | gaagtga | | | | 1587 |

<210> SEQ ID NO 163
<211> LENGTH: 1323
<212> TYPE: DNA
<213> ORGANISM: Escherichia coli

<400> SEQUENCE: 163

| | | | | | | |
|---|---|---|---|---|---|---|
| atgcaagcct | attttgacca | gctcgatcgc | gttcgttatg | aaggctcaaa | atcctcaaac | 60 |
| ccgttagcat | tccgtcacta | caatcccgac | gaactggtgt | ggggtaagcg | tatggaagag | 120 |
| cacttgcgtt | ttgccgcctg | ctactggcac | accttctgct | ggaacggggc | ggatatgttt | 180 |
| ggtgtggggg | cgtttaatcg | tccgtggcag | cagcctggtg | aggcactggc | gttggcgaag | 240 |
| cgtaaagcag | atgtcgcatt | tgagtttttc | cacaagttac | atgtgccatt | ttattgcttc | 300 |

-continued

```
cacgatgtgg atgtttcccc tgagggcgcg tcgttaaaag agtacatcaa taattttgcg    360
caaatggttg atgtcctggc aggcaagcaa gaagagagcg gcgtgaagct gctgtgggga    420
acggccaact gctttacaaa ccctcgctac ggcgcgggtg cggcgacgaa cccagatcct    480
gaagtcttca gctgggcggc aacgcaagtt gttacagcga tggaagcaac ccataaattg    540
ggcggtgaaa actatgtcct gtggggcggt cgtgaaggtt acgaaacgct gttaaatacc    600
gacttgcgtc aggagcgtga acaactgggc cgctttatgc agatggtggt tgagcataaa    660
cataaaatcg gtttccaggg cacgttgctt atcgaaccga aaccgcaaga accgaccaaa    720
catcaatatg attacgatgc cgcgacggtc tatggcttcc tgaaacagtt tggtctggaa    780
aaagagatta aactgaacat tgaagctaac cacgcgacgc tggcaggtca ctctttccat    840
catgaaatag ccaccgccat tgcgcttggc ctgttcggtt ctgtcgacgc caaccgtggc    900
gatgcgcaac tgggctggga caccgaccag ttcccgaaca gtgtggaaga gaatgcgctg    960
gtgatgtatg aaattctcaa agcaggcggt ttcaccaccg gtggtctgaa cttcgatgcc   1020
aaagtacgtc gtcaaagtac tgataaatat gatctgtttt acggtcatat cggcgcgatg   1080
gatacgatgg cactggcgct gaaaattgca gcgcgcatga ttgaagatgg cgagctggat   1140
aaacgcatcg cgcagcgtta ttccggctgg aatagcgaat tgggccagca aatcctgaaa   1200
ggccaaatgt cactggcaga tttagccaaa tatgctcagg aacatcattt gtctccggtg   1260
catcagagtg gtcgccagga acaactggaa aatctggtaa accattatct gttcgacaaa   1320
taa                                                                 1323
```

<210> SEQ ID NO 164
<211> LENGTH: 1455
<212> TYPE: DNA
<213> ORGANISM: Escherichia coli

<400> SEQUENCE: 164

```
atgtatatcg ggatagatct tggcacctcg ggcgtaaaag ttattttgct caacgagcag     60
ggtgaggtgg ttgctgcgca aacggaaaag ctgaccgttt cgcgcccgca tccactctgg    120
tcggaacaag acccggaaca gtggtggcag gcaactgatc gcgcaatgaa agctctgggc    180
gatcagcatt ctctgcagga cgttaaagca ttgggtattg ccggccagat gcacggagca    240
accttgctgg atgctcagca acgggtgtta cgccctgcca ttttgtggaa cgacgggcgc    300
tgtgcgcaag agtgcacttt gctggaagcg cgagttccgc aatcgcgggt gattaccggc    360
aacctgatga tgcccggatt tactgcgcct aaattgctat gggttcagcg gcatgagccg    420
gagatattcc gtcaaatcga caaagtatta ttaccgaaag attacttgcg tctgcgtatg    480
acgggggagt ttgccagcga tatgtctgac gcagctggca ccatgtggct ggatgtcgca    540
aagcgtgact ggagtgacgt catgctgcag gcttgcgact tatctcgtga ccagatgccc    600
gcattatacg aaggcagcga aattactggt gctttgttac ctgaagttgc gaaagcgtgg    660
ggtatggcga cggtgccagt tgtcgcaggc ggtggcgaca atgcagctgg tgcagttggt    720
gtgggaatgg ttgatgctaa tcaggcaatg ttatcgctgg ggacgtcggg ggtctatttt    780
gctgtcagcg aagggttctt aagcaagcca gaaagcgccg tacatagctt ttgccatgcg    840
ctaccgcaac gttggcattt aatgtctgtg atgctgagtg cagcgtcgtg tctggattgg    900
gccgcgaaat taaccggcct gagcaatgtc ccagctttaa tcgctgcagc tcaacaggct    960
gatgaaagtg ccgagccagt ttggtttctg ccttatcttt ccggcgagcg tacgccacac   1020
aataatcccc aggcgaaggg ggttttcttt ggtttgactc atcaacatgg ccccaatgaa   1080
```

```
ctggcgcgag cagtgctgga aggcgtgggt tatgcgctgg cagatggcat ggatgtcgtg   1140
catgcctgcg gtattaaacc gcaaagtgtt acgttgattg ggggcggggc gcgtagtgag   1200
tactggcgtc agatgctggc ggatatcagc ggtcagcagc tcgattaccg tacgggggg    1260 gatgtggggc cagcactggg cgcagcaagg ctggcgcaga tcgcggcgaa tccagagaaa   1320
tcgctcattg aattgttgcc gcaactaccg ttagaacagt cgcatctacc agatgcgcag   1380
cgttatgccg cttatcagcc acgacgagaa acgttccgtc gcctctatca gcaacttctg   1440
ccattaatgg cgtaa                                                    1455
```

<210> SEQ ID NO 165
<211> LENGTH: 906
<212> TYPE: DNA
<213> ORGANISM: Escherichia coli

<400> SEQUENCE: 165

```
atgaaaaaat tcagcggcat tattccaccg gtatccagca cgtttcatcg tgacggaacc    60
cttgataaaa aggcaatgcg cgaagttgcc gacttcctga ttaataaagg ggtcgacggg   120 ctgtttttatc tgggtaccgg tgtgaattt  agccaaatga atacagccca gcgcatggca   180
ctcgccgaag aagctgtaac cattgtcgac gggcgagtgc cggtattgat tggcgtcggt   240 tcccctcca ctgacgaagc ggtcaaactg gcgcagcatg cgcaagccta cggcgctgat    300
ggtatcgtcg ccatcaaccc ctactactgg aaagtcgcac cacgaaatct tgacgactat   360
taccagcaga tcgcccgtag cgtcacccta ccggtgatcc tgtacaactt tccggatctg   420
acgggtcagg acttaaccc ggaaaccgtg acgcgtctgg ctctgcaaaa cgagaatatc   480
gttggcatca agacaccat cgacagcgtt ggtcacttgc gtacgatgat caacacagtt   540
aagtcggtac gcccgtcgtt ttcggtattc tgcggttacg atgatcattt gctgaatacg   600
atgctgctgg gcggcgacgg tgcgataacc gccagcgcta actttgctcc ggaactctcc   660
gtcggcatct accgcgcctg gcgtgaaggc gatctggcga ccgctgcgac gctgaataaa   720
aaactactac aactgcccgc tatttacgcc ctcgaaacac cgtttgtctc actgatcaaa   780
tacagcatgc agtgtgtcgg gctgcctgta gagacatatt gcttaccacc gattcttgaa   840
gcatctgaag aagcaaaaga taaagtccac gtgctgctta ccgcgcaggg catttttacca   900 gtctga                                                              906
```

<210> SEQ ID NO 166
<211> LENGTH: 909
<212> TYPE: DNA
<213> ORGANISM: Escherichia coli

<400> SEQUENCE: 166

```
atgccgcagt ccgcgttgtt cacgggaatc attcccctg  tctccaccat ttttaccgcc    60
gacggccagc tcgataagcc gggcaccgcc gcgctgatcg acgatctgat caaagcaggc   120
gttgacggcc tgttcttcct gggcagcggt ggcgagttct cccagctcgg cgccgaagag   180
cgtaaagcca ttgcccgctt tgctatcgat catgtcgatc gtcgcgtgcc ggtgctgatc   240
ggcaccggcg gcaccaacgc ccgggaaacc atcgaactca gccagcacgc gcagcaggcg   300
ggcgcggacg gcatcgtggt gatcaacccc tactactgga aagtgtcgga agcgaacctg   360
atccgctatt tcgagcaggt ggccgacagc gtcacgctgc cggtgatgct ctataacttc   420
ccggcgctga ccgggcagga tctgactccg gcgctggtga aaaccctcgc cgactcgcgc   480
```

-continued

```
agcaatatta tcggcatcaa agacaccatc gactccgtcg cccacctgcg cagcatgatc      540
cataccgtca aaggtgccca tccgcacttc accgtgctct gcggctacga cgatcatctg      600
ttcaataccc tgctgctcgg cggcgacggg gcgatatcgg cgagcggcaa ctttgccccg      660
caggtgtcgg tgaatcttct gaaagcctgg cgcgacgggg acgtggcgaa agcggccggg      720
tatcatcaga ccttgctgca aattccgcag atgtatcagc tggatacgcc gtttgtgaac      780
gtgattaaag aggcgatcgt gctctgcggt cgtcctgtct ccacgcacgt gctgccgccc      840
gcctcgccgc tggacgagcc gcgcaaggcg cagctgaaaa ccctgctgca acagctcaag      900
ctttgctga                                                              909
```

<210> SEQ ID NO 167
<211> LENGTH: 975
<212> TYPE: DNA
<213> ORGANISM: Escherichia coli

<400> SEQUENCE: 167

```
atgaagccgt ccgttatcct ctacaaagcc ttacctgatg atttactgca acgcctgcaa       60
gagcatttca ccgttcacca ggtggcaaac ctcagcccac aaaccgtcga acaaaatgca      120 gcaattttg ccgaagctga aggtttactg ggttcaaacg agaatgtaaa tgccgcattg      180
ctggaaaaaa tgccgaaact gcgtgccaca tcaacgatct ccgtcggcta tgacaatttt      240
gatgtcgatg cgcttaccgc ccgaaaaatt ctgctgatgc acacgccaac cgtattaaca      300
gaaaccgtcg ccgatacgct gatggcgctg gtgttgtcta ccgctcgtcg ggttgtggag      360
gtagcagaac gggtaaaagc aggcgaatgg accgcgagca taggcccgga ctggtacggc      420
actgacgttc accataaaac actgggcatt gtcgggatgg acggatcgg catggcgctg      480 gcacaacgtg cgcactttgg cttcaacatg cccatcctct ataacgcgcg ccgccaccat      540
aaagaagcag aagaacgctt caacgcccgc tactgcgatt tggatactct gttacaagag      600
tcagatttcg tttgcctgat cctgccgtta actgatgaga cgcatcatct gtttggcgca      660
gaacaattcg ccaaaatgaa atcctccgcc attttcatta atgccggacg tggcccggtg      720
gttgacgaaa atgcactgat cgcagcattg cagaaaggcg aaattcacgc tgccgggctg      780
gatgtcttcg aacaagagcc actgtccgta gattcgccgt tgctctcaat ggccaacgtc      840
gtcgcagtac cgcatattgg atctgccacc catgagacgc gttatggcat ggccgcctgt      900
gccgtggata atttgattga tgcgttacaa ggaaaggttg agaagaactg tgtgaatccg      960
cacgtcgcgg actaa                                                       975
```

<210> SEQ ID NO 168
<211> LENGTH: 939
<212> TYPE: DNA
<213> ORGANISM: Escherichia coli

<400> SEQUENCE: 168

```
atggatatca tcttttatca cccaacgttc gatacccaat ggtggattga ggcactgcgc       60
aaagctattc ctcaggcaag agtcagagca tggaaaagcg agataatga ctctgctgat      120 tatgctttag tctggcatcc tcctgttgaa atgctggcag ggcgcgatct aaagcggtg      180 ttcgcactcg gggccggtgt tgattctatt ttgagcaagc tacaggcaca ccctgaaatg      240 ctgaacccctt ctgttccact ttttcgcctg gaagataccg gtatgggcga gcaaatgcag      300
gaatatgctg tcagtcaggt gctgcattgg tttcgacgtt ttgacgatta tcgcatccag      360
caaaatagtt cgcattggca accgctgcct gaatatcatc gggaagattt taccatcggc      420
```

```
atttgggcg caggcgtact gggcagtaaa gttgctcaga gtctgcaaac ctggcgcttt    480
ccgctgcgtt gctggagtcg aacccgtaaa tcgtggcctg gcgtgcaaag ctttgccgga    540
cgggaagaac tgtctgcatt tctgagccaa tgtcgggtat tgattaattt gttaccgaat    600 accccctgaaa ccgtcggcat tattaatcaa caattactcg aaaaattacc ggatggcgcg    660
tatctcctca acctggcgcg tggtgttcat gttgtggaag atgacctgct cgcggcgctg    720
gatagcggca aagttaaagg cgcaatgttg atgttttta atcgtgaacc cttaccgcct    780
gaaagtccgc tctggcaaca tccacgcgtg acgataacac cacatgtcgc cgcgattacc    840
cgtcccgctg aagctgtgga gtacatttct cgcaccattg cccagctcga aaaaggggag    900
agggtctgcg ggcaagtcga ccgcgcacgc ggctactaa                           939
```

<210> SEQ ID NO 169
<211> LENGTH: 1434
<212> TYPE: DNA
<213> ORGANISM: Escherichia coli

<400> SEQUENCE: 169

```
atgtttaaga atgcatttgc taacctgcaa aaggtcggta atcgctgat gctgccggta     60 tccgtactgc ctatcgcagg tattctgctg ggcgtcggtt ccgcgaattt cagctggctg    120
cccgccgttg tatcgcatgt tatggcagaa gcaggcggtt ccgtctttgc aaacatgcca    180 ctgattttg cgatcggtgt cgccctcggc tttaccaata cgatggcgt atccgcgctg    240 gccgcagttg ttgcctatgg catcatggtt aaaaccatgg ccgtggttgc gccactggta    300
ctgcatttac ctgctgaaga atcgcctct aaacacctgg cggatactgg cgtactcgga    360
gggattatct ccggtgcgat cgcagcgtac atgtttaacc gtttctaccg tattaagctg    420
cctgagtatc ttggcttctt tgccggtaaa cgctttgtgc cgatcatttc tggcctggct    480
gccatcttta ctggcgttgt gctgtccttc atttggccgc cgattggttc tgcaatccag    540
accttctctc agtgggctgc ttaccagaac ccggtagttg cgtttggcat ttacggtttc    600
atcgaacgtt gcctggtacc gtttggtctg caccacatct ggaacgtacc tttccagatg    660
cagattggtg aatacaccaa cgcagcaggt caggttttcc acggcgacat tccgcgttat    720
atggcgggtg acccgactgc gggtaaactg tcctggtggct tcctgttcaa aatgtacggt    780
ctgccagctg ccgcaattgc tatctggcac tctgctaaac agaaaaccg cgcgaaagtg    840 ggcggtatta tgatctccgc ggcgctgacc tcgttcctga ccggtatcac cgagccgatc    900
gagttctcct tcatgttcgt tgcgccgatc ctgtacatca tccacgcgat tctggcaggc    960
ctggcattcc caatctgtat tcttctgggg atgcgtgacg gtacgtcgtt ctcgcacggt   1020
ctgatcgact tcatcgttct gtctggtaac agcagcaaac tgtggctgtt cccgatcgtc   1080
ggtatcggtt atgcgattgt ttactacacc atcttccgcg tgctgattaa agcactggat   1140
ctgaaaacgc cgggtcgtga agacgcgact gaagatgcaa aagcgacagg taccagcgaa   1200
atggcaccgg ctctggttgc tgcatttggt ggtaaagaaa acattactaa cctcgacgca   1260
tgtattaccc gtctgcgcgt cagcgttgct gatgtgtcta agtggatca ggccggcctg   1320 aagaaactgg gcgcagcggg cgtagtggtt gctggttctg tgttcaggc gattttcggt   1380 actaaatccg ataacctgaa aaccgagatg gatgagtaca tccgtaacca ctaa         1434
```

<210> SEQ ID NO 170
<211> LENGTH: 510
<212> TYPE: DNA

<213> ORGANISM: Escherichia coli

<400> SEQUENCE: 170

```
atgggtttgt tcgataaact gaaatctctg gtttccgacg acaagaagga taccggaact    60
attgagatca ttgctccgct ctctggcgag atcgtcaata tcgaagacgt gccggatgtc   120
gttttttgcgg aaaaaatcgt tggtgatggt attgctatca aaccaacggg taacaaaatg   180
gtcgcgccag tagacggcac cattggtaaa atctttgaaa ccaaccacgc attctctatc   240
gaatctgata gcggcgttga actgttcgtc cacttcggta tcgacaccgt tgaactgaaa   300
ggcgaaggct tcaagcgtat tgctgaagaa ggtcagcgcg tgaaagttgg cgatactgtc   360
attgaatttg atctgccgct gctggaagag aaagccaagt ctaccctgac tccggttgtt   420
atctccaaca tggacgaaat caagaactg atcaaactgt ccggtagcgt aaccgtgggt   480
gaaaccccgg ttatccgcat caagaagtaa                                    510
```

<210> SEQ ID NO 171
<211> LENGTH: 258
<212> TYPE: DNA
<213> ORGANISM: Escherichia coli

<400> SEQUENCE: 171

```
atgttccagc aagaagttac cattaccgct ccgaacggtc tgcacacccg ccctgctgcc    60
cagtttgtaa agaagctaa gggcttcact tctgaaatta ctgtgacttc aacggcaaa   120
agcgccagcg cgaaaagcct gtttaaactg cagactctgg cctgactca aggtaccgtt   180
gtgactatct ccgcagaagg cgaagacgag cagaaagcgg ttgaacatct ggttaaactg   240
atggcggaac tcgagtaa                                                 258
```

<210> SEQ ID NO 172
<211> LENGTH: 1254
<212> TYPE: DNA
<213> ORGANISM: Escherichia coli

<400> SEQUENCE: 172

```
atgtactatt taaaaaacac aaacttttgg atgttcggtt tattctttttt cttttacttt    60
tttatcatgg gagcctactt cccgttttc ccgatttggc tacatgacat caaccatatc   120
agcaaaagtg atacgggtat tatttttgcc gctatttctc tgttctcgct attattccaa   180
ccgctgtttg gtctgctttc tgacaaactc gggctgcgca atacctgct gtggattatt   240
accggcatgt tagtgatgtt tgcgccgttc tttattttta tcttcgggcc actgttacaa   300
tacaacattt tagtaggatc gattgttggt ggtatttatc taggcttttg ttttaacgcc   360
ggtgcgccag cagtagaggc atttattgag aaagtcagcc gtcgcagtaa tttcgaattt   420
ggtcgcgcgc ggatgtttgg ctgtgttggc tgggcgctgt gtgcctcgat tgtcggcatc   480
atgttcacca tcaataatca gtttgttttc tggctgggct ctggctgtgc actcatcctc   540
gccgttttac tctttttcgc caaaacggat gcgccctctt ctgccacggt tgccaatgcg   600
gtaggtgcca accattcggc atttagcctt aagctggcac tggaactgtt cagacagcca   660
aaactgtggg ttttgtcact gtatgttatt ggcgtttcct gcacctacga tgttttttgac   720
caacagtttg ctaatttctt tacttcgttc tttgctaccg gtgaacaggg tacgcgggta   780
tttggctacg taacgacaat gggcgaatta cttaacgcct cgattatgtt ctttgcgcca   840
ctgatcatta atcgcatcgg tgggaaaaac gccctgctgc tggctggcac tattatgtct   900
gtacgtatta ttggctcatc gttcgccacc tcagcgctgg aagtggttat tctgaaaacg   960
```

```
ctgcatatgt tgaagtacc gttcctgctg gtgggctgct ttaaatatat taccagccag    1020
tttgaagtgc gttttcagc gacgatttat ctggtctgtt tctgcttctt taagcaactg    1080
gcgatgattt ttatgtctgt actggcgggc aatatgtatg aaagcatcgg tttccagggc    1140
gcttatctgg tgctgggtct ggtggcgctg ggcttcacct taatttccgt gttcacgctt    1200
agcggccccg gcccgctttc cctgctgcgt cgtcaggtga atgaagtcgc ttaa          1254
```

<210> SEQ ID NO 173
<211> LENGTH: 1545
<212> TYPE: DNA
<213> ORGANISM: Escherichia coli

<400> SEQUENCE: 173

```
atggatgtca ttaaaaagaa acattggtgg caaagcgacg cgctgaaatg gtcagtgcta     60
ggtctgctcg gcctgctggt gggttacctt gttgttttaa tgtacgcaca aggggaatac    120
ctgttcgcca ttaccacgct gatattgagt tcagcggggc tgtatatttt cgccaatcgt    180
aaagcctacg cctggcgcta tgtttacccg gaatggctg aatgggatt attcgtcctc      240 ttccctctgg tctgcaccat cgccattgcc ttcaccaact acagcagcac taaccagctg    300
acttttgaac gtgcgcagga agtgttgtta gatcgctcct ggcaagcagg caaaacctat    360
aactttggtc tttacccggc gggcgatgag tggcaactgg cgctcagcga cggcgaaacc    420
ggcaaaaatt acctctccga cgcttttaaa tttggcggcg agcaaaaact gcaactgaaa    480
gaaacgaccg cccagcccga aggcgaacgc gcgaatctgc gcgtgattac ccagaatcgt    540
caggcgctga gtgacattac cgccattctg ccggatggca caaagtgat gatgagctcc    600 ctgcgccagt tttctggcac gcagccgctc tacacactcg acggtgacgg cacgttgacg    660
aataatcaga gcggcgtgaa atatcgtccg aataaccaaa ttggcttta ccagtccatt    720 accgccgacg gcaactgggg tgatgaaaag ctaagccccg gttacaccgt gaccaccggc    780
tggaaaaact ttacccgcgt ctttaccgac gaaggcattc agaaaccgtt cctcgccatt    840
ttcgtctgga ccgtggtgtt ctcgctgatc actgtcttt taacggtggc ggtcggcatg    900
gttctggcgt gtctggtgca gtgggaagcg ttgcgcggca aagcggtcta tcgcgtcctg    960
ctgattctgc cctacgcggt gccatcgttc atttcaatct tgattttcaa agggttgttt    1020
aaccagagct tcggtgaaat caacatgatg ttgagcgcgc tgtttggcgt gaagcccgcc    1080
tggttcagcg atccgaccac cgcccgcacg atgctaatta tcgtcaatac ctggctgggt    1140
tatccgtaca tgatgatcct ctgcatgggc ttgctgaaag cgattccgga cgatttgtat    1200
gaagcctcag caatggatgg cgcaggtccg ttccagaact tctttaagat tacgctgccg    1260
ctgctgatta aaccgctgac gccgctgatg atcgccagct tcgcctttaa ctttaacaac    1320
ttcgtgctga ttcaactgtt aaccaacggc ggcccggatc gtcttggcac gaccacgcca    1380
gccggttata ccgacctgct tgttaactac acctaccgca tcgcttttga aggcggcggg    1440
ggtcaggact tcggtctggc ggcagcaatt gccacgctga tcttcctgct ggtgggtgcg    1500
ctggcgatag tgaacctgaa agccacgcga atgaagtttg attaa                    1545
```

<210> SEQ ID NO 174
<211> LENGTH: 891
<212> TYPE: DNA
<213> ORGANISM: Escherichia coli

<400> SEQUENCE: 174

```
atggcaatgg tccaaccgaa atcgcaaaaa gctcgtttat ttattactca cctgctactg    60
ctactttta  tcgcagcgat tatgttcccg ctgctgatgg tcgtcgctat ctcgctgcgt   120
cagggaaact tgcgaccgg  cagcctgatc ccggagcaaa tctcctggga tcactggaaa   180
ctggcgttag gttttagcgt tgaacaggct gatggtcgca ttacgccacc gccattcccg   240
gtactgctgt ggctgtggaa ctcggtaaag gtcgccggga tttccgcgat tggcattgtg   300
gcgctctcca ccacctgcgc ctacgctttc gcccgtatgc gctttccagg caaagcgacg   360
ctgctgaaag gaatgctgat tttccagatg ttcccggcag tactttcact ggtcgcgttg   420
tatgcgttgt ttgatcgtct gggtgagtac attccattca ttggcctgaa tactcacggc   480
ggcgtaattt tcgcgtatct gggtgggatt gcgctgcatg tctggaccat caaaggctat   540
ttcgaaacca tcgacagttc gctggaagaa gctgctgcgc tggatggtgc acaccgtgg   600
caggccttcc gccttgtcct gttgccgctg tcagtaccga ttctggcggt ggtattcatc   660
ctgtcgttta tcgctgccat tactgaagtt ccggtcgcgt cgctgttact gcgtgacgta   720
aacagctaca ccctggccgt ggggatgcag caatacctca acccgcaaaa ctacctgtgg   780
ggtgactttg ccgccgctgc cgtgatgtct gcattaccga tcaccatcgt cttcttgctg   840
gctcaacgct ggctggtcaa cggcctgacg gcaggtggtg tgaaaggtta a          891
```

<210> SEQ ID NO 175
<211> LENGTH: 6546
<212> TYPE: DNA
<213> ORGANISM: Salmonella typhimurium

<400> SEQUENCE: 175

```
atgaatgcaa aagtttgggt tctgggcgac gcggtggtgg acctgctgcc ggagagcgaa    60
gggcgcctgc tgcagtgccc tggaggcgcg ccggctaacg tggcggtagg ggttgcccgc   120
cttggcggca acagcggatt tatcggcgcc gtcggcggtg acccgtttgg ccgctacatg   180
cgtcatacccc tgcaacagga gcaggtcgac gtcagccata tgtatctcga cgatcagcac   240
cgcacgtcca ctgtggtcgt cgaccttgac gaccagggg  aacgcacctt tacctttatg   300
gtacgcccca cgcggacct  gttcctggtt gaagaagacc tgccacagtt tgccgccgga   360
cagtggttgc acgtctgctc catcgcgctc agcgccgagc ccagccgtag cactaccttc   420
gcggcgatgg agagcatcag gtctgccggc ggtcgggtca gctttgaccc taatattcgt   480
cccgatctct ggcaggatca ggctttgctg ctagcctgcc tcgatcgcgc tttgcacatg   540
gccaacgtgg taaagctatc ggaagaggag ctggtcttca tcagcagcag taatgattta   600
gcatacggaa tcgccagcgt aacggagcgc tatcagccag aattgctact ggtgacccgg   660
ggcaaagcgg gggtgcttgc cgcgtttcag cagaagttta cccattttcaa cgcccggcct   720
gtggccagcg tggacaccac cggcgcggga gacgcatttg tcgccggact gctcgccagc   780
cttgcggcta cgggatgcc  aacggacatg accgcactgg aaccgacact cacgcttgca   840
cagacctgcg gcgccctggc caccacagcc aaaggtgcga tgaccgcctt gccttatcag   900
cgcgatctca accgtcagtt ttaatcctta agccgctttg cgcggctca  ctttgttgca   960
tgcatcacat ttattaaacc ggtttagcat atttgtttta agaaaaacaa aggtcgggct  1020
taacatagcg cctaaaccgg tttagcaaaa attataattt tccatttta  cttttgggat  1080
gccaacagca tgtacagaaa aagcacactt gcgatgctta tcgctttgct aaccagcgct  1140
gcctcagccc atgcgcaaac ggatataagc accattgaag cccgactcaa cgcgctgaa   1200
aaacgcctgc aggaggcaga aacagggcg  caaacggcgg aaaaccgcgc cggggcggcg  1260
```

```
gagaaaaaag ttcagcaact caccgcgcag cagcaaaaaa accagaactc gactcaggaa    1320
gtggctcagc gtaccgccag acttgagaaa aaagccgatg acaaaagcgg atttgagttt    1380
cacggttacg cccgctccgg cgtgataatg aatgattccg gcgccagcac caaatccgga    1440
gcctacataa cgccggcagg tgaaaccggc ggagctatcg gccgtctggg aaaccaggcc    1500
gataccfatg ttgaaatgaa tcttgaacat aagcagaccc tggataatgg ggccacgacc    1560
cgctttaagg tgatggtcgc cgacgggcaa acctcttata cgactggac tgcaagcacc     1620
agcgatctga acgttcgtca ggcctttgtc gaattgggta acctgccgac gttcgctggg    1680
ccatttaagg gctccaccct gtgggccggg aaacgtttcg accgcgacaa tttcgatatt    1740
cactggattg actctgatgt cgtgttcctc gccggtaccg tggtggtat ctatgacgtg     1800
aagtggaacg acggcctgcg gagtaatttc tccctgtacg ggcgtaactt cggcgacatt    1860
gatgattcca gcaacagcgt gcagaactat atcctcacca tgaatcactt cgcaggtccg    1920
ctgcagatga tggtcagcgg tctgcgggcg aaggataacg acgagcgtaa agatagcaac    1980
ggcaatctgg caaaaggcga tgcggcaaac accggcgtgc atgcgctgct cggcctgcat    2040
aacgacagtt tctacggcct gcgcgacggt agcagtaaaa ccgctctgct ttatggtcat    2100
ggtctgggcg cagaggttaa aggtatcgga tctgatggcg cacttcgtcc gggagccgac    2160
acatggcgca ttgccagtta cggcaccacg ccgctcagcg aaaactggtc tgttgccccg    2220
gcaatgctgg cgcaacgcag taaagaccgc tatgccgatg gcgacagcta tcagtgggca    2280
acattcaacc tgcgtctgat tcaggcaatc aatcagaatt cgctctcgc ctacgaaggc     2340
agctaccagt acatggatct taaacccgaa ggttataacg atcgtcaggc ggtgaacggt    2400
agcttctaca agctcacctt cgccccgaca tttaaggtcg gcagtatcgg tgatttcttc    2460
agtcgcccgg agattcgttt ctatacctcc tggatggact ggagcaaaaa actgaataat    2520
tacgccagcg acgacgccct gggcagtgac ggttttaact cgggcggcga atggtctttc    2580
ggtgtgcaga tggaaacctg gttctgacgc ttacgcctga tgacaggaat agccgggggt    2640
cagagcatct ttgtcacccc ggactcaact aagacgcaga aaaagcgctc ccgtgaacgc    2700
gggacgacaa cataaaaatg tttaagcctt aagagggtac tatggatttt gaacagattt    2760
cctgctcgct gcttccgctt cttggaggca agaaaatat cgccagcgcc gcgcactgcg     2820
ccacgcgcct gcgcctggtg ctggtcgatg attcgctggc cgaccagcag gccatcggca    2880
aagttgaagg ggtgaagggc tgttttcgta atgccggaca gatgcagatt attttcggca    2940
ccggggtggt aaataaggtc tacgctgcct ttactcaggc ggcgggtatt agcgaatcca    3000
gcaaatcgga agccgccgac atcgcggcaa aaaagctcaa tccgttccag cgcatcgccc    3060
gcctgctatc aaacatcttc gtgccgataa tccctgccat cgtcgcctct ggtctgctga    3120
tgggcctgct gggaatggtc aaaacatacg ctgggttga cccgggcaac gccatctaca     3180
tcatgctgga tatgtgcagc tcggcggcat ttatcattct gccgattctg attggcttta    3240
ccgccgcccg cgaattcggc ggtaatcctt atctcggcgc gacgcttggc ggcattctga    3300
ctcatccagc gctgactaac gcctggggcg tggccgcggg tttccacacc atgaactttt    3360
tcggcttcga aattgccatg atcggctatc agggtacggt gttccggta ctgctggcag     3420
tatggtttat gagcatcgtt gagaagcagt tgcgtcgcgc aatccccgat gccctggatt    3480
tgatcctgac gccgttcctg acggtgatta tatccggttt tatcgccctg ttgattatcg    3540
gcccggccgg tcgcgcactg ggcgacggta tctcgtttgt cctcagcacc ctgattagcc    3600
```

```
acgccggctg gctcgccggg ttactgtttg gcggtctcta ttcagttatc gtcattaccg    3660
gtattcatca cagcttccat gcggttgaag ccgggttgct gggcaatccc tccatcggcg    3720
tcaacttcct gctgccgatt tgggcgatgg ccaacgtcgc tcagggcgga gcctgtctgg    3780
cggtgtggtt caaaaccaaa gatgcaaaaa ttaaagccat tactctgccc tcggcgtttt    3840
ccgccatgct gggcatcacc gaggcggcga tttttggtat taacctgcgc tttgtgaagc    3900
catttattgc ggcgctgatt ggtggtgcgg cgggcggcgc atgggtggta tctgtacacg    3960
tctacatgac cgcggtcggc ttgacagcga tccccggcat ggccatcgtg caggccagtt    4020
cgctgttgaa ctacattatc gggatggtta tcgcctttgg cgtcgccttt acggtctccc    4080
tggttttgaa atacaaaacg gacgctgaat aatgtctctt ccatcacgac tgcctgcgat    4140
tttgcaggcc gtaatgcagg ccagccgcg cgcgctggcc gatagccact atccgcgctg    4200
gcaccatgcg ccggtcaccg ggctgatgaa cgaccccaac ggctttatcg aatttgccgg    4260
acgctatcat ctgtttttatc agtggaaccc gctcgcctgc gatcatacgt ttaagtgctg    4320
ggcgcactgg agttccatcg atctgctgca ctggcagcat gagcccattg cgctgatgcc    4380
ggacgaagag tatgaccgta acggctgcta ctccggcagc gcggtggata caacggtac    4440 gcttaccctg tgctataccg gcaacgtgaa gtttgccgag ggagggcgaa ccgcctggca    4500
atgcctggca acggaaaacg ctgacggcac cttccgcaaa atcggtccgg tcctgccgct    4560
gccggagggc tacaccggcc acgtgcgcga cccaaaagtc tggcgacacg aagacctgtg    4620
gtacatggtg ctgggcgcgc aggatcggca aaagcgcggc aaggtgctgc tgttcagctc    4680
tgcggatctc catcagtgga cgagtatggg tgaaatcgcc ggccacggca tcaatggcct    4740
cgacgacgtc ggctatatgt gggagtgccc ggatcttttt ccactcggcg accagcatat    4800
tctaatctgc tgtccgcagg ggattgcccg tgaggaagag tgctacctga cacctaccc    4860 ggcagtatgg atgcgggcg agtttgatta cgctgctggc gctttcagac acggcgaact    4920
gcacgaactg gacgccgggt ttgagttcta cgccccgcaa accatgctta ccagtgatgg    4980
ccgtcgtctg ctggtcggct ggatgggcgt gccggagggc gaagagatgc ttcagccgac    5040
cctgaacaac ggctggatcc atcagatgac ctgcctgcgt gagctggagt ttatcaacgg    5100
tcagctctat cagcgtccgc tacgggaact gagcgccctg cgcggtgaag cgaacggctg    5160
gtcggggaac gccctgccgc tggcaccgat ggaaatcgat ttgcaaaccc gcggggggcga    5220 tatgttgagc ctcgattttg gcggcgtatt aacccttgag tgcgatgcca gcggactccg    5280
cctggcccga cgcagtctcg ccagtgacga gatgcattat cgttactggc gcggaaacgt    5340
ccgctcgctg cgtgttttca tcgaccagtc gagcgtggag attttcataa acggcggtga    5400
aggggtgatg agcagccgct acttcccggc ctgctccggt cagctaacat tctccggcat    5460
cacgccggac gcattctgct actggccgct gcgaacttgc atggtagaat aagcgttttg    5520
cttcaggctc atggcgtcgt aatgaaaacc aaacgcgtaa ccattaaaga tatagccgaa    5580
caggctggcg tctccaaagc gaccgccagc ttggtactga atggtcgtgg caaggagctg    5640
cgcgtggcgc aggaaacgcg tgagcgcgta ctgtcgattg cccgtaagca tcactatcag    5700
ccaagcattc atgcccgctc gctgcgcaac aaccgcagcc acaccatcgg gctggtggtg    5760
ccggagatca ccaaccacgg ctttgcggtc tttgcccatg agctggagat gctgtgccgc    5820
gaggcgggcg tccagctgtt gatctcttgt actgatgaaa accccggtca ggagagcgtg    5880
gtggtcaata atatgattgc cgccaggtc gacgggatga tcgtcgcttc ctgtatgcac    5940
aacgatgccg actatctcaa actcagccaa cagctgccag tggtgctgtt tgaccggtgc    6000
```

```
cccaatgaaa gcgcgctgcc gctggtaatg accgattcga ttaccccaac ggcggaactg    6060
atttcccgca tcgcgcctca gcatagcgat gagttctggt ttttaggcgg tcaggcgcgt    6120
ctgtcgccct cccgcgatcg tctgaccggg ttcacgcagg gtttggctca ggcgggtatt    6180
gccctgcgcc cggaatgggt gatcaacggc aattaccacc ccagctccgg ctatgagatg    6240
tttgccgcac tctgcgcgcg ccttgggcgg ccgcctaagg cgctattcac cgccgcctgc    6300
gggctgctcg aagggttctc gcgctatatg agccagcacc atttactcga ttccgatatt    6360
catctgacga gctttgacga tcactatctt tatgattcgc tgtcgctgcg tatcgacact    6420
gtccagcagg ataatcgcca gctggcctgg cactgctacg atctgataag ccagctgatc    6480
gagggcgata cgcccgaaac gctacaacgc tacctgcccg caaccctgca gtttcggcat    6540
cagtaa                                                                6546
```

<210> SEQ ID NO 176
<211> LENGTH: 4885
<212> TYPE: DNA
<213> ORGANISM: Escherichia coli

<400> SEQUENCE: 176

```
ctatattgct gaaggtacag gcgtttccat aactatttgc tcgcgttttt tactcaggaa      60
gaaaatgcca atagcaaca tcaggcagac aatacccgaa attgcgaaga aaactgtctg     120
gtagcctgcg tggtcaaaga gtatcccagt cggcgttgaa agcagcacaa tcccaagcga     180
actggcaatt tgaaaaccaa tcagaaagat cgtcgacgac aggcgcttat caaagtttgc     240
cacgctgtat ttgaagacgg atatgacaca agtggaacc tcaatggcat gtaacagctt      300
cactaatgaa ataatccagg ggttaacgaa caacgcgcag gaaaggatac gcaacgccat     360
aatcacaaca ccgataagta atgcattttt tggccctacc cgattcacaa agaaaggaat     420
aatcgccatg cacagcgctt cgagtaccac ctggaatgag ttgagataac catacaggcg     480
cgttcctaca tcgtgtgatt cgaataaacc tgcataaaag acaggaaaga gttgttgatc     540
aaaaatgtta tagaaagacc acgtccccac aataaatatg acgaaaaccc agaagtttcg     600
atccttgaaa actgcgataa aatcctctct ttttaccccct cccgcatccg ccgctatgca     660
ctggtgatcc ttatctttaa aacgcatgtt gatcatcata atacagcgc caaatagcga      720 gaccaaccag aagttgatat ggggactgat actaaaaaat ataccggcaa agaacgcgcc     780
aatagcatag ccaaaagatc cccaggcgcg cgctgttcca tattcgaaat gaaaatttcg     840
cgccattttt tcggtgaagc tgtcaagcaa accgcatccc gccagatacc ccaggccaaa     900
aaagagcgcc cccagaatta gacctacaga aaaattgctt tgcagtaacg gttcataaac     960
gtaaatcata aacggtccgg tcaagaccag aatgaaactc atacaccaga tgagcggttt    1020
cttcagaccg agtttatcct gaacgatgcc gtagaacatc ataaatagaa tgctggtaaa    1080
ctggttgacc gaataaagtg tacctaattc cgtccctgtt aatcctagat gtcctttcag    1140
ccaaatagcg tataacgacc accacagcga ccaggaaata aaaagagaa atgagtaact    1200 ggatgcaaaa cgatagtacg catttctgaa tggaatattc agtgccataa ttacctgcct    1260
gtcgttaaaa aattcatgtc ctatttagag ataagagcgg cctcgccgtt tacttctcac    1320
tttccagttc ttgtcgacat ggcagcgctg tcattgcccc tttcgctgtt actgcaagcg    1380
ctccgcaacg ttgagcgaga tcgataattc gtcgcatttc tctctcatct gtagataatc    1440
ccgtagagga cagacctgtg agtaacccgg caacgaacgc atctcccgcc ccagtgctat    1500
```

```
cgacacaatt cacagacatt ccagcaaaat ggtggacttg tcctcgataa cagaccacca    1560 cccccttctgc acctttagtc accaacagca tggcgatctc atactctttt gccagggcgc    1620
atatatcccg atcgttctgt gttttccac tgataagtcg ccattcttct tccgagagct     1680
tgacgacatc cgccagttgt agcgcctgcc gcaaacacaa gcggagcaaa tgctcgtctt    1740
gccatagatc ttcacgaata ttgggatcga agctgacaaa acctccggca tgccggatcg    1800
ccgtcatcgc agtaaatgcg ctggtacgcg aaggctcggc agacaacgca attgaacaga    1860
gatgtaacca ttcgccatgt cgccagcagg gcaagtctgt cgtctctaaa aaagatcgg     1920 cactggggcg gaccataaac gtaaatgaac gttctccttg atcgttcaga tcgacaagca    1980
ccgtggatgt ccggtgccat tcatcttgct tcagatacg gatatcgaca ccctcagtta     2040
gcagcgttct ttgcattaac gcaccaaaag gatcatcacc gacccgacct ataaacccac    2100
ttgttccgcc taatctggcg attcccaccg caacgttagc tggcgcgccg ccaggacaag    2160
gcagtagccg cccgtctgat tctggcaaga gatctacgac cgcatcccct aaaacccata    2220
ctttggctga cattttttc ccttaaattc atctgactta cgcatagtga taaacctctt     2280
tttcgcaaaa tcgtcatgga tttactaaaa catgcatatt cgatcacaaa acgtcatagt    2340
taacgttaac atttgtgata ttcatcgcat ttatgaaagt aagggacttt attttttataa   2400 aagttaacgt taacaattca ccaaatttgc ttaaccagga tgattaaaat gacgcaatct    2460
cgattgcatg cggcgcaaaa cgcactagca aaacttcacg agcgccgagg taacactttc    2520
tatccccatt ttcacctcgc gcctcctgcc gggtggatga acgatccaaa cggcctgatc    2580
tggtttaacg atcgttatca cgcgttttat caacatcacc cgatgagcga cactggggg    2640 ccaatgcact ggggacatgc caccagcgac gatatgatcc actggcagca tgagcctatt    2700
gcgctagcgc caggagacga gaatgacaaa gacgggtgtt tttcaggtag tgctgtcgat    2760
gacaatggtg tcctctcact tatctacacc ggacacgtct ggctcgatgg tgcaggtaat    2820
gacgatgcaa ttcgcgaagt acaatgtctg gctaccagtc gggatggtat tcatttcgag    2880
aaacagggtg tgatcctcac tccaccagaa ggcatcatgc acttccgcga tcctaaagtg    2940
tggcgtgaag ccgacacatg gtggatggta gtcggggcga aagacccagg caacacgggg    3000
cagatcctgc tttatcgcgg cagttcattg cgtgaatgga ctttcgatcg cgtactggcc    3060
cacgctgatg cgggtgaaag ctatatgtgg gaatgtccgg acttttttcag ccttggcgat   3120 cagcattatc tgatgttttc cccgcaggga atgaatgccg agggatacag ttatcgaaat    3180
cgctttcaaa gtggcgtaat acccggaatg tggtcgccag gacgacttt tgcacaatcc     3240 gggcatttta ctgaacttga taacgggcat gacttttatg caccacaaag ctttgtagcg    3300
aaggatggtc ggcgtattgt tatcggctgg atggatatgt gggaatcgcc aatgccctca    3360
aaacgtgaag gctgggcagg ctgcatgacg ctggcgcgcg agctatcaga gagcaatggc    3420
aaactcctac aacgcccggt acacgaagct gagtcgttac gccagcagca tcaatctatc    3480
tctccccgca caatcagcaa taaatatgtt ttgcaggaaa acgcgcaagc agttgagatt    3540
cagttgcagt gggcgctgaa gaacagtgat gccgaacatt acggattaca gctcggcgct    3600
ggaatgcggc tgtatattga taaccatatct gagcgacttg ttttgtggcg gtattaccca    3660
cacgagaatt tagatggcta ccgtagtatt cccctcccgc agggtgacat gctcgcccta    3720 aggatatta tcgatacatc atccgtggaa gtatttatta acgacgggga ggcggtgatg     3780
agtagccgaa tatatccgca gccagaagaa cgggaactgt cgctctatgc ctcccacgga    3840
gtggctgtgc tgcaacatgg agcactctgg caactgggtt aacataatat caggtggaac    3900
```

| | |
|---|---|
| aacggatcaa cagcgggcaa gggatccgcg tcactcttcc cccttcacga ccttcaataa | 3960 |
| tatgcaatgc agcttccgc ccgataatgt catgtggaag ctgaattgtg gtcagcggcg | 4020 |
| gtaaaaacag atgcccgacg ccaaccagat tatcaaagcc cattacggcg acatcctgcg | 4080 |
| ggatacgtac cccttcgcc aaagaacct gataagccac aaaggctgcg cgatcgttac | 4140 |
| cacatatcag aacatcaaaa tctggtttgc ccgatttgaa gtgggcattg agtaaacttg | 4200 |
| cgagatcggt gtagtgatca tcacctgttg ccatgtgaaa ttgtttcacc tcagccagat | 4260 |
| ctcgtccagc atcacgccag gcctgctcaa atccctgccg acgataccct gttgccaacg | 4320 |
| cactttccgg tagccagaag cataacggtt gacgatagcc cgccgcgagc aaatgctgtg | 4380 |
| ttgattcata ttgtgcagtg taatcatcag ggatataact gggtaacgct gggtcatccg | 4440 |
| ccacacagtt cgccaataca atattttcac catacagaga ctcaggcagc gtgatatgtc | 4500 |
| gcagccccat tgtagtatag ataatgccat ccggacggtg ggcaagcagc tgacgtgccg | 4560 |
| cgcgggcagc gtcatcttca gaaaaaatat tgattaaaaa actattccag ccgaactcgc | 4620 |
| tggcggtttg ctcaatggca agcagaatat caacagagaa aggagtggta gcagtgtcct | 4680 |
| gcgccagcac ggcgagagtc gacggcttac gtccttgagc gcgcatctta cgggcggaaa | 4740 |
| gatcaggaac ataattcagg gtctggattg cctgcaatac gcggtcacgc gttgcaggac | 4800 |
| gcacagattc tgcattatgc atcacccggg agactgtcat catcgacact cccgccaggc | 4860 |
| gtgcgacatc ctttaatgaa gccat | 4885 |

<210> SEQ ID NO 177
<211> LENGTH: 3771
<212> TYPE: DNA
<213> ORGANISM: Escherichia coli

<400> SEQUENCE: 177

| | |
|---|---|
| atgaaaataa agaacattct actcacccctt tgcacctcac tcctgcttac caacgttgct | 60 |
| gcacacgcca aagaagtcaa aataggtatg gcgattgatg atctccgtct tgaacgctgg | 120 |
| caaaaagatc gagatatctt tgtgaaaaag gcagaatctc tcggcgcgaa agtatttgta | 180 |
| cagtctgcaa atggcaatga agaaacacaa atgtcgcaga ttgaaaacat gataaaccgg | 240 |
| ggtgtcgatg ttcttgtcat tattccgtat aacggtcagg tattaagtaa cgttgtaaaa | 300 |
| gaagccaaac aagaaggcat taagtatta gcttacgacc gtatgattaa cgatgcggat | 360 |
| atcgatttt atatttcttt cgataacgaa aaagtcggtg aactgcaggc aaaagccctg | 420 |
| gtcgatattg ttccgcaagg taattacttc ctgatgggcg gctcgccggt agataacaac | 480 |
| gccaagctgt tccgcgccgg acaaatgaaa gtgttaaaac cttacgttga ttccggaaaa | 540 |
| attaaagtcg ttggtgacca atgggttgat ggctggttac cggaaaacgc attgaaaatt | 600 |
| atggaaaacg cgctaaccgc caataataac aaaattgatg ctgtagttgc ctcaaacgat | 660 |
| gccaccgcag gtgggcaat tcaggcatta agcgcgcaag gttatcagg gaaagtagca | 720 |
| atctccggcc aggatgcgga tctcgcaggt attaaacgta ttgctgccgg tacgcaaact | 780 |
| atgacggtgt ataaacctat tacgttgttg gcaaatactg ccgcagaaat tgccgttgag | 840 |
| ttgggcaatg gtcaggaacc aaaagcagat accacactga ataatggcct gaaagatgtc | 900 |
| ccctccccgc tcctgacacc gatcgatgtg aataaaaaca acatcaaaga tacggtaatt | 960 |
| aaagacggat tccacaaaga gagcgagctg taagcgttac gccccagcgc ggagcggggg | 1020 |
| cgtgatttct ctccatgccg cgtgaatgaa ttggcttagg tggagtcgtt atgccttatc | 1080 |

```
tacttgaaat gaagaacatt accaaaacct tcggcagtgt gaaggcgatt gataacgtct   1140
gcttgcggtt gaatgctggc gaaatcgtct cactttgtgg ggaaaatggg tctggtaaat   1200
caacgctgat gaaagtgctg tgtggtattt atccccatgg ctcctacgaa ggcgaaatta   1260
tttttgcggg agaagagatt caggcgagtc acatccgcga taccgaacgc aaaggtatcg   1320
ccatcattca tcaggaattg gccctggtga agaattgac cgtgctggaa aatatcttcc    1380
tgggtaacga aataacccac aatggcatta tggattatga cctgatgacg ctacgctgtc   1440
agaagctgct cgcacaggtc agtttatcca tttcacctga tacccgcgtt ggcgatttag   1500
ggcttgggca acaacaactg gttgaaattg ccaaggcact aataaacag gtgcgcttgt    1560
taattctcga tgaaccgaca gcctcattaa ctgagcagga aacgtcgatt ttactggata   1620
ttattcgcga tctacaacag cacggtatcg cctgtattta tatttcgcac aaactcaacg   1680
aagtcaaagc gatttccgat acgatttgcg ttattcgcga cggacagcac attggtacgc   1740
gtgatgctgc cggaatgagt gaagacgata ttatcaccat gatggtcggg cgagagttaa   1800
ccgcgcttta ccctaatgaa ccacatacca ccggagatga aatattacgt attgaacatc   1860
tgacggcatg gcatccggtt aatcgtcata ttaaacgagt taatgatgtc tcgttttccc   1920
tgaaacgtgg cgaaatattg ggtattgccg gactcgttgg tgccggacgt accgagacca   1980
ttcagtgcct gtttggtgtg tggcccggac aatgggaagg aaaaatttat attgatggca   2040
aacaggtaga tattcgtaac tgtcagcaag ccatcgccca ggggattgcg atggtccccg   2100
aagacagaaa gcgcgacggc atcgttccgg taatggcggt tggtaaaaat attaccctcg   2160
ccgcactcaa taaatttacc ggtggcatta gccagcttga tgacgcggca gagcaaaaat   2220
gtattctgga atcaatccag caactcaaag ttaaaacgtc gtccccgac cttgctattg    2280
gacgtttgag cggcggcaat cagcaaaaag cgatcctcgc tcgctgtctg ttacttaacc   2340
cgcgcattct cattcttgat gaacccacca ggggtatcga tattggcgcg aaatacgaga   2400
tctacaaatt aattaaccaa ctcgtccagc agggtattgc cgttattgtc atctcttccg   2460
aattacctga agtgctcggc cttagcgatc gtgtactggt gatgcatgaa gggaaactaa   2520
aagccaacct gataaatcat aacctgactc aggagcaggt gatggaagcc gcattgagga   2580
gcgaacatca tgtcgaaaag caatccgtct gaagtgaaat tggccgtacc gacatccggt   2640
ggcttctccg gctgaaatc actgaatttg caggtcttcg tgatgattgc agctatcatc    2700
gcaatcatgc tgttctttac ctggaccacc gatggtgcct acttaagcgc ccgtaacgtc   2760
tccaacctgt tacgccagac cgcgattacc ggcatcctcg cggtaggaat ggtgttcgtc   2820
ataatttctg ctgaaatcga cctttccgtc ggctcaatga tggggctgtt aggtggcgtc   2880
gcggcgattt gtgacgtctg gttaggctgg cctttgccac ttaccatcat tgtgacgctg   2940
gttctgggac tgcttctcgg tgcctggaac ggatggtggg tcgcgtaccg taaagtccct   3000
tcatttattg tcaccctcgc gggcatgttg gcatttcgcg gcatactcat ggcatcacc    3060
aacggcacga ctgtatcccc caccagcgcc gcgatgtcac aaattgggca agctatctc    3120
cccgccagta ccggcttcat cattggcgcg cttggcttaa tggcttttgt tggttggcaa   3180
tggcgcggaa gaatgcgccg tcaggctttg gtttacagt ctccggcctc taccgcagta    3240
gtcggtcgcc aggctttaac cgctatcatc gtattaggcg caatctggct gttgaatgat   3300
taccgtggcg ttcccactcc tgttctgctg ctgacgttgc tgttactcgg cggaatgttt   3360
atggcaacgc ggacggcatt tggacgacgc atttatgcca tcggcggcaa tctgaaagca   3420
gcacgtctct ccgggattaa cgttgaacgc accaaacttg ccgtgttcgc gattaacgga   3480
```

```
ttaatggtag ccatcgccgg attaatcctt agttctcgac ttggcgctgg ttcaccttct    3540
gcgggaaata tcgccgaact ggacgcaatt gcagcatgcg tgattggcgg caccagcctg    3600
gctggcggtg tgggaagcgt tgccggagca gtaatggggg catttatcat ggcttcactg    3660
gataacggca tgagtatgat ggatgtaccg accttctggc agtatatcgt taaaggtgcg    3720
attctgttgc tggcagtatg gatggactcc gcaaccaaac gccgttcttg a             3771
```

<210> SEQ ID NO 178
<211> LENGTH: 1395
<212> TYPE: DNA
<213> ORGANISM: Escherichia coli

<400> SEQUENCE: 178

```
atgcctgacg ctaaaaaaca ggggcggtca acaaggcaa tgacgttttt cgtctgcttc      60
cttgccgctc tggcgggatt actctttggc ctggatatcg gtgtaattgc tggcgcactg    120
ccgtttattg cagatgaatt ccagattact tcgcacacgc aagaatgggt cgtaagctcc    180
atgatgttcg gtgcggcagt cggtgcggtg gcagcggct ggctctcctt taaactcggg    240
cgcaaaaaga gcctgatgat cggcgcaatt ttgtttgttg ccggttcgct gttctctgcg    300
gctgcgccaa acgttgaagt actgattctt tcccgcgttc tactggggct ggcggtgggt    360
gtggcctctt ataccgcacc gctgtacctc tctgaaattg cgccggaaaa aattcgtggc    420
agtatgatct cgatgtatca gttgatgatc actatcggga tcctcggtgc ttatctttct    480
gataccgcct tcagctacac cggtgcatgg cgctggatgc tgggtgtgat tatcatcccg    540 gcaatttttgc tgctgattgg tgtcttcttc ctgccagaca gcccacgttg gtttgccgcc    600
aaacgccgtt ttgttgatgc cgaacgcgtg ctgctacgcc tgcgtgacac cagcgcggaa    660
gcgaaacgcg aactggatga atccgtgaa agtttgcagg ttaaacagag tggctgggcg    720
ctgtttaaag agaacagcaa cttccgccgc gcggtgttcc ttggcgtact gttgcaggta    780
atgcagcaat tcaccgggat gaacgtcatc atgtattacg cgccgaaaat cttcgaactg    840
gcgggttata ccaacactac cgagcaaatg tgggggaccg tgattgtcgg cctgaccaac    900
gtacttgcca cctttatcgc aatcggcctt gttgaccgct ggggacgtaa accaacgcta    960
acgctgggct tcctggtgat ggctgctggc atgggcgtac tcggtacaat gatgcatatc   1020
ggtattcact ctccgtcggc gcagtatttc gccatcgcca tgctgctgat gtttattgtc   1080
ggttttgcca tgagtgccgg tccgctgatt tgggtactgt gctccgaaat tcagccgctg   1140
aaaggccgcg attttggcat cacctgctcc actgccacca actggattgc caacatgatc   1200
gttggcgcaa cgttcctgac catgctcaac acgctgggta acgccaacac cttctgggtg   1260
tatgcggctc tgaacgtact gtttatcctg ctgacattgt ggctggtacc ggaaaccaaa   1320
cacgtttcgc tggaacatat tgaacgtaat ctgatgaaag tcgtaaact gcgcgaaata   1380 ggcgctcacg attaa                                                    1395
```

<210> SEQ ID NO 179
<211> LENGTH: 1422
<212> TYPE: DNA
<213> ORGANISM: Zymomonas mobilis

<400> SEQUENCE: 179

```
atgagttctg aaagtagtca gggtctagtc acgcgactag ccctaatcgc tgctataggc     60
ggcttgcttt tcggttacga ttcagcggtt atcgctgcaa tcggtacacc ggttgatatc    120
```

```
cattttattg ccccctcgtca cctgtctgct acggctgcgg cttcccttc tgggatggtc      180
gttgttgctg ttttggtcgg ttgtgttacc ggttctttgc tgtctggctg gattggtatt      240
cgcttcggtc gtcgcggcgg attgttgatg agttccattt gtttcgtcgc cgccggtttt      300
ggtgctgcgt taaccgaaaa attatttgga accggtggtc cggctttaca aattttttgc      360
tttttccggt ttcttgccgg tttaggtatc ggtgtcgttt caaccttgac cccaacctat      420
attgctgaaa ttcgtccgcc agacaaacgt ggtcagatgg tttctggtca gcagatggcc      480
attgtgacgg gtgctttaac cggttatatc tttacctggt tactggctca tttcggttct      540
atcgattggg ttaatgccag tggttggtgc tggtctccgg cttcagaagg cctgatcggt      600
attgccttct tattgctgct gttaaccgca ccggatacgc cgcattggtt ggtgatgaag      660
ggacgtcatt ccgaggctag caaaatcctt gctcgtctgg aaccgcaagc cgatcctaat      720
ctgacgattc aaaagattaa agctggcttt gataaagcca tggacaaaag cagcgcaggt      780
ttgtttgctt ttggtatcac cgttgttttt gccggtgtat ccgttgctgc cttccagcag      840
ttagtcggta ttaacgccgt gctgtattat gcaccgcaga tgttccagaa tttaggtttt      900
ggagctgata cggcattatt gcagaccatc tctatcggtg ttgtgaactt catcttcacc      960
atgattgctt cccgtgttgt tgaccgcttc ggccgtaaac ctctgctat ttggggtgct     1020
ctcggtatgg ctgcaatgat ggctgtttta ggctgctgtt tctggttcaa agtcggtggt     1080
gttttgcctt tggcttctgt gcttcttat attgcagtct ttggtatgtc atggggccct     1140
gtctgctggg ttgttctgtc agaaatgttc ccgagttcca tcaagggcgc agctatgcct     1200
atcgctgtta ccggacaatg gttagctaat atcttggtta acttcctgtt taaggttgcc     1260
gatggttctc cagcattgaa tcagactttc aaccacggtt tctcctatct cgttttcgca     1320
gcattaagta tcttaggtgg cttgattgtt gctcgcttcg tgccggaaac caaaggtcgg     1380
agcctggatg aaatcgagga gatgtggcgc tcccagaagt ag                        1422

<210> SEQ ID NO 180
<211> LENGTH: 984
<212> TYPE: DNA
<213> ORGANISM: Zymomonas mobilis

<400> SEQUENCE: 180
atggaaattg ttgcgattga catcggtgga acgcatgcgc gtttctctat tgcggaagta       60
agcaatggtc gggttctttc tcttggagaa gaaacaactt ttaaaacggc agaacatgct      120
agcttgcagt tagcttggga acgtttcggt gaaaaactgg gtcgtcctct gccacgtgcc      180
gcagctattg catgggctgg cccggttcat ggtgaagttt aaaacttac caataaccct      240
tgggtattaa gaccagctac tctgaatgaa aagctggaca tcgatacgca tgttctgatc      300
aatgacttcg gcgcggttgc ccacgcggtt gcgcatatgg attcttctta tctggatcat      360
atttgtggtc ctgatgaagc gcttcctagc gatggtgtta tcactattct ggtccgggga      420
acgggcttgg gtgttgccca tctgttgcgg actgaaggcc gttatttcgt catcgaaact      480
gaaggcggtc atatcgactt tgctccgctt gacagacttg aagacaaaat tctggcacgt      540
ttacgtgaac gtttccgccg cgtttctatc gaacgcatta tttctggccc gggtcttggt      600
aatatctacg aagcactggc tgccattgaa ggcgttccgt tcagcttgct ggatgatatt      660
aaattatgcc agatggcttt ggaaggtaaa gacaaccttg ctgaagccgc tttggatcgc      720
ttctgcttga gccttggcgc tatcgctggt gatcttgctt tggcacaggg tcgaaccagt      780
gttgttattg gcggtggtgt cggtcttcgt atcgcttccc atttgccaga atctggtttc      840
```

```
cgtcagcgct ttgtttcaaa aggacgcttt gaacgcgtca tgtccaagat tccggttaag    900
ttgattactt atccgcagcc tggactgttg ggtgcgcagc tgcctatgcc aacaaatatt    960
ctgaagttga ataatatttt ttaa                                          984
```

<210> SEQ ID NO 181
<211> LENGTH: 966
<212> TYPE: DNA
<213> ORGANISM: Escherichia coli

<400> SEQUENCE: 181

```
atgacaaagt atgcattagt cggtgatgtg ggcggcacca acgcacgtct tgctctgtgt     60
gatattgcca gtggtgaaat ctcgcaggct aagacctatt cagggcttga ttaccccagc    120
ctcgaagcgg tcattcgcgt ttatcttgaa aacataagg tcgaggtgaa agacggctgt     180
attgccatcg cttgcccaat taccggtgac tgggtggcga tgaccaacca tacctgggcg    240
ttctcaattg ccgaaatgaa aaagaatctc ggttttagcc atctggaaat tattaacgat    300
tttaccgctg tatcgatggc gatcccgatg ctgaaaaaag agcatctgat tcagtttggt    360
ggcgcagaac cggtcgaagg taagcctatt gcggtttacg gtgccggaac ggggcttggg    420
gttgcgcatc tggtccatgt cgataagcgt tgggtaagct tgccaggcga aggcggtcac    480
gttgattttg cgccgaatag tgaagaagag gccattatcc tcgaaatatt gcgtgcggaa    540
attggtcatg tttcggcgga gcgcgtgctt tctggccctg ggctggtgaa tttgtatcgc    600
gcaattgtga agctgacaa ccgcctgcca gaaaatctca gccaaaaga tattaccgaa      660
cgcgcgctgg ctgacagctg caccgattgc cgccgcgcat tgtcgctgtt ttgcgtcatt    720
atgggccgtt ttggcggcaa tctggcgctc aatctcggga catttggcgg cgtgtttatt    780
gcgggcggta tcgtgccgcg cttccttgag ttcttcaaag cctccggttt ccgtgccgca    840
tttgaagata aagggcgctt taagaatat gtccatgata ttccggtgta tctcatcgtc     900
catgacaatc cgggccttct cggttccggt gcacatttac gccagacctt aggtcacatt    960
ctgtaa                                                              966
```

<210> SEQ ID NO 182
<211> LENGTH: 2547
<212> TYPE: DNA
<213> ORGANISM: Escherichia coli

<400> SEQUENCE: 182

```
ttgtacctct atattgagac tctgaaacag agactggatg ccataaatca attgcgtgtg     60
gatcgcgcgc ttgctgctat ggggcctgca ttccaacagg tctacagtct actgccgaca    120
ttgttgcact atcaccatcc gctaatgccg ggttaccttg atggtaacgt tcccaaaggc    180
atttgccttt acacgcctga tgaaactcaa cgccactacc tgaacgagct tgaactgtat    240
cgtggaatgt cagtacagga tccgccgaaa ggtgagcttc caattactgg tgtatacacc    300
atgggcagca cctcgtccgt agggcaaagt tgttcctctg acctggatat ctgggtctgt    360
catcaatcct ggctcgatag cgaagagcgc caattgctac aacgtaaatg tagcctgctg    420
gaaaactggg ccgcctcgct gggtgtggaa gtcagcttct tcctgattga tgaaaaccgc    480
ttccgtcata tgaaagcgg cagcctgggg ggcgaagatt gtggctccac ccagcatata    540
ctgctgcttg acgaatttta tcgtaccgcc gtgcgtctcg ccggtaagcg tattctgtgg    600
aatatggtgc cgtgcgacga agaagagcat tacgacgact atgtgatgac gctttacgcg    660
```

```
cagggcgtgc tgacgccaaa tgaatggctg gatctcggtg gcttaagctc gctttctgct    720
gaagagtact ttggtgccag cctttggcag ctctacaaga gtatcgattc cccatacaaa    780
gcggtactga aaacactgct gctggaagcc tattcctggg aatacccgaa cccacgtctg    840
ctggcgaaag atatcaaaca gcgtttgcac gacggcgaga ttgtatcgtt tggtctcgat    900
ccatactgca tgatgctgga gcgtgttact gaatacctga cggcgattga agattttacc    960
cgtctggatt tagtacgtcg ctgcttctat ttaaaagtgt gcgaaaagct cagccgtgaa    1020
cgcgcctgcg taggctggcg tcgcgcagtg ttgagccagt tagtgagcga gtggggttgg    1080
gacgaagctc gtctggcaat gctcgataac cgcgctaact ggaagattga tcaggtgcgt    1140
gaggcgcaca acgagttgct cgacgcgatg atgcagagct accgtaatct gatccgcttt    1200
gcgcgtcgca ataaccttag cgtctccgcc agtccgcagg atatcggcgt gctgacgcgt    1260
aagctgtatg ccgcgtttga agcattacca ggtaaagtga cgctggtaaa cccgcagatt    1320
tcacccgatc tctcggaacc gaatctgacc tttatttatg tgccgccggg ccgggctaac    1380
cgttcaggtt ggtatctgta taccgcgcg ccaaatattg agtcgatcat cagccatcag    1440
ccgctggaat ataaccgtta cctgaataaa ctggtggcgt gggcatggtt aacggcctg    1500 ctgacctcgc gcacccgttt gtatattaaa ggtaacggca ttgtcgattt gcctaagttg    1560
caggagatgg tcgccgacgt gtcgcaccat ttcccgctgc gcttacctgc accgacaccg    1620
aaggcgctct acagcccgtg tgagatccgc catctggcga ttatcgttaa cctgaatat    1680 gaccccgacag cggcgttccg caatcaggtg gtgcatttcg atttccgtaa gctggatgtc    1740
ttcagctttg gcgagaatca aaattgcctg gtaggtagcg ttgacctgct gtaccgcaac    1800
tcgtggaacg aagtgcgtac gctgcacttc aacggcgagc aatcgatgat cgaagccctg    1860
aaaactattc tcggcaaaat gcatcaggac gccgcaccgc cagatagcgt ggaagtcttc    1920
tgttatagcc agcatctgcg cggcttaatt cgtactcgcg tgcagcaact ggtttctgag    1980
tgtattgaat tgcgtctttc cagcacccgc caggaaaccg gcgtttcaa ggcgctgcgc    2040 gtttctggtc aaacctgggg gttgttcttc gaacgcctga atgtatcggt acagaaactg    2100
gaaaacgcca tcgagttttta tggcgcgatt tcgcataaca actgcacgg cctgtcagtg    2160 caggttgaaa ccaatcacgt caaattaccg gcggtggtgg acggctttgc cagcgaaggg    2220
atcatccagt tcttttttcga agaaacgcaa gacgagaatg gctttaatat ctacattctc    2280
gacgaaagca accgggttga ggtatatcac cactgcgaag gcagcaaaga ggagctggta    2340
cgtgacgtca gtcgcttcta ctcgtcatcg catgaccgtt ttacctacgg ctcaagcttc    2400
atcaacttca acctgccgca gttctatcag attgtgaagg ttgatggtcg tgaacaggtg    2460
attccgttcc gcacaaaatc tatcggtaac atgccgcctg ccaatcagga tcacgatacg    2520
ccgctattac agcaatattt ttcgtga                                         2547
```

<210> SEQ ID NO 183
<211> LENGTH: 210
<212> TYPE: PRT
<213> ORGANISM: Escherichia coli

<400> SEQUENCE: 183

```
Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
```

```
            35                  40                  45
Ala Val Leu Ile Lys Asp Glu Glu Gly Lys Glu Met Ile Leu Ser Tyr
         50                  55                  60

Leu Asn Gln Gly Asp Phe Ile Gly Glu Leu Gly Leu Phe Glu Glu Gly
 65                  70                  75                  80

Gln Glu Arg Ser Ala Trp Val Arg Ala Lys Thr Ala Cys Glu Val Ala
                 85                  90                  95

Glu Ile Ser Tyr Lys Lys Phe Arg Gln Leu Ile Gln Val Asn Pro Asp
                100                 105                 110

Ile Leu Met Arg Leu Ser Ala Gln Met Ala Arg Arg Leu Gln Val Thr
                115                 120                 125

Ser Glu Lys Val Gly Asn Leu Ala Phe Leu Asp Val Thr Gly Arg Ile
            130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                    165                 170                 175

Val Gly Cys Ser Arg Glu Thr Val Gly Arg Ile Leu Lys Met Leu Glu
                180                 185                 190

Asp Gln Asn Leu Ile Ser Ala His Gly Lys Thr Ile Val Val Tyr Gly
                195                 200                 205

Thr Arg
    210

<210> SEQ ID NO 184
<211> LENGTH: 210
<212> TYPE: PRT
<213> ORGANISM: artificial
<220> FEATURE:
<223> OTHER INFORMATION: Crp* mutant

<400> SEQUENCE: 184

Met Val Leu Gly Lys Pro Gln Thr Asp Pro Thr Leu Glu Trp Phe Leu
  1               5                  10                  15

Ser His Cys His Ile His Lys Tyr Pro Ser Lys Ser Thr Leu Ile His
                 20                  25                  30

Gln Gly Glu Lys Ala Glu Thr Leu Tyr Tyr Ile Val Lys Gly Ser Val
             35                  40                  45

Ala Val Leu Ile Lys His Glu Glu Gly Lys Glu Met Ile Leu Ser Tyr
         50                  55                  60

Leu Asn Gln Gly Asp Phe Ile Gly Glu Leu Gly Leu Phe Glu Glu Gly
 65                  70                  75                  80

Gln Glu Arg Ser Ala Trp Val Arg Ala Lys Thr Ala Cys Glu Val Ala
                 85                  90                  95

Glu Ile Ser Tyr Lys Lys Phe Arg Gln Leu Ile Gln Val Asn Pro Asp
                100                 105                 110

Ile Leu Met Arg Leu Ser Ala Gln Met Ala Arg Arg Leu Gln Val Thr
                115                 120                 125

Ser Glu Lys Val Gly Asn Leu Ala Phe Leu Asp Val Thr Gly Arg Ile
            130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                    165                 170                 175

Val Gly Cys Ser Arg Glu Thr Val Gly Arg Ile Leu Lys Met Leu Glu
```

```
                180                 185                 190
Asp Gln Asn Leu Ile Ser Ala His Gly Lys Thr Ile Val Val Tyr Gly
        195                 200                 205

Thr Arg
    210

<210> SEQ ID NO 185
<211> LENGTH: 210
<212> TYPE: PRT
<213> ORGANISM: artificial
<220> FEATURE:
<223> OTHER INFORMATION: Crp* mutant

<400> SEQUENCE: 185

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45

Ala Val Leu Ile Lys Asp Glu Glu Gly Lys Glu Met Ile Leu Phe Tyr
50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
        115                 120                 125

Ser Glu Lys Val Gly Asn Leu Ala Phe Leu Asp Val Thr Gly Arg Ile
130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
    210

<210> SEQ ID NO 186
<211> LENGTH: 210
<212> TYPE: PRT
<213> ORGANISM: artificial
<220> FEATURE:
<223> OTHER INFORMATION: Crp* mutant

<400> SEQUENCE: 186

Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45
```

```
Ala Val Leu Ile Lys Asp Glu Glu Gly Lys Glu Met Ile Leu Ser Tyr
         50                  55                  60

Leu Asn Gln Gly Asp Phe Ile Gly Glu Leu Gly Leu Phe Glu Glu Gly
 65                  70                  75                  80

Gln Glu Arg Ser Ala Trp Val Arg Ala Lys Thr Ala Cys Glu Val Ala
                 85                  90                  95

Glu Ile Ser Tyr Lys Lys Phe Arg Gln Leu Ile Gln Val Asn Pro Asp
                100                 105                 110

Ile Leu Met Arg Leu Ser Ala Gln Met Ala Arg Arg Leu Gln Val Thr
                115                 120                 125

Ser Glu Lys Val Gly Asn Leu Ala Phe Leu Asp Val Thr Asp Arg Ile
        130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
                180                 185                 190

Asp Gln Asn Leu Ile Ser Ala His Gly Lys Thr Ile Val Val Tyr Gly
                195                 200                 205

Thr Arg
    210

<210> SEQ ID NO 187
<211> LENGTH: 210
<212> TYPE: PRT
<213> ORGANISM: artificial
<220> FEATURE:
<223> OTHER INFORMATION: Crp* mutant

<400> SEQUENCE: 187

Met Val Leu Gly Lys Pro Gln Thr Asp Pro Thr Leu Glu Trp Phe Leu
 1               5                  10                  15

Ser His Cys His Ile His Lys Tyr Pro Ser Lys Ser Thr Leu Ile His
                 20                  25                  30

Gln Gly Glu Lys Ala Glu Thr Leu Tyr Tyr Ile Val Lys Gly Ser Val
         35                  40                  45

Ala Val Leu Ile Lys Asp Glu Glu Gly Lys Glu Met Ile Leu Ser Tyr
         50                  55                  60

Leu Asn Gln Gly Asp Phe Ile Gly Glu Leu Gly Leu Phe Glu Glu Gly
 65                  70                  75                  80

Gln Glu Arg Ser Ala Trp Val Arg Ala Lys Thr Ala Cys Glu Val Ala
                 85                  90                  95

Glu Ile Ser Tyr Lys Lys Phe Arg Gln Leu Ile Gln Val Asn Pro Asp
                100                 105                 110

Ile Leu Met Arg Leu Ser Ala Gln Met Ala Arg Arg Leu Gln Val Thr
                115                 120                 125

Ser Glu Lys Val Gly Asn Leu Ala Phe Leu Asp Val Thr Gly Asp Ile
        130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
                180                 185                 190
```

Asp Gln Asn Leu Ile Ser Ala His Gly Lys Thr Ile Val Val Tyr Gly
            195                 200                 205

Thr Arg
    210

<210> SEQ ID NO 188
<211> LENGTH: 2932
<212> TYPE: DNA
<213> ORGANISM: Escherichia coli

<400> SEQUENCE: 188

| | | | | | |
|---|---|---|---|---|---|
| atgcgaattg | gcataccaag | agaacggtta | accaatgaaa | cccgtgttgc | agcaacgcca | 60 |
| aaaacagtgg | aacagctgct | gaaactgggt | tttaccgtcg | cggtagagag | cggcgcgggt | 120 |
| caactggcaa | gttttgacga | taaagcgttt | gtgcaagcgg | gcgctgaaat | tgtagaaggg | 180 |
| aatagcgtct | ggcagtcaga | gatcattctg | aaggtcaatg | cgccgttaga | tgatgaaatt | 240 |
| gcgttactga | tcctgggac | aacgctggtg | agttttatct | ggcctgcgca | gaatccggaa | 300 |
| ttaatgcaaa | aacttgcgga | acgtaacgtg | accgtgatgc | cgatggactc | tgtgccgcgt | 360 |
| atctcacgcg | cacaatcgct | ggacgcacta | agctcgatgg | cgaacatcgc | cggttatcgc | 420 |
| gccattgttg | aagcggcaca | tgaatttggg | cgcttcttta | ccgggcaaat | tactgcggcc | 480 |
| gggaaagtgc | caccggcaaa | agtgatggtg | attggtgcgg | gtgttgcagg | tctggccgcc | 540 |
| attggcgcag | caaacagtct | cggcgcgatt | gtgcgtgcat | cgacacccg | cccggaagtg | 600 |
| aaagaacaag | ttcaaagtat | gggcgcggaa | ttcctcgagc | tggattttaa | agaggaagct | 660 |
| ggcagcggcg | atggctatgc | caaagtgatg | tcggacgcg | tcatcaaagc | ggaaatggaa | 720 |
| ctctttgccg | cccaggcaaa | agaggtcgat | atcattgtca | ccaccgcgct | tattccaggc | 780 |
| aaaccagcgc | cgaagctaat | tacccgtgaa | atggttgact | ccatgaaggc | gggcagtgtg | 840 |
| attgtcgacc | tggcagccca | aaacggcggc | aactgtgaat | acaccgtgcc | gggtgaaatc | 900 |
| ttcactacga | aaaatggtgt | caaagtgatt | ggttataccg | atcttccggg | ccgtctgccg | 960 |
| acgcaatcct | cacagcttta | cggcacaaac | ctcgttaatc | tgctgaaact | gttgtgcaaa | 1020 |
| gagaaagacg | gcaatatcac | tgttgatttt | gatgatgtgg | tgattcgcgg | cgtgaccgtg | 1080 |
| atccgtgcgg | gcgaaattac | ctggccggca | ccgccgattc | aggtatcagc | tcagccgcag | 1140 |
| gcggcacaaa | aagcggcacc | ggaagtgaaa | actgaggaaa | aatgtacctg | ctcaccgtgg | 1200 |
| cgtaaatacg | cgttgatggc | gctggcaatc | attcttttg | gctggatggc | aagcgttgcg | 1260 |
| ccgaaagaat | tccttgggca | cttcaccgtt | ttcgcgctgg | cctgcgttgt | cggttattac | 1320 |
| gtggtgtgga | atgtatcgca | cgcgctgcat | acaccgttga | tgtcggtcac | caacgcgatt | 1380 |
| tcagggatta | ttgttgtcgg | agcactgttg | cagattggcc | agggcggctg | ggttagcttc | 1440 |
| cttagtttta | tcgcggtgct | tatagccagc | attaatattt | tcggtggctt | caccgtgact | 1500 |
| cagcgcatgc | tgaaaatgtt | ccgcaaaaat | taagggtaa | catatgtctg | gaggattagt | 1560 |
| tacagctgca | tacattgttg | ccgcgatcct | gtttatcttc | agtctggccg | gtctttcgaa | 1620 |
| acatgaaacg | tctcgccagg | gtaacaactt | cggtatcgcc | gggatggcga | ttgcgttaat | 1680 |
| cgcaaccatt | tttggaccgg | atacgggtaa | tgttggctgg | atcttgctgg | cgatggtcat | 1740 |
| tggtgggca | attggtatcc | gtctggcgaa | gaaagttgaa | atgaccgaaa | tgccagaact | 1800 |
| ggtggcgatc | ctgcatagct | tcgtgggtct | ggcggcagtg | ctggttggct | taacagcta | 1860 |
| tctgcatcat | gacgcgggaa | tggcaccgat | tctggtcaat | attcacctga | cggaagtgtt | 1920 |
| cctcggtatc | ttcatcgggg | cggtaacgtt | cacgggttcg | gtggtggcgt | tcggcaaact | 1980 |

```
gtgtggcaag atttcgtcta aaccattgat gctgccaaac cgtcacaaaa tgaacctggc    2040
ggctctggtc gtttccttcc tgctgctgat tgtatttgtt cgcacggaca gcgtcggcct    2100
gcaagtgctg gcattgctga taatgaccgc aattgcgctg gtattcggct ggcatttagt    2160
cgcctccatc ggtggtgcag atatgccagt ggtggtgtcg atgctgaact cgtactccgg    2220
ctgggcggct gcggctgcgg gctttatgct cagcaacgac ctgctgattg tgaccggtgc    2280
gctggtcggt tcttcggggg ctatccttc ttacattatg tgtaaggcga tgaaccgttc     2340
ctttatcagc gttattgcgg gtggtttcgg caccgacggc tcttctactg gcgatgatca    2400
ggaagtgggg gagcaccgcg aaatcaccgc agaagagaca gcggaactgc tgaaaaactc    2460
ccattcagtg atcattactc cggggtacgg catggcagtc gcgcaggcgc aatatcctgt    2520
cgctgaaatt actgagaaat tgcgcgctcg tggtattaat gtgcgtttcg gtatccaccc    2580
ggtcgcgggg cgtttgcctg acatatgaa cgtattgctg gctgaagcaa aagtaccgta     2640
tgacatcgtg ctggaaatgg acgagatcaa tgatgacttt gctgataccg ataccgtact    2700
ggtgattggt gctaacgata cggttaaccc ggcggcgcag gatgatccga gagtccgat     2760 tgctggtatg cctgtgctgg aagtgtggaa agcgcagaac gtgattgtct ttaaacgttc    2820
gatgaacact ggctatgctg gtgtgcaaaa cccgctgttc ttcaaggaaa acacccacat    2880
gctgtttggt gacgccaaag ccagcgtgga tgcaatcctg aaagctctgt aa            2932

<210> SEQ ID NO 189
<211> LENGTH: 1401
<212> TYPE: DNA
<213> ORGANISM: Escherichia coli

<400> SEQUENCE: 189
atgccacatt cctacgatta cgatgccata gtaataggtt ccggccccgg cggcgaaggc     60
gctgcaatgg gcctggttaa gcaaggtgcg cgcgtcgcag ttatcgagcg ttatcaaaat    120
gttggcggcg gttgcaccca ctggggcacc atcccgtcga agctctccg tcacgccgtc     180 agccgcatta tagaattcaa tcaaaaccca ctttacagcg accattcccg actgctccgc    240
tcttcttttg ccgatatcct taaccatgcc gataacgtga ttaatcaaca aacgcgcatg    300
cgtcagggat tttacgaacg taatcactgt gaaatattgc agggaaacgc tcgctttgtt    360
gacgagcata cgttggcgct ggattccccg acggcagcg ttgaaacact aaccgctgaa     420
aaatttgtta ttgcctgcgg ctctcgtcca tatcatccaa cagatgttga tttcacccat    480
ccacgcattt acgacagcga ctcaattctc agcatgcacc acgaaccgcg ccatgtactt    540
atctatggtg ctggagtgat cggctgtgaa tatgcgtcga tcttccgcgg tatggatgta    600
aaagtggatc tgatcaacac ccgcgatcgc ctgctggcat ttctcgatca agagatgtca    660
gattctctct cctatcactt ctggaacagt ggcgtagtga ttcgtcacaa cgaagagtac    720
gagaagatcg aaggctgtga cgatggtgtg atcatgcatc tgaagtcggg taaaaaactg    780
aaagctgact gcctgctcta tgccaacggt cgcaccggta taccgattc gctggcgtta     840 cagaacattg gctagaaaac tgacagccgc ggacagctga aggtcaacag catgtatcag    900
accgcacagc cacacgttta cgcggtgggc gacgtgattg gttatccgag cctggcgtcg    960
gcggcctatg accaggggcg cattgccgcg caggcgctgg taaaaggcga agccaccgca   1020
catctgatta agatatcccc taccggtatt tacaccatcc cggaaatcag ctctgtgggc   1080 aaaccgaac agcagctgac cgcaatgaaa gtgccatatg aagtgggccg cgcccagttt    1140
```

| | |
|---|---:|
| aaacatctgg cacgcgcaca atcgtcggc atgaacgtgg gcacgctgaa aattttgttc | 1200 |
| catcgggaaa caaagagat tctgggtatt cactgctttg cgagcgcgc tgccgaaatt | 1260 |
| attcatatcg gtcaggcgat tatggaacag aaaggtggcg gcaacactat tgagtacttc | 1320 |
| gtcaacacca cctttaacta cccgacgatg gcggaagcct atcgggtagc tgcgttaaac | 1380 |
| ggtttaaacc gcctgtttta a | 1401 |

<210> SEQ ID NO 190
<211> LENGTH: 1434
<212> TYPE: DNA
<213> ORGANISM: Streptococcus mutans

<400> SEQUENCE: 190

| | |
|---|---:|
| atggcaatga caaaacaata taaaaattat gtcaatggcg agtggaagct ttcagaaaat | 60 |
| gaaattaaaa tctacgaacc agccagtgga gctgaattgg gttcagttcc agcaatgagt | 120 |
| actgaagaag tagattatgt ttatgcttca gccaagaaag ctcaaccagc ttggcgagca | 180 |
| ctttcataca tagaacgtgc tgcctacctt cataaggtag cagatatttt gatgcgtgat | 240 |
| aaagaaaaaa taggtgctat tctttccaaa gaggttgcta aaggttataa atcagcagtc | 300 |
| agcgaagttg ttcgtactgc agaaatcatt aattatgcag ctgaagaagg tcttcgtatg | 360 |
| gaaggtgaag tccttgaagg cggcagtttt gaagcagcca gcaagaaaaa aattgccgtt | 420 |
| gttcgtcgtg aaccagtagg tcttgtatta gctatttcac catttaacta ccctgttaac | 480 |
| ttggcaggtt cgaaaattgc accggctctt attgcgggaa atgttattgc ttttaaacca | 540 |
| ccgacgcaag gatcaatctc agggctctta cttgctgaag catttgctga agctggactt | 600 |
| cctgcaggtg tctttaatac cattacaggt cgtggttctg aaattggaga ctatattgta | 660 |
| gaacatcaag ccgttaactt tatcaatttc actggttcaa caggaattgg cgaacgtatt | 720 |
| ggcaaaatgg ctggtatgcg tccgattatg cttgaactcg gtggaaaaga ttcagccatc | 780 |
| gttcttgaag atgcggacct tgaattgact gctaaaaata ttattgcagg tgcttttggt | 840 |
| tattcaggtc aacgctgtac agcagttaaa cgtgttcttg tgatggaaag tgttgctgat | 900 |
| gaactggtcg aaaaaatccg tgaaaaagtt cttgcattaa caattggtaa tccagaagac | 960 |
| gatgcagata ttacaccgtt gattgataca aaatcagctg attatgtaga aggtcttatt | 1020 |
| aatgatgcca atgataaagg agccactgcc cttactgaaa tcaaacgtga aggtaatctt | 1080 |
| atctgtccaa tcctctttga taaggtaacg acagatatgc gtcttgcttg ggaagaacca | 1140 |
| tttggtcctg ttcttccgat cattcgtgtg acatctgtag aagaagccat tgaaatttct | 1200 |
| aacaaatcgg aatatggact tcaggcttct atctttacaa atgatttccc acgcgctttt | 1260 |
| ggtattgctg agcagcttga agttggtaca gttcatatca ataataagac acagcgcggc | 1320 |
| acggacaact tcccattctt aggggctaaa aaatcaggtg caggtattca aggggtaaaa | 1380 |
| tattctattg aagctatgac aactgttaaa tccgtcgtat ttgatatcaa ataa | 1434 |

<210> SEQ ID NO 191
<211> LENGTH: 996
<212> TYPE: DNA
<213> ORGANISM: Escherichia coli

<400> SEQUENCE: 191

| | |
|---|---:|
| atgactatca aagtaggtat caacggtttt ggccgtatcg gtcgcattgt tttccgtgct | 60 |
| gctcagaaac gttctgacat cgagatcgtt gcaatcaacg acctgttaga cgctgattac | 120 |
| atggcataca tgctgaaata tgactccact cacggccgtt tcgacggtac cgttgaagtg | 180 |

```
aaagacggtc atctgatcgt taacggtaaa aaaatccgtg ttaccgctga acgtgatccg    240
gctaacctga aatgggacga agttggtgtt gacgttgtcg ctgaagcaac tggtctgttc    300
ctgactgacg aaactgctcg taaacacatc accgctggtg cgaagaaagt ggttatgact    360
ggtccgtcta aagacaacac tccgatgttc gttaaaggcg ctaacttcga caaatatgct    420
ggccaggaca tcgtttccaa cgcttcctgc accaccaact gcctggctcc gctggctaaa    480
gttatcaacg ataacttcgg catcatcgaa ggtctgatga ccaccgttca cgctactacc    540
gctactcaga aaccgttga tggcccgtct cacaaagact ggcgcggcgg ccgcggcgct    600
tcccagaaca tcatcccgtc ctctaccggt gctgctaaag ctgtaggtaa agtactgcca    660
gaactgaatg gcaaactgac tggtatggcg ttccgcgttc cgaccccgaa cgtatctgta    720
gttgacctga ccgttcgtct ggaaaaagct gcaacttacg agcagatcaa agctgccgtt    780
aaagctgctg ctgaaggcga atgaaaggc gttctgggct acaccgaaga tgacgtagta    840
tctaccgatt tcaacggcga agtttgcact tccgtgttcg atgctaaagc tggtatcgct    900
ctgaacgaca acttcgtgaa actggtatcc tggtacgaca cgaaaccgg ttactccaac    960 aaagttctgg acctgatcgc tcacatctcc aaataa    996
```

`<210>` SEQ ID NO 192
`<211>` LENGTH: 1650
`<212>` TYPE: DNA
`<213>` ORGANISM: Escherichia coli

`<400>` SEQUENCE: 192

```
atgaaaaaca tcaatccaac gcagaccgct gcctggcagg cactacagaa acacttcgat     60
gaaatgaaag acgttacgat cgccgatctt tttgctaaag acggcgatcg ttttttctaag   120 ttctccgcaa ccttcgacga tcagatgctg gtggattact ccaaaaaccg catcactgaa   180
gagacgctgg cgaaattaca ggatctggcg aaagagtgcg atctggcggg cgcgattaag   240
tcgatgttct ctggcgagaa gatcaaccgc actgaaaacc gcgccgtgct gcacgtagcg   300
ctgcgtaacc gtagcaatac cccgattttg gttgatggca agacgtaat gccggaagtc   360 aacgcggtgc tggagaagat gaaaaccttc tcagaagcga ttatttccgg tgagtggaaa   420
ggttataccg gcaaagcaat cactgacgta gtgaacatcg ggatcggcgg ttctgacctc   480
ggcccataca tggtgaccga agctctgcgt ccgtacaaaa accacctgaa catgcacttt   540
gtttctaacg tcgatgggac tcacatcgcg gaagtgctga aaaagtaaa cccggaaacc   600 acgctgttct tggtagcatc taaaaccttc accactcagg aaactatgac caacgcccat   660
agcgcgcgtg actggttcct gaaagcggca ggtgatgaaa acacgttgc aaaacacttt   720 gcggcgcttt ccaccaatgc caaagccgtt ggcgagtttg gtattgatac tgccaacatg   780
ttcgagttct gggactgggt tggcggccgt tactctttgt ggtcagcgat tggcctgtcg   840
attgttctct ccatcggctt tgataacttc gttgaactgc tttccggcgc acacgcgatg   900
gacaagcatt tctccaccac gcctgccgag aaaaacctgc ctgtactgct ggcgctgatt   960
ggcatctggt acaacaattt ctttggtgcg gaaactgaag cgattctgcc gtatgaccag  1020
tatatgcacc gtttcgcggc gtacttccag cagggcaata tggagtccaa cggtaagtat  1080
gttgaccgta acgtaacgt tgtggattac cagactggcc cgattatctg gggtgaacca  1140
ggcactaacg tcagcacgc gttctaccag ctgatccacc agggaaccaa aatggtaccg  1200
tgcgatttca tcgctccggc tatcacccat aaccccgctct ctgatcatca ccagaaactg  1260
```

| | |
|---|---:|
| ctgtctaact tcttcgccca gaccgaagcg ctggcgtttg gtaaatcccg cgaagtggtt | 1320 |
| gagcaggaat atcgtgatca gggtaaagat ccggcaacgc ttgactacgt ggtgccgttc | 1380 |
| aaagtattcg aaggtaaccg cccgaccaac tccatcctgc tgcgtgaaat cactccgttc | 1440 |
| agcctgggtg cgttgattgc gctgtatgag cacaaaatct ttactcaggg cgtgatcctg | 1500 |
| aacatcttca ccttcgacca gtggggcgtg gaactgggta acagctggc gaaccgtatt | 1560 |
| ctgccagagc tgaaagatga taagaaatc agcagccacg atagctcgac caatggtctg | 1620 |
| attaaccgct ataaagcgtg gcgcggttaa | 1650 |

<210> SEQ ID NO 193
<211> LENGTH: 963
<212> TYPE: DNA
<213> ORGANISM: Escherichia coli

<400> SEQUENCE: 193

| | |
|---|---:|
| atgattaaga aaatcggtgt gttgacaagc ggcggtgatg cgccaggcat gaacgccgca | 60 |
| attcgcgggg ttgttcgttc tgcgctgaca gaaggtctgg aagtaatggg tatttatgac | 120 |
| ggctatctgg gtctgtatga agaccgtatg gtacagctag accgttacag cgtgtctgac | 180 |
| atgatcaacc gtgcggtac gttcctcggt tctgcgcgtt tcccggaatt ccgcgacgag | 240 |
| aacatccgcg ccgtggctat cgaaaacctg aaaaacgtg gtatcgacgc gctggtggtt | 300 |
| atcggcggtg acggttccta catggtgca atgcgtctga ccgaaatggg cttcccgtgc | 360 |
| atcggtctgc cgggcactat cgacaacgac atcaaaggca ctgactacac tatcggtttc | 420 |
| ttcactgcgc tgagcaccgt tgtagaagcg atcgaccgtc tgcgtgacac ctcttcttct | 480 |
| caccagcgta tttccgtggt ggaagtgatg ggccgttatt gtggagatct gacgttggct | 540 |
| gcggccattg ccgtggctg tgaattcgtt gtggttccgg aagttgaatt cagccgtgaa | 600 |
| gacctggtaa acgaaatcaa agcgggtatc gcgaaaggta aaaacacgc gatcgtggcg | 660 |
| attaccgaac atatgtgtga tgttgacgaa ctggcgcatt tcatcgagaa agaaaccggt | 720 |
| cgtgaaaccc gcgcaactgt gctgggccac atccagcgcg gtggttctcc ggtgccttac | 780 |
| gaccgtattc tggcttcccg tatgggcgct tacgctatcg atctgctgct ggcaggttac | 840 |
| ggcggtcgtt gtgtaggtat ccagaacgaa cagctggttc accacgacat catcgacgct | 900 |
| atcgaaaaca tgaagcgtcc gttcaaaggt gactggctgg actgcgcgaa aaaactgtat | 960 |
| taa | 963 |

<210> SEQ ID NO 194
<211> LENGTH: 1476
<212> TYPE: DNA
<213> ORGANISM: Escherichia coli

<400> SEQUENCE: 194

| | |
|---|---:|
| atggcggtaa cgcaaacagc ccaggcctgt gacctggtca ttttcggcgc gaaaggcgac | 60 |
| cttgcgcgtc gtaaattgct gccttccctg tatcaactga aaaagccgg tcagctcaac | 120 |
| ccggacaccc ggattatcgg cgtagggcgt gctgactggg ataaagcggc atataccaaa | 180 |
| gttgtccgcg aggcgctcga aactttcatg aaagaaacca ttgatgaagg tttatgggac | 240 |
| accctgagtg cacgtctgga tttttgtaat ctcgatgtca atgacactgc tgcattcagc | 300 |
| cgtctcggcg cgatgctgga tcaaaaaaat cgtatcacca ttaactactt tgccatgccg | 360 |
| cccagcactt ttgcgcaat ttgcaaaggg cttggcgagg caaaactgaa tgctaaaccg | 420 |
| gcacgcgtag tcatggagaa accgctgggg acgtcgctgg cgacctcgca ggaaatcaat | 480 |

```
gatcaggttg gcgaatactt cgaggagtgc caggtttacc gtatcgacca ctatcttggt      540
aaagaaacgg tgctgaacct gttggcgctg cgttttgcta actccctgtt tgtgaataac      600
tgggacaatc gcaccattga tcatgttgag attaccgtgg cagaagaagt ggggatcgaa      660
gggcgctggg gctattttga taaagccggt cagatgcgcg acatgatcca gaaccacctg      720
ctgcaaattc tttgcatgat tgcgatgtct ccgccgtctg acctgagcgc agacagcatc      780
cgcgatgaaa aagtgaaagt actgaagtct ctgcgccgca tcgaccgctc caacgtacgc      840
gaaaaaaccg tacgcgggca atatactgcg ggcttcgccc agggcaaaaa agtgccggga      900
tatctggaag aagagggcgc gaacaagagc agcaatacag aaactttcgt ggcgatccgc      960
gtcgacattg ataactggcg ctgggccggt gtgccattct acctgcgtac tggtaaacgt     1020
ctgccgacca atgttctgaa gtcgtggtc tatttcaaaa cacctgaact gaatctgttt     1080
aaagaatcgt ggcaggatct gccgcagaat aaactgacta ccgtctgca acctgatgaa     1140 ggcgtggata tccaggtact gaataaagtt cctggccttg accacaaaca taacctgcaa     1200
atcaccaagc tggatctgag ctattcagaa acctttaatc agacgcatct ggcggatgcc     1260
tatgaacgtt tgctgctgga aaccatgcgt ggtattcagg cactgtttgt acgtcgcgac     1320
gaagtggaag aagcctggaa atgggtagac tccattactg aggcgtgggc gatggacaat     1380
gatgcgccga aaccgtatca ggccggaacc tggggacccg ttgcctcggt ggcgatgatt     1440
acccgtgatg gtcgttcctg gaatgagttt gagtaa                              1476
```

<210> SEQ ID NO 195
<211> LENGTH: 474
<212> TYPE: PRT
<213> ORGANISM: Escherichia coli

<400> SEQUENCE: 195

```
Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
                20                  25                  30

Val Ile Val Glu Arg Tyr Asn Thr Leu Gly Gly Val Cys Leu Asn Val
            35                  40                  45

Gly Cys Ile Pro Ser Lys Ala Leu Leu His Val Ala Lys Val Ile Glu
        50                  55                  60

Glu Ala Lys Ala Leu Ala Glu His Gly Ile Val Phe Gly Glu Pro Lys
    65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
                100                 105                 110

Val Asn Gly Leu Gly Lys Phe Thr Gly Ala Asn Thr Leu Glu Val Glu
            115                 120                 125

Gly Glu Asn Gly Lys Thr Val Ile Asn Phe Asp Asn Ala Ile Ile Ala
        130                 135                 140

Ala Gly Ser Arg Pro Ile Gln Leu Pro Phe Ile Pro His Glu Asp Pro
    145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
                180                 185                 190
```

```
Val Tyr His Ala Leu Gly Ser Gln Ile Asp Val Val Glu Met Phe Asp
        195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 196
<211> LENGTH: 474
<212> TYPE: PRT
<213> ORGANISM: artificial
<220> FEATURE:
<223> OTHER INFORMATION: Lpd mutant

<400> SEQUENCE: 196

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
                20                  25                  30

Val Ile Val Glu Arg Tyr Asn Thr Leu Gly Gly Val Cys Leu Asn Val
            35                  40                  45

Gly Cys Ile Pro Ser Lys Ala Leu Leu His Val Ala Lys Val Ile Glu
        50                  55                  60

Glu Ala Lys Ala Leu Ala Glu His Gly Ile Val Phe Gly Glu Pro Lys
65                  70                  75                  80
```

```
Thr Asp Ile Asp Lys Ile Arg Thr Trp Lys Glu Lys Val Ile Asn Gln
             85                  90                  95

Leu Thr Gly Gly Leu Ala Gly Met Ala Lys Gly Arg Lys Val Lys Val
        100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
        130                 135                 140

Ala Gly Ser Arg Pro Ile Gln Leu Pro Phe Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Ile Ile Ala Leu Glu Met Ala Thr
                180                 185                 190

Val Tyr His Ala Leu Gly Ser Gln Ile Asp Val Val Arg Lys His
        195                 200                 205

Gln Val Ile Arg Ala Ala Asp Lys Asp Ile Val Lys Val Phe Thr Lys
        210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
                260                 265                 270

Arg Val Pro Asn Gly Lys Asn Leu Asp Ala Gly Lys Ala Gly Val Glu
                275                 280                 285

Val Asp Asp Arg Gly Phe Ile Arg Val Asp Lys Gln Leu Arg Thr Asn
        290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
                340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
        370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
                420                 425                 430

Cys Asp Ala Glu Asp Ile Ala Leu Thr Ile His Ala His Pro Thr Leu
                435                 440                 445

His Glu Ser Val Gly Leu Ala Ala Glu Val Phe Glu Gly Ser Ile Thr
        450                 455                 460

Asp Leu Pro Asn Pro Lys Ala Lys Lys Lys
465                 470

<210> SEQ ID NO 197
<211> LENGTH: 1548
<212> TYPE: DNA
```

<213> ORGANISM: Escherichia coli

<400> SEQUENCE: 197

```
atgacggacc atacaatgaa gaaaaacccc gtaagtatac cacacaccgt ctggtacgcc      60
gacgatatcc gccgcggaga acgcgaggcg gcagatgtgc tggggctcac actctatgag     120
ctgatgcttc gcgctggcga ggccgcattc caggtgtgtc gttcggcgta tcctgacgcc     180
cgccactggc tggtgctgtg cggtcatggt aataacggcg gcgatggcta cgtggtcgcg     240
cgactggcca aagcggtcgg cattgaggtc acgttgttgg cccaggagag cgacaaaccg     300
ttgccggaag aggccgcgct ggcacgcgaa gcatggttaa acgcgggtgg cgagatccat     360
gcttcgaata ttgtctggcc cgaatcggta gatctgattg ttgatgcgct gctcggtacc     420
ggtttgcggc aagcgccccg cgaatccatt agccagttaa tcgaccacgc taattcccat     480
cctgcgccga ttgtggcggt tgatatccct tccggcctgc tggctgaaac tggcgctacg     540
ccaggcgcgg tgatcaacgc cgatcacacc atcacttttta ttgcgctgaa accaggcttg     600
ctcactggaa aagcgcggga tgttaccgga caactgcatt ttgactcact ggggctggat     660
agttggctgg caggtcagga gacgaaaatt cagcggtttt cagcagaaca actttctcac     720
tggctaaaac cgcgtcgccc gacttcgcat aaaggcgatc acgggcggct ggtaattatc     780
ggtggcgatc acggcacggc gggggctatt cgtatgacgg gggaagcggc gctgcgtgct     840
ggtgctggtt tagtccgagt actgacccgc agtgaaaaca ttgcgccgct gctgactgca     900
cgaccggaat tgatggtgca tgaactgacg atggactctc ttaccgaaag cctggaatgg     960
gccgatgtgg tggtgattgg tcccggtctg ggccagcaag agtgggggaa aaaagcactg    1020
caaaaagttg agaattttcg caaaccgatg ttgtgggatg ccgatgcatt gaacctgctg    1080
gcaatcaatc ccgataagcg tcacaatcgc gtgatcacgc cgcatcctgg cgaggccgca    1140
cggttgttag gctgttccgt cgctgaaatt gaaagtgacc gcttacattg cgccaaacgt    1200
ctggtacaac gttatggcgg cgtagcggtg ctgaaaggtg ccggaaccgt ggtcgccgcc    1260
catcctgacg ctttaggcat tattgatgcc ggaaatgcag gcatggcgag cggcggcatg    1320
ggcgatgtgc tctctggtat tattggcgca ttgcttgggc aaaaaactgtc gccgtatgat    1380
gcagcctgtg caggctgtgt cgcgcacggt gcggcagctg acgtactggc ggcgcgtttt    1440
ggaacgcgcg ggatgctggc aaccgatctc ttttccacgc tacagcgtat tgttaacccg    1500
gaagtgactg ataaaaacca tgatgaatcg agtaattccg ctccctga                 1548
```

<210> SEQ ID NO 198
<211> LENGTH: 449
<212> TYPE: PRT
<213> ORGANISM: Escherichia coli

<400> SEQUENCE: 198

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80
```

```
Pro Asn Val Ile Arg Glu Glu Ile Glu Arg Leu Leu Glu Asn Ile Thr
             85                  90                  95

Val Leu Ala Glu Ala Ala Leu Ala Thr Ser Pro Ala Leu Thr Asp
        100                 105                 110

Glu Leu Val Ser His Gly Gly Leu Met Ser Thr Leu Leu Phe Val Glu
            115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Lys Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
    275                 280                 285

Val Cys Asn Lys Thr Glu Asn Pro Pro Leu Phe Arg Ala Leu Ala Leu
290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
            325                 330                 335

Ile Ser Val Asp Leu Ile Thr Thr Ser Glu Val Ser Val Ala Leu Thr
        340                 345                 350

Leu Asp Thr Thr Gly Ser Thr Ser Thr Gly Asp Thr Leu Leu Thr Gln
    355                 360                 365

Ser Leu Leu Met Glu Leu Ser Ala Leu Cys Arg Val Glu Val Glu Glu
370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
        435                 440                 445

Glu

<210> SEQ ID NO 199
<211> LENGTH: 367
<212> TYPE: PRT
<213> ORGANISM: Escherichia coli

<400> SEQUENCE: 199
```

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Gln Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
        355                 360                 365

<210> SEQ ID NO 200
<211> LENGTH: 360
<212> TYPE: PRT
<213> ORGANISM: Metallosphaera sedula

<400> SEQUENCE: 200

Met Lys Ala Ala Val Leu His Thr Tyr Lys Glu Pro Leu Ser Ile Glu
1               5                   10                  15

Asp Val Asn Ile Ser Gln Pro Lys Ala Gly Glu Val Lys Ile Lys Val
                20                  25                  30

Lys Ala Thr Gly Leu Cys Arg Ser Asp Val His Val Phe Glu Gly Lys
            35                  40                  45

Thr Pro Val Pro Pro Val Ala Gly His Glu Ile Ser Gly Ile
50                  55                  60

Val Glu Glu Val Gly Pro Gly Val Thr Arg Val Lys Pro Gly Asp Arg
65                  70                  75                  80

Val Ile Ser Ala Phe Ile His Pro Cys Gly Lys Cys Gly Asn Cys Val
                85                  90                  95

Ala Gly Lys Glu Asn Leu Cys Glu Thr Phe Ser Gln Val Arg Leu Lys
            100                 105                 110

Gly Val Met Pro Asp Gly Thr Ser Arg Leu Ser Lys Asp Gly Lys Glu
        115                 120                 125

Ile Arg Thr Phe Leu Gly Gly Phe Ala Glu Tyr Ala Ile Val Gly
    130                 135                 140

Glu Asn Ala Leu Thr Arg Val Pro Glu Asp Met Asp Leu Glu Lys Val
145                 150                 155                 160

Ala Val Leu Gly Cys Ala Gly Leu Thr Gly Tyr Gly Ala Ile Ser Ser
                165                 170                 175

Ser Lys Ile Glu Pro Gly Asp Thr Val Ala Val Ile Gly Val Gly Gly
            180                 185                 190

Val Gly Leu Ser Thr Ile Gln Leu Leu Arg Ala Ser Gly Ala Gly Arg
        195                 200                 205

Ile Ile Ala Val Gly Thr Lys Lys Trp Lys Leu Asp Arg Ala Met Glu
    210                 215                 220

Leu Gly Ala Thr Asp Val Val Asn Ser Lys Glu Ile Asp Pro Val Lys
225                 230                 235                 240

Ala Ile Lys Glu Ile Thr Gly Gly Pro Gln Val Val Ile Glu Ala
                245                 250                 255

Gly Gly Asn Glu Asp Thr Ile His Met Ala Leu Asp Ser Val Arg Ile
            260                 265                 270

Gly Gly Lys Val Val Leu Val Gly Leu Pro Pro Ala Thr Ala Met Ile
        275                 280                 285

Pro Ile Arg Val Ala Ser Ile Val Arg Gly Gly Ile Glu Val Val Gly
    290                 295                 300

Asn Tyr Gly Gly Arg Pro Arg Val Asp Met Pro Lys Leu Leu Glu Leu
305                 310                 315                 320

Val Arg Gln Gly Arg Tyr Asp Pro Ser Arg Leu Val Thr Gly Arg Phe
                325                 330                 335

Arg Leu Glu Glu Ile Asn Glu Ala Val Lys Met Leu Glu Glu Gly Glu
            340                 345                 350

Ala Ile Arg Ser Leu Ile Ile Pro
        355                 360

<210> SEQ ID NO 201
<211> LENGTH: 359
<212> TYPE: PRT
<213> ORGANISM: Sulfolobus tokodaii

<400> SEQUENCE: 201

Met Ile Leu Met Arg Arg Thr Leu Lys Ala Ala Ile Leu Gly Ala Thr
1               5                   10                  15

Gly Leu Val Gly Ile Glu Tyr Val Arg Met Leu Ser Asn His Pro Tyr

```
            20                  25                  30
Ile Lys Pro Ala Tyr Leu Ala Gly Lys Gly Ser Val Gly Lys Pro Tyr
            35                  40                  45
Gly Glu Val Val Arg Trp Gln Thr Val Gly Gln Val Pro Lys Glu Ile
 50                  55                  60
Ala Asp Met Glu Ile Lys Pro Thr Asp Pro Lys Leu Met Asp Asp Val
 65                  70                  75                  80
Asp Ile Ile Phe Ser Pro Leu Pro Gln Gly Ala Ala Gly Pro Val Glu
                 85                  90                  95
Glu Gln Phe Ala Lys Glu Gly Phe Pro Val Ile Ser Asn Ser Pro Asp
                100                 105                 110
His Arg Phe Asp Pro Asp Val Pro Leu Leu Val Pro Glu Leu Asn Pro
                115                 120                 125
His Thr Ile Ser Leu Ile Asp Glu Gln Arg Lys Arg Glu Trp Lys
                130                 135                 140
Gly Phe Ile Val Thr Thr Pro Leu Cys Thr Ala Gln Gly Ala Ala Ile
145                 150                 155                 160
Pro Leu Gly Ala Ile Phe Lys Asp Tyr Lys Met Asp Gly Ala Phe Ile
                165                 170                 175
Thr Thr Ile Gln Ser Leu Ser Gly Ala Gly Tyr Pro Gly Ile Pro Ser
                180                 185                 190
Leu Asp Val Val Asp Asn Ile Leu Pro Leu Gly Asp Gly Pro Asp Ala
                195                 200                 205
Lys Thr Ile Lys Glu Ile Phe Arg Ile Leu Ser Glu Val Lys Arg Asn
210                 215                 220
Val Asp Glu Pro Lys Leu Glu Asp Val Ser Leu Ala Ala Thr Thr His
225                 230                 235                 240
Arg Ile Ala Thr Ile His Gly His Tyr Glu Val Leu Tyr Val Ser Phe
                245                 250                 255
Lys Glu Glu Thr Ala Ala Glu Lys Val Lys Glu Thr Leu Glu Asn Phe
                260                 265                 270
Arg Gly Glu Pro Gln Asp Leu Lys Leu Pro Thr Ala Pro Ser Lys Pro
                275                 280                 285
Ile Ile Val Met Asn Glu Asp Thr Arg Pro Gln Val Tyr Phe Asp Arg
                290                 295                 300
Trp Ala Gly Asp Ile Pro Gly Met Ser Val Val Gly Arg Leu Lys
305                 310                 315                 320
Gln Val Asn Lys Arg Met Ile Arg Leu Val Ser Leu Ile His Asn Thr
                325                 330                 335
Val Arg Gly Ala Ala Gly Gly Ile Leu Ala Ala Glu Leu Leu Val
                340                 345                 350
Glu Lys Gly Tyr Ile Glu Lys
            355

<210> SEQ ID NO 202
<211> LENGTH: 324
<212> TYPE: PRT
<213> ORGANISM: Methylobacter extorquens

<400> SEQUENCE: 202

Met Ser Phe Thr Leu Ile Gln Gln Ala Thr Pro Arg Leu His Arg Ser
 1               5                  10                  15
Glu Leu Ala Val Pro Gly Ser Asn Pro Thr Phe Met Glu Lys Ser Ala
             20                  25                  30
```

Ala Ser Lys Ala Asp Val Ile Phe Leu Asp Leu Glu Asp Val Ala
        35                  40                  45

Pro Asp Asp Lys Glu Gln Ala Arg Lys Asn Ile Ile Gln Ala Leu Asn
 50                  55                  60

Asp Leu Asp Trp Gly Asn Lys Thr Met Met Ile Arg Ile Asn Gly Leu
 65                  70                  75                  80

Asp Thr His Tyr Met Tyr Arg Asp Val Val Asp Ile Val Glu Ala Cys
                 85                  90                  95

Pro Arg Leu Asp Met Ile Leu Ile Pro Lys Val Gly Val Pro Ala Asp
            100                 105                 110

Val Tyr Ala Ile Asp Val Leu Thr Thr Gln Ile Glu Gln Ala Lys Lys
        115                 120                 125

Arg Glu Lys Lys Ile Gly Phe Glu Val Leu Ile Glu Thr Ala Leu Gly
130                 135                 140

Met Ala Asn Val Glu Ala Ile Ala Thr Ser Ser Lys Arg Leu Glu Ala
145                 150                 155                 160

Met Ser Phe Gly Val Ala Asp Tyr Ala Ala Ser Thr Arg Ala Arg Ser
                165                 170                 175

Thr Val Ile Gly Gly Val Asn Ala Asp Tyr Ser Val Leu Thr Asp Lys
            180                 185                 190

Asp Glu Ala Gly Asn Arg Gln Thr His Trp Gln Asp Pro Trp Leu Phe
        195                 200                 205

Ala Gln Asn Arg Met Leu Val Ala Cys Arg Ala Tyr Gly Leu Arg Pro
    210                 215                 220

Ile Asp Gly Pro Phe Gly Asp Phe Ser Asp Pro Asp Gly Tyr Thr Ser
225                 230                 235                 240

Ala Ala Arg Arg Cys Ala Ala Leu Gly Phe Glu Gly Lys Trp Ala Ile
                245                 250                 255

His Pro Ser Gln Ile Asp Leu Ala Asn Glu Val Phe Thr Pro Ser Glu
            260                 265                 270

Ala Glu Val Thr Lys Ala Arg Arg Ile Leu Glu Ala Met Glu Glu Ala
        275                 280                 285

Ala Lys Ala Gly Arg Gly Ala Val Ser Leu Asp Gly Arg Leu Ile Asp
    290                 295                 300

Ile Ala Ser Ile Arg Met Ala Glu Ala Leu Ile Gln Lys Ala Asp Ala
305                 310                 315                 320

Met Gly Gly Lys

<210> SEQ ID NO 203
<211> LENGTH: 309
<212> TYPE: PRT
<213> ORGANISM: Escherichia coli

<400> SEQUENCE: 203

Met Thr Thr Lys Lys Ala Asp Tyr Ile Trp Phe Asn Gly Glu Met Val
 1               5                  10                  15

Arg Trp Glu Asp Ala Lys Val His Val Met Ser His Ala Leu His Tyr
                20                  25                  30

Gly Thr Ser Val Phe Glu Gly Ile Arg Cys Tyr Asp Ser His Lys Gly
            35                  40                  45

Pro Val Val Phe Arg His Arg Glu His Met Gln Arg Leu His Asp Ser
        50                  55                  60

Ala Lys Ile Tyr Arg Phe Pro Val Ser Gln Ser Ile Asp Glu Leu Met
 65                  70                  75                  80

```
Glu Ala Cys Arg Asp Val Ile Arg Lys Asn Asn Leu Thr Ser Ala Tyr
                85                  90                  95

Ile Arg Pro Leu Ile Phe Val Gly Asp Val Gly Met Gly Val Asn Pro
            100                 105                 110

Pro Ala Gly Tyr Ser Thr Asp Val Ile Ile Ala Ala Phe Pro Trp Gly
            115                 120                 125

Ala Tyr Leu Gly Ala Glu Ala Leu Glu Gln Gly Ile Asp Ala Met Val
            130                 135                 140

Ser Ser Trp Asn Arg Ala Pro Asn Thr Ile Pro Thr Ala Ala Lys
145                 150                 155                 160

Ala Gly Gly Asn Tyr Leu Ser Ser Leu Val Gly Ser Glu Ala Arg
                165                 170                 175

Arg His Gly Tyr Gln Glu Gly Ile Ala Leu Asp Val Asn Gly Tyr Ile
            180                 185                 190

Ser Glu Gly Ala Gly Glu Asn Leu Phe Glu Val Lys Asp Gly Val Leu
            195                 200                 205

Phe Thr Pro Pro Phe Thr Ser Ser Ala Leu Pro Gly Ile Thr Arg Asp
    210                 215                 220

Ala Ile Ile Lys Leu Ala Lys Glu Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270

Val Gly Glu Gly Arg Cys Gly Pro Val Thr Lys Arg Ile Gln Gln Ala
            275                 280                 285

Phe Phe Gly Leu Phe Thr Gly Glu Thr Glu Asp Lys Trp Gly Trp Leu
    290                 295                 300

Asp Gln Val Asn Gln
305

<210> SEQ ID NO 204
<211> LENGTH: 329
<212> TYPE: PRT
<213> ORGANISM: Lactococcus lactis

<400> SEQUENCE: 204

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
            35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
            115                 120                 125

Asp Ala Asn Phe Ser Leu Glu Gly Leu Thr Gly Phe Thr Met Tyr Gly
            130                 135                 140
```

-continued

```
Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325

<210> SEQ ID NO 205
<211> LENGTH: 50
<212> TYPE: DNA
<213> ORGANISM: artificial
<220> FEATURE:
<223> OTHER INFORMATION: primer deletion xylAB 1

<400> SEQUENCE: 205
acgacatcat ccatcacccg cggcattacc tgattatgga gttcaatatg            50

<210> SEQ ID NO 206
<211> LENGTH: 50
<212> TYPE: DNA
<213> ORGANISM: artificial
<220> FEATURE:
<223> OTHER INFORMATION: primer deletion xylAB 2

<400> SEQUENCE: 206
cccccacccg gtcaggcagg ggataacgtt tacgccatta atggcagaag            50

<210> SEQ ID NO 207
<211> LENGTH: 50
<212> TYPE: DNA
<213> ORGANISM: artificial
<220> FEATURE:
<223> OTHER INFORMATION: primer deletion yjhH 1

<400> SEQUENCE: 207
aatgcgcgaa gttgccgact tcctgattaa taaaggggtc gacgggctgt            50

<210> SEQ ID NO 208
<211> LENGTH: 50
<212> TYPE: DNA
<213> ORGANISM: artificial
<220> FEATURE:
```

<223> OTHER INFORMATION: primer deletion yjhH 2

<400> SEQUENCE: 208
gtaccgactt aactgtgttg atcatcgtac gcaagtgacc aacgctgtcg    50

<210> SEQ ID NO 209
<211> LENGTH: 50
<212> TYPE: DNA
<213> ORGANISM: artificial
<220> FEATURE:
<223> OTHER INFORMATION: primer deletion yagE 1

<400> SEQUENCE: 209
ggcggcacca acgcccggga aaccatcgaa ctcagccagc acgcgcagca    50

<210> SEQ ID NO 210
<211> LENGTH: 50
<212> TYPE: DNA
<213> ORGANISM: artificial
<220> FEATURE:
<223> OTHER INFORMATION: primer deletion yagE 2

<400> SEQUENCE: 210
agcacggtga agtgcggatg ggcacctttg acggtatgga tcatgctgcg    50

<210> SEQ ID NO 211
<211> LENGTH: 50
<212> TYPE: DNA
<213> ORGANISM: artificial
<220> FEATURE:
<223> OTHER INFORMATION: primer deletion yiaE 1

<400> SEQUENCE: 211
catatttcag gctaaggtga tcgccttatc agtgaatgga gagaagcatg    50

<210> SEQ ID NO 212
<211> LENGTH: 50
<212> TYPE: DNA
<213> ORGANISM: artificial
<220> FEATURE:
<223> OTHER INFORMATION: primer deletion yiaE 2

<400> SEQUENCE: 212
tatcgggctt tactctacgc agtcgcggct tagtccgcga cgtgcggatt    50

<210> SEQ ID NO 213
<211> LENGTH: 50
<212> TYPE: DNA
<213> ORGANISM: artificial
<220> FEATURE:
<223> OTHER INFORMATION: primer deletion ycdW 1

<400> SEQUENCE: 213
aacgataagt gcgaataaat ttcgcacaac gcttttcggg agtcagtatg    50

<210> SEQ ID NO 214
<211> LENGTH: 50
<212> TYPE: DNA
<213> ORGANISM: artificial
<220> FEATURE:
<223> OTHER INFORMATION: primer deletion ycdW 2

<400> SEQUENCE: 214
ccaaggatag caggaatcct gatgctttat tagtagccgc gtgcgcggtc    50

-continued

```
<210> SEQ ID NO 215
<211> LENGTH: 100
<212> TYPE: DNA
<213> ORGANISM: artificial
<220> FEATURE:
<223> OTHER INFORMATION: primer deletion ptsG 1

<400> SEQUENCE: 215
atgtttaaga atgcatttgc taacctgcaa aaggtcggta aatcgctgat gctgccggta      60
tccgtactgc ctatcgcagg tgtaggctgg agctgcttcg                           100

<210> SEQ ID NO 216
<211> LENGTH: 100
<212> TYPE: DNA
<213> ORGANISM: artificial
<220> FEATURE:
<223> OTHER INFORMATION: primer deletion ptsG 2

<400> SEQUENCE: 216
ttagtggtta cggatgtact catccatctc ggttttcagg ttatcggatt tagtaccgaa      60
aatcgcctga acaccagaac catatgaata tcctccttag                           100

<210> SEQ ID NO 217
<211> LENGTH: 21
<212> TYPE: DNA
<213> ORGANISM: artificial
<220> FEATURE:
<223> OTHER INFORMATION: RBS120

<400> SEQUENCE: 217
atccggtata ggaggtatag a                                                21

<210> SEQ ID NO 218
<211> LENGTH: 100
<212> TYPE: DNA
<213> ORGANISM: artificial
<220> FEATURE:
<223> OTHER INFORMATION: primer deletion udhA 1

<400> SEQUENCE: 218
ggtgcgcgcg tcgcagttat cgagcgttat caaaatgttg gcggcggttg cacccactgg      60
ggcaccatcc cgtcgaaagc catatgaata tcctccttag                           100

<210> SEQ ID NO 219
<211> LENGTH: 100
<212> TYPE: DNA
<213> ORGANISM: artificial
<220> FEATURE:
<223> OTHER INFORMATION: primer deletion udhA 2

<400> SEQUENCE: 219
cccagaatct cttttgtttc ccgatggaac aaaattttca gcgtgcccac gttcatgccg      60
acgatttgtg cgcgtgccag tgtaggctgg agctgcttcg                           100

<210> SEQ ID NO 220
<211> LENGTH: 101
<212> TYPE: DNA
<213> ORGANISM: artificial
<220> FEATURE:
<223> OTHER INFORMATION: primer deletion pfkA 1

<400> SEQUENCE: 220
gttcctcggt tctgcgcgtt tcccggaatt ccgcgacgag aacatccgcg ccgtggctat      60
```

```
cgaaaacctg aaaaaacgtg gtgtaggctg gagctgcttc g              101
```

```
<210> SEQ ID NO 221
<211> LENGTH: 102
<212> TYPE: DNA
<213> ORGANISM: artificial
<220> FEATURE:
<223> OTHER INFORMATION: primer deletion pfkA 2

<400> SEQUENCE: 221
ggcctgataa gcgaagcgca tcaggcattt ttgcttctgt catcggtttc agggtaaagg    60
aatctgcctt tttccgaaat cacatatgaa tatcctcctt ag                     102

<210> SEQ ID NO 222
<211> LENGTH: 2463
<212> TYPE: DNA
<213> ORGANISM: Escherichia coli

<400> SEQUENCE: 222
atgagagtgt tgaagttcgg cggtacatca gtggcaaatg cagaacgttt tctgcgtgtt    60
gccgatattc tggaaagcaa tgccaggcag gggcaggtgg ccaccgtcct ctctgccccc   120
gccaaaatca ccaaccacct ggtggcgatg attgaaaaaa ccattagcgg ccaggatgct   180
ttacccaata tcagcgatgc cgaacgtatt tttgccgaac ttttgacggg actcgccgcc   240
gcccagccgg ggttcccgct ggcgcaattg aaaactttcg tcgatcagga atttgcccaa   300
ataaaacatg tcctgcatgg cattagtttg ttggggcagt gcccggatag catcaacgct   360
gcgctgattt gccgtggcga aaaatgtcg atcgccatta tggccggcgt attagaagcg   420
cgcggtcaca acgttactgt tatcgatccg gtcgaaaaac tgctggcagt ggggcattac   480
ctcgaatcta ccgtcgatat tgctgagtcc acccgccgta ttgcggcaag ccgcattccg   540
gctgatcaca tggtgctgat ggcaggtttc accgccggta atgaaaaagg cgaactggtg   600
gtgcttggac gcaacggttc cgactactct gctgcggtgc tggctgcctg tttacgcgcc   660
gattgttgcg agatttggac ggacgttgac ggggtctata cctgcgaccc gcgtcaggtg   720
cccgatgcga ggttgttgaa gtcgatgtcc taccaggaag cgatggagct ttcctacttc   780
ggcgctaaag ttcttcaccc ccgcaccatt accccatcg cccagttcca gatcccttgc   840
ctgattaaaa ataccggaaa tcctcaagca ccaggtacgc tcattggtgc cagccgtgat   900
gaagacgaat accggtcaa gggcatttcc aatctgaata acatggcaat gtccagcgtt   960
tctggtccgg ggatgaaagg gatggtcggc atggcggcgc gcgtctttgc agcgatgtca  1020
cgcgcccgta tttccgtggt gctgattacg caatcatctt ccgaatacag catcagtttc  1080
tgcgttccac aaagcgactg tgtgcgagct gaacgggcaa tgcaggaaga gttctacctg  1140
gaactgaaag aaggcttact ggagccgctg gcagtgacgg aacggctggc cattatctcg  1200
gtggtaggtg atggtatgcg caccttgcgt gggatctcgg cgaaattctt tgccgcactg  1260
gcccgcgcca atatcaacat tgtcgccatt gctcagggat cttctgaacg ctcaatctct  1320
gtcgtggtaa ataacgatga tgcgaccact ggcgtgcgcg ttactcatca gatgctgttc  1380
aataccgatc aggttatcga agtgtttgtg attggcgtcg gtggcgttgg cggtgcgctg  1440
ctggagcaac tgaagcgtca gcaaagctgg ctgaagaata acatatcga cttacgtgtc  1500
tgcggtgttg ccaactcgaa ggctctgctc accaatgtac atggccttaa tctggaaaac  1560
tggcaggaag aactggcgca agccaaagag ccgtttaatc tcgggcgctt aattcgcctc  1620
gtgaaagaat atcatctgct gaacccggtc attgttgact gcacttccag ccaggcagtg  1680
```

```
gcggatcaat atgccgactt cctgcgcgaa ggtttccacg ttgtcacgcc gaacaaaaag    1740
gccaacacct cgtcgatgga ttactaccat cagttgcgtt atgcggcgga aaaatcgcgg    1800
cgtaaattcc tctatgacac caacgttggg gctggattac cggttattga aacctgcaa    1860 aatctgctca atgcaggtga tgaattgatg aagttctccg gcattctttc tggttcgctt    1920
tcttatatct tcggcaagtt agacgaaggc atgagtttct ccgaggcgac cacgctggcg    1980
cgggaaatgg gttataccga accggacccg cgagatgatc tttctggtat ggatgtggcg    2040
cgtaaactat tgattctcgc tcgtgaaacg ggacgtgaac tggagctggc ggatattgaa    2100
attgaacctg tgctgcccgc agagtttaac gccgagggtg atgttgccgc ttttatggcg    2160
aatctgtcac aactcgacga tctctttgcc gcgcgcgtgg cgaaggcccg tgatgaagga    2220
aaagttttgc gctatgttgg caatattgat gaagatggcg tctgccgcgt gaagattgcc    2280
gaagtggatg gtaatgatcc gctgttcaaa gtgaaaaatg gcgaaaacgc cctggccttc    2340
tatagccact attatcagcc gctgccgttg gtactgcgcg gatatggtgc gggcaatgac    2400
gttacagctg ccggtgtctt tgctgatctg ctacgtaccc tctcatggaa gttaggagtc    2460
tga                                                                   2463
```

<210> SEQ ID NO 223
<211> LENGTH: 3465
<212> TYPE: DNA
<213> ORGANISM: Rhizobium etli

<400> SEQUENCE: 223

```
atgcccatat ccaagatact cgttgccaat cgctctgaaa tagccatccg cgtgttccgc     60
gcggccaacg agcttggaat aaaaacggtg gcgatctggg cggaagagga caagctggcg    120
ctgcaccgct tcaaggcgga cgagagttat caggtcggcc gcggaccgca tcttgcccgc    180
gacctcgggc cgatcgaaag ctatctgtcg atcgacgagg tgatccgcgt cgccaagctt    240
tccggtgccg acgccatcca tccgggctac ggcctcttgt cggaaagccc cgaattcgtc    300
gatgcctgca caaggccgg catcatcttc atcggcccga aggccgatac gatgcgccag    360
cttggcaaca aggtcgcagc gcgcaacctg gcgatctcgg tcggcgtacc ggtcgtgccg    420
gcgaccgagc cactgccgga cgatatggcc gaagtggcga agatggcggc ggcgatcggc    480
tatcccgtca tgctgaaggc atcctggggc ggcggcggtc gcggcatgcg cgtcattcgt    540
tccgaggccg acctcgccaa ggaagtgacg gaagccaagc gcgaggcgat ggcggccttc    600
ggcaaggacg aggtctatct cgaaaaactg gtcgagcgcg cccgccacgt cgaaagccag    660
atcctcggcg acacccacgg caatgtcgtg catctcttcg agcgcgactg ttccgttcag    720
cgccgcaatc agaaggtcgt cgagcgcgcg cccgcaccct atctttcgga agcgcagcgc    780
caggaactcg ccgcctattc gctgaagatc gcaggggcga ccaactatat cggcgccggc    840
accgtcgaat atctgatgga tgccgatacc ggcaaatttt acttcatcga agtcaatccg    900
cgcatccagg tcgagcacac ggtgaccgaa gtcgtcaccg gcatcgatat cgtcaaggcg    960
cagatccaca tcctggacgg cgccgcgatc ggcacgccgc aatccggcgt gccgaaccag   1020
gaagacatcc gtctcaacgg tcacgccctg cagtgccgcg tgacgacgga agatccggag   1080
cacaacttca ttccggatta cggccgcatc accgcctatc gctcggcttc cggcttcggc   1140
atccggcttg acgcggcac ctcttattcc ggcgccatca tcacccgcta ttacgatccg   1200
ctgctcgtca aggtcacggc ctgggcgccg aacccgctgg aagccatttc ccgcatggac   1260
```

-continued

```
cgggcgctgc gcgaattccg catccgtggc gtcgccacca acctgacctt cctcgaagcg   1320
atcatcggcc atccgaaatt ccgcgacaac agctacacca cccgcttcat cgacacgacg   1380
ccggagctct tccagcaggt caagcgccag gaccgcgcga cgaagcttct gacctatctc   1440
gccgacgtca ccgtcaatgg ccatcccgag gccaaggaca ggccgaagcc cctcgagaat   1500
gccgccaggc cggtggtgcc ctatgccaat ggcaacgggg tgaaggacgg caccaagcag   1560
ctgctcgata cgctcggccc gaaaaaattc ggcgaatgga tgcgcaatga aagcgcgtg    1620
cttctgaccg acaccacgat gcgcgacggc caccagtcgc tgctcgcaac ccgcatgcgt   1680
acctatgaca tcgccaggat cgccggcacc tattcgcatg cgctgccgaa cctcttgtcg   1740
ctcgaatgct ggggcggcgc caccttcgac gtctcgatgc gcttcctcac cgaagatccg   1800
tgggagcggc tggcgctgat ccgagagggg gcgccgaacc tgctcctgca gatgctgctg   1860
cgcggcgcca atggcgtcgg ttacaccaac tatcccgaca atgtcgtcaa atacttcgtc   1920
cgccaggcgg ccaaaggcgg catcgatctc ttccgcgtct tcgactgcct gaactgggtc   1980
gagaatatgc gggtgtcgat ggatgcgatt gccgaggaga acaagctctg cgaggcggcg   2040
atctgctaca ccggcgatat cctcaattcc gcccgcccga aatacgactt gaaatattac   2100
accaaccttg ccgtcgagct tgagaaggcc ggcgcccata tcattgcggt caaggatatg   2160
gcgggccttc tgaagccggc tgctgccaag gttctgttca aggcgctgcg tgaagcaacc   2220
ggcctgccga tccatttcca cacgcatgac acctcgggca ttgcggcggc aacggttctt   2280
gccgccgtcg aagccggtgt cgatgccgtc gatgcggcga tggatgcgct ctccggcaac   2340
acctcgcaac cctgtctcgg ctcgatcgtc gaggcgctct ccggctccga gcgcgatccc   2400
ggcctcgatc cggcatggat ccgccgcatc tccttctatt gggaagcggt gcgcaaccag   2460
tatgccgcct tcgaaagcga cctcaaggga ccggcatcgg aagtctatct gcatgaaatg   2520
ccgggcggcc agttcaccaa cctcaaggag caggcccgct cgctggggct ggaaacccgc   2580
tggcaccagg tggcgcaggc ctatgccgac gccaaccaga tgttcggcga tatcgtcaag   2640
gtgacgccat cctccaaggt cgtcggcgac atggcgctga tgatggtctc ccaggacctg   2700
accgtcgccg atgtcgtcag ccccgaccgc gaagtctcct tcccggaatc ggtcgtctcg   2760
atgctgaagg gcgatctcgg ccagcctccg tctggatggc cggaagcgct gcagaagaaa   2820
gcattgaagg gcgaaaagcc ctatacggtg cgcccccggct cgctgctcaa ggaagccgat   2880
ctcgatgcgg aacgcaaagt catcgagaag aagcttgagc gcgaggtcag cgacttcgaa   2940
ttcgcttcct atctgatgta tccgaaggtc ttcaccgact ttgcgcttgc ctccgatacc   3000
tacggtccgg tttcggtgct gccgacgccc gcctattttt acgggttggc ggacggcgag   3060
gagctgttcg ccgacatcga aagggcaag acgctcgtca tcgtcaatca ggcggtgagc   3120
gccaccgaca gccagggcat ggtcactgtc ttcttcgagc tcaacggcca gccgcgccgt   3180
atcaaggtgc ccgatcgggc ccacggggcg acgggagccg ccgtgcgccg caaggccgaa   3240
cccggcaatg ccgccatgt cggtgcgccg atgccgggcg tcatcagccg tgtctttgtc   3300
tcttcaggcc aggccgtcaa tgccggcgac gtgctcgtct ccatcgaggc catgaagatg   3360
gaaaccgcga tccatgcgga aaaggacggc accattgccg aagtgctggt caaggccggc   3420
gatcagatcg atgccaagga cctgctggcg gtttacggcg gatga                   3465
```

<210> SEQ ID NO 224
<211> LENGTH: 62
<212> TYPE: DNA
<213> ORGANISM: artificial

```
<220> FEATURE:
<223> OTHER INFORMATION: promoter Ptrc

<400> SEQUENCE: 224
gagctgttga caattaatca tccggctcgt ataatgtgtg gaattgtgag cggataacaa      60
tt                                                                    62

<210> SEQ ID NO 225
<211> LENGTH: 121
<212> TYPE: DNA
<213> ORGANISM: Escherichia coli

<400> SEQUENCE: 225
caagcccaaa ggaagagtga ggcgagtcag tcgcgtaatg cttaggcaca ggattgattt     60
gtcgcaatga ttgacacgat tccgcttgac gctgcgtaag gttttttgtaa ttttacaggc  120 a                                                                    121

<210> SEQ ID NO 226
<211> LENGTH: 933
<212> TYPE: DNA
<213> ORGANISM: Escherichia coli

<400> SEQUENCE: 226
atggttaaag tttatgcccc ggcttccagt gccaatatga gcgtcgggtt tgatgtgctc      60
ggggcggcgg tgacacctgt tgatggtgca ttgctcggag atgtagtcac ggttgaggcg    120
gcagagacat tcagtctcaa caacctcgga cgctttgccg ataagctgcc gtcagaacca    180
cgggaaaata tcgtttatca gtgctgggag cgttttttgcc aggaactggg taagcaaatt    240
ccagtggcga tgaccctgga aaagaatatg ccgatcggtt cgggcttagg ctccagtgcc    300
tgttcggtgg tcgcggcgct gatggcgatg aatgaacact gcggcaagcc gcttaatgac    360
actcgtttgc tggcttttga tgggcgagctg gaaggccgta tctccggcag cattcattac    420
gacaacgtgg caccgtgttt tctcggtggt atgcagttga tgatcgaaga aaacgacatc    480
atcagccagc aagtgccagg gtttgatgag tggctgtggg tgctggcgta tccggggatt    540
aaagtctcga cggcagaagc cagggctatt ttaccggcgc agtatcgccg ccaggattgc    600
attgcgcacg gcgacatctc ggcaggcttc attcacgcct gctattcccg tcagcctgag    660
cttgccgcga agctgatgaa agatgttatc gctgaaccct accgtgaacg gttactgcca    720
ggcttccggc aggcgcggca ggcggtcgcg gaaatcggcg cggtagcgag cggtatctcc    780
ggctccggcc cgaccttgtt cgctctgtgt gacaagccgg aaaccgccca gcgcgttgcc    840
gactggttgg gtaagaacta cctgcaaaat caggaaggtt ttgttcatat ttgccggctg    900
gatacggcgg gcgcacgagt actggaaaac taa                                 933

<210> SEQ ID NO 227
<211> LENGTH: 1287
<212> TYPE: DNA
<213> ORGANISM: Escherichia coli

<400> SEQUENCE: 227
atgaaactct acaatctgaa agatcacaac gagcaggtca gctttgcgca agccgtaacc     60
caggggttgg gcaaaaatca ggggctgttt tttccgcacg acctgccgga attcagcctg    120
actgaaattg atgagatgct gaagctggat tttgtcaccc gcagtgcgaa gatcctctcg    180
gcgtttattg gtgatgaaat cccacaggaa atcctggaag agcgcgtgcg cgcggcgttt    240
```

-continued

```
gccttcccgg ctccggtcgc caatgttgaa agcgatgtcg gttgtctgga attgttccac      300
gggccaacgc tggcatttaa agatttcggc ggtcgcttta tggcacaaat gctgacccat      360
attgcgggtg ataagccagt gaccattctg accgcgacct ccggtgatac cggagcggca      420
gtggctcatg ctttctacgg tttaccgaat gtgaaagtgg ttatcctcta tccacgaggc      480
aaaatcagtc cactgcaaga aaaactgttc tgtacattgg gcggcaatat cgaaactgtt      540
gccatcgacg gcgatttcga tgcctgtcag gcgctggtga agcaggcgtt tgatgatgaa      600
gaactgaaag tggcgctagg gttaaactcg gctaactcga ttaacatcag ccgtttgctg      660
gcgcagattt gctactactt tgaagctgtt gcgcagctgc cgcaggagac gcgcaaccag      720
ctggttgtct cggtgccaag cggaaacttc ggcgatttga cggcgggtct gctggcgaag      780
tcactcggtc tgccggtgaa acgttttatt gctgcgacca acgtgaacga taccgtgcca      840
cgtttcctgc acgacggtca gtggtcaccc aaagcgactc aggcgacgtt atccaacgcg      900
atggacgtga gtcagccgaa caactggccg cgtgtggaag agttgttccg ccgcaaaatc      960
tggcaactga aagagctggg ttatgcagcc gtggatgatg aaaccacgca acagacaatg     1020
cgtgagttaa agaactggg ctacacttcg gagccgcacg ctgccgtagc ttatcgtgcg     1080
ctgcgtgatc agttgaatcc aggcgaatat ggcttgttcc tcggcaccgc gcatccggcg     1140
aaatttaaag agagcgtgga agcgattctc ggtgaaacgt tggatctgcc aaaagagctg     1200
gcagaacgtg ctgatttacc cttgctttca cataatctgc ccgccgattt tgctgcgttg     1260
cgtaaattga tgatgaatca tcagtaa                                        1287
```

<210> SEQ ID NO 228
<211> LENGTH: 930
<212> TYPE: DNA
<213> ORGANISM: Escherichia coli

<400> SEQUENCE: 228

```
atgccgattc gtgtgccgga cgagctaccc gccgtcaatt tcttgcgtga agaaaacgtc       60
tttgtgatga caacttctcg tgcgtctggt caggaaattc gtccacttaa ggttctgatc      120
cttaacctga tgccgaagaa gattgaaact gaaaatcagt ttctgcgcct gctttcaaac      180
tcacctttgc aggtcgatat tcagctgttg cgcatcgatt cccgtgaatc gcgcaacacg      240
cccgcagagc atctgaacaa cttctactgt aactttgaag atattcagga tcagaacttt      300
gacggtttga ttgtaactgg tgcgccgctg gcctggtgg agtttaatga tgtcgcttac      360
tggccgcaga tcaaacaggt gctggagtgg tcgaaagatc acgtcacctc gacgctgttt      420
gtctgctggg cggtacaggc cgcgctcaat atcctctacg gcattcctaa gcaaactcgc      480
accgaaaaac tctctggcgt ttacgagcat catattctcc atcctcatgc gcttctgacg      540
cgtggctttg atgattcatt cctggcaccg cattcgcgct atgctgactt tccggcagcg      600
ttgattcgtg attacaccga tctggaaatt ctggcagaga cggaagaagg ggatgcatat      660
ctgtttgcca gtaaagataa gcgcattgcc tttgtgacgg gccatcccga atatgatgcg      720
caaacgctgg cgcaggaatt tttccgcgat gtggaagccg actagaccc ggatgtaccg      780 tataactatt ccccgcacaa tgatccgcaa aatacaccgc gagcgagctg gcgtagtcac      840
ggtaatttac tgtttaccaa ctggctcaac tattacgtct accagatcac gccatacgat      900
ctacggcaca tgaatccaac gctggattaa                                      930
```

<210> SEQ ID NO 229
<211> LENGTH: 34

<212> TYPE: DNA
<213> ORGANISM: T7 bacteriophage

<400> SEQUENCE: 229
tcacactggc tcaccttcgg gtgggccttt ctgc         34

<210> SEQ ID NO 230
<211> LENGTH: 66
<212> TYPE: DNA
<213> ORGANISM: artificial
<220> FEATURE:
<223> OTHER INFORMATION: promoter for attenuation of thrBC and metA
      expression

<400> SEQUENCE: 230
gagctgttgg cgattaatca tccggctcgt atattgtgtg gggttgcatg tactggagga    60
cagacc                                                              66

<210> SEQ ID NO 231
<211> LENGTH: 50
<212> TYPE: DNA
<213> ORGANISM: artificial
<220> FEATURE:
<223> OTHER INFORMATION: primer attenuation thrBC 1

<400> SEQUENCE: 231
atggttaaag tttatgcccc ggcttccagt gccaatatga gcgtcgggtt              50

<210> SEQ ID NO 232
<211> LENGTH: 66
<212> TYPE: DNA
<213> ORGANISM: artificial
<220> FEATURE:
<223> OTHER INFORMATION: primer attenuation thrBC 2

<400> SEQUENCE: 232
gacgttacag ctgccggtgt ctttgctgat ctgctacgta ccctctcatg gaagttagga    60
gtctga                                                              66

<210> SEQ ID NO 233
<211> LENGTH: 50
<212> TYPE: DNA
<213> ORGANISM: artificial
<220> FEATURE:
<223> OTHER INFORMATION: primer attenuation metA 1

<400> SEQUENCE: 233
atgccgattc gtgtgccgga cgagctaccc gccgtcaatt tcttgcgtga              50

<210> SEQ ID NO 234
<211> LENGTH: 66
<212> TYPE: DNA
<213> ORGANISM: artificial
<220> FEATURE:
<223> OTHER INFORMATION: primer attenuation metA 2

<400> SEQUENCE: 234
tttctggtta tcttcagcta tctggatgtc taaacgtata agcgtatgta gtgaggtaat    60
caggtt                                                              66

<210> SEQ ID NO 235
<211> LENGTH: 54
<212> TYPE: DNA
<213> ORGANISM: artificial

```
<220> FEATURE:
<223> OTHER INFORMATION: promoter Ptac

<400> SEQUENCE: 235
tgacaattaa tcatcggctc gtataatgtg tggaattgtg agcggataac aatt         54

<210> SEQ ID NO 236
<211> LENGTH: 17
<212> TYPE: DNA
<213> ORGANISM: T7 bacteriophage

<400> SEQUENCE: 236
ttaactttaa gaaggag                                                   17

<210> SEQ ID NO 237
<211> LENGTH: 329
<212> TYPE: PRT
<213> ORGANISM: Escherichia coli

<400> SEQUENCE: 237
```

| | | | | | | | | | | | | | | | |
|---|---|---|---|---|---|---|---|---|---|---|---|---|---|---|---|
| Met | Lys | Leu | Ala | Val | Tyr | Ser | Thr | Lys | Gln | Tyr | Asp | Lys | Lys | Tyr | Leu |
| 1 | | | | 5 | | | | | 10 | | | | | 15 | |
| Gln | Gln | Val | Asn | Glu | Ser | Phe | Gly | Phe | Glu | Leu | Glu | Phe | Phe | Asp | Phe |
| | | | 20 | | | | | 25 | | | | | 30 | | |
| Leu | Leu | Thr | Glu | Lys | Thr | Ala | Lys | Thr | Ala | Asn | Gly | Cys | Glu | Ala | Val |
| | | | 35 | | | | | 40 | | | | | 45 | | |
| Cys | Ile | Phe | Val | Asn | Asp | Asp | Gly | Ser | Arg | Pro | Val | Leu | Glu | Glu | Leu |
| | 50 | | | | | 55 | | | | | 60 | | | | |
| Lys | Lys | His | Gly | Val | Lys | Tyr | Ile | Ala | Leu | Arg | Cys | Ala | Gly | Phe | Asn |
| 65 | | | | | 70 | | | | | 75 | | | | | 80 |
| Asn | Val | Asp | Leu | Asp | Ala | Ala | Lys | Glu | Leu | Gly | Leu | Lys | Val | Val | Arg |
| | | | | 85 | | | | | 90 | | | | | 95 | |
| Val | Pro | Ala | Tyr | Asp | Pro | Glu | Ala | Val | Ala | Glu | His | Ala | Ile | Gly | Met |
| | | | 100 | | | | | 105 | | | | | 110 | | |
| Met | Met | Thr | Leu | Asn | Arg | Arg | Ile | His | Arg | Ala | Tyr | Gln | Arg | Thr | Arg |
| | | | 115 | | | | | 120 | | | | | 125 | | |
| Asp | Ala | Asn | Phe | Ser | Leu | Glu | Gly | Leu | Thr | Gly | Phe | Thr | Met | Tyr | Gly |
| | 130 | | | | | 135 | | | | | 140 | | | | |
| Lys | Thr | Ala | Gly | Val | Ile | Gly | Thr | Gly | Lys | Ile | Gly | Val | Ala | Met | Leu |
| 145 | | | | | 150 | | | | | 155 | | | | | 160 |
| Arg | Ile | Leu | Lys | Gly | Phe | Gly | Met | Arg | Leu | Leu | Ala | Phe | Asp | Pro | Tyr |
| | | | | 165 | | | | | 170 | | | | | 175 | |
| Pro | Ser | Ala | Ala | Ala | Leu | Glu | Leu | Gly | Val | Glu | Tyr | Val | Asp | Leu | Pro |
| | | | 180 | | | | | 185 | | | | | 190 | | |
| Thr | Leu | Phe | Ser | Glu | Ser | Asp | Val | Ile | Ser | Leu | His | Cys | Pro | Leu | Thr |
| | | | 195 | | | | | 200 | | | | | 205 | | |
| Pro | Glu | Asn | Tyr | His | Leu | Leu | Asn | Glu | Ala | Ala | Phe | Glu | Gln | Met | Lys |
| | 210 | | | | | 215 | | | | | 220 | | | | |
| Asn | Gly | Val | Met | Ile | Val | Asn | Thr | Ser | Arg | Gly | Ala | Leu | Ile | Asp | Ser |
| 225 | | | | | 230 | | | | | 235 | | | | | 240 |
| Gln | Ala | Ala | Ile | Glu | Ala | Leu | Lys | Asn | Gln | Lys | Ile | Gly | Ser | Leu | Gly |
| | | | | 245 | | | | | 250 | | | | | 255 | |
| Met | Asp | Val | Tyr | Glu | Asn | Glu | Arg | Asp | Leu | Phe | Phe | Glu | Asp | Lys | Ser |
| | | | 260 | | | | | 265 | | | | | 270 | | |
| Asn | Asp | Val | Ile | Gln | Asp | Asp | Val | Phe | Arg | Arg | Leu | Ser | Ala | Cys | His |
| | | | 275 | | | | | 280 | | | | | 285 | | |

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325

<210> SEQ ID NO 238
<211> LENGTH: 2676
<212> TYPE: DNA
<213> ORGANISM: Escherichia coli

<400> SEQUENCE: 238

| | |
|---|---|
| atggctgtta ctaatgtcgc tgaacttaac gcactcgtag agcgtgtaaa aaaagcccag | 60 |
| cgtgaatatg ccagtttcac tcaagagcaa gtagacaaaa tcttccgcgc cgccgctctg | 120 |
| gctgctgcag atgctcgaat cccactcgcg aaaatggccg ttgccgaatc cggcatgggt | 180 |
| atcgtcgaag ataaagtgat caaaaaccac tttgcttctg aatatatcta caacgcctat | 240 |
| aaagatgaaa aacctgtggt gttctgtct gaagacgaca cttttggtac catcactatc | 300 |
| gctgaaccaa tcggtattat ttgcggtatc gttccgacca ctaacccgac ttcaactgct | 360 |
| atcttcaaat cgctgatcag tctgaagacc cgtaacgcca ttatcttctc cccgcacccg | 420 |
| cgtgcaaaag atgccaccaa caagcggct gatatcgttc tgcaggctgc tatcgctgcc | 480 |
| ggtgctccga agatctgat cggctggatc gatcaacctt ctgttgaact gtctaacgca | 540 |
| ctgatgcacc acccagacat caacctgatc ctcgcgactg gtggtccggg catggttaaa | 600 |
| gccgcataca gctccggtaa accagctatc ggtgtaggcg cgggcaacac tccagttgtt | 660 |
| atcgatgaaa ctgctgatat caaacgtgca gttgcatctg tactgatgtc caaaaccttc | 720 |
| gacaacggcg taatctgtgc ttctgaacag tctgttgttg ttgttgactc tgtttatgac | 780 |
| gctgtacgtg aacgttttgc aacccacggc ggctatctgt tgcagggtaa agagctgaaa | 840 |
| gctgttcagg atgttatcct gaaaaacggt gcgctgaacg cggctatcgt tggtcagcca | 900 |
| gcctataaaa ttgctgaact ggcaggcttc tctgtaccag aaaacaccaa gattctgatc | 960 |
| ggtgaagtga ccgttgttga tgaaagcgaa ccgttcgcac atgaaaaact gtccccgact | 1020 |
| ctggcaatgt accgcgctaa agatttcgaa gacgcggtag aaaagcaga gaaactggtt | 1080 |
| gctatgggcg gtatcggtca tacctcttgc ctgtacactg accaggataa ccaaccggct | 1140 |
| cgcgtttctt acttcggtca gaaatgaaa acggcgcgta tcctgattaa cacccccagcg | 1200 |
| tctcagggtg gtatcggtga cctgtataac ttcaaactcg caccttccct gactctgggt | 1260 |
| tgtggttctt ggggtggtaa ctccatctct gaaaacgttg gtccgaaaca cctgatcaac | 1320 |
| aagaaaaccg ttgctaagcg agctgaaaac atgttgtggc acaaacttcc gaaatctatc | 1380 |
| tacttccgcc gtggctccct gccaatcgcg ctggatgaag tgattactga tggccacaaa | 1440 |
| cgtgcgctca tcgtgactga ccgcttcctg ttcaacaatg ttatgctga tcagatcact | 1500 |
| tccgtactga aagcagcagg cgttgaaact gaagtcttct cgaagtaga agcggacccg | 1560 |
| accctgagca tcgttcgtaa aggtgcagaa ctggcaaact ccttcaaacc agacgtgatt | 1620 |
| atcgcgctgg gtggtggttc cccgatggac gccgcgaaga tcatgtgggt tatgtacgaa | 1680 |
| catccggaaa ctcacttcga agagctggcg ctgcgcttta tggatatccg taaacgtatc | 1740 |
| tacaagttcc cgaaaatggg cgtgaaagcg aaaatgatcg ctgtcaccac cacttctggt | 1800 |
| acaggttctg aagtcactcc gtttgcggtt gtaactgacg acgctactgg tcagaaatat | 1860 |

```
ccgctggcag actatgcgct gactccggat atggcgattg tcgacgccaa cctggttatg    1920
gacatgccga agtccctgtg tgctttcggt ggtctggacg cagtaactca cgccatggaa    1980
gcttatgttt ctgtactggc atctgagttc tctgatggtc aggctctgca ggcactgaaa    2040
ctgctgaaag aatatctgcc agcgtcctac cacgaagggt ctaaaaatcc ggtagcgcgt    2100
gaacgtgttc acagtgcagc gactatcgcg ggtatcgcgt ttgcgaacgc cttcctgggt    2160
gtatgtcact caatggcgca caaactgggt tcccagttcc atattccgca cggtctggca    2220
aacgccctgc tgatttgtaa cgttattcgc tacaatgcga acgacaaccc gaccaagcag    2280
actgcattca gccagtatga ccgtccgcag gctcgccgtc gttatgctga aattgccgac    2340
cacttgggtc tgagcgcacc gggcgaccgt actgctgcta agatcgagaa actgctggca    2400
tggctggaaa cgctgaaagc tgaactgggt attccgaaat ctatccgtga agctggcgtt    2460
caggaagcag acttcctggc gaacgtggat aaactgtctg aagatgcatt cgatgaccag    2520
tgcaccggcg ctaaccccgcg ttacccgctg atctccgagc tgaaacagat tctgctggat    2580
acctactacg gtcgtgatta tgtagaaggt gaaactgcag cgaagaaaga agctgctccg    2640
gctaaagctg agaaaaaagc gaaaaaatcc gcttaa                             2676
```

<210> SEQ ID NO 239
<211> LENGTH: 1443
<212> TYPE: DNA
<213> ORGANISM: Escherichia coli

<400> SEQUENCE: 239

```
atgtccagaa ggcttcgcag aacaaaaatc gttaccacgt taggcccagc aacagatcgc      60
gataataatc ttgaaaaagt tatcgcggcg ggtgccaacg ttgtacgtat gaacttttct     120
cacggctcgc ctgaagatca caaaatgcgc gcggataaag ttcgtgagat tgccgcaaaa     180
ctggggcgtc atgtggctat tctgggtgac ctccaggggc ccaaaatccg tgtatccacc     240
tttaaagaag gcaaagtttt cctcaatatt ggggataaat tcctgctcga cgccaacctg     300
ggtaaaggtg aaggcgacaa agaaaaagtc ggtatcgact acaaaggcct gcctgctgac     360
gtcgtgcctg tgacatcct gctgctggac gatggtcgcg tccagttaaa agtactggaa     420
gttcagggca tgaaagtgtt caccgaagtc accgtcggtg gtcccctctc caacaataaa     480
ggtatcaaca aacttggcgg cggttttgtcg gctgaagcgc tgaccgaaaa agacaaagca     540
gacattaaga ctgcggcgtt gattggcgta gattacctgg ctgtctcctt cccacgctgt     600
ggcgaagatc tgaactatgc ccgtcgcctg gcacgcgatg caggatgtga tgcgaaaatt     660
gttgccaagg ttgaacgtgc ggaagccgtt tgcagccagg atgcaatgga tgacatcatc     720
ctcgcctctg acgtggtaat ggttcacgt ggcgacctcg tgtggaaat tggcgacccg     780 gaactggtcg gcattcagaa agcgttgatc cgtcgtgcgc gtcagctaaa ccgagcggta     840
atcacggcga cccagatgat ggagtcaatg attactaacc cgatgccgac gcgtgcagaa     900
gtcatggacg tagcaaacgc cgttctggat ggtactgacg ctgtgatgct gtctgcagaa     960
actgccgctg ggcagtatcc gtcagaaacc gttgcagcca tggcgcgcgt ttgcctgggt    1020
gcggaaaaaa tcccgagcat caacgtttct aaacaccgtc tggacgttca gttcgacaat    1080
gtggaagaag ctattgccat gtcagcaatg tacgcagcta accacctgaa aggcgttacg    1140
gcgatcatca ccatgaccga atcgggtcgt accgcgctga tgacctcccg tatcagctct    1200
ggtctgccaa ttttcgccat gtcgcgccat gaacgtacgc tgaacctgac tgctctctat    1260
cgtggcgtta cgccggtgca ctttgatagc gctaatgacg gcgtagcagc tgccagcgaa    1320
```

```
gcggttaatc tgctgcgcga taaaggttac ttgatgtctg gtgacctggt gattgtcacc    1380
cagggcgacg tgatgagtac cgtgggttct actaatacca cgcgtatttt aacggtagag    1440
taa                                                                  1443
```

<210> SEQ ID NO 240
<211> LENGTH: 1413
<212> TYPE: DNA
<213> ORGANISM: Escherichia coli

<400> SEQUENCE: 240

```
atgaaaaaga ccaaaattgt ttgcaccatc ggaccgaaaa ccgaatctga agagatgtta     60
gctaaaatgc tggacgctgg catgaacgtt atgcgtctga acttctctca tggtgactat    120
gcagaacacg tcagcgcat tcagaatctg cgcaacgtga tgagcaaaac tggtaaaacc    180
gccgctatcc tgcttgatac caaaggtccg gaaatccgca ccatgaaact ggaaggcggt    240
aacgacgttt ctctgaaagc tggtcagacc tttactttca ccactgataa atctgttatc    300
ggcaacagcg aaatggttgc ggtaacgtat gaaggtttca ctactgacct gtctgttggc    360
aacaccgtac tggttgacga tggtctgatc ggtatggaag ttaccgccat gaaggtaac    420 aaagttatct gtaaagtgct gaacaacggt gacctgggcg aaaacaaagg tgtgaacctg    480
cctggcgttt ccattgctct gcagcactg gctgaaaaag acaaacagga cctgatcttt    540
ggttgcgaac aaggcgtaga ctttgttgct gcttccttta ttcgtaagcg ttctgacgtt    600
atcgaaatcc gtgagcacct gaaagcgcac ggcggcgaaa acatccacat catctccaaa    660
atcgaaaacc aggaaggcct caacaacttc gacgaaatcc tcgaagcctc tgacggcatc    720
atggttgcgc gtggcgacct gggtgtgaaa atcccggtag aagaagttat cttcgcccag    780
aagatgatga tcgaaaaatg tatccgtgca cgtaaagtcg ttatcactgc gacccagatg    840
ctggattcca tgatcaaaaa cccacgcccc actcgcgcag aagccggtga cgttgcaaac    900
gccatcctcg acggtactga cgcagtgatg ctgtctggtg aatccgcaaa aggtaaatac    960
ccgctggaag cggtttctat catggcgacc atctgcgaac gtaccgaccg cgtgatgaac   1020
agccgtctcg agttcaacaa tgacaaccgt aaactgcgca ttaccgaagc ggtatgccgt   1080
ggtgccgttg aaactgctga aaaactggat gctccgctga tcgtggttgc tactcagggc   1140
ggtaaatctg ctcgcgcagt acgtaaatac ttcccggatg ccaccatcct ggcactgacc   1200
accaacgaaa aacggctca tcagttggta ctgagcaaag cgttgtgcc gcagcttgtt   1260 aaagagatca cttctactga tgatttctac cgtctgggta agaactggc tctgcagagc   1320 ggtctggcac acaaaggtga cgttgtagtt atggtttctg gtgcactggt accgagcggc   1380
actactaaca ccgcatctgt tcacgtcctg taa                                 1413
```

<210> SEQ ID NO 241
<211> LENGTH: 1221
<212> TYPE: DNA
<213> ORGANISM: Escherichia coli

<400> SEQUENCE: 241

```
gtggttgctg aaaaccagcc tgggcacatt gatcaaataa agcagaccaa cgcgggcgcg     60
gtttatcgcc tgattgatca gcttggtcca gtctcgcgta tcgatctttc ccgtctggcg    120
caactggctc ctgccagtat cactaaaatt gtccgtgaga tgctcgaagc acacctggtg    180
caagagctgg aaatcaaaga agcggggaac cgtggccgtc cggcggtggg gctggtggtt    240
```

```
gaaactgaag cctggcacta tctttctctg cgcattagtc gcggggagat tttccttgct      300
ctgcgcgatc tgagcagcaa actggtggtg aagagtcgc  aggaactggc gttaaaagat      360
gacttgccat tgctggatcg tattatttcc catatcgatc agttttttat ccgccaccag      420
aaaaaacttg agcgtctaac ttcgattgcc ataaccttgc cgggaattat tgatacggaa      480
aatggtattg tacatcgcat gccgttctac gaggatgtaa aagagatgcc gctcggcgag      540
gcgctggagc agcataccgg cgttccggtt tatattcagc atgatatcag cgcatggacg      600
atggcagagg ccttgtttgg tgcctcacgc ggggcgcgcg atgtgattca ggtggttatc      660
gatcacaacg tggggcggg  cgtcattacc gatggtcatc tgctacacgc aggcagcagt      720
agtctcgtgg aaataggcca cacacaggtc gacccgtatg ggaaacgctg ttattgcggg      780
aatcacggct gcctcgaaac catcgccagc gtggacagta ttcttgagct ggcacagctg      840
cgtcttaatc aatccatgag ctcgatgtta catggacaac cgttaaccgt ggactcattg      900
tgtcaggcgg cattgcgcgg cgatctactg gcaaaagaca tcattaccgg ggtgggcgcg      960
catgtcgggc gcattcttgc catcatggtg aatttattta cccacaaaa  aatactgatt     1020 ggctcaccgt taagtaaagc ggcagatatc ctcttcccgg tcatctcaga cagcatccgt     1080
cagcaggccc ttcctgcgta tagtcagcac atcagcgttg agagtactca gttttctaac     1140
cagggcacga tggcaggcgc tgcactggta aaagacgcga tgtataacgg ttctttgttg     1200
attcgtctgt tgcagggtta a                                               1221

<210> SEQ ID NO 242
<211> LENGTH: 2145
<212> TYPE: DNA
<213> ORGANISM: Escherichia coli

<400> SEQUENCE: 242
gtgtcccgta ttattatgct gatccctacc ggaaccagcg tcggtctgac cagcgtcagc       60
cttggcgtga tccgtgcaat ggaacgcaaa ggcgttcgtc tgagcgtttt caaacctatc      120
gctcagccgc gtaccggtgg cgatgcgccc gatcagacta cgactatcgt gcgtgcgaac      180
tcttccacca cgacggccgc tgaaccgctg aaaatgagct acgttgaagg tctgctttcc      240
agcaatcaga aagatgtgct gatggaagag atcgtcgcaa actaccacgc taacaccaaa      300
gacgctgaag tcgttctggt tgaaggtctg gtcccgacac gtaagcacca gtttgcccag      360
tctctgaact acgaaatcgc taaaacgctg aatgcggaaa tcgtcttcgt tatgtctcag      420
ggcactgaca ccccggaaca gctgaaagag cgtatcgaac tgacccgcaa cagcttcggc      480
ggtgccaaaa acaccaacat caccggcgtt atcgttaaca aactgaacgc accggttgat      540
gaacagggtc gtactcgccc ggatctgtcc gagattttcg acgactcttc caaagctaaa      600
gtaaacaatg ttgatccggc gaagctgcaa gaatccagcc cgctgccggt tctcggcgct     660
gtgccgtgga gctttgacct gatcgcgact cgtgcgatcg atatggctcg ccacctgaat     720
gcgaccatca tcaacgaagg cgacatcaat actcgccgcg ttaaatccgt cactttctgc     780
gcacgcagca ttccgcacat gctggagcac ttccgtgccg ttctctgct  ggtgacttcc      840 gcagaccgtc ctgacgtgct ggtggccgct tgcctggcag ccatgaacgg cgtagaaatc      900
ggtgccctgc tgctgactgg cggttacgaa atggacgcgc gcatttctaa actgtgcgaa      960
cgtgctttcg ctaccggcct gccggtattt atggtgaaca ccaacacctg gcagacctct     1020
ctgagcctga gagcttcaa  cctggaagtt ccggttgacg atcacgaacg tatcgagaaa     1080
gttcaggaat acgttgctaa ctacatcaac gctgactgga tcgaatctct gactgccact     1140
```

```
tctgagcgca gccgtcgtct gtctccgcct gcgttccgtt atcagctgac tgaacttgcg    1200
cgcaaagcgg gcaaacgtat cgtactgccg gaaggtgacg aaccgcgtac cgttaaagca    1260
gccgctatct gtgctgaacg tggtatcgca acttgcgtac tgctgggtaa tccggcagag    1320
atcaaccgtg ttgcagcgtc tcagggtgta gaactgggtg cagggattga aatcgttgat    1380
ccagaagtgg ttcgcgaaag ctatgttggt cgtctggtcg aactgcgtaa gaacaaaggc    1440
atgaccgaaa ccgttgcccg cgaacagctg gaagacaacg tggtgctcgg tacgctgatg    1500
ctggaacagg atgaagttga tggtctggtt ccggtgctg ttcacactac cgcaaacacc    1560
atccgtccgc cgctgcagct gatcaaaact gcaccgggca gctccctggt atcttccgtg    1620
ttcttcatgc tgctgccgga acaggtttac gtttacggtg actgtgcgat caacccggat    1680
ccgaccgctg aacagctggc agaaatcgcg attcagtccg ctgattccgc tgcggccttc    1740
ggtatcgaac gcgcgttgc tatgctctcc tactccaccg gtacttctgg tgcaggtagc    1800
gacgtagaaa aagttcgcga agcaactcgt ctggcgcagg aaaaacgtcc tgacctgatg    1860
atcgacggtc cgctgcagta cgacgctgcg gtaatggctg acgttgcgaa atccaaagcg    1920
ccgaactctc cggttgcagg tcgcgctacc gtgttcatct cccggatct gaacaccggt    1980 aacaccacct acaaagcggt acagcgttct gccgacctga tctccatcgg gccgatgctg    2040
cagggtatgc gcaagccggt taacgacctg tcccgtggcg cactggttga cgatatcgtc    2100
tacaccatcg cgctgactgc gattcagtct gcacagcagc agtaa    2145

<210> SEQ ID NO 243
<211> LENGTH: 1602
<212> TYPE: DNA
<213> ORGANISM: Escherichia coli

<400> SEQUENCE: 243
atgactgaac aggcaacaac aaccgatgaa ctggctttca caaggccgta tggcgagcag     60
gagaagcaaa ttcttactgc cgaagcggta gaatttctga ctgagctggt gacgcatttt    120
acgccacaac gcaataaact tctggcagcg cgcattcagc agcagcaaga tattgataac    180
ggaacgttgc ctgattttat ttcggaaaca gcttccattc gcgatgctga ttggaaaatt    240
cgcgggattc ctgcggactt agaagaccgc cgcgtagaga taactggccc ggtagagcgc    300
aagatggtga tcaacgcgct caacgccaat gtgaaagtct ttatgccga tttcgaagat    360 tcactggcac cagactggaa caaagtgatc gacgggcaaa ttaacctgcg tgatgcggtt    420
aacggcacca tcagttacac caatgaagca ggcaaaattt accagctcaa gcccaatcca    480
gcggttttga tttgtcgggt acgcggtctg cacttgccgg aaaaacatgt cacctggcgt    540
ggtgaggcaa tccccggcag cctgtttgat tttgcgctct atttcttcca caactatcag    600
gcactgttgg caagggcag tggtccctat ttctatctgc gaaaacccca gtcctggcag    660
gaagcggcct ggtggagcga agtcttcagc tatgcagaag atcgctttaa tctgccgcgc    720
ggcaccatca aggcgacgtt gctgattgaa acgctgcccg ccgtgttcca gatggatgaa    780
atccttcacg cgctgcgtga ccatattgtt ggtctgaact gcggtcgttg ggattacatc    840
ttcagctata tcaaaacgtt gaaaaactat cccgatcgcg tcctgccaga cagacaggca    900
gtgacgatgg ataaaccatt cctgaatgct tactcacgcc tgttgattaa aacctgccat    960
aaacgcggtg ctttttgcgat gggcggcatg gcggcgttta ttccgagcaa agatgaagag   1020
cacaataacc aggtgctcaa caaagtaaaa gcggataaat cgctggaagc caataacggt   1080
```

```
cacgatggca catggatcgc tcacccaggc cttgcggaca cggcaatggc ggtattcaac   1140
gacattctcg gctcccgtaa aaatcagctt gaagtgatgc gcgaacaaga cgcgccgatt   1200
actgccgatc agctgctggc accttgtgat ggtgaacgca ccgaagaagg tatgcgcgcc   1260
aacattcgcg tggctgtgca gtacatcgaa gcgtggatct ctggcaacgg ctgtgtgccg   1320
atttatggcc tgatggaaga tgcggcgacg gctgaaattt cccgtacctc gatctggcag   1380
tggatccatc atcaaaaaac gttgagcaat ggcaaaccgg tgaccaaagc cttgttccgc   1440
cagatgctgg gcgaagagat gaaagtcatt gccagcgaac tgggcgaaga acgtttctcc   1500
caggggcgtt ttgacgatgc cgcacgcttg atggaacaga tcaccacttc cgatgagtta   1560
attgatttcc tgaccctgcc aggctaccgc ctgttagcgt aa                      1602

<210> SEQ ID NO 244
<211> LENGTH: 825
<212> TYPE: DNA
<213> ORGANISM: Escherichia coli

<400> SEQUENCE: 244
atggtcgcac ccattcccgc gaaacgcggc agaaaacccg ccgttgccac cgcaccagcg     60
actggacagg ttcagtcttt aacgcgtggc ctgaaattac tggagtggat tgccgaatcc    120
aatggcagtg tggcactcac ggaactggcg caacaagccg ggttacccaa ttccacgacc    180
caccgcctgc taaccacgat gcaacagcag ggtttcgtgc gtcaggttgg cgaactggga    240
cattgggcaa tcggcgcaca tgcctttatg gtcggcagca gctttctcca gagccgtaat    300
ttgttagcga ttgttcaccc tatcctgcgc aatctaatgg aagagtctgg cgaaacggtc    360
aatatggcgg tgcttgatca aagcgatcac gaagcgatta ttatcgacca ggtacagtgt    420
acgcatctga tgcgaatgtc cgcgccatc ggcggtaaat tgccgatgca cgcttccggt    480
gcgggtaaag ccttttttagc ccaactgagc gaagaacagg tgacgaagct gctgcaccgc    540
aaagggttac atgcctatac ccacgcaacg ctggtgtctc ctgtgcattt aaaagaagat    600
ctcgcccaaa cgcgcaaacg gggttattca tttgacgatg aggaacatgc actggggcta    660
cgttgccttg cagcgtgtat tttcgatgag caccgtgaac cgtttgccgc aatttctatt    720
tccggaccga tttcacgtat taccgatgac cgcgtgaccg agtttggcgc gatggtgatt    780
aaagcggcga aggaagtgac gctggcgtac ggtggaatgc gctga                    825

<210> SEQ ID NO 245
<211> LENGTH: 50
<212> TYPE: DNA
<213> ORGANISM: artificial
<220> FEATURE:
<223> OTHER INFORMATION: primer deletion kgtP 1

<400> SEQUENCE: 245
ggctataccg tctggcaact gacccgtcac taaagacgca tccccttccc                50

<210> SEQ ID NO 246
<211> LENGTH: 50
<212> TYPE: DNA
<213> ORGANISM: artificial
<220> FEATURE:
<223> OTHER INFORMATION: primer deletion kgtP 2

<400> SEQUENCE: 246
aaaagcgacc gacaaaagca tcggattacg gcaggagaca taatggcatg                50
```

```
<210> SEQ ID NO 247
<211> LENGTH: 50
<212> TYPE: DNA
<213> ORGANISM: artificial
<220> FEATURE:
<223> OTHER INFORMATION: primer deletion llgP 1

<400> SEQUENCE: 247
gtctgacagg cgtctgggta aaacaatcat taaggaatca tccacgttaa            50

<210> SEQ ID NO 248
<211> LENGTH: 50
<212> TYPE: DNA
<213> ORGANISM: artificial
<220> FEATURE:
<223> OTHER INFORMATION: primer deletion llgP 2

<400> SEQUENCE: 248
agcaacagac tcattacacg atgtgcgtgg actccaggag acctgcaatg            50

<210> SEQ ID NO 249
<211> LENGTH: 50
<212> TYPE: DNA
<213> ORGANISM: artificial
<220> FEATURE:
<223> OTHER INFORMATION: primer deletion glcA 1

<400> SEQUENCE: 249
gatattaacg atcatccggc tttattgatt tacgagacta acatcccggt            50

<210> SEQ ID NO 250
<211> LENGTH: 50
<212> TYPE: DNA
<213> ORGANISM: artificial
<220> FEATURE:
<223> OTHER INFORMATION: primer deletion glcA 2

<400> SEQUENCE: 250
aaccttaagt atatcaagca tataaagata ataagagact gaacaatatg            50
```